US008834880B2

(12) United States Patent
Green et al.

(10) Patent No.: US 8,834,880 B2
(45) Date of Patent: Sep. 16, 2014

(54) ANTIBODIES DIRECTED TO ANGIOPOIETIN-2 AND USES THEREOF

(71) Applicant: MedImmune Limited, Cambridge (GB)

(72) Inventors: Larry L. Green, San Francisco, CA (US); Qing Zhou, Fremont, CA (US); Bruce A. Keyt, Hillsborough, CA (US); Xiao-Dong Yang, Palo Alto, CA (US); Stephen Charles Emery, Winterley (GB); David Charles Blakey, Macclesfield (GB)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 13/690,120

(22) Filed: Nov. 30, 2012

(65) Prior Publication Data

US 2013/0171160 A1 Jul. 4, 2013

Related U.S. Application Data

(63) Continuation of application No. 13/169,400, filed on Jun. 27, 2011, now abandoned, which is a continuation of application No. 11/311,939, filed on Dec. 19, 2005, now Pat. No. 7,973,140.

(60) Provisional application No. 60/711,289, filed on Aug. 25, 2005, provisional application No. 60/638,354, filed on Dec. 21, 2004.

(51) Int. Cl.
*A61K 39/395* (2006.01)
*C07K 16/22* (2006.01)

(52) U.S. Cl.
CPC ............ *A61K 39/39558* (2013.01); *C07K 16/22* (2013.01)
USPC ...................................................... 424/141.1

(58) Field of Classification Search
CPC .......................... A61K 39/39558; C07K 16/22
See application file for complete search history.

(56) References Cited

U.S. PATENT DOCUMENTS

| | | |
|---|---|---|
| 5,650,490 A | 7/1997 | Davis et al. |
| 5,814,464 A | 9/1998 | Davis et al. |
| 6,166,185 A | 12/2000 | Davis et al. |
| 6,455,035 B1 | 9/2002 | Suri et al. |
| 7,067,475 B2 | 6/2006 | Cerretti et al. |
| 7,205,275 B2 | 4/2007 | Oliner |
| 7,485,297 B2 | 2/2009 | Wood et al. |
| 7,521,053 B2 | 4/2009 | Oliner |
| 7,658,924 B2 | 2/2010 | Oliner et al. |
| 2003/0124129 A1 | 7/2003 | Oliner |
| 2006/0057138 A1 | 3/2006 | Wood et al. |

FOREIGN PATENT DOCUMENTS

| | | |
|---|---|---|
| EP | 0784683 B1 | 2/2001 |
| EP | 1165115 B1 | 5/2003 |
| EP | 0821728 B1 | 8/2004 |
| WO | WO 00/75323 A1 | 12/2000 |
| WO | WO 03/030833 | 4/2003 |

OTHER PUBLICATIONS

Ahmad, Syed A. et al., 2001, "The Effects of Angiopoietin-1 and -2 on Tumor Growth and Angiogenesis in Human Colon Cancer", Cancer Research, 61:1255-1259.
Ahmad, Syed A. et al., 2001, "Differential Expression of Angiopoietin-1 and Angiopoietin-2 in Colon Carcinoma", Cancer, 92:1138-1143.
Asahara, Takayuki et al., 1998, "Tie2 Receptor Ligands, Angiopoietin-1 and Angiopoietin-2, Modulate VEGF-Induced Postnatal Neovascularization", Circ. Res. 83:233-240.
Bunone, Giuseppe et al., 1999, "Expression of Angiogenesis Stimulators and Inhibitors in Human Thyroid Tumors and Correlation with Clinical Pathological Features", American Journal of Pathology, 155(6):1967-1976.
Cai, Mingqing, et al., 2003, "Single chain Fv antibody against angiopoietin-2 inhibits VEGF-induced endothelial cell proliferation and migration in vitro", Biochemical and Biophysical Research Communications, 309:946-951.
Chen, Yvonne et al., 1999, "Selection and Analysis of an Optimized Anti-VEGF Antibody: Crystal Structure of an Affinity-matured Fab in Complex with Antigen", J. Mol. Biol., 293:865-881.
Chen, L. et al., 2001, "Expression of angiopoietin-2 gene and its receptor Tie2 in hepatocellular carcinoma", J. Tongji Med. Univ., 21(3):228-230, 235. English Abstract Only.
Davis, Samuel et al., 1996, "Isolation of Angiopoietin-1, a Ligand for the TIE2 Receptor, by Secretion-Trap Expression Cloning", Cell, 87:1161-1169.
Dumont, Daniel J., et al., 1994, "Dominant-negative and targeted null mutations in the endothelial receptor tyrosine kinase, tek, reveal a critical role in vasculogenesis of the embryo", Genes & Development, 8:1897-1909.
Etoh, Tsuyoshi et al., 2001, "Angiopoietin-2 is Related to Tumor Angiogenesis in Gastric Carcinoma: Possible in Vivo Regulation via Induction of Proteases", Cancer Research, 61:2145-2153.
Flessner, Michael F. et al., 2005, "Resistance of Tumor Interstitial Pressure to the Penetration of Intraperitoneally Delivered Antibodies into Metastatic Ovarian Tumors", Clin Cancer Res., 11(8):3117-3125.
Fiedler, Ulrike et al., 2003, "Angiopoietin-1 and Angiopoietin-2 Share the Same Binding Domains in the Tie-2 Receptor Involving the First Ig-like Loop and the Epidermal Growth Factor-like Repeats", The Journal of Biological Chemistry 278(3):1721-1727.

(Continued)

*Primary Examiner* — Marianne P Allen

(57) ABSTRACT

Antibodies directed to the antigen Ang-2 and uses of such antibodies are described. In particular, fully human monoclonal antibodies directed to the antigen Ang-2. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3. Hybridomas or other cell lines expressing such immunoglobulin molecules and monoclonal antibodies.

4 Claims, 13 Drawing Sheets

(56) References Cited

OTHER PUBLICATIONS

Gale, Nicholas W. et al., 2002, "Angiopoietin-2 Is Required for Postnatal Angiogenesis and Lymphatic Patterning, and Only the Latter Role is Rescued by Angiopoietin-1", Developmental Cell, 3:411-423.

Gura, Trisha, 1997, "Systems for Identifying New Drugs Are Often Faulty", Science, 278:1041-1042.

Hanahan, Douglas, 1997, "Signaling Vascular Morphogenesis and Maintenance", Science, 277 (5322):48-50.

Holash, J. et al., 1999, Vessel Cooption, Regression, and Growth in Tumors Mediated by Angiopoietins and VEGF, Science, 284:1994-1998.

Holash, J. et al., 1999, "New model of tumor angiogenesis: dynamic balance between vessel regression and growth mediated by angiopoietins and VEGF", Oncogene, 18:5356-5362.

Jain, Rakesh K. 1990, "Physiological Barriers to Delivery of Monoclonal Antibodies and Other Macromolecules in Tumors", Cancer Research, 50:814s-819s.

Kim, Injune et al., 1999, "Molecular cloning and characterization of a novel angiopoietin family protein, angiopoietin-3", FEBS Letters 443:353-356.

Kim, Injune et al., 1999, "Molecular Cloning, Expression, and Characterization of Angiopoietin-related Protein", The Journal of Biological Chemistry, 274(37):26523-26528.

Kim, Injune et al., 2000, "Angiopoietin-2 at high concentration can enhance endothelial cell survival through the phosphatidylinositol 3'-kinase/AKT signal transduction pathway", Oncogene, 19:4549-4552.

Koga, Kazunari et al., 2001, "Expression of Angiopoietin-2 in Human Glioma Cells and Its Role for Angiogenesis", Cancer Research 61:6248-6254.

Korff, Thomas et al., 2001, "Blood vessel maturation in a 3-dimensional spheroidal coculture model: direct contact with smooth muscle cells regulates endothelial cell quiescence and abrogates VEGF responsiveness", The FASEB Journal, 15:447-457.

Kwak, Hee Jin et al., 1999, "Angiopoietin-1 is an apoptosis survival factor for endothelial cells", FEBS Letters, 448:249-253.

Lee, Ji Hee et al., 2001, "Comparative study of angiostatic and anti-invasive gene expressions as prognostic factors in gastric cancer", International Journal of Oncology, 18:355-361.

Lewis, Claire E. et al., 2007, "Tie2-Expressing Monocytes and Tumor Angiogenesis: Regulation by Hypoxia and Angiopoietin-2", Cancer Research, 67(18):8429-8432.

Lin, Pengnian et al., 1997, "Inhibition of Tumor Angiogenesis Using a Soluable Receptor Establishes a Role for Tie2 in Pathologic Vascular Growth", The American Society for Clinical Investigation, Inc., 100(8):2072-2078.

Lin, Pengnian et al., 1998, "Antiangiogenic gene therapy targeting the endothelium-specific receptor tyrosine kinase Tie2", Proc. Natl. Acad. Sci. USA, 95:8829-8834.

Lobov, Ivan B. et al., 2002, "Angiopoietin-2 displays VEGF-dependent modulation of capillary structure and endothelial cell survival in vivo:", Proc. Natl. Acad. Sci. USA, 99:11205-11210.

Maisonpierre, Peter C. et al., 1997, "Angiopoietin-2, a Natural Antagonist for Tie2 That Disrupts in vivo Angiogenesis", Science, 277:55-60.

Mochizuki, Yasushi et al., 2002, "Angiopoietin 2 stimulates migration and tube-like structure formation of murine brain capillary endothelial cells through c-Fes and c-Fyn", Journal of Cell Science, 115:175-183.

Oliner et al., 2004, "Peptide-Fc Protein Expression", Cancer Cell, Cancer Cell Supplemental Data.

Oliner, Jonathan et al., 2004, "Suppression of angiogenesis and tumor growth by selective inhibition of angiopoietin-2", Cancer Cell, 6:507-516.

Osada, Hideo, et al., 2001, "Gene expression of angiogenesis related factors in glioma", International Journal of Oncology, 18:305-309.

Rudikoff, Stuart et al., 1982, "Single amino acid substitution altering antigen-binding specificity", Proc. Natl. Acad. Sci. USA, 79:1979-1983.

Sato, Thomas N., et al., 1995, "Distinct roles of the receptor tyrosine kinases Tie-1 and Tie-2 in blood vessel formation", Nature, 376:70-74.

Shim, Winston S.N. et al., 2007, "Angiopoietin: A TIE(d) Balance in Tumor Angiogenesis", Mol. Cancer Research, 5(7):655-665.

Sfiligoi, Christian et al., 2003, "Angiopoietin-2 Expression in Breast Cancer Correlates With Lymph Node Invasion and Short Survival", Int. J. Cancer, 103:466-474.

Siemeister, Gerhard et al., 1999, "Two Independent Mechanisms Essential for Tumor Angiogenesis: Inhibition of Human Melanoma Xenograft Growth by Interfering with either the Vascular Endothelial Growth Factor Receptor Pathway or the Tie-2 Pathway", Cancer Research, 59:3185-3191.

Spinelli, Gian Paolo et al., 2006, "Long-Term Survival in Metastatic Pancreatic Cancer", Journal of the Pancreas, 7(5):486-491.

Suri, Chitra et al., 1998, "Increased Vascularization in Mice Overexpressing Angiopoietin-1", Science, 282:468-71.

Tanaka, Shinji et al., 1999, "Biologic significance of angiopoietin-2 expression in human hepatocellular carcinoma", The Journal of Clinical Investigation, 103(3):341-345.

Tanaka, Fumihiro et al., 2002, "Expression of Angiopoietins and Its Clinical Significance in Non-Small Cell Lung Cancer", Cancer Research, 62:7124-7129.

Teichert-Kuliszewska, Krystyna et al., 2001, "Biological action of angiopoietin-2 in a fibrin matrix model of angiogenesis is associated with activation of Tie2", Cardiovascular Research 49:659-670.

Thurston, G. et al., 1999, "Leakage-Resistant Blood Vessels in Mice Transgenically Overexpressing Angiopoietin-1", Science, 286:2511-2514.

Thurston, G. et al., 2000, "Angiopoietin-1 protects the adult vasculature against plasma leakage", 6(4):460-463.

Vajkoczy, Peter et al., 2002, "Microtumor growth initiates angiogenic sprouting with simultaneous expression of VEGF, VEGF receptor-2, and angiopoietin-2", The Journal of Clinical Investigation, 109(6):777-785.

Wong, Maria Pik et al., 2000, "The angiopoietins, tie2 and vascular endothlial growth factor are differently expressed in the transformation of normal lung to non-small cell lung carcinomas", Lung Cancer 29:11-12/.

Wurmbach, Jan-Henner et al., 2000, The Expression of Angiopoietins and their Receptor Tie-2 in Human Prostate Carcinoma, Anticancer Research, 20:5217-5220.

Yancopoulos, George D. et al., 2000, "Vascular-specific growth factors and blood vessel formation", Nature, 407:242-248.

Zagzag, David et al., 1999, "In Situ Expression of Angiopoietins in Astrocytomas Identifies Angiopoietin-2 as an Early Marker of Tumor Angiogenesis", Experimental Neurology, 159:391-400.

Robinson, Candy S. et al., 2001, "The Effects of Angiopoietin-2 and Neutralizing Anti-Tie-2 Antibody on Microvessel Growth, Branching, and Regression in the Ex Vivo Rat Aortic Ring Explant Model of Angiogenesis", Proceedings of the American Association for Cancer Research, vol. 42, Abstract.

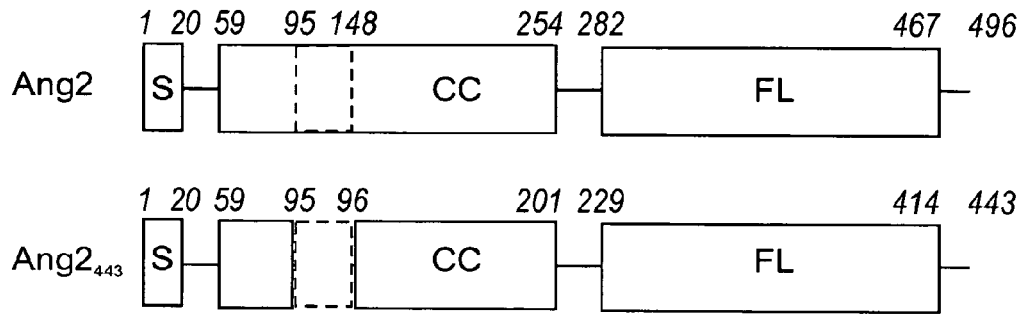

FIG. 6

```
  1   MWQIIFLTFG  WDLVLASAYS  NFRKSVDSTG  RRQYQVQNGP  CSYTFLLPET
 51   DSCRSSSSPY  MSNAVQRDAP  LDYDDSVQRL  QVLENILENN  TQWLMKLENY
101   IQDNMKKEMV  EIQQNVVQNQ  TAVMIEIGTS  LLNQTAAQTR  KLTDVEAQVL
151   NQTTRLELQL  LQHSISTNKL  EKQILDQTSE  INKLQNKNSF  LEQKVLDMEG
201   KHSEQLQSMK  EQKDELQVLV  SKQSSVIDEL  EKKLVTATVN  NSLLQKQQHD
251   LMETVNSLLT  MMSSPNSKSS  VAIRKEEQTT  FRDCAEIFKS  GLTTSGIYTL
301   TFPNSTEEIK  AYCDMEAGGG  GWTIIQRRED  GSVDFQRTWK  EYKVGFGNPS
351   GEYWLGNEFV  SQLTNQQRYV  LKIHLKDWEG  NEAYSLYEHF  YLSSEELNYR
401   IHLTGLTGTA  AKISSISQPG  SDFSTKDSDN  DKCICKCSQM  LSGGWWFDAC
451   GPSNLNGQYY  PQKQNTNKFN  GIKWYYWKGS  GYSLKATTMM  IRPADF
```

FIG. 7

```
Ang1       (1)   MTVFLSFAFLAAITHIGCSNQRRSPENSGRRYNRIQHGQCAYTFILPEH
Ang2       (1)   MWQIVFFTLSCDLVLAAAYNNFRKSMDSIGKKQYQVQHGSCSYTFLLPEM
Mouse Ang2 (1)   MWQIIFLTFGWDLVLASAYSNFRKSVDSTGRRQYQVQNGPCSYTFLLPET
                                                                      100
Ang1       (51)  DGNCRESTTDQYNTNALQRDAPHVEPDFSSQKLQHLEHVMENYIQWLQKL
Ang2       (51)  D-NCRSSISS-PYVSNAVQRDAP-LEYDDSVQRLQVLENIMENNIQWLMKL
Mouse Ang2 (51)  D-SCRSSSS-PYMSNAVQRDAP-LDYDDSVQRLQVLENILENNIQWLMKL
                                          BsmI                        150
Ang1       (101) ENYIVENMKSEMAQIQQNAVQQNHTATMLEIGTSLLSQTAEQTRKLTDVET
Ang2       (98)  ENYIQDNMKKEMVEIQQNAVQQNQTAVMIEIGTNLLNQTAEQTRKLTDVEA
Mouse Ang2 (98)  ENYIQDNMKKEMVEIQQNVVQNQTAVMIEIGTSLLNQTAAQTRKLTDVEA
                                                                      200
Ang1       (151) QVLNQTSRLEIQLLENSLSTYKLEKQLLQQTNEILKIHEKNSLLEHKILE
Ang2       (148) QVLNQTTRLELQLLEHSLSTNKLEKQILDQTSEINKLQDKNSFLEKKVLA
Mouse Ang2 (148) QVLNQTTRLELQLLQHSISTNKLEKQILDQTSEINKLQNKNSFLEQKVLD
                                                                      250
Ang1       (201) MEGKHKEELDTLKEEKENLQGLVTRQTYIIQELEKQLNRATTNNSVLQKQ
Ang2       (198) MEDKHIIQLSIKEEKDQLQVLVSKQNSIEELEKKIVTATVNNSVLQKQ
Mouse Ang2 (198) MEGKHSEQLQSMKEQKDELQVLVSKQSSVIDELEKKLVTATVNNSLLQKQ
                                                                      300
Ang1       (251) QLELMDTVHNLVNLCTKEVLLKG--GKREEKPFRDCADVYQAGFNKSGI
Ang2       (248) QHDLMETVNNLLTMMSTSNSAKDPTVAKEEQISFRDCAEVFKSGHTTNGI
Mouse Ang2 (248) QHDLMETVNSLLTMMSSPNSKSSVAIRKEEQTFRDCAEIFKSGLTTSGI
```

FIG. 8

```
                                                        StuI                                          V345
           301
Ang1 (299) YTLYIYINMPEPKKVFCNMDVNGGWTVIQHREDGSLDFQRGWKEYKMGFG
Ang2 (298) YTLTFPNSTEEIKAYCDMEAGGGWTIIQRREDGSVDFQRTWKEBYKVGFG
Mouse Ang2 (298) YTLTFPNSTEEIKAYCDMDVGGGGWTVIQHREDGSVDFQRTWKEYKEGFG 351     SspI           NQ365/7   H375
Ang1 (349) NPSGEYWLGNEFIFAITSQRQVMLRIELMDWEGNRAYSQYDRFHIGNEKQ
Ang2 (348) NPSGEYWLGNEFVSQLTNQQRYVLKIHLKDWEGNEAYSLYEHFYLSEEL
Mouse Ang2 (348) NPLGEYWLGNEFVSQLTGQHRYVLKIIQLKDWEGNEAHSLYDHFYLAGEES TfiI                                        450
Ang1 (399) NYRLYLKGHTGTAGKQSSLILHGADFSTKDADNDNCMCKCALMLTGGWWF
Ang2 (398) NYRIHLKGLTGTAGKISSISSISQPGNDFSTKDGDNDKCICKCSQMLTGGWWF
Mouse Ang2 (398) NYRIHLTGLTGTAAKISSISQPGSDFSTKDSDNDKCICKCSQMLSGGWWF 451                                                         499
Ang1 (449) DACGPSNLNGMFYTAGQNHGKLNGIKWHYFKGPSYSLRSTTMMIRPLDF
Ang2 (448) DACGPSNLNGMYVPQRQNTNKFNGIKWYYWKGSGYSLKATTMMIRPADF
Mouse Ang2 (448) DACGPSNLNGQYYPQKQNTNKFNGIKWYYWKGSGYSLKATTMMIRPADF
```

FIG. 8
(CONTINUED)

```
h Ang2   MWQIVFFTLS CDLVLAAAYN NFRKSMDSIG KKQYQVQHGS CSYTFLLPEM D-NCR-SSSS  58
m Ang2   ....i.l.fg w......s..s ......v..t. rr.....n.p .........t .-s..-....  58
h Ang1   .tvfls.afl aailthigcs .q.r.pens. rrynri...q .a...i...h .g...e.ttd  60
m Ang1   .tvfls.aff aailthigcs .q.rnpeng. rrynri...q .a...i...h .g...e.ate  60
```
Coiled-coil domain
```
h Ang2   PYVSNAVQRD AP-LEYDDSV QRLQVLENIM ENNTQWLMKL ENYIQDNMKK EMVEIQQNAV 117
m Ang2   ..m....... ...-.d..... ..........l .......... .......... .........v. 117
h Ang1   q.nt..1... ..hv.p.f.s .k..h..hv. ...y....q.. ....ve...s ..aq...... 120
m Ang1   q.nt..1... ..hv.p.f.s .k..n..nv. ...y....q.. ....ve...s ..aq...... 120
```
Coiled-coil domain
```
h Ang2   QNQTAVMIEI GTNLLNQTAE QTRKLTDVEA QVLNQTTRLE LQLLEHSLST NKLEKQILDQ 177
m Ang2   .......... ..s......a .......... .......... ....q..i.. .......... 177
h Ang1   ..h..t.l.. ..s..s.... .........t ......s... i....n.... y.....l.q. 180
m Ang1   ..h..t.l.. ..s..s.... .........t ......s... i....n.... y.....l.q. 180
```
Coiled-coil domain
```
h Ang2   TSEINKLQDK NSFLEKKVLA MEDKHIIQLQ SIKEEKDQLQ VLVSKQNSII EELEKKIVTA 237
m Ang2   ........n. .....q...d ..g..se... .m..q..e.. ......s.v. d.....l... 237
h Ang1   .n..l.ihe. ..l..h.i.e ..g..kee.d tl....en.. g..tr.ty.. q....qlnr. 240
m Ang1   .n..l.ihe. ..l..h.i.e ..g..kee.d tl....en.. g...r.tf.. q....qlsr. 240 h Ang2   TVNNSVLQKQ QHDLMETVNN LLTMMSTSNS AKDPTVAKEE QISFRDCAEV FKSGHTTNGI 297
m Ang2   .....l.... ..........s ......sp.. kssvair... .tt......i ....l...s.. 297
h Ang1   .t........ .le..d..h. .vnl-c.keg vllkggkr.. ekp......d. yqa.fnks.. 299
m Ang1   .n...i.... .le..d..h. .vsl-c.keg vllkggkr.. ekp......d. yqa.fnks.. 299
```
Fibrinogen-like domain
```
h Ang2   YTLTFPNSTE EIKAYCDMEA GGGGWTIIQR REDGSVDFQR TWKEYKVGFG NPSGEYWLGN 357
m Ang2   .......... ........dv ......v..h .......... ......e.... ..l....... 357
h Ang1   ..iyin.mp. pk.vf.n.dv n.....v..h .....l.... g......m... .......... 359
m Ang1   ..iy.n.mp. pk.vf.n.dv n.....v..h .....l.... g......m... .......... 359
```
Fibrinogen-like domain
```
h Ang2   EFVSQLTNQQ RYVLKIHLKD WEGNEAYSLY EHFYLSSEEL NYRIHLKGLT GTAGKISSIS 417
m Ang2   .......g.h ......q... ......h... d....ag..s ......t.... ...a...... 417
h Ang1   ..ifai.s.r q.m.r.e.m. ....r...q. dr.hign.kq ...ly...h. .....q..li 419
m Ang1   ..ifai.s.r q.m.r.e.m. ....r...q. dr.hign.kq ...ly...h. .....q..li 419 h Ang2   QPGNDFSTKD GDNDKCICKC SQMLTGGWWF DACGPSNLNG MYYPQRQNTN KFNGIKWYYW 477
m Ang2   ...s...... s......... ....s..... .......... q....k.... .......... 477
h Ang1   lh.a...... a...n.m... al........ .......... .f.tag..hg .l.....h.f 479
m Ang1   lh.a...... a...n.m... al........ .......... .f.tag..hg .l.....h.f 479 h Ang2   KGSGYSLKAT TMMIRPADF 496
m Ang2   .......... ......... 496
h Ang1   ..ps...rs. ......l.. 498
m Ang1   ..ps...rs. ......l.. 498
```

FIG. 9

HT29 Xenograft Model

ANTIBODIES DIRECTED TO ANGIOPOIETIN-2 AND USES THEREOF

This application is a continuation of U.S. application Ser. No. 13/169,400 filed on Jun. 27, 2011, said application Ser. No. 13/169,400 is a continuation of U.S. application Ser. No. 11/311,939 filed on Dec. 19, 2005, now U.S. Pat. No. 7,973,140 issued on Jul. 5, 2011, said application Ser. No. 11/311,939 claims benefit under 35 U.S.C. §119(e) of the following U.S. Provisional Application Nos. 60/711,289 filed Aug. 25, 2005 and 60/638,354 filed on Dec. 21, 2004. Each of the above listed applications is incorporated by reference herein in its entirety for all purposes.

REFERENCE TO THE SEQUENCE LISTING

This application incorporates by reference a Sequence Listing submitted with this application as text file entitled ANG_100US4_seq_listing created on Nov. 14, 2012 and having a size of 538 kilobytes.

FIELD

The invention relates to monoclonal antibodies against Angiopoietin-2 (Ang-2) and uses of such antibodies. More specifically, the invention relates to fully human monoclonal antibodies directed to Ang-2. The described antibodies are useful as diagnostics and for the treatment of diseases associated with the activity and/or overproduction of Ang-2.

BACKGROUND

Angiogenesis is the process of forming new capillaries from preexisting blood vessels and is an essential component of embryogenesis, normal physiological growth, repair, and tumor expansion. Although a variety of factors can modulate endothelial cell (EC) responses in vitro and blood vessel growth in vivo, only vascular endothelial growth factor (VEGF) family members and the angiopoietins are believed to act almost exclusively on vascular ECs. Yancopoulos et al., *Nature* 407:242-48 (2000).

The angiopoietins were discovered as ligands for the Ties, a family of tyrosine kinases that is selectively expressed within the vascular endothelium. Yancopoulos et al., *Nature* 407:242-48 (2000). There are now four definitive members of the angiopoietin family. Angiopoietin-3 and -4 (Ang-3 and Ang-4) may represent widely diverged counterparts of the same gene locus in mouse and man. Kim et al., *FEBS Let,* 443:353-56 (1999); Kim et al., *J Biol Chem* 274:26523-28 (1999). Ang-1 and Ang-2 were originally identified in tissue culture experiments as agonist and antagonist, respectively. Davis et al., *Cell* 87:1161-69 (1996); Maisonpierre et al., *Science* 277:55-60 (1997). All of the known angiopoietins bind primarily to Tie2, and both Ang-1 and -2 bind to Tie2 with an affinity of 3 nM (Kd). Maisonpierre et al., *Science* 277:55-60 (1997). Ang-1 was shown to support EC survival and to promote endothelium integrity, Davis et al., *Cell* 87:1161-69 (1996); Kwak et al., *FEBS Lett* 448:249-53 (1999); Suri et al., *Science* 282:468-71 (1998); Thurston et al., *Science* 286: 2511-14 (1999); Thurston et al., *Nat. Med.* 6:460-63 (2000), whereas Ang-2 had the opposite effect and promoted blood vessel destabilization and regression in the absence of the survival factors VEGF or basic fibroblast growth factor. Maisonpierre et al., *Science* 277:55-60 (1997). However, many studies of Ang-2 function have suggested a more complex situation. Ang-2 might be a complex regulator of vascular remodeling that plays a role in both vessel sprouting and vessel regression. Supporting such roles for Ang-2, expression analyses reveal that Ang-2 is rapidly induced, together with VEGF, in adult settings of angiogenic sprouting, whereas Ang-2 is induced in the absence of VEGF in settings of vascular regression. Holash et al., *Science* 284:1994-98 (1999); Holash et al., *Oncogene* 18:5356-62 (1999). Consistent with a context-dependent role, Ang-2 binds to the same endothelial-specific receptor, Tie-2, which is activated by Ang-1, but has context-dependent effects on its activation. Maisonpierre et al., *Science* 277:55-60 (1997).

Corneal angiogenesis assays have shown that both Ang-1 and Ang-2 had similar effects, acting synergistically with VEGF to promote growth of new blood vessels. Asahara et al., *Circ. Res.* 83:233-40 (1998). The possibility that there was a dose-dependent endothelial response was raised by the observation that in vitro at high concentration, Ang-2 can also be pro-angiogenic. Kim et al., *Oncogene* 19:4549-52 (2000). At high concentration, Ang-2 acts as an apoptosis survival factor for endothelial cells during serum deprivation apoptosis through activation of Tie2 via PI-3 kinase and Akt pathway. Kim et al., *Oncogene* 19:4549-52 (2000).

Other in vitro experiments suggested that during sustained exposure, the effects of Ang-2 may progressively shift from that of an antagonist to an agonist of Tie2, and at later time points, it may contribute directly to vascular tube formation and neovessel stabilization. Teichert-Kuliszewska et al., *Cardiovasc. Res.* 49:659-70 (2001). Furthermore, if ECs were cultivated on fibrin gel, activation of Tie2 with Ang-2 was also observed, perhaps suggesting that the action of Ang-2 could depend on EC differentiation state. Teichert-Kuliszewska et al., *Cardiovasc. Res.* 49:659-70 (2001). In microvascular EC cultured in a three-dimensional collagen gel, Ang-2 can also induce Tie2 activation and promote formation of capillary-like structures. Mochizuki et al., *J. Cell. Sci.* 115:175-83 (2002). Use of a 3-D spheroidal coculture as an in vitro model of vessel maturation demonstrated that direct contact between ECs and mesenchymal cells abrogates responsiveness to VEGF, whereas the presence of VEGF and Ang-2 induced sprouting. Korff et al., *Faseb J.* 15:447-57 (2001). Etoh et al. demonstrated that ECs that constitutively express Tie2, the expression of MMP-1, -9 and u-PA were strongly up-regulated by Ang-2 in the presence of VEGF. Etoh, et al., *Cancer Res.* 61:2145-53 (2001). With an in vivo pupillary membrane model, Lobov et al. showed that Ang-2 in the presence of endogenous VEGF promotes a rapid increase in capillary diameter, remodeling of the basal lamina, proliferation and migration of endothelial cells, and stimulates sprouting of new blood vessels. Lobov et al., *Proc. Natl. Acad. Sci. USA* 99:11205-10 (2002). By contrast, Ang-2 promotes endothelial cell death and vessel regression without endogenous VEGF. Lobov et al., *Proc. Natl. Acad. Sci. USA* 99:11205-10 (2002). Similarly, with an in vivo tumor model, Vajkoczy et al. demonstrated that multicellular aggregates initiate vascular growth by angiogenic sprouting via the simultaneous expression of VEGFR-2 and Ang-2 by host and tumor endothelium. Vajkoczy et al., *J. Clin. Invest.* 109:777-85 (2002). This model illustrated that the established microvasculature of growing tumors is characterized by a continuous remodeling, putatively mediated by the expression of VEGF and Ang-2. Vajkoczy et al., *J. Clin. Invest.* 109:777-85 (2002).

Knock-out mouse studies of Tie-2 and Angiopoietin-1 show similar phenotypes and suggest that Angiopoietin-1 stimulated Tie-2 phosphorylation mediates remodeling and stabilization of developing vessel, promoting blood vessel maturation during angiogenesis and maintenance of endothelial cell-support cell adhesion (Dumont et al., *Genes & Devel-* opment, 8:1897-1909 (1994); Sato, *Nature*, 376:70-74 (1995); (Thurston, G. et al., 2000 Nature Medicine: 6, 460-463)). The role of Angiopoietin-1 is thought to be conserved in the adult, where it is expressed widely and constitutively (Hanahan, *Science*, 277:48-50 (1997); Zagzag, et al., *Exp Neurology*, 159:391-400 (1999)). In contrast, Angiopoietin-2 expression is primarily limited to sites of vascular remodeling where it is thought to block the constitutive stabilizing or maturing function of Angiopoietin-1, allowing vessels to revert to, and remain in, a plastic state which may be more responsive to sprouting signals (Hanahan, 1997; Holash et al., *Oncogene* 18:5356-62 (1999); Maisonpierre, 1997). Studies of Angiopoietin-2 expression in pathological angiogenesis have found many tumor types to show vascular Angiopoietin-2 expression (Maisonpierre et al., *Science* 277:55-60 (1997)). Functional studies suggest Angiopoietin-2 is involved in tumor angiogenesis and associate Angiopoietin-2 overexpression with increased tumor growth in a mouse xenograft model (Ahmad, et al., *Cancer Res.*, 61:1255-1259 (2001)). Other studies have associated Angiopoietin-2 over-expression with tumor hypervascularity (Etoh, et al., *Cancer Res.* 61:2145-53 (2001); Tanaka et al., *Cancer Res.* 62:7124-29 (2002)).

In recent years Angiopoietin-1, Angiopoietin-2 and/or Tie-2 have been proposed as possible anti-cancer therapeutic targets. For example U.S. Pat. No. 6,166,185, U.S. Pat. No. 5,650,490 and U.S. Pat. No. 5,814,464 each disclose anti-Tie-2 ligand and receptor antibodies. Studies using soluble Tie-2 were reported to decrease the number and size of tumors in rodents (Lin, 1997; Lin 1998). Siemester et al. (1999) generated human melanoma cell lines expressing the extracellular domain of Tie-2, injected these into nude mice and reported soluble Tie-2 to result in significant inhibition of tumor growth and tumor angiogenesis. Given both Angiopoietin-1 and Angiopoietin-2 bind to Tie-2, it is unclear from these studies whether Angiopoietin-1, Angiopoietin-2 or Tie-2 would be an attractive target for anti-cancer therapy. However, effective anti-Angiopoietin-2 therapy is thought to be of benefit in treating diseases such as cancer, in which progression is dependant on aberrant angiogenesis where blocking the process can lead to prevention of disease advancement (Folkman, J., *Nature Medicine*. 1: 27-31 (1995). In addition some groups have reported the use of antibodies that bind to Angiopoietin-2, See, for example, U.S. Pat. No. 6,166,185 and U.S. Patent Application Publication No. 2003/0124129 A1. Study of the effect of focal expression of Angiopoietin-2 has shown that antagonizing the Angiopoietin-1/Tie-2 signal loosens the tight vascular structure thereby exposing ECs to activating signals from angiogenesis inducers, e.g. VEGF (Hanahan, 1997). This pro-angiogenic effect resulting from inhibition of Angiopoietin-1 indicates that anti-Angiopoietin-1 therapy would not be an effective anti-cancer treatment.

Ang-2 is expressed during development at sites where blood vessel remodeling is occurring. Maisonpierre et al., *Science* 277:55-60 (1997). In adult individuals, Ang-2 expression is restricted to sites of vascular remodeling as well as in highly vascularized tumors, including glioma, Osada et al., *Int. J. Oncol.* 18:305-09 (2001); Koga et al., *Cancer Res.* 61:6248-54 (2001), hepatocellular carcinoma, Tanaka et al, *J. Clin. Invest.* 103:341-45 (1999), gastric carcinoma, Etoh, et al., *Cancer Res.* 61:2145-53 (2001); Lee et al, *Int. J. Oncol.* 18:355-61 (2001), thyroid tumor, Bunone et al., *Am J Pathol* 155:1967-76 (1999), non-small cell lung cancer, Wong et al., *Lung Cancer* 29:11-22 (2000), and cancer of colon, Ahmad et al., *Cancer* 92:1138-43 (2001), and prostate Wurmbach et al., *Anticancer Res.* 20:5217-20 (2000). Some tumor cells are found to express Ang-2. For example, Tanaka et al., *J. Clin. Invest.* 103:341-45 (1999) detected Ang-2 mRNA in 10 out of 12 specimens of human hepatocellular carcinoma (HCC). Ellis' group reported that Ang-2 is expressed ubiquitously in tumor epithelium. Ahmad et al., *Cancer* 92:1138-43 (2001). Other investigators reported similar findings. Chen et al., *J. Tongji Med. Univ.* 21:228-30, 235 (2001). By detecting Ang-2 mRNA levels in archived human breast cancer specimens, Sfilogoi et al., *Int. J. Cancer* 103:466-74 (2003) reported that Ang-2 mRNA is significantly associated with auxiliary lymph node invasion, short disease-free time and poor overall survival. Tanaka et al., *Cancer Res.* 62:7124-29 (2002) reviewed a total of 236 patients of non-small cell lung cancer (NSCLC) with pathological stage-I to -IIIA, respectively. Using immunohistochemistry, they found that 16.9% of the NSCLC patients were Ang-2 positive. The microvessel density for Ang-2 positive tumor is significantly higher than that of Ang-2 negative. Such an angiogenic effect of Ang-2 was seen only when VEGF expression was high. Moreover, positive expression of Ang-2 was a significant factor to predict a poor postoperative survival. Tanaka et al., *Cancer Res.* 62:7124-29 (2002). However, they found no significant correlation between Ang-1 expression and the microvessel density. Tanaka et al., *Cancer Res.* 62:7124-29 (2002). These results suggest that Ang-2 is an indicator of poor prognosis patients with several types of cancer.

Recently, using an Ang-2 knockout mouse model, Yancopoulos' group reported that Ang-2 is required for postnatal angiogenesis. Gale et al., *Dev. Cell* 3:411-23 (2002). They showed that the developmentally programmed regression of the hyaloid vasculature in the eye does not occur in the Ang-2–/– mice and their retinal blood vessels fail to sprout out from the central retinal artery. Gale et al., *Dev. Cell* 3:411-23 (2002). They also found that deletion of Ang-2 results in profound defects in the patterning and function of the lymphatic vasculature. Gale et al., *Dev. Cell* 3:411-23 (2002). Genetic rescue with Ang-1 corrects the lymphatic, but not the angiogenesis defects. Gale et al., *Dev. Cell* 3:411-23 (2002).

Peters and his colleagues reported that soluble Tie2, when delivered either as recombinant protein or in a viral expression vector, inhibited in vivo growth of murine mammary carcinoma and melanoma in mouse models. Lin et al., *Proc. Natl. Acad. Sci. USA* 95:8829-34 (1998); Lin et al., *J. Clin. Invest.* 100:2072-78 (1997). Vascular densities in the tumor tissues so treated were greatly reduced. In addition, soluble Tie2 blocked angiogenesis in the rat corneal stimulated by tumor cell conditioned media. Lin et al., *J. Clin. Invest.* 100: 2072-78 (1997). Furthermore, Isner and his team demonstrated that addition of Ang-2 to VEGF promoted significantly longer and more circumferential neovascularity than VEGF alone. Asahara et al., *Circ. Res.* 83:233-40 (1998). Excess soluble Tie2 receptor precluded modulation of VEGF-induced neovascularization by Ang-2. Asahara et al., *Circ. Res.* 83:233-40 (1998). Siemeister et al., *Cancer Res.* 59:3185-91 (1999) showed with nude mouse xenografts that overexpression of the extracellular ligand-binding domains of either Flt-1 or Tie2 in the xenografts results in significant inhibition of pathway could not be compensated by the other one, suggesting that the VEGF receptor pathway and the Tie2 pathway should be considered as two independent mediators essential for the process of in vivo angiogenesis. Siemeister et al., *Cancer Res.* 59:3185-91 (1999). This is proven by a more recent publication by White et al., *Proc. Natl. Acad. Sci. USA* 100:5028-33 (2003). In their study, it was demonstrated that a nuclease-resistant RNA aptamer that specifically binds and inhibits Ang-2 significantly inhibited neovascularization induced by bFGF in the rat corneal micropocket angiogenesis model.

SUMMARY

Embodiments of the invention relate to targeted binding agents that specifically bind to Angiopoietin-2 and therein inhibit tumor angiogenesis and reduce tumor growth. Mechanisms by which this can be achieved can include and are not limited to either inhibition of binding of Ang-2 to its receptor Tie2, inhibition of Ang-2 induced Tie2 signaling, or increased clearance of Ang-2, therein reducing the effective concentration of Ang-2.

One embodiment of the invention, the targeted binding agent is a fully human antibody that binds to Ang-2 and prevents Ang-2 binding to Tie2. Yet another embodiment of the invention is a fully human monoclonal antibody that binds to Ang-2 and Ang-1, and also inhibits Ang-2 induced Tie2 phosphorylation. The antibody may bind Ang-2 with a $K_d$ of less than 100 pM, 30 pM, 20 pM, 10 pM or 5 pM.

The antibody may comprise a heavy chain amino acid sequence having a complementarity determining region (CDR) with one of the sequences shown in Table 11. It is noted that those of ordinary skill in the art can readily accomplish CDR determinations. See for example, Kabat et al., *Sequences of Proteins of Immunological Interest*, Fifth Edition, NIH Publication 91-3242, Bethesda Md. (1991), vols. 1-3.

One embodiment of the invention comprises fully human monoclonal antibodies 3.3.2 (ATCC Accession Number PTA-7258), 3.1-9.3 (ATCC Accession Number PTA-7260) and 5.88.3 (ATCC Accession Number PTA-7259) which specifically bind to Ang-2, as discussed in more detail below.

Monoclonal antibodies 3.3.2, 5.88.3, and 3.19.3 were deposited with the American Type Culture Collection (ATCC®, 10801 University Boulevard, Manassas, Va. 20110-2209) on Dec. 5, 2005, and assigned Accession Nos. PTA-7258, PTA-7259, and PTA-7260, respectively. These deposits will be maintained under the terms of the Budapest Treaty on the International Recognition of the Deposit of Microorganisms for the Purposes of Patent Procedure. Since the strains referred to are being maintained under the terms of the Budapest Treaty, they will be made available to a patent office signatory to the Budapest Treaty.

Yet another embodiment is an antibody that binds to Ang-2 and comprises a light chain amino acid sequence having a CDR comprising one of the sequences shown in Table 12. In certain embodiments the antibody is a fully human monoclonal antibody.

A further embodiment is an antibody that binds to Ang-2 and comprises a heavy chain amino acid sequence having one of the CDR sequences shown in Table 11 and a light chain amino acid sequence having one of the CDR sequences shown in Table 12. In certain embodiments the antibody is a fully human monoclonal antibody. A further embodiment of the invention is an antibody that cross-competes for binding to Ang-2 with the fully human antibodies of the invention, preferably an antibody comprising a heavy chain amino acid sequence having one of the CDR sequences shown in Table 11 and a light chain amino acid sequence having one of the CDR sequences shown in Table 12. A further embodiment of the invention is an antibody that binds to the same epitope on Ang-2 as a fully human antibodies of the invention, preferably an antibody comprising a heavy chain amino acid sequence having one of the CDR sequences shown in Table 11 and a light chain amino acid sequence having one of the CDR sequences shown in Table 12.

Further embodiments of the invention include human monoclonal antibodies that specifically bind to Angiopoietin-2, wherein the antibodies comprise a heavy chain complementarity determining region 1 (CDR1) corresponding to canonical class 1. The antibodies provided herein can also include a heavy chain complementarity determining region 2 (CDR2) corresponding to canonical class 3, a light chain complementarity determining region 1 (CDR1) corresponding to canonical class 2, a light chain complementarity determining region 2 (CDR2) corresponding to canonical class 1, and a light chain complementarity determining region 3 (CDR3) corresponding to canonical class 1.

The invention further provides methods for assaying the level of Angiopoietin-2 (Ang-2) in a patient sample, comprising contacting an anti-Ang-2 antibody with a biological sample from a patient, and detecting the level of binding between said antibody and Ang-2 in said sample. In more specific embodiments, the biological sample is blood.

In other embodiments the invention provides compositions, including an antibody or functional fragment thereof, and a pharmaceutically acceptable carrier.

Still further embodiments of the invention include methods of effectively treating an animal suffering from an angiogenesis-related disease, including selecting an animal in need of treatment for a neoplastic or non-neoplastic disease, and administering to said animal a therapeutically effective dose of a fully human monoclonal antibody that specifically binds to Angiopoietin-2 (Ang-2).

Treatable angiogenesis-related diseases can include neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

Additional embodiments of the invention include methods of inhibiting Angiopoietin-2 (Ang-2) induced angiogenesis in an animal. These methods include selecting an animal in need of treatment for Ang-2 induced angiogenesis, and administering to said animal a therapeutically effective dose of a fully human monoclonal antibody wherein said antibody specifically binds to Ang-2.

Further embodiments of the invention include the use of an antibody of in the preparation of medicament for the treatment of angiogenesis-related diseases in an animal, wherein said monoclonal antibody specifically binds to Angiopoietin-2 (Ang-2). Treatable angiogenesis-related diseases can include neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, cholangiocarcinoma, small bowel adenocarcinoma, pediatric malignancies and epidermoid carcinoma.

In still further embodiments, the antibodies described herein can be used for the preparation of a medicament for the effective treatment of Angiopoietin-2 induced angiogenesis in an animal, wherein said monoclonal antibody specifically binds to Angiopoietin-2 (Ang-2).

Embodiments of the invention described herein relate to monoclonal antibodies that bind Ang-2 and affect Ang-2 function. Other embodiments relate to fully human anti-Ang-2 antibodies and anti-Ang-2 antibody preparations with desirable properties from a therapeutic perspective, including high binding affinity for Ang-2, the ability to neutralize Ang-2 in vitro and in vivo, and the ability to inhibit Ang-2 induced angiogenesis.

In a preferred embodiment, antibodies described herein bind to Ang-2 with very high affinities (Kd). For example a human, rabbit, mouse, chimeric or humanized antibody that is capable of binding Ang-2 with a Kd less than, but not limited to, $10^{-5}$, $10^{-6}$, $10^{-7}$, $10^{-8}$, $10^{-9}$, $10^{10}$, $10^{-11}$, $10^{-12}$, $10^{-13}$ or $10^{-14}$ M, or any range or value therein. Affinity and/or avidity measurements can be measured by KinExA® and/or BIA-CORE®, as described herein.

Accordingly, one embodiment described herein includes isolated antibodies, or fragments of those antibodies, that bind to Ang-2. As known in the art, the antibodies can advantageously be, for example, polyclonal, oligoclonal, monoclonal, chimeric, humanized, and/or fully human antibodies. Embodiments of the invention described herein also provide cells for producing these antibodies.

Another embodiment of the invention is a fully human antibody that binds to other Angiopoietin-2 family members including, but not limited to, Angiopoietin-1, Angiopoietin-3, and Angiopoietin-4. A further embodiment herein is an antibody that cross-competes for binding to Tie2 with Ang-2 with the fully human antibodies of the invention. In one embodiment of the invention, the antibody binds to and neutralizes Angiopoietin-2, and also binds to and neutralizes, Angiopoietin-1.

It will be appreciated that embodiments of the invention are not limited to any particular form of an antibody or method of generation or production. For example, the anti-Ang-2 antibody may be a full-length antibody (e.g., having an intact human Fc region) or an antibody fragment (e.g., a Fab, Fab' or $F(ab')_2$). In addition, the antibody may be manufactured from a hybridoma that secretes the antibody, or from a recombinantly produced cell that has been transformed or transfected with a gene or genes encoding the antibody.

Other embodiments of the invention include isolated nucleic acid molecules encoding any of the antibodies described herein, vectors having isolated nucleic acid molecules encoding anti-Ang-2 antibodies or a host cell transformed with any of such nucleic acid molecules. In addition, one embodiment of the invention is a method of producing an anti-Ang-2 antibody by culturing host cells under conditions wherein a nucleic acid molecule is expressed to produce the antibody followed by recovering the antibody. It should be realized that embodiments of the invention also include any nucleic acid molecule which encodes an antibody or fragment of an antibody of the invention including nucleic acid sequences optimized for increasing yields of antibodies or fragments thereof when transfected into host cells for antibody production.

A further embodiment herein includes a method of producing high affinity antibodies to Ang-2 by immunizing a mammal with human Ang-2, or a fragment thereof, and one or more orthologous sequences or fragments thereof.

Other embodiments are based upon the generation and identification of isolated antibodies that bind specifically to Ang-2. Ang-2 is expressed at elevated levels in angiogenesis-related diseases, such as neoplastic diseases. Inhibition of the biological activity of Ang-2 can prevent Ang-2 induced angiogenesis and other desired effects.

Another embodiment of the invention includes a method of diagnosing diseases or conditions in which an antibody prepared as described herein is utilized to detect the level of Ang-2 in a patient sample. In one embodiment, the patient sample is blood or blood serum. In further embodiments, methods for the identification of risk factors, diagnosis of disease, and staging of disease is presented which involves the identification of the overexpression of Ang-2 using anti-Ang-2 antibodies.

Another embodiment of the invention includes a method for diagnosing a condition associated with the expression of Ang-2 in a cell by contacting the serum or a cell with an anti-Ang-2 antibody, and thereafter detecting the presence of Ang-2. Preferred conditions include angiogenesis-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

In another embodiment, the invention includes an assay kit for detecting Angiopoietin-2 and Angiopoietin family members in mammalian tissues, cells, or body fluids to screen for angiogenesis-related diseases. The kit includes an antibody that binds to Angiopoietin-2 and a means for indicating the reaction of the antibody with Angiopoietin-2, if present. Preferably the antibody is a monoclonal antibody. In one embodiment, the antibody that binds Ang-2 is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radiopaque material.

Yet another embodiment includes methods for treating diseases or conditions associated with the expression of Ang-2 in a patient, by administering to the patient an effective amount of an anti-Ang-2 antibody. The anti-Ang-2 antibody can be administered alone, or can be administered in combination with additional antibodies or chemotherapeutic drug or radiation therapy. For example, a monoclonal, oligoclonal or polyclonal mixture of Ang-2 antibodies that block angiogenesis can be administered in combination with a drug shown to inhibit tumor cell proliferation directly. The method can be performed in vivo and the patient is preferably a human patient. In a preferred embodiment, the method concerns the treatment of angiogenesis-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

In another embodiment, the invention provides an article of manufacture including a container. The container includes a composition containing an anti-Ang-2 antibody, and a package insert or label indicating that the composition can be used to treat angiogenesis-related diseases characterized by the overexpression of Ang-2.

In some embodiments, the anti-Ang-2 antibody is administered to a patient, followed by administration of a clearing agent to remove excess circulating antibody from the blood.

Yet another embodiment is the use of an anti-Ang-2 antibody in the preparation of a medicament for the treatment of diseases such as angiogenesis-related diseases. In one embodiment, the angiogenesis-related diseases include carcinoma, such as breast, ovarian, stomach, endometrial, salivary gland, lung, kidney, colon, colorectum, esophageal, thyroid, pancreatic, prostate and bladder cancer. In another embodiment, the angiogenesis-related diseases include, but are not limited to, neoplastic diseases, such as, melanoma, small cell lung cancer, non-small cell lung cancer, glioma, hepatocellular (liver) carcinoma, sarcoma, head and neck cancers, mesothelioma, biliary (cholangiocarcinoma), small bowel adenocarcinoma, pediatric malignancies and glioblastoma.

Ang-2 is an important "on-switch" of angiogenesis. Accordingly, antagonizing this molecule is expected to inhibit pathophysiological procedures, and thereby act as a potent therapy for various angiogenesis-dependent diseases. Besides solid tumors and their metastases, haematologic malignancies, such as leukemias, lymphomas and multiple myeloma, are also angiogenesis-dependent. Excessive vascular growth contributes to numerous non-neoplastic disorders. These non-neoplastic angiogenesis-dependent diseases include: atherosclerosis, haemangioma, haemangioendothelioma, angiofibroma, vascular malformations (e.g. Hereditary Hemorrhagic Teleangiectasia (HHT), or Osler-Weber syndrome), warts, pyogenic granulomas, excessive hair growth, Kaposis' sarcoma, scar keloids, allergic oedema, psoriasis, dysfunctional uterine bleeding, follicular cysts, ovarian hyperstimulation, endometriosis, respiratory distress, ascites, peritoneal sclerosis in dialysis patients, adhesion formation result from abdominal surgery, obesity, rheumatoid arthritis, synovitis, osteomyelitis, pannus growth, osteophyte, hemophilic joints, inflammatory and infectious processes (e.g. hepatitis, pneumonia, glomerulonephritis), asthma, nasal polyps, liver regeneration, pulmonary hypertension, retinopathy of prematurity, diabetic retinopathy, age-related macular degeneration., leukomalacia, neovascular glaucoma, corneal graft neovascularization, trachoma, thyroiditis, thyroid enlargement, and lymphoproliferative disorders.

BRIEF DESCRIPTION OF THE DRAWINGS

FIG. 6 is a schematic diagram of the protein structure of human Ang-2 and Ang-2$_{443}$. The upper numbers denote amino acid sequences (diagram taken from Injune et al., (2000) *JBC* 275: 18550).

FIG. 7 displays the amino acid sequence of a Mouse/Human chimeric molecule (SEQ ID NO: 1). The human residues (cloned as StuI-TfiI fragment) 310-400 are underlined.

FIG. 8 is an amino acid sequence comparison of human Ang-1 (SEQ ID NO: 2), human Ang-2 (SEQ ID NO: 3), and mouse Ang-2 (SEQ ID NO: 4) proteins. The fusion points of Ang-2 chimeric molecules and point mutations are noted in bold.

FIG. 9 is an amino acid sequence comparison of mouse Ang-1 (SEQ ID NO: 5), human Ang-1 (SEQ ID NO: 2), mouse Ang-2 (SEQ ID NO: 4), and human Ang-2 (SEQ ID NO: 3). The arrowhead shows the cleavage site for hydrophobic leader sequences. The arrows define the limits of the coiled-coil and fibrinogen like domains. The solid circles show the conserved cysteine residues (image taken from Maisonpierre et al., 1997, *Science* 277:55).

FIG. 12A shows the effect of anti-Ang-2 antibodies on the number of blood vessel ends where the x axis indicates the experimental groups and the y axis indicates the mean number of vessel ends (+/−SD). FIG. 12B demonstrates the effect of anti-Ang-2 antibodies on blood vessel length where the x axis indicates the experimental groups and the y axis indicates the mean vessel length (+/−SD).

DETAILED DESCRIPTION

Figure 1:
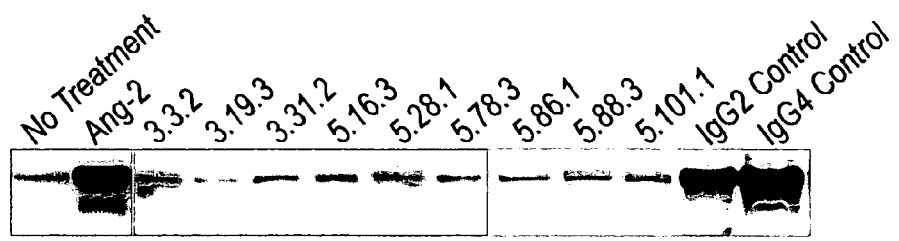
FIG. 1 is a Western Blot showing that Ang-2 mAbs inhibit Ang-2-induced phosphorylation of Tie2 ectopically expressed in HEK293F cells.

Embodiments of the invention described herein relate to monoclonal antibodies that bind to Ang-2. In some embodiments, the antibodies bind to Ang-2 and inhibit the binding of Ang-2 to its receptor, Tie2. Other embodiments of the invention include fully human anti-Ang-2 antibodies, and antibody preparations that are therapeutically useful. Such anti-Ang-2 antibody preparations preferably have desirable therapeutic properties, including strong binding affinity for Ang-2, the ability to neutralize Ang-2 in vitro, and the ability to inhibit Ang-2-induced angiogenesis in vivo.

One embodiment of the invention includes an antibody that binds to and neutralizes Ang-2, but does not bind to Ang-1. In another embodiment, the antibody binds to both Ang-2 and Ang-1, but only neutralizes Ang-2. In another embodiment, the antibody binds to both Ang-2 and Ang-1, and neutralizes binding of both Ang-1 and Ang-2 to Tie2.

Embodiments of the invention also include isolated binding fragments of anti-Ang-2 antibodies. Preferably, the binding fragments are derived from fully human anti-Ang-2 antibodies. Exemplary fragments include Fv, Fab' or other well know antibody fragments, as described in more detail below. Embodiments of the invention also include cells that express fully human antibodies against Ang-2. Examples of cells include hybridomas, or recombinantly created cells, such as Chinese hamster ovary (CHO) cells, variants of CHO cells (for example DG44) and NS0 cells that produce antibodies against Ang-2. Additional information about variants of CHO cells can be found in Andersen and Reilly (2004) Current Opinion in Biotechnology 15, 456-462 which is incorporated herein in its entirety by reference.

In addition, embodiments of the invention include methods of using these antibodies for treating diseases. Anti-Ang-2 antibodies are useful for preventing Ang-2 mediated Tie2 signal transduction, thereby inhibiting angiogenesis. The mechanism of action of this inhibition may include inhibition of Ang-2 from binding to its receptor, Tie2, inhibition of Ang-2 induced Tie2 signaling, or enhanced clearance of Ang-2 therein lowering the effective concentration of Ang-2 for binding to Tie-2. Diseases that are treatable through this inhibition mechanism include, but are not limited to, neoplastic diseases, such as, melanoma, small cell lung cancer, non-small cell lung cancer, glioma, hepatocellular (liver) carcinoma, glioblastoma, and cancers and tumors of the thyroid, stomach, prostate, breast, ovary, bladder, lung, uterus, kidney, colon, and pancreas, salivary gland, and colorectal.

Other embodiments of the invention include diagnostic assays for specifically determining the quantity of Ang-2 in a biological sample. The assay kit can include anti-Ang-2 antibodies along with the necessary labels for detecting such antibodies. These diagnostic assays are useful to screen for angiogenesis-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

According to one aspect of the invention there is provided an antagonist of the biological activity of Angiopoietin-1 and Angiopoietin-2 wherein the antagonist does not bind to the ATP-binding site of Tie-2.

According to another aspect of the invention there is provided an antagonist of the biological activity of Angiopoietin-1 and Angiopoietin-2 wherein the antagonist binds to Angiopoietin-1 and Angiopoietin-2.

According to another aspect of the invention there is provided an antagonist of the biological activity of Angiopoietin-1 and Angiopoietin-2 wherein the antagonist is not a compound.

In one embodiment there is provided an antagonist of the biological activity of Angiopoietin-1 and Angiopoietin-2 wherein the Angiopoietin-1 antagonist activity and the Angiopoietin-2 antagonist activity is comprised within one molecule. In an alternative embodiment there is provided an antagonist wherein the Angiopoietin-1 antagonist activity and the Angiopoietin-2 antagonist activity is comprised within more than one molecule.

In one embodiment there is provided an antagonist of the biological activity of Angiopoietin-1 and Angiopoietin-2 wherein the antagonist may bind to:
  i) the Tie-2 receptor;
  ii) Angiopoietin-1 and/or Angiopoietin-2;
  iii) Tie-2 receptor-Angiopoietin-1 complex; or
  iv) Tie-2 receptor-Angiopoietin-2 complex,
  or any combination of these.

In one embodiment the antagonist of the biological activity of Angiopoietin-1 and Angiopoietin-2 may bind to Angiopoietin-1 and/or Angiopoietin-2 and/or Tie-2 and thereby prevent Angiopoietin-1 and Angiopoietin-2 mediated Tie-2 signal transduction, thereby inhibiting angiogenesis. The mechanism of action of this inhibition may include;
  i) binding of the antagonist to Angiopoietin-1 and inhibiting the binding of Angiopoietin-1 to its receptor, Tie-2, and/or
  ii) binding of the antagonist to Angiopoietin-2 and inhibit the binding of Angiopoietin-2 to its receptor, Tie-2, and/or
  iii) enhancing the clearance of Angiopoietin-1 and/or Angiopoietin-2 therein lowering the effective concentration of Angiopoietin-1 and/or Angiopoietin-2 available for binding to Tie-2,
  or any combination of these, sufficient to antagonize the biological activity of Angiopoietin-1 and Angiopoietin-2.

Without wishing to be bound by theoretical considerations mechanisms by which antagonism of the biological activity of Angiopoietin-1 and Angiopoietin-2 can be achieved include, but are not limited to, inhibition of binding of Angiopoietin-1 and Angiopoietin-2 to the receptor Tie-2, inhibition of Angiopoietin-1 and Angiopoietin-2 induced Tie-2 signaling, or increased clearance of Angiopoietin-1 and Angiopoietin-2, therein reducing the effective concentration of Angiopoietin-1 and Angiopoietin-2.

In one embodiment there is provided an antagonist of the biological activity of Angiopoietin-1 and Angiopoietin-2 wherein the antagonist is an antibody. Preferably the antibody is able to antagonize the biological activity of Angiopoietin-1 and/or Angiopoietin-2 in vitro and in vivo. Preferably the antibody is a polyclonal or monoclonal antibody. More preferably the antibody is a monoclonal antibody and more preferably the antibody is a fully human monoclonal antibody. Most preferably the antibody is the fully human monoclonal antibody 3.19.3.

In one embodiment there is provided an antibody which binds to the same epitope or epitopes as fully human monoclonal antibody 3.19.3.

In one embodiment of the invention there is provided a fully human antibody that binds to Angiopoietin-1 and prevents Angiopoietin-1 binding to Tie-2. Yet another embodiment of the invention is a fully human monoclonal antibody that binds to Angiopoietin-1 and inhibits Angiopoietin-1 induced Tie-2 phosphorylation. In one embodiment, the antibody binds Angiopoietin-1 with a $K_d$ of less than 1 nanomolar (nM). More preferably, the antibody binds with a Kd less than 500 picomolar (pM). More preferably, the antibody binds with a Kd less than 100 picomolar (pM). More preferably, the antibody binds with a Kd less than 30 picomolar (pM). More preferably, the antibody binds with a IQ of less than 20 pM. Even more preferably, the antibody binds with a IQ of less than 10 or 5 pM.

In one embodiment of the invention there is provided a fully human antibody that binds to Angiopoietin-2 and prevents Angiopoietin-2 binding to Tie-2. Yet another embodiment of the invention is a fully human monoclonal antibody that binds to Angiopoietin-2 and inhibits Angiopoietin-2 induced Tie-2 phosphorylation. In one embodiment, the antibody binds Angiopoietin-2 with a $K_d$ of less than 1 nanomolar (nM). More preferably, the antibody binds with a Kd less than 500 picomolar (pM). More preferably, the antibody binds with a Kd less than 100 picomolar (pM). More preferably, the antibody binds with a Kd less than 30 picomolar (pM). More preferably, the antibody binds with a $K_d$ of less than 20 pM. Even more preferably, the antibody binds with a $K_d$ of less than 10 or 5 pM.

In one embodiment there is provided a hybridoma that produces the light chain and/or the heavy chain of antibody as described hereinabove. Preferably the hybridoma produces the light chain and/or the heavy chain of a fully human monoclonal antibody. More preferably the hybridoma produces the light chain and/or the heavy chain of the fully human monoclonal antibody 3.19.3, 3.3.2 or 5.88.3. Alternatively the hybridoma produces an antibody which binds to the same epitope or epitopes as fully human monoclonal antibody 3.19.3, 3.3.2 or 5.88.3.

In one embodiment there is provided a nucleic acid molecule encoding the light chain or the heavy chain of the antibody as described hereinabove. Preferably there is provided a nucleic acid molecule encoding the light chain or the heavy chain of a fully human monoclonal antibody. More preferably there is provided a nucleic acid molecule encoding the light chain or the heavy chain of the fully human monoclonal antibody 3.19.3.

In one embodiment of the invention there is provided a vector comprising a nucleic acid molecule or molecules as described hereinabove, wherein the vector encodes a light chain and/or a heavy chain of an antibody as defined hereinabove.

In one embodiment of the invention there is provided a host cell comprising a vector as described hereinabove. Alternatively the host cell may comprise more than one vector.

In addition, one embodiment of the invention is a method of producing an antibody by culturing host cells under conditions wherein a nucleic acid molecule is expressed to produce the antibody, followed by recovery of the antibody.

In one embodiment of the invention there is provided a method of making an antibody comprising transfecting at least one host cell with at least one nucleic acid molecule encoding the antibody as described hereinabove, expressing the nucleic acid molecule in said host cell and isolating said antibody.

According to another aspect of the invention there is provided a method of antagonising the biological activity of Angiopoietin-1 and Angiopoietin-2 comprising administering an antagonist as described hereinabove. The method may include selecting an animal in need of treatment for disease-related angiogenesis, and administering to said animal a therapeutically effective dose of an antagonist of the biological activity of Angiopoietin-1 and Angiopoietin-2.

According to another aspect of the invention there is provided a method of antagonising the biological activity of Angiopoietin-1 and Angiopoietin-2 comprising administering an antibody as described hereinabove. The method may include selecting an animal in need of treatment for disease-related angiogenesis, and administering to said animal a therapeutically effective dose of an antibody which antagonises the biological activity of Angiopoietin-1 and Angiopoietin-2.

According to another aspect there is provided a method of treating disease-related angiogenesis in a mammal comprising administering a therapeutically effective amount of an antagonist of the biological activity of Angiopoietin-1 and Angiopoietin-2. The method may include selecting an animal in need of treatment for disease-related angiogenesis, and administering to said animal a therapeutically effective dose of an antagonist of the biological activity of Angiopoietin-1 and Angiopoietin-2.

According to another aspect there is provided a method of treating disease-related angiogenesis in a mammal comprising administering a therapeutically effective amount of an antibody which antagonizes the biological activity of Angiopoietin-1 and Angiopoietin-2. The method may include selecting an animal in need of treatment for disease-related angiogenesis, and administering to said animal a therapeutically effective dose of an antibody which antagonises the biological activity of Angiopoietin-1 and Angiopoietin-2. The antibody can be administered alone, or can be administered in combination with additional antibodies or chemotherapeutic drug or radiation therapy.

According to another aspect there is provided a method of treating cancer in a mammal comprising administering a therapeutically effective amount of an antagonist of the biological activity of Angiopoietin-1 and Angiopoietin-2. The method may include selecting an animal in need of treatment for cancer, and administering to said animal a therapeutically effective dose of an antagonist which antagonises the biological activity of Angiopoietin-1 and Angiopoietin-2. The antagonist can be administered alone, or can be administered in combination with additional antibodies or chemotherapeutic drug or radiation therapy.

According to another aspect there is provided a method of treating cancer in a mammal comprising administering a therapeutically effective amount of an antibody which antagonizes the biological activity of Angiopoietin-1 and Angiopoietin-2. The method may include selecting an animal in need of treatment for cancer, and administering to said animal a therapeutically effective dose of an antibody which antagonises the biological activity of Angiopoietin-1 and Angiopoietin-2. The antibody can be administered alone, or can be administered in combination with additional antibodies or chemotherapeutic drug or radiation therapy.

According to another aspect of the invention there is provided the use of an antagonist of the biological activity of Angiopoietin-1 and Angiopoietin-2 for the manufacture of a medicament for the treatment of disease-related angiogenesis.

According to another aspect of the invention there is provided the use of an antibody which antagonizes the biological activity of Angiopoietin-1 and Angiopoietin-2 for the manufacture of a medicament for the treatment of disease-related angiogenesis.

In a preferred embodiment the present invention is particularly suitable for use in antagonizing Angiopoietin-1 or Angiopoietin-2, in patients with a tumour which is dependent alone, or in part, on a Tie-2 receptor.

Another embodiment of the invention includes an assay kit for detecting Angiopoietin-1 and/or Angiopoietin-2 in mammalian tissues, cells, or body fluids to screen for angiogenesis-related diseases. The kit includes an antibody that binds to Angiopoietin-1 and/or Angiopoietin-1 and a means for indicating the reaction of the antibody with Angiopoietin-1 and/or Angiopoietin-2, if present. The antibody may be a monoclonal antibody. In one embodiment, the antibody that binds Angiopoietin-2 is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radio-opaque material.

Further embodiments, features, and the like regarding anti-Ang-2 antibodies are provided in additional detail below.

SEQUENCE LISTING

Embodiments of the invention include the specific anti-Ang-2 antibodies listed below in Table 1. This table reports the identification number of each anti-Ang-2 antibody, along with the SEQ ID number of the corresponding heavy chain and light chain genes.

Each antibody has been given an identification number that includes either two or three numbers separated by one or two decimal points. For most of the antibodies, only two identification numbers, separated by one decimal point, are listed.

However, in some cases, several clones of one antibody were prepared. Although the clones have the identical nucleic acid and amino acid sequences as the parent sequence, they may also be listed separately, with the clone number indicated by the number to the right of a second decimal point. Thus, for example, the nucleic acid and amino acid sequences of antibody 5.35 are identical to the sequences of antibody 5.35.1, 5.35.2, and 5.35.3.

TABLE 1

| mAb ID No.: | Sequence | SEQ ID NO: |
|---|---|---|
| 3.1 | Nucleotide sequence encoding the variable region of the heavy chain | 6 |
| | Amino acid sequence encoding the variable region of the heavy chain | 7 |
| | Nucleotide sequence encoding the variable region of the light chain | 8 |
| | Amino acid sequence encoding the variable region of the light chain | 9 |
| 3.2 | Nucleotide sequence encoding the variable region of the heavy chain | 10 |
| | Amino acid sequence encoding the variable region of the heavy chain | 11 |
| | Nucleotide sequence encoding the variable region of the light chain | 12 |
| | Amino acid sequence encoding the variable region of the light chain | 13 |
| 3.3 | Nucleotide sequence encoding the variable region of the heavy chain | 14 |
| | Amino acid sequence encoding the variable region of the heavy chain | 15 |
| | Nucleotide sequence encoding the variable region of the light chain | 16 |
| | Amino acid sequence encoding the variable region of the light chain | 17 |
| 3.3.1 | Nucleotide sequence encoding the variable region of the heavy chain | 18 |
| | Amino acid sequence encoding the variable region of the heavy chain | 19 |
| | Nucleotide sequence encoding the variable region of the light chain | 20 |
| | Amino acid sequence encoding the variable region of the light chain | 21 |
| 3.3.2 | Nucleotide sequence encoding the variable region of the heavy chain | 22 |
| | Amino acid sequence encoding the variable region of the heavy chain | 23 |
| | Nucleotide sequence encoding the variable region of the light chain | 24 |
| | Amino acid sequence encoding the variable region of the light chain | 25 |
| 3.6 | Nucleotide sequence encoding the variable region of the heavy chain | 26 |
| | Amino acid sequence encoding the variable region of the heavy chain | 27 |
| | Nucleotide sequence encoding the variable region of the light chain | 28 |
| | Amino acid sequence encoding the variable region of the light chain | 29 |
| 3.7 | Nucleotide sequence encoding the variable region of the heavy chain | 30 |
| | Amino acid sequence encoding the variable region of the heavy chain | 31 |
| | Nucleotide sequence encoding the variable region of the light chain | 32 |
| | Amino acid sequence encoding the variable region of the light chain | 33 |
| 3.8 | Nucleotide sequence encoding the variable region of the heavy chain | 34 |
| | Amino acid sequence encoding the variable region of the heavy chain | 35 |
| | Nucleotide sequence encoding the variable region of the light chain | 36 |
| | Amino acid sequence encoding the variable region of the light chain | 37 |
| 3.9 | Nucleotide sequence encoding the variable region of the heavy chain | 38 |
| | Amino acid sequence encoding the variable region of the heavy chain | 39 |
| | Nucleotide sequence encoding the variable region of the light chain | 40 |
| | Amino acid sequence encoding the variable region of the light chain | 41 |
| 3.10 | Nucleotide sequence encoding the variable region of the heavy chain | 42 |
| | Amino acid sequence encoding the variable region of the heavy chain | 43 |
| | Nucleotide sequence encoding the variable region of the light chain | 44 |
| | Amino acid sequence encoding the variable region of the light chain | 45 |
| 3.11 | Nucleotide sequence encoding the variable region of the heavy chain | 46 |
| | Amino acid sequence encoding the variable region of the heavy chain | 47 |
| | Nucleotide sequence encoding the variable region of the light chain | 48 |
| | Amino acid sequence encoding the variable region of the light chain | 49 |
| 3.12 | Nucleotide sequence encoding the variable region of the heavy chain | 50 |
| | Amino acid sequence encoding the variable region of the heavy chain | 51 |
| | Nucleotide sequence encoding the variable region of the light chain | 52 |
| | Amino acid sequence encoding the variable region of the light chain | 53 |
| 3.13 | Nucleotide sequence encoding the variable region of the heavy chain | 54 |
| | Amino acid sequence encoding the variable region of the heavy chain | 55 |
| | Nucleotide sequence encoding the variable region of the light chain | 56 |
| | Amino acid sequence encoding the variable region of the light chain | 57 |
| 3.14 | Nucleotide sequence encoding the variable region of the heavy chain | 58 |
| | Amino acid sequence encoding the variable region of the heavy chain | 59 |
| | Nucleotide sequence encoding the variable region of the light chain | 60 |
| | Amino acid sequence encoding the variable region of the light chain | 61 |
| 3.15 | Nucleotide sequence encoding the variable region of the light chain | 62 |
| | Amino acid sequence encoding the variable region of the light chain | 63 |

TABLE 1-continued

| mAb ID No.: | Sequence | SEQ ID NO: |
|---|---|---|
| 3.16 | Nucleotide sequence encoding the variable region of the light chain | 64 |
| | Amino acid sequence encoding the variable region of the light chain | 65 |
| 3.17 | Nucleotide sequence encoding the variable region of the heavy chain | 66 |
| | Amino acid sequence encoding the variable region of the heavy chain | 67 |
| | Nucleotide sequence encoding the variable region of the light chain | 68 |
| | Amino acid sequence encoding the variable region of the light chain | 69 |
| 3.18 | Nucleotide sequence encoding the variable region of the heavy chain | 70 |
| | Amino acid sequence encoding the variable region of the heavy chain | 71 |
| | Nucleotide sequence encoding the variable region of the light chain | 72 |
| | Amino acid sequence encoding the variable region of the light chain | 73 |
| 3.19.1 | Nucleotide sequence encoding the variable region of the heavy chain | 74 |
| | Amino acid sequence encoding the variable region of the heavy chain | 75 |
| | Nucleotide sequence encoding the variable region of the light chain | 76 |
| | Amino acid sequence encoding the variable region of the light chain | 77 |
| 3.19.3 | Nucleotide sequence encoding the variable region of the heavy chain | 78 |
| | Amino acid sequence encoding the variable region of the heavy chain | 79 |
| | Nucleotide sequence encoding the variable region of the light chain | 80 |
| | Amino acid sequence encoding the variable region of the light chain | 81 |
| 3.20 | Nucleotide sequence encoding the variable region of the light chain | 82 |
| | Amino acid sequence encoding the variable region of the light chain | 83 |
| 3.21 | Nucleotide sequence encoding the variable region of the heavy chain | 84 |
| | Amino acid sequence encoding the variable region of the heavy chain | 85 |
| | Nucleotide sequence encoding the variable region of the light chain | 86 |
| | Amino acid sequence encoding the variable region of the light chain | 87 |
| 3.22 | Nucleotide sequence encoding the variable region of the heavy chain | 88 |
| | Amino acid sequence encoding the variable region of the heavy chain | 89 |
| | Nucleotide sequence encoding the variable region of the light chain | 90 |
| | Amino acid sequence encoding the variable region of the light chain | 91 |
| 3.26 | Nucleotide sequence encoding the variable region of the heavy chain | 92 |
| | Amino acid sequence encoding the variable region of the heavy chain | 93 |
| | Nucleotide sequence encoding the variable region of the light chain | 94 |
| | Amino acid sequence encoding the variable region of the light chain | 95 |
| 3.28.1 | Nucleotide sequence encoding the variable region of the heavy chain | 96 |
| | Amino acid sequence encoding the variable region of the heavy chain | 97 |
| 3.31.1 | Nucleotide sequence encoding the variable region of the heavy chain | 98 |
| | Amino acid sequence encoding the variable region of the heavy chain | 99 |
| | Nucleotide sequence encoding the variable region of the light chain | 100 |
| | Amino acid sequence encoding the variable region of the light chain | 101 |
| 3.31.2 | Nucleotide sequence encoding the variable region of the heavy chain | 102 |
| | Amino acid sequence encoding the variable region of the heavy chain | 103 |
| | Nucleotide sequence encoding the variable region of the light chain | 104 |
| | Amino acid sequence encoding the variable region of the light chain | 105 |
| 3.32 | Nucleotide sequence encoding the variable region of the heavy chain | 106 |
| | Amino acid sequence encoding the variable region of the heavy chain | 107 |
| | Nucleotide sequence encoding the variable region of the light chain | 108 |
| | Amino acid sequence encoding the variable region of the light chain | 109 |
| 3.33 | Nucleotide sequence encoding the variable region of the heavy chain | 110 |
| | Amino acid sequence encoding the variable region of the heavy chain | 111 |
| | Nucleotide sequence encoding the variable region of the light chain | 112 |
| | Amino acid sequence encoding the variable region of the light chain | 113 |
| 3.34 | Nucleotide sequence encoding the variable region of the heavy chain | 114 |
| | Amino acid sequence encoding the variable region of the heavy chain | 115 |
| | Nucleotide sequence encoding the variable region of the light chain | 116 |
| | Amino acid sequence encoding the variable region of the light chain | 117 |
| 3.35 | Nucleotide sequence encoding the variable region of the heavy chain | 118 |
| | Amino acid sequence encoding the variable region of the heavy chain | 119 |
| 3.37 | Nucleotide sequence encoding the variable region of the heavy chain | 120 |
| | Amino acid sequence encoding the variable region of the heavy chain | 121 |
| | Nucleotide sequence encoding the variable region of the light chain | 122 |
| | Amino acid sequence encoding the variable region of the light chain | 123 |
| 3.39 | Nucleotide sequence encoding the variable region of the heavy chain | 124 |
| | Amino acid sequence encoding the variable region of the heavy chain | 125 |
| | Nucleotide sequence encoding the variable region of the light chain | 126 |
| | Amino acid sequence encoding the variable region of the light chain | 127 |
| 3.40 | Nucleotide sequence encoding the variable region of the heavy chain | 128 |
| | Amino acid sequence encoding the variable region of the heavy chain | 129 |
| | Nucleotide sequence encoding the variable region of the light chain | 130 |
| | Amino acid sequence encoding the variable region of the light chain | 131 |
| 3.41 | Nucleotide sequence encoding the variable region of the heavy chain | 132 |
| | Amino acid sequence encoding the variable region of the heavy chain | 133 |
| | Nucleotide sequence encoding the variable region of the light chain | 134 |
| | Amino acid sequence encoding the variable region of the light chain | 135 |
| 3.42 | Nucleotide sequence encoding the variable region of the heavy chain | 136 |
| | Amino acid sequence encoding the variable region of the heavy chain | 137 |
| | Nucleotide sequence encoding the variable region of the light chain | 138 |
| | Amino acid sequence encoding the variable region of the light chain | 139 |

TABLE 1-continued

| mAb ID No.: | Sequence | SEQ ID NO: |
|---|---|---|
| 4.2 | Nucleotide sequence encoding the variable region of the heavy chain | 140 |
| | Amino acid sequence encoding the variable region of the heavy chain | 141 |
| | Nucleotide sequence encoding the variable region of the light chain | 142 |
| | Amino acid sequence encoding the variable region of the light chain | 143 |
| 4.3 | Nucleotide sequence encoding the variable region of the heavy chain | 144 |
| | Amino acid sequence encoding the variable region of the heavy chain | 145 |
| | Nucleotide sequence encoding the variable region of the light chain | 146 |
| | Amino acid sequence encoding the variable region of the light chain | 147 |
| 4.4 | Nucleotide sequence encoding the variable region of the light chain | 148 |
| | Amino acid sequence encoding the variable region of the light chain | 149 |
| 4.5 | Nucleotide sequence encoding the variable region of the heavy chain | 150 |
| | Amino acid sequence encoding the variable region of the heavy chain | 151 |
| | Nucleotide sequence encoding the variable region of the light chain | 152 |
| | Amino acid sequence encoding the variable region of the light chain | 153 |
| 4.6 | Nucleotide sequence encoding the variable region of the heavy chain | 154 |
| | Amino acid sequence encoding the variable region of the heavy chain | 155 |
| 4.7 | Nucleotide sequence encoding the variable region of the heavy chain | 156 |
| | Amino acid sequence encoding the variable region of the heavy chain | 157 |
| 4.8 | Nucleotide sequence encoding the variable region of the heavy chain | 158 |
| | Amino acid sequence encoding the variable region of the heavy chain | 159 |
| | Nucleotide sequence encoding the variable region of the light chain | 160 |
| | Amino acid sequence encoding the variable region of the light chain | 161 |
| 4.9 | Nucleotide sequence encoding the variable region of the heavy chain | 162 |
| | Amino acid sequence encoding the variable region of the heavy chain | 163 |
| | Nucleotide sequence encoding the variable region of the light chain | 164 |
| | Amino acid sequence encoding the variable region of the light chain | 165 |
| 4.11 | Nucleotide sequence encoding the variable region of the heavy chain | 166 |
| | Amino acid sequence encoding the variable region of the heavy chain | 167 |
| | Nucleotide sequence encoding the variable region of the light chain | 168 |
| | Amino acid sequence encoding the variable region of the light chain | 169 |
| 4.13 | Nucleotide sequence encoding the variable region of the heavy chain | 170 |
| | Amino acid sequence encoding the variable region of the heavy chain | 171 |
| | Nucleotide sequence encoding the variable region of the light chain | 172 |
| | Amino acid sequence encoding the variable region of the light chain | 173 |
| 4.14 | Nucleotide sequence encoding the variable region of the heavy chain | 174 |
| | Amino acid sequence encoding the variable region of the heavy chain | 175 |
| | Nucleotide sequence encoding the variable region of the light chain | 176 |
| | Amino acid sequence encoding the variable region of the light chain | 177 |
| 4.15 | Nucleotide sequence encoding the variable region of the heavy chain | 178 |
| | Amino acid sequence encoding the variable region of the heavy chain | 179 |
| | Nucleotide sequence encoding the variable region of the light chain | 180 |
| | Amino acid sequence encoding the variable region of the light chain | 181 |
| 4.16 | Nucleotide sequence encoding the variable region of the heavy chain | 182 |
| | Amino acid sequence encoding the variable region of the heavy chain | 183 |
| | Nucleotide sequence encoding the variable region of the light chain | 184 |
| | Amino acid sequence encoding the variable region of the light chain | 185 |
| 4.18 | Nucleotide sequence encoding the variable region of the heavy chain | 186 |
| | Amino acid sequence encoding the variable region of the heavy chain | 187 |
| | Nucleotide sequence encoding the variable region of the light chain | 188 |
| | Amino acid sequence encoding the variable region of the light chain | 189 |
| 5.1 | Nucleotide sequence encoding the variable region of the heavy chain | 190 |
| | Amino acid sequence encoding the variable region of the heavy chain | 191 |
| | Nucleotide sequence encoding the variable region of the light chain | 192 |
| | Amino acid sequence encoding the variable region of the light chain | 193 |
| 5.2 | Nucleotide sequence encoding the variable region of the heavy chain | 194 |
| | Amino acid sequence encoding the variable region of the heavy chain | 195 |
| 5.2.1 | Nucleotide sequence encoding the variable region of the heavy chain | 196 |
| | Amino acid sequence encoding the variable region of the heavy chain | 197 |
| 5.3 | Nucleotide sequence encoding the variable region of the light chain | 198 |
| | Amino acid sequence encoding the variable region of the light chain | 199 |
| 5.4 | Nucleotide sequence encoding the variable region of the heavy chain | 200 |
| | Amino acid sequence encoding the variable region of the heavy chain | 201 |
| 5.5 | Nucleotide sequence encoding the variable region of the heavy chain | 202 |
| | Amino acid sequence encoding the variable region of the heavy chain | 203 |
| 5.6 | Nucleotide sequence encoding the variable region of the heavy chain | 204 |
| | Amino acid sequence encoding the variable region of the heavy chain | 205 |
| | Nucleotide sequence encoding the variable region of the light chain | 206 |
| | Amino acid sequence encoding the variable region of the light chain | 207 |
| 5.7 | Nucleotide sequence encoding the variable region of the heavy chain | 208 |
| | Amino acid sequence encoding the variable region of the heavy chain | 209 |
| 5.8 | Nucleotide sequence encoding the variable region of the heavy chain | 210 |
| | Amino acid sequence encoding the variable region of the heavy chain | 211 |
| | Nucleotide sequence encoding the variable region of the light chain | 212 |
| | Amino acid sequence encoding the variable region of the light chain | 213 |
| 5.9 | Nucleotide sequence encoding the variable region of the heavy chain | 214 |
| | Amino acid sequence encoding the variable region of the heavy chain | 215 |

TABLE 1-continued

| mAb ID No.: | Sequence | SEQ ID NO: |
|---|---|---|
| 5.10 | Nucleotide sequence encoding the variable region of the heavy chain | 216 |
| | Amino acid sequence encoding the variable region of the heavy chain | 217 |
| | Nucleotide sequence encoding the variable region of the light chain | 218 |
| | Amino acid sequence encoding the variable region of the light chain | 219 |
| 5.11 | Nucleotide sequence encoding the variable region of the heavy chain | 220 |
| | Amino acid sequence encoding the variable region of the heavy chain | 221 |
| | Nucleotide sequence encoding the variable region of the light chain | 222 |
| | Amino acid sequence encoding the variable region of the light chain | 223 |
| 5.12 | Nucleotide sequence encoding the variable region of the heavy chain | 224 |
| | Amino acid sequence encoding the variable region of the heavy chain | 225 |
| | Nucleotide sequence encoding the variable region of the light chain | 226 |
| | Amino acid sequence encoding the variable region of the light chain | 227 |
| 5.13.1 | Nucleotide sequence encoding the variable region of the heavy chain | 228 |
| | Amino acid sequence encoding the variable region of the heavy chain | 229 |
| | Nucleotide sequence encoding the variable region of the light chain | 230 |
| | Amino acid sequence encoding the variable region of the light chain | 231 |
| 5.14.1 | Nucleotide sequence encoding the variable region of the heavy chain | 232 |
| | Amino acid sequence encoding the variable region of the heavy chain | 233 |
| 5.15 | Nucleotide sequence encoding the variable region of the heavy chain | 234 |
| | Amino acid sequence encoding the variable region of the heavy chain | 235 |
| | Nucleotide sequence encoding the variable region of the light chain | 236 |
| | Amino acid sequence encoding the variable region of the light chain | 237 |
| 5.16.1 | Nucleotide sequence encoding the variable region of the heavy chain | 238 |
| | Amino acid sequence encoding the variable region of the heavy chain | 239 |
| | Nucleotide sequence encoding the variable region of the light chain | 240 |
| | Amino acid sequence encoding the variable region of the light chain | 241 |
| 5.17 | Nucleotide sequence encoding the variable region of the heavy chain | 242 |
| | Amino acid sequence encoding the variable region of the heavy chain | 243 |
| | Nucleotide sequence encoding the variable region of the light chain | 244 |
| | Amino acid sequence encoding the variable region of the light chain | 245 |
| 5.18 | Nucleotide sequence encoding the variable region of the heavy chain | 246 |
| | Amino acid sequence encoding the variable region of the heavy chain | 247 |
| | Nucleotide sequence encoding the variable region of the light chain | 248 |
| | Amino acid sequence encoding the variable region of the light chain | 249 |
| 5.19 | Nucleotide sequence encoding the variable region of the heavy chain | 250 |
| | Amino acid sequence encoding the variable region of the heavy chain | 251 |
| 5.20 | Nucleotide sequence encoding the variable region of the heavy chain | 252 |
| | Amino acid sequence encoding the variable region of the heavy chain | 253 |
| 5.21 | Nucleotide sequence encoding the variable region of the heavy chain | 254 |
| | Amino acid sequence encoding the variable region of the heavy chain | 255 |
| | Nucleotide sequence encoding the variable region of the light chain | 256 |
| | Amino acid sequence encoding the variable region of the light chain | 257 |
| 5.22 | Nucleotide sequence encoding the variable region of the heavy chain | 258 |
| | Amino acid sequence encoding the variable region of the heavy chain | 259 |
| | Nucleotide sequence encoding the variable region of the light chain | 260 |
| | Amino acid sequence encoding the variable region of the light chain | 261 |
| 5.23 | Nucleotide sequence encoding the variable region of the heavy chain | 262 |
| | Amino acid sequence encoding the variable region of the heavy chain | 263 |
| | Nucleotide sequence encoding the variable region of the light chain | 264 |
| | Amino acid sequence encoding the variable region of the light chain | 265 |
| 5.24 | Nucleotide sequence encoding the variable region of the heavy chain | 266 |
| | Amino acid sequence encoding the variable region of the heavy chain | 267 |
| | Nucleotide sequence encoding the variable region of the light chain | 268 |
| | Amino acid sequence encoding the variable region of the light chain | 269 |
| 5.25 | Nucleotide sequence encoding the variable region of the light chain | 270 |
| | Amino acid sequence encoding the variable region of the light chain | 271 |
| 5.26 | Nucleotide sequence encoding the variable region of the heavy chain | 272 |
| | Amino acid sequence encoding the variable region of the heavy chain | 273 |
| 5.27 | Nucleotide sequence encoding the variable region of the light chain | 274 |
| | Amino acid sequence encoding the variable region of the light chain | 275 |
| 5.28.1 | Nucleotide sequence encoding the variable region of the heavy chain | 276 |
| | Amino acid sequence encoding the variable region of the heavy chain | 277 |
| | Nucleotide sequence encoding the variable region of the light chain | 278 |
| | Amino acid sequence encoding the variable region of the light chain | 279 |
| 5.29 | Nucleotide sequence encoding the variable region of the heavy chain | 280 |
| | Amino acid sequence encoding the variable region of the heavy chain | 281 |
| | Nucleotide sequence encoding the variable region of the light chain | 282 |
| | Amino acid sequence encoding the variable region of the light chain | 283 |
| 5.30 | Nucleotide sequence encoding the variable region of the heavy chain | 284 |
| | Amino acid sequence encoding the variable region of the heavy chain | 285 |
| | Nucleotide sequence encoding the variable region of the light chain | 286 |
| | Amino acid sequence encoding the variable region of the light chain | 287 |
| 5.31 | Nucleotide sequence encoding the variable region of the heavy chain | 288 |
| | Amino acid sequence encoding the variable region of the heavy chain | 289 |
| | Nucleotide sequence encoding the variable region of the light chain | 290 |
| | Amino acid sequence encoding the variable region of the light chain | 291 |
| 5.33 | Nucleotide sequence encoding the variable region of the heavy chain | 292 |
| | Amino acid sequence encoding the variable region of the heavy chain | 293 |

TABLE 1-continued

| mAb ID No.: | Sequence | SEQ ID NO: |
|---|---|---|
| 5.34 | Nucleotide sequence encoding the variable region of the light chain | 294 |
| | Amino acid sequence encoding the variable region of the light chain | 295 |
| 5.35.1 | Nucleotide sequence encoding the variable region of the heavy chain | 296 |
| | Amino acid sequence encoding the variable region of the heavy chain | 297 |
| | Nucleotide sequence encoding the variable region of the light chain | 298 |
| | Amino acid sequence encoding the variable region of the light chain | 299 |
| 5.36 | Nucleotide sequence encoding the variable region of the heavy chain | 300 |
| | Amino acid sequence encoding the variable region of the heavy chain | 301 |
| | Nucleotide sequence encoding the variable region of the light chain | 302 |
| | Amino acid sequence encoding the variable region of the light chain | 303 |
| 5.37 | Nucleotide sequence encoding the variable region of the heavy chain | 304 |
| | Amino acid sequence encoding the variable region of the heavy chain | 305 |
| | Nucleotide sequence encoding the variable region of the light chain | 306 |
| | Amino acid sequence encoding the variable region of the light chain | 307 |
| 5.38 | Nucleotide sequence encoding the variable region of the heavy chain | 308 |
| | Amino acid sequence encoding the variable region of the heavy chain | 309 |
| | Nucleotide sequence encoding the variable region of the light chain | 310 |
| | Amino acid sequence encoding the variable region of the light chain | 311 |
| 5.39.1 | Nucleotide sequence encoding the variable region of the heavy chain | 312 |
| | Amino acid sequence encoding the variable region of the heavy chain | 313 |
| | Nucleotide sequence encoding the variable region of the light chain | 314 |
| | Amino acid sequence encoding the variable region of the light chain | 315 |
| 5.40.2 | Nucleotide sequence encoding the variable region of the heavy chain | 316 |
| | Amino acid sequence encoding the variable region of the heavy chain | 317 |
| | Nucleotide sequence encoding the variable region of the light chain | 318 |
| | Amino acid sequence encoding the variable region of the light chain | 319 |
| 5.41.1 | Nucleotide sequence encoding the variable region of the heavy chain | 320 |
| | Amino acid sequence encoding the variable region of the heavy chain | 321 |
| | Nucleotide sequence encoding the variable region of the light chain | 322 |
| | Amino acid sequence encoding the variable region of the light chain | 323 |
| 5.43 | Nucleotide sequence encoding the variable region of the heavy chain | 324 |
| | Amino acid sequence encoding the variable region of the heavy chain | 325 |
| | Nucleotide sequence encoding the variable region of the light chain | 326 |
| | Amino acid sequence encoding the variable region of the light chain | 327 |
| 5.44 | Nucleotide sequence encoding the variable region of the heavy chain | 328 |
| | Amino acid sequence encoding the variable region of the heavy chain | 329 |
| | Nucleotide sequence encoding the variable region of the light chain | 330 |
| | Amino acid sequence encoding the variable region of the light chain | 331 |
| 5.45 | Nucleotide sequence encoding the variable region of the heavy chain | 332 |
| | Amino acid sequence encoding the variable region of the heavy chain | 333 |
| | Nucleotide sequence encoding the variable region of the light chain | 334 |
| | Amino acid sequence encoding the variable region of the light chain | 335 |
| 5.46 | Nucleotide sequence encoding the variable region of the heavy chain | 336 |
| | Amino acid sequence encoding the variable region of the heavy chain | 337 |
| 5.47 | Nucleotide sequence encoding the variable region of the heavy chain | 338 |
| | Amino acid sequence encoding the variable region of the heavy chain | 339 |
| 5.48 | Nucleotide sequence encoding the variable region of the heavy chain | 340 |
| | Amino acid sequence encoding the variable region of the heavy chain | 341 |
| | Nucleotide sequence encoding the variable region of the light chain | 342 |
| | Amino acid sequence encoding the variable region of the light chain | 343 |
| 5.51 | Nucleotide sequence encoding the variable region of the heavy chain | 344 |
| | Amino acid sequence encoding the variable region of the heavy chain | 345 |
| 5.52 | Nucleotide sequence encoding the variable region of the heavy chain | 346 |
| | Amino acid sequence encoding the variable region of the heavy chain | 347 |
| | Nucleotide sequence encoding the variable region of the light chain | 348 |
| | Amino acid sequence encoding the variable region of the light chain | 349 |
| 5.52.1 | Nucleotide sequence encoding the variable region of the heavy chain | 350 |
| | Amino acid sequence encoding the variable region of the heavy chain | 351 |
| | Nucleotide sequence encoding the variable region of the light chain | 352 |
| | Amino acid sequence encoding the variable region of the light chain | 353 |
| 5.53 | Nucleotide sequence encoding the variable region of the heavy chain | 354 |
| | Amino acid sequence encoding the variable region of the heavy chain | 355 |
| 5.54.1 | Nucleotide sequence encoding the variable region of the heavy chain | 356 |
| | Amino acid sequence encoding the variable region of the heavy chain | 357 |
| | Nucleotide sequence encoding the variable region of the light chain | 358 |
| | Amino acid sequence encoding the variable region of the light chain | 359 |
| 5.55 | Nucleotide sequence encoding the variable region of the heavy chain | 360 |
| | Amino acid sequence encoding the variable region of the heavy chain | 361 |
| 5.56.1 | Nucleotide sequence encoding the variable region of the heavy chain | 362 |
| | Amino acid sequence encoding the variable region of the heavy chain | 363 |
| | Nucleotide sequence encoding the variable region of the light chain | 364 |
| | Amino acid sequence encoding the variable region of the light chain | 365 |
| 5.58 | Nucleotide sequence encoding the variable region of the heavy chain | 366 |
| | Amino acid sequence encoding the variable region of the heavy chain | 367 |
| | Nucleotide sequence encoding the variable region of the light chain | 368 |
| | Amino acid sequence encoding the variable region of the light chain | 369 |
| 5.59 | Nucleotide sequence encoding the variable region of the heavy chain | 370 |
| | Amino acid sequence encoding the variable region of the heavy chain | 371 |

TABLE 1-continued

| mAb ID No.: | Sequence | SEQ ID NO: |
|---|---|---|
| 5.60 | Nucleotide sequence encoding the variable region of the heavy chain | 372 |
|  | Amino acid sequence encoding the variable region of the heavy chain | 373 |
|  | Nucleotide sequence encoding the variable region of the light chain | 374 |
|  | Amino acid sequence encoding the variable region of the light chain | 375 |
| 5.61 | Nucleotide sequence encoding the variable region of the heavy chain | 376 |
|  | Amino acid sequence encoding the variable region of the heavy chain | 377 |
|  | Nucleotide sequence encoding the variable region of the light chain | 378 |
|  | Amino acid sequence encoding the variable region of the light chain | 379 |
| 5.62.1 | Nucleotide sequence encoding the variable region of the heavy chain | 380 |
|  | Amino acid sequence encoding the variable region of the heavy chain | 381 |
|  | Nucleotide sequence encoding the variable region of the light chain | 382 |
|  | Amino acid sequence encoding the variable region of the light chain | 383 |
| 5.64 | Nucleotide sequence encoding the variable region of the heavy chain | 384 |
|  | Amino acid sequence encoding the variable region of the heavy chain | 385 |
|  | Nucleotide sequence encoding the variable region of the light chain | 386 |
|  | Amino acid sequence encoding the variable region of the light chain | 387 |
| 5.66 | Nucleotide sequence encoding the variable region of the heavy chain | 388 |
|  | Amino acid sequence encoding the variable region of the heavy chain | 389 |
|  | Nucleotide sequence encoding the variable region of the light chain | 390 |
|  | Amino acid sequence encoding the variable region of the light chain | 391 |
| 5.67 | Nucleotide sequence encoding the variable region of the heavy chain | 392 |
|  | Amino acid sequence encoding the variable region of the heavy chain | 393 |
|  | Nucleotide sequence encoding the variable region of the light chain | 394 |
|  | Amino acid sequence encoding the variable region of the light chain | 395 |
| 5.68 | Nucleotide sequence encoding the variable region of the heavy chain | 396 |
|  | Amino acid sequence encoding the variable region of the heavy chain | 397 |
| 5.70 | Nucleotide sequence encoding the variable region of the heavy chain | 398 |
|  | Amino acid sequence encoding the variable region of the heavy chain | 399 |
| 5.71 | Nucleotide sequence encoding the variable region of the heavy chain | 400 |
|  | Amino acid sequence encoding the variable region of the heavy chain | 401 |
|  | Nucleotide sequence encoding the variable region of the light chain | 402 |
|  | Amino acid sequence encoding the variable region of the light chain | 403 |
| 5.72 | Nucleotide sequence encoding the variable region of the heavy chain | 404 |
|  | Amino acid sequence encoding the variable region of the heavy chain | 405 |
|  | Nucleotide sequence encoding the variable region of the light chain | 406 |
|  | Amino acid sequence encoding the variable region of the light chain | 407 |
| 5.73 | Nucleotide sequence encoding the variable region of the heavy chain | 408 |
|  | Amino acid sequence encoding the variable region of the heavy chain | 409 |
|  | Nucleotide sequence encoding the variable region of the light chain | 410 |
|  | Amino acid sequence encoding the variable region of the light chain | 411 |
| 5.74 | Nucleotide sequence encoding the variable region of the heavy chain | 412 |
|  | Amino acid sequence encoding the variable region of the heavy chain | 413 |
|  | Nucleotide sequence encoding the variable region of the light chain | 414 |
|  | Amino acid sequence encoding the variable region of the light chain | 415 |
| 5.75 | Nucleotide sequence encoding the variable region of the heavy chain | 416 |
|  | Amino acid sequence encoding the variable region of the heavy chain | 417 |
| 5.76 | Nucleotide sequence encoding the variable region of the heavy chain | 418 |
|  | Amino acid sequence encoding the variable region of the heavy chain | 419 |
|  | Nucleotide sequence encoding the variable region of the light chain | 420 |
|  | Amino acid sequence encoding the variable region of the light chain | 421 |
| 5.77 | Nucleotide sequence encoding the variable region of the light chain | 422 |
|  | Amino acid sequence encoding the variable region of the light chain | 423 |
| 5.78 | Nucleotide sequence encoding the variable region of the heavy chain | 424 |
|  | Amino acid sequence encoding the variable region of the heavy chain | 425 |
|  | Nucleotide sequence encoding the variable region of the light chain | 426 |
|  | Amino acid sequence encoding the variable region of the light chain | 427 |
| 5.78.1 | Nucleotide sequence encoding the variable region of the heavy chain | 428 |
|  | Amino acid sequence encoding the variable region of the heavy chain | 429 |
|  | Nucleotide sequence encoding the variable region of the light chain | 430 |
|  | Amino acid sequence encoding the variable region of the light chain | 431 |
| 5.79 | Nucleotide sequence encoding the variable region of the heavy chain | 432 |
|  | Amino acid sequence encoding the variable region of the heavy chain | 433 |
| 5.80 | Nucleotide sequence encoding the variable region of the heavy chain | 434 |
|  | Amino acid sequence encoding the variable region of the heavy chain | 435 |
|  | Nucleotide sequence encoding the variable region of the light chain | 436 |
|  | Amino acid sequence encoding the variable region of the light chain | 437 |
| 5.81 | Nucleotide sequence encoding the variable region of the heavy chain | 438 |
|  | Amino acid sequence encoding the variable region of the heavy chain | 439 |
|  | Nucleotide sequence encoding the variable region of the light chain | 440 |
|  | Amino acid sequence encoding the variable region of the light chain | 441 |
| 5.82 | Nucleotide sequence encoding the variable region of the heavy chain | 442 |
|  | Amino acid sequence encoding the variable region of the heavy chain | 443 |
|  | Nucleotide sequence encoding the variable region of the light chain | 444 |
|  | Amino acid sequence encoding the variable region of the light chain | 445 |
| 5.83 | Nucleotide sequence encoding the variable region of the heavy chain | 446 |
|  | Amino acid sequence encoding the variable region of the heavy chain | 447 |

TABLE 1-continued

| mAb ID No.: | Sequence | SEQ ID NO: |
|---|---|---|
| 5.83.1 | Nucleotide sequence encoding the variable region of the heavy chain | 448 |
| | Amino acid sequence encoding the variable region of the heavy chain | 449 |
| | Nucleotide sequence encoding the variable region of the light chain | 450 |
| | Amino acid sequence encoding the variable region of the light chain | 451 |
| 5.86.1 | Nucleotide sequence encoding the variable region of the heavy chain | 452 |
| | Amino acid sequence encoding the variable region of the heavy chain | 453 |
| | Nucleotide sequence encoding the variable region of the light chain | 454 |
| | Amino acid sequence encoding the variable region of the light chain | 455 |
| 5.87 | Nucleotide sequence encoding the variable region of the heavy chain | 456 |
| | Amino acid sequence encoding the variable region of the heavy chain | 457 |
| | Nucleotide sequence encoding the variable region of the light chain | 458 |
| | Amino acid sequence encoding the variable region of the light chain | 459 |
| 5.88 | Nucleotide sequence encoding the variable region of the heavy chain | 460 |
| | Amino acid sequence encoding the variable region of the heavy chain | 461 |
| | Nucleotide sequence encoding the variable region of the light chain | 462 |
| | Amino acid sequence encoding the variable region of the light chain | 463 |
| 5.88.1 | Nucleotide sequence encoding the variable region of the heavy chain | 464 |
| | Amino acid sequence encoding the variable region of the heavy chain | 465 |
| | Nucleotide sequence encoding the variable region of the light chain | 466 |
| | Amino acid sequence encoding the variable region of the light chain | 467 |
| 5.88.3 | Nucleotide sequence encoding the variable region of the heavy chain | 468 |
| | Amino acid sequence encoding the variable region of the heavy chain | 469 |
| | Nucleotide sequence encoding the variable region of the light chain | 470 |
| | Amino acid sequence encoding the variable region of the light chain | 471 |
| 5.89 | Nucleotide sequence encoding the variable region of the heavy chain | 472 |
| | Amino acid sequence encoding the variable region of the heavy chain | 473 |
| 5.90 | Nucleotide sequence encoding the variable region of the heavy chain | 474 |
| | Amino acid sequence encoding the variable region of the heavy chain | 475 |
| | Nucleotide sequence encoding the variable region of the light chain | 476 |
| | Amino acid sequence encoding the variable region of the light chain | 477 |
| 5.91 | Nucleotide sequence encoding the variable region of the heavy chain | 478 |
| | Amino acid sequence encoding the variable region of the heavy chain | 479 |
| 5.92 | Nucleotide sequence encoding the variable region of the heavy chain | 480 |
| | Amino acid sequence encoding the variable region of the heavy chain | 481 |
| | Nucleotide sequence encoding the variable region of the light chain | 482 |
| | Amino acid sequence encoding the variable region of the light chain | 483 |
| 5.93 | Nucleotide sequence encoding the variable region of the light chain | 484 |
| | Amino acid sequence encoding the variable region of the light chain | 485 |
| 5.94 | Nucleotide sequence encoding the variable region of the heavy chain | 486 |
| | Amino acid sequence encoding the variable region of the heavy chain | 487 |
| 5.95 | Nucleotide sequence encoding the variable region of the light chain | 488 |
| | Amino acid sequence encoding the variable region of the light chain | 489 |
| 5.97 | Nucleotide sequence encoding the variable region of the heavy chain | 490 |
| | Amino acid sequence encoding the variable region of the heavy chain | 491 |
| | Nucleotide sequence encoding the variable region of the light chain | 492 |
| | Amino acid sequence encoding the variable region of the light chain | 493 |
| 5.99 | Nucleotide sequence encoding the variable region of the light chain | 494 |
| | Amino acid sequence encoding the variable region of the light chain | 495 |
| 5.101.1 | Nucleotide sequence encoding the variable region of the heavy chain | 496 |
| | Amino acid sequence encoding the variable region of the heavy chain | 497 |
| | Nucleotide sequence encoding the variable region of the light chain | 498 |
| | Amino acid sequence encoding the variable region of the light chain | 499 |
| 5.102 | Nucleotide sequence encoding the variable region of the heavy chain | 500 |
| | Amino acid sequence encoding the variable region of the heavy chain | 501 |
| 5.103.1 | Nucleotide sequence encoding the variable region of the heavy chain | 502 |
| | Amino acid sequence encoding the variable region of the heavy chain | 503 |
| | Nucleotide sequence encoding the variable region of the light chain | 504 |
| | Amino acid sequence encoding the variable region of the light chain | 505 |
| 5.104 | Nucleotide sequence encoding the variable region of the heavy chain | 506 |
| | Amino acid sequence encoding the variable region of the heavy chain | 507 |
| 5.106 | Nucleotide sequence encoding the variable region of the heavy chain | 508 |
| | Amino acid sequence encoding the variable region of the heavy chain | 509 |
| 5.107 | Nucleotide sequence encoding the variable region of the heavy chain | 510 |
| | Amino acid sequence encoding the variable region of the heavy chain | 511 |
| 5.108.1 | Nucleotide sequence encoding the variable region of the heavy chain | 512 |
| | Amino acid sequence encoding the variable region of the heavy chain | 513 |
| | Nucleotide sequence encoding the variable region of the light chain | 514 |
| | Amino acid sequence encoding the variable region of the light chain | 515 |
| 5.109 | Nucleotide sequence encoding the variable region of the heavy chain | 516 |
| | Amino acid sequence encoding the variable region of the heavy chain | 517 |
| | Nucleotide sequence encoding the variable region of the light chain | 518 |
| | Amino acid sequence encoding the variable region of the light chain | 519 |
| 5.111 | Nucleotide sequence encoding the variable region of the heavy chain | 520 |
| | Amino acid sequence encoding the variable region of the heavy chain | 521 |
| | Nucleotide sequence encoding the variable region of the light chain | 522 |
| | Amino acid sequence encoding the variable region of the light chain | 523 |
| 5.112 | Nucleotide sequence encoding the variable region of the heavy chain | 524 |
| | Amino acid sequence encoding the variable region of the heavy chain | 525 |

TABLE 1-continued

| mAb ID No.: | Sequence | SEQ ID NO: |
|---|---|---|
| 5.114 | Nucleotide sequence encoding the variable region of the light chain | 526 |
| | Amino acid sequence encoding the variable region of the light chain | 527 |
| 5.115 | Nucleotide sequence encoding the variable region of the heavy chain | 528 |
| | Amino acid sequence encoding the variable region of the heavy chain | 529 |
| | Nucleotide sequence encoding the variable region of the light chain | 530 |
| | Amino acid sequence encoding the variable region of the light chain | 531 |
| 6.1 | Nucleotide sequence encoding the variable region of the heavy chain | 532 |
| | Amino acid sequence encoding the variable region of the heavy chain | 533 |
| 6.2 | Nucleotide sequence encoding the variable region of the heavy chain | 534 |
| | Amino acid sequence encoding the variable region of the heavy chain | 535 |
| | Nucleotide sequence encoding the variable region of the light chain | 536 |
| | Amino acid sequence encoding the variable region of the light chain | 537 |
| 6.3.1 | Nucleotide sequence encoding the variable region of the heavy chain | 538 |
| | Amino acid sequence encoding the variable region of the heavy chain | 539 |
| | Nucleotide sequence encoding the variable region of the light chain | 540 |
| | Amino acid sequence encoding the variable region of the light chain | 541 |
| 6.4 | Nucleotide sequence encoding the variable region of the light chain | 542 |
| | Amino acid sequence encoding the variable region of the light chain | 543 |
| 6.5 | Nucleotide sequence encoding the variable region of the heavy chain | 544 |
| | Amino acid sequence encoding the variable region of the heavy chain | 545 |
| 6.6 | Nucleotide sequence encoding the variable region of the heavy chain | 546 |
| | Amino acid sequence encoding the variable region of the heavy chain | 547 |
| | Nucleotide sequence encoding the variable region of the light chain | 548 |
| | Amino acid sequence encoding the variable region of the light chain | 549 |
| 6.7 | Nucleotide sequence encoding the variable region of the heavy chain | 550 |
| | Amino acid sequence encoding the variable region of the heavy chain | 551 |
| 6.8 | Nucleotide sequence encoding the variable region of the heavy chain | 552 |
| | Amino acid sequence encoding the variable region of the heavy chain | 553 |
| 6.9 | Nucleotide sequence encoding the variable region of the heavy chain | 554 |
| | Amino acid sequence encoding the variable region of the heavy chain | 555 |
| 6.10 | Nucleotide sequence encoding the variable region of the light chain | 556 |
| | Amino acid sequence encoding the variable region of the light chain | 557 |

DEFINITIONS

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

An antagonist may be a polypeptide, nucleic acid, carbohydrate, lipid, small molecular weight compound, an oligonucleotide, an oligopeptide, RNA interference (RNAi), antisense, a recombinant protein, an antibody, or conjugates or fusion proteins thereof. For a review of RNAi see Milhavet O, Gary D S, Mattson M P. (Pharmacol Rev. 2003 December; 55(4):629-48. Review.) and antisense see Opalinska J B, Gewirtz A M. (Sci STKE. 2003 Oct. 28; 2003(206):pe47.)

Disease-related angiogenesis may be any abnormal, undesirable or pathological angiogenesis, for example tumor-related angiogenesis. Angiogenesis-related diseases include, but are not limited to, non-solid tumors such as leukaemia, multiple myeloma or lymphoma, and also solid tumors such as melanoma, small cell lung cancer, non-small cell lung cancer, glioma, hepatocellular (liver) carcinoma, glioblastoma, carcinoma of the thyroid, bile duct, bone, gastric, brain/CNS, head and neck, hepatic, stomach, prostate, breast, renal, testicular, ovarian, skin, cervical, lung, muscle, neuronal, oesophageal, bladder, lung, uterine, vulval, endometrial, kidney, colorectal, pancreatic, pleural/peritoneal membranes, salivary gland, and epidermoid tumors.

A compound refers to any small molecular weight compound with a molecular weight of less than about 2000 Daltons.

The term "Ang-2" refers to the molecule Angiopoietin-2.

The term "neutralizing" when referring to an antibody relates to the ability of an antibody to eliminate, or significantly reduce, the activity of a target antigen. Accordingly, a "neutralizing" anti-Ang-2 antibody is capable of eliminating or significantly reducing the activity of Ang-2. A neutralizing Ang-2 antibody may, for example, act by blocking the binding of Ang-2 to its receptor Tie2. By blocking this binding, the Tie2 mediated signal transduction is significantly, or completely, eliminated. Ideally, a neutralizing antibody against Ang-2 inhibits angiogenesis.

The term "isolated polynucleotide" as used herein shall mean a polynucleotide that has been isolated from its naturally occurring environment. Such polynucleotides may be genomic, cDNA, or synthetic. Isolated polynucleotides preferably are not associated with all or a portion of the polynucleotides they associate with in nature. The isolated polynucleotides may be operably linked to another polynucleotide that it is not linked to in nature. In addition, isolated polynucleotides preferably do not occur in nature as part of a larger sequence.

The term "isolated protein" referred to herein means a protein that has been isolated from its naturally occurring environment. Such proteins may be derived from genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "control sequence" as used herein refers to polynucleotide sequences that are necessary either to effect or to affect the expression and processing of coding sequences to which they are connected. The nature of such control sequences differs depending upon the host organism; in prokaryotes, such control sequences generally include promoter, ribosomal binding site, and transcription termination sequence; in eukaryotes, generally, such control sequences may include promoters, enhancers, introns, transcription termination sequences, polyadenylation signal sequences, and 5' and '3 untranslated regions. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison. A reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least about 18 contiguous nucleotide positions or about 6 amino acids wherein the polynucleotide sequence or amino acid sequence is compared to a reference sequence of at least 18 contiguous nucleotides or 6 amino acid sequences and wherein the portion of the polynucleotide sequence in the comparison window may include additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), GENEWORKS™, or MACVECTOR® software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a Ang-2, under suitable binding conditions, (2) ability to block appropriate Ang-2 binding, or (3) ability to inhibit Ang-2 activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

As used herein, the term "antibody" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site.

As used herein, a "targeted binding agent" is an antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope.

"Binding fragments" of an antibody are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

An antibody may be oligoclonal, a polyclonal antibody, a monoclonal antibody, a chimeric antibody, a CDR-grafted antibody, a multi-specific antibody, a bispecific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and disulphide stabilized variable region (dsFv).

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is ≤0.1 µM, preferably ≤100 nM and most preferably ≤10 nM.

The term "agent" is used herein to denote a chemical compound, a mixture of chemical compounds, a biological macromolecule, or an extract made from biological materials.

"Active" or "activity" in regard to an Ang-2 polypeptide refers to a portion of an Ang-2 polypeptide that has a biological or an immunological activity of a native Ang-2 polypeptide. "Biological" when used herein refers to a biological function that results from the activity of the native Ang-2 polypeptide. A preferred Ang-2 biological activity includes, for example, Ang-2 induced angiogenesis.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites.

"Fab" when used herein refers to a fragment of an antibody that comprises the constant domain of the light chain and the CH1 domain of the heavy chain.

The term "mAb" refers to monoclonal antibody.

"Liposome" when used herein refers to a small vesicle that may be useful for delivery of drugs that may include the Ang-2 polypeptide of the invention or antibodies to such an Ang-2 polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3$H, $^{14}$C, $^{15}$N, $^{35}$S, $^{90}$Y, $^{99}$Tc, $^{125}$I, $^{131}$I, fluorescent labels may include rhodamine, lanthanide phosphors or FITC and enzymatic labels may include horseradish peroxidase, β-galactosidase, luciferase, alkaline phosphatase.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al. *Nature Genetics* 15:146-156 (1997) and Green and Jakobovits *J. Exp. Med.* 188:483-495 (1998). The XenoMouse® strains are available from Abgenix, Inc. (Fremont, Calif.).

The production of the XenoMouse® strains of mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. No. 07/574,748, filed Aug. 29, 1990, Ser. No. 07/575, 962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™—mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

Preparation of Antibodies

Antibodies, as described herein, were prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. Ang-2), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to Ang-1 and Ang-2. Further, provided herein are characterization of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by ELISA for reactivity against the Ang-2 immunogen. The supernatants might also be screened for immunoreactivity against fragments of Ang-2 to further map the different antibodies for binding to domains of functional interest on Ang-2. The antibodies may also be screened against Ang-1, Ang-3 or Ang-4, other related human chemokines and against the rat, the mouse, and non-human primate, such as Cynomolgus monkey, orthologues of Ang-2, the last to determine species cross-reactivity. B cells from wells containing antibodies of interest may be immortalized by various methods including fusion to make hybridomas either from individual or from pooled wells, or by infection with EBV or transfection by known immortalizing genes and then plating in suitable medium. Alternatively, single plasma cells secreting antibodies with the desired specificities are then isolated using an Ang-1 or Ang-2-specific hemolytic plaque assay (see for example Babcook et al., *Proc. Natl. Acad. Sci. USA* 93:7843-48 (1996)). Cells targeted for lysis are preferably sheep red blood cells (SRBCs) coated with the Ang-2 antigen. In screening for an antibody also able to antagonize Angiopoietin-1 the above methods can equally be used substituting Angiopoietin-2 with Angiopoietin-1.

In the presence of a B-cell culture containing plasma cells secreting the immunoglobulin of interest and complement, the formation of a plaque indicates specific Ang-1/Ang-2-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunglobulin heavy and light chain. The generated vector can then be transfected into host cells, e.g., HEK293 cells, CHO cells, and cultured in conventional nutrient media modified as appropriate for inducing transcription, selecting transformants, or amplifying the genes encoding the desired sequences.

In general, antibodies produced by the fused hybridomas were human IgG2 heavy chains with fully human kappa or lambda light chains. Antibodies described herein possess human IgG4 heavy chains as well as IgG2 heavy chains. Antibodies can also be of other human isotypes, including IgG1. The antibodies possessed high affinities, typically possessing a Kd of from about $10^{-6}$ through about $10^{-12}$ M or below, when measured by solid phase and solution phase techniques. Antibodies possessing a KD of at least $10^{-11}$ M are preferred to inhibit the activity of Ang-1 and/or Ang-2.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive Ang-2 binding properties.

Based on the ability of mAbs to significantly neutralize Angiopoietin-1 and Angiopoietin-2 activity (as demonstrated in the Examples below), these antibodies will have therapeutic effects in treating symptoms and conditions resulting from Angiopoietin-1 and/or Angiopoietin-2 expression. In specific embodiments, the antibodies and methods herein relate to the treatment of symptoms resulting from Angiopoietin-1 and/or Angiopoietin-2 induced angiogenesis.

According to another aspect of the invention there is provided a pharmaceutical composition comprising an antagonist of the biological activity of Angiopoietin-1 and Angiopoietin-2, and a pharmaceutically acceptable carrier. In one embodiment the antagonist comprises an antibody. According to another aspect of the invention there is provided a pharmaceutical composition comprising an antagonist of the biological activity of Angiopoietin-2, and a pharmaceutically acceptable carrier. In one embodiment the antagonist comprises an antibody.

Anti-Ang-2 antibodies are useful in the detection of Ang-2 in patient samples and accordingly are useful as diagnostics for disease states as described herein. In addition, based on their ability to significantly neutralize Ang-2 activity (as demonstrated in the Examples below), anti-Ang-2 antibodies have therapeutic effects in treating symptoms and conditions resulting from Ang-2 expression. In specific embodiments, the antibodies and methods herein relate to the treatment of symptoms resulting from Ang-2 induced angiogenesis. Further embodiments involve using the antibodies and methods described herein to treat angiogenesis-related diseases including neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, and pancreatic cancer.

Therapeutic Administration and Formulations

Embodiments of the invention include sterile pharmaceutical formulations of anti-Ang-2 antibodies or antibodies which bind to both Ang-1 and Ang-2 that are useful as treatments for diseases. Such formulations would inhibit the binding of Ang-2 or Ang-1 and Ang-2 to its receptor Tie2, thereby effectively treating pathological conditions where, for example, serum or tissue Ang-1 and/or Ang-2 is abnormally elevated. Anti-Ang-2 antibodies preferably possess adequate affinity to potently neutralize Ang-2, and preferably have an adequate duration of action to allow for infrequent dosing in humans. Anti-Ang-1/Ang-2 antibodies preferably possess adequate affinity to potently neutralize Ang-1 and Ang-2, and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* (20*th* ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2): 210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Combinations

The anti-angiogenic treatment defined herein may be applied as a sole therapy or may involve, in addition to the compounds of the invention, conventional surgery or radiotherapy or chemotherapy. Such chemotherapy may include one or more of the following categories of anti tumor agents:

(i) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5* reductase such as finasteride;

(ii) agents which inhibit cancer cell invasion (for example metalloproteinase inhibitors like marimastat and inhibitors of urokinase plasminogen activator receptor function);

(iii) inhibitors of growth factor function, for example such inhibitors include growth factor antibodies, growth factor receptor antibodies (for example the anti erbb2 antibody trastuzumab [Herceptin™] and the anti erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N (3 chloro 4 fluorophenyl) 7 methoxy 6 (3 morpholinopropoxy)quinazolin 4 amine (gefitinib, AZD1839), N (3 ethynylphenyl) 6,7 bis (2 methoxyethoxy)quinazolin 4 amine (erlotinib, OSI 774) and 6 acrylamido N (3 chloro 4 fluorophenyl) 7 (3 morpholinopropoxy)quinazolin 4 amine (CI 1033)), for example inhibitors of the platelet derived growth factor family and for example inhibitors of the hepatocyte growth factor family;

(iv) antiangiogenic agents such as those which inhibit the effects of vascular endothelial growth factor, (for example the anti vascular endothelial cell growth factor antibody bevacizumab [Avastin™], anti-vascular endothelial growth factor receptor antibodies such anti-KDR antibodies and anti-flt1 antibodies, compounds such as those disclosed in International Patent Applications WO 97/22596, WO 97/30035, WO 97/3285, WO 98/13354, WO00/47212 and WO01/32651) and compounds that work by other mechanisms (for example linomide, inhibitors of integrin avb3 function and angiostatin);

(v) vascular damaging agents such as Combretastatin A4 and compounds disclosed in International Patent Applications WO 99/02166, WO 00/40529, WO 00/41669, WO 01/92224, WO 02/04434 and WO 02/08213;

(vi) antisense therapies, for example those which are directed to the targets listed above, such as ISIS 2503, an anti ras antisense;

(vii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (viii) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies.

In one embodiment of the invention the anti-angiogenic treatments of the invention are combined with agents which inhibit the effects of vascular endothelial growth factor (VEGF), (for example the anti-vascular endothelial cell growth factor antibody bevacizumab (Avastin®), anti-vascular endothelial growth factor receptor antibodies such anti-KDR antibodies and anti-flt1 antibodies, compounds such as those disclosed in International Patent Applications WO 97/22596, WO 97/30035, WO 97/3285, WO 98/13354, WO00/47212 and WO01/32651) and compounds that work by other mechanisms (for example linomide, inhibitors of integrin avb3 function and angiostatin); In another embodiment of the invention the anti-angiogenic treatments of the invention are combined agents which inhibit the tyrosine kinase activity of the vascular endothelial growth factor receptor, KDR (for example AZD2171 or AZD6474). Additional details on AZD2171 may be found in Wedge et al (2005) Cancer Research. 65(10):4389-400. Additional details on AZD6474 may be found in Ryan & Wedge (2005) British Journal of Cancer. 92 Suppl 1:S6-13. Both publications are herein incorporated by reference in their entireties. In another embodiment of the invention the fully human antibodies 3.19.3, 3.3.2 or 5.88.3 are combined alone or in combination with Avastin™, AZD2171 or AZD6474.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

EXAMPLES

The following examples, including the experiments conducted and results achieved are provided for illustrative purposes only and are not to be construed as limiting upon the teachings herein.

Example 1

Immunization and Titering

Immunization

Recombinant human Ang-2 obtained from R&D Systems, Inc. (Minneapolis, Minn. Cat. No. 623-AM/CF) was used as an antigen. Monoclonal antibodies against Ang-2 were developed by sequentially immunizing XenoMouse® mice (XenoMouse strains XMG2 and XMG4 (3C-1 strain), Abgenix, Inc. Fremont, Calif.). XenoMouse animals were immunized via footpad route for all injections. The total volume of each injection was 50 µl per mouse, 25 µl per footpad. The first injection was with 2.35 µg recombinant human Ang-2 (rhAng-2, cat #623-AM/CF; lot #BN023202A) in pyrogen-free Dulbecco's PBS (DPBS) and admixed 1:1 v/v with 10 µg CpG (15 µl of ImmunEasy Mouse Adjuvant, catalog #303101; lot #11553042; Qiagen) per mouse. The next 6 boosts were with 2.35 µg rhANG-2 in pyrogen-free DPBS, admixed with 25 µg of Adju-Phos (aluminum phosphate gel, Catalog #1452-250, batch #8937, HCl Biosector) and 10 µg CpG per mouse, followed by a final boost of 2.35 µg rhAng-2 in pyrogen-free DPBS, without adjuvant. The XenoMouse mice were immunized on days 0, 3, 6, 10, 13, 17, 20, and 24 for this protocol and fusions were performed on day 29.

Selection of Animals for Harvest by Titer

Anti-Ang-2 antibody titers in the serum from immunized XenoMouse mice were determined by ELISA. Briefly, recombinant Ang-2 (1 µg/ml) was coated onto Costar Labcoat Universal Binding Polystyrene 96-well plates (Corning, Acton, Mass.) overnight at four degrees in Antigen Coating Buffer (0.1 M Carbonate Buffer, pH 9.6 $NaHCO_3$ 8.4 g/L). The next day, the plates were washed 3 times with washing buffer (0.05% Tween 20 in 1×PBS) using a Biotek plate washer. The plates were then blocked with 200 µl/well blocking buffer (0.5% BSA, 0.1% Tween 20, 0.01% Thimerosal in 1×PBS) and incubated at room temperature for 1 h. After the one-hour blocking, the plates were washed 3 times with washing buffer using a Biotek plate washer. Sera from either Ang-2 immunized XenoMouse mice or naïve XenoMouse animals were titrated in 0.5% BSA/PBS buffer at 1:3 dilutions in duplicate from a 1:100 initial dilution. The last well was left blank. These plates were incubated at room temperature for 2 hr, and the plates were then washed 3 times with washing buffer using a Biotek plate washer. A goat anti-human IgG Fc-specific horseradish peroxidase (HRP, Pierce, Rockford, Ill.) conjugated antibody was added at a final concentration of 1 µg/ml and incubated for 1 hour at room temperature. Then the plates were washed 3 times with washing buffer using a Biotek plate washer.

After washing, the plates were developed with the addition of TMB chromogenic substrate (BioFx BSTP-0100-01) for 10-20 min or until negative control wells start to show color. Then the ELISA was stopped by the addition of Stop Solution (650 nM Stop reagent for TMB (BioFx BSTP-0100-01), reconstituted with 100 ml $H_2O$ per bottle). The specific titer of each XenoMouse animal was determined from the optical density at 650 nm and is shown in Tables 2 and 3 below. The titer value is the reciprocal of the greatest dilution of sera with an OD reading two-fold that of background. Therefore, the higher the number, the greater was the humoral immune response to Ang-2.

TABLE 2

| Group 1: 10 mice (XMG2 strain) | | |
|---|---|---|
| | After 4 injections | After 6 injections |
| | Reactivity to rhAng-2 | |
| Mouse ID | Titers via hIgG | |
| O825-1 | 92,000 | 231,000 |
| O825-2 | 56,000 | 212,000 |
| O825-3 | 73,000 | 331,000 |
| O825-4 | 16,000 | 175,000 |
| O825-5 | 95,000 | 236,000 |
| O825-6 | 27,000 | 119,000 |
| O825-7 | 100,000 | 239,000 |
| O825-8 | 25,000 | 165,000 |
| O825-9 | 68,000 | 136,000 |
| O825-10 | 120,000 | 264,000 |
| NC | 35 | 65 |
| PC | Sensitivity: 10 ng/ml | Sensitivity: 9 ng/ml |

* NC = xmg2 strain, ova gp2, fp
* PC = goat AB, anti-huAng-2 (R&D Systems, Catalog No. AF623) 1 mg/ml

TABLE 3

| Group 2: 10 mice (XMG4 strain) | | |
|---|---|---|
| | After 4 injections | After 6 injections |
| | Reactivity to rhAng-2 | |
| Mouse ID | Titers via hIgG | |
| O824-1 | 750 | 4,600 |
| O824-2 | 200 | 5,800 |
| O824-3 | 500 | 7,400 |

TABLE 3-continued

| Group 2: 10 mice (XMG4 strain) | | |
|---|---|---|
| | After 4 injections | After 6 injections |
| | Reactivity to rhAng-2 | |
| Mouse ID | Titers via hIgG | |
| O824-4 | 225 | 4,700 |
| O824-5 | 300 | 5,800 |
| O824-6 | 550 | 7,400 |
| O824-7 | 1,600 | 11,000 |
| O824-8 | 45 | 2,400 |
| O824-9 | 600 | 6,900 |
| O824-10 | 225 | 2,300 |
| NC | <100 | 35 |
| PC | Sensitivity: 12 ng/ml | Sensitivity: 8 ng/ml |

* NC = 3c-1 N128-3
* PC = goat AB, anti-huAng-2 (R&D Systems, Catalog No. AF623) 1 mg/ml Example 2

Recovery of Lymphocytes, B-Cell Isolations, Fusions and Generation of Hybridomas Immunized mice were sacrificed by cervical dislocation, and the draining lymph nodes harvested and pooled from each cohort. The lymphoid cells were dissociated by grinding in DMEM to release the cells from the tissues and the cells were suspended in DMEM. The cells were counted, and 0.9 ml DMEM per 100 million lymphocytes added to the cell pellet to resuspend the cells gently but completely. Using 100 µl of CD90+ magnetic beads per 100 million cells, the cells were labeled by incubating the cells with the magnetic beads at 4° C. for 15 minutes. The magnetically labeled cell suspension containing up to $10^8$ positive cells (or up to $2 \times 10^9$ total cells) was loaded onto a LS+ column and the column washed with DMEM. The total effluent was collected as the CD90-negative fraction (most of these cells were expected to be B cells).

The fusion was performed by mixing washed enriched B cells from above and nonsecretory myeloma P3X63Ag8.653 cells purchased from ATCC, cat. # CRL 1580 (Kearney et al, J. Immunol. 123, 1979, 1548-1550) at a ratio of 1:1. The cell mixture was gently pelleted by centrifugation at 800×g. After complete removal of the supernatant, the cells were treated with 2-4 mL of Pronase solution (CalBiochem, cat. #53702; 0.5 mg/ml in PBS) for no more than 2 minutes. Then 3-5 ml of FBS was added to stop the enzyme activity and the suspension was adjusted to 40 ml total volume using electro cell fusion solution, (ECFS, 0.3M Sucrose, Sigma, Cat #S7903, 0.1 mM Magnesium Acetate, Sigma, Cat #M2545, 0.1 mM Calcium Acetate, Sigma, Cat #C4705). The supernatant was removed after centrifugation and the cells were resuspended in 40 ml ECFS. This wash step was repeated and the cells again were resuspended in ECFS to a concentration of $2 \times 10^6$ cells/ml.

Electro-cell fusion was performed using a fusion generator (model ECM2001, Genetronic, Inc., San Diego, Calif.). The fusion chamber size used was 2.0 ml, using the following instrument settings:

Alignment condition: voltage: 50 V, time: 50 sec.
Membrane breaking at: voltage: 3000 V, time: 30 µsec
Post-fusion holding time: 3 sec After ECF, the cell suspensions were carefully removed from the fusion chamber under sterile conditions and transferred into a sterile tube containing the same volume of Hybridoma Culture Medium (DMEM, JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim). The cells were incubated for 15-30 minutes at 37° C., and then centrifuged at 400×g (1000 rpm) for five minutes. The cells were gently resuspended in a small volume of Hybridoma Selection Medium (Hybridoma Culture Medium supplemented with 0.5×HA (Sigma, cat. #A9666)), and the volume adjusted appropriately with more Hybridoma Selection Medium, based on a final plating of $5 \times 10^6$ B cells total per 96-well plate and 200 µl per well. The cells were mixed gently and pipetted into 96-well plates and allowed to grow. On day 7 or 10, one-half the medium was removed, and the cells re-fed with Hybridoma Selection Medium.

Example 3

Selection of Candidate Antibodies by ELISA

After 14 days of culture, hybridoma supernatants were screened for Ang-2-specific monoclonal antibodies. The ELISA plates (Fisher, Cat. No. 12-565-136) were coated with 50 µl/well of human Ang-2 (2 µg/ml) in Coating Buffer (0.1 M Carbonate Buffer, pH 9.6, NaHCO$_3$ 8.4 g/L), then incubated at 4° C. overnight. After incubation, the plates were washed with Washing Buffer (0.05% Tween 20 in PBS) 3 times. 200 µl/well Blocking Buffer (0.5% BSA, 0.1% Tween 20, 0.01% Thimerosal in 1×PBS) were added and the plates incubated at room temperature for 1 hour. After incubation, the plates were washed with Washing Buffer three times. 50 µl/well of hybridoma supernatants, and positive and negative controls were added and the plates incubated at room temperature for 2 hours. The positive control used throughout was serum from the Ang-2 immunized XenoMouse mouse, XMG2 Ang-2 Group 1, footpad (fp) N160-7, and the negative control was serum from the KLH-immunized XenoMouse mouse, XMG2 KLH Group 1, footpad (fp) L627-6.

After incubation, the plates were washed three times with Washing Buffer. 100 µl/well of detection antibody goat anti-huIgGFc-HRP (Caltag, Cat. No. H10507), was added and the plates incubated at room temperature for 1 hour. In the secondary screen, the positives in first screening were screened in two sets, one for hIgG detection and the other for human Ig kappa light chain detection (goat anti-hIg kappa-HRP (Southern Biotechnology, Cat. No. 2060-05) in order to demonstrate fully human composition for both IgG and Ig kappa. After incubation, the plates were washed three times with Washing Buffer. 100 µl/well of TMB (BioFX Lab. Cat. No. TMSK-0100-01) were added and the plates allowed to develop for about 10 minutes (until negative control wells barely started to show color). 50 µl/well stop solution (TMB Stop Solution, (BioFX Lab. Cat. No. STPR-0100-01) was then added and the plates read on an ELISA plate reader at 450 nm. There were 185 fully human IgG kappa antibodies against Ang-2.

All antibodies that bound in the ELISA assay were counter screened for binding to Ang-1 by ELISA in order to exclude those that cross-reacted with Ang-1. The ELISA plates (Fisher, Cat. No. 12-565-136) were coated with 50 µl/well of recombinant Ang-1 (2 µg/ml, obtained from R&D Systems, Cat. #293-AN-025/CF) in Coating Buffer (0.1 M Carbonate Buffer, pH 9.6, NaHCO$_3$ 8.4 g/L), then incubated at 4° C. overnight. Under the experimental conditions described here, when the recombinant Ang-1 molecule was immobilized on the ELISA plate, no antibodies were found to bind to Ang-1. However, the counter screening described here has technical limitations. First, the antibodies derive from line materials, but not a cloned hybridoma. Binding signals from a particular clone, which only account for a minor percentage of the line, may fall below the detection sensitivity threshold. Second, certain epitopes in the antigen may be concealed from the antibodies in this experiment due to slight conformational changes induced by immobilization of the antigen. For all of these reasons, the cross-reactivity of each antibody to Ang-1 was further examined using cloned antibodies and a Biacore system (see Example 8). As described in Example 8, one clone (mAb 3.19.3) was in fact found to have strong cross-reactivity to human recombinant Ang-1 (Examples 8, 9 and 12).

Example 4

Inhibition of Ang-2 Binding to Tie2

As discussed above, Ang-2 exerts its biological effect by binding to the Tie2 receptor. Monoclonal antibodies that inhibited Ang-2/Tie2 binding were identified by a competitive binding assay using a modified ELISA. The mAbs used were products of micro-purification from 50 ml of exhaustive supernatants of the hybridoma pools that were specific for Ang-2 (see Example 3). 96-well Nunc Immplates™ were coated with 100 µl of recombinant human Tie2/Fc fusion protein (R&D Systems, Inc., Cat. No. 313-TI-100) at 4 µg/ml by incubating overnight at 4° C. The plates were washed four times using Phosphate Buffer Saline (PBS) with a Skan™ Washer 300 station (SKATRON). The wells were blocked by 100 µl of ABX-blocking buffer (0.5% BSA, 0.1% Tween, 0.01% Thimerosal in PBS) for 1 hour.

Biotinylated recombinant human Ang-2 (R&D Systems, Inc. Cat. No. BT623) at 100 ng/ml was added in each well with or without the anti Ang-2 mAbs at 100 µg/ml. The plates were incubated at room temperature for two hours before the unbound molecules were washed off. Bound biotinylated Ang-2 was then detected using 100 µl/well of Streptavidin-HRP conjugate at 1:200 by incubating at room temperature for half an hour. After washing twice, the bound Streptavidin was detected by HRP substrate (R&D Systems, Cat. No. DY998). The plates were incubated for 30 minutes before 450 stop solution (100 µl/well, BioFX, Cat #BSTP-0100-01) was added to terminate the reaction. The light absorbance at 450 nm was determined by a Spectramax Plus reader.

Soluble recombinant Tie2/Fc fusion protein at 10-fold molar excess to Ang-2 was used as a positive control. At this concentration, Tie2/Fc inhibited binding of Ang-2 to immobilized Tie2 by 80%. With this as an arbitrary criterion, 74 out of 175 Ang-2 binding mAbs showed inhibitory activity. For the convenience of operation, the top 27 neutralizers were selected for subsequent hybridoma cloning.

Each hybridoma was cloned using a limited dilution method by following standard procedures. Three sister clones were collected from each hybridoma. For each clone, the supernatant was tested using ELISA binding to human Ang-2 and counter binding to Ang-1, as described above, to ensure that each antibody was only specific for Ang-2. Concentrations of IgG in the exhaustive supernatants were determined, and one clone with the highest yield among the three sister clones from each hybridoma was selected for IgG purification. 0.5 to 1 mg of IgG was purified from each supernatant for further characterization.

To quantitate the inhibitory activities of the mAbs on Ang-2 binding to Tie2, the titer was determined for purified mAbs from the top 27 candidates using a competitive binding assay. Each concentration of the mAb was tested in duplicate. The concentration-response relationship was found by curve fitting using Graphpad Prism™ graphic software (non-linear, Sigmoid curve). The maximal inhibition (efficacy) and IC$_{50}$ (potency) were calculated by the software. Ten monoclonal antibodies that exhibited both relative high efficacy and potency were selected for further investigation. The efficacy and potency of these 10 mAbs are listed in Table 4.

TABLE 4

Efficacy and potency of top 10 mAbs

| Clone | Efficacy* | EC50 (µg/ml) |
|---|---|---|
| 3.31.2 | 0.3751 | 0.04169 |
| 5.16.3 | 0.3279 | 0.08532 |
| 5.86.1 | 0.3844 | 0.1331 |
| 5.88.3 | 0.4032 | 0.1557 |
| 3.3.2 | 0.3881 | 0.1684 |
| 5.103.1 | 0.2317 | 0.3643 |
| 5.101.1 | 0.3639 | 0.3762 |
| 3.19.3 | 0.3945 | 0.7976 |
| 5.28.1 | 0.3892 | 2.698 |
| 5.78.3 | 0.2621 | 5.969 |

*Efficacy is expressed as the ratio of bound Ang-2 with mAbs (30 µg/ml) versus without mAbs.

Example 5

Binning of Antibodies

Epitope binning was performed to determine which of the anti-Ang-2 antibodies would cross compete with one another, and thus were likely to bind to the same epitope on Ang-2. The binning process is described in U.S. Patent Application 20030175760, also described in Jia et al., J. Immunol. Methods, (2004) 288:91-98, both of which are incorporated by reference in entirety. Briefly, Luminex beads were coupled with mouse anti-huIgG (Pharmingen #555784) following the protein coupling protocol provided on the Luminex website. Pre-coupled beads were prepared for coupling to primary unknown antibody using the following procedure, protecting the beads from light. Individual tubes were used for each unknown supernatant. The volume of supernatant needed was calculated using the following formula: (n×2+10)×50 µl (where n=total number of samples). A concentration of 0.1 µg/ml was used in this assay. The bead stock was gently vortexed, and diluted in supernatant to a concentration of 2500 of each bead in 50 µl per well or $0.5 \times 10^5$ beads/ml.

Samples were incubated on a shaker in the dark at room temperature overnight.

The filter plate was pre-wetted by adding 200 µl wash buffer per well, which was then aspirated. 50 µl of each bead was added to each well of the filter plate. Samples were washed once by adding 100 µl/well wash buffer and aspirating. Antigen and controls were added to the filter plate at 50 µl/well. The plate was covered, incubated in the dark for 1 hour on a shaker, and then samples were washed 3 times. A secondary unknown antibody was then added at 50 µl/well. A concentration of 0.1 µg/ml was used for the primary antibody. The plate was then incubated in the dark for 2 hours at room temperature on a shaker, and then samples were washed 3 times. 50 µl/well of biotinylated mouse anti-human IgG (Pharmingen #555785) diluted at 1:500 was added, and samples were incubated in the dark for 1 hour with shaking at room temperature.

Samples were washed 3 times. 50 µl/well Streptavidin-PE at a 1:1000 dilution was added, and samples were incubated in the dark for 15 minutes with shaking at room temperature. After running two wash cycles on the Luminex100, samples were washed 3 times. Contents in each well were resuspended in 80 µl blocking buffer. Samples were carefully mixed with pipetting several times to resuspend the beads. Samples were then analyzed on the Luminex100. Results are presented below in Table 5.

TABLE 5

Bins for top 24 of Ang-2 antibodies positive in functional assay

| Bin 1 | Bin 2 | Bin 3 | Bin 4 | Bin 5 | Bin 6 | Bin 7 | Bin 8 |
|---|---|---|---|---|---|---|---|
| 3.3 | 3.38 | 5.56* | 5.28 | 5.78 | 3.19 | 6.3 | 5.35 |
| 3.28 | 5.103 | | | | | | 5.40 |
| 3.31 | | | | | | | |
| 5.14 | 5.2 | | | | | | |
| 5.16 | | | | | | | |
| 5.39 | | | | | | | |
| 5.41 | | | | | | | |
| 5.49 | | | | | | | |
| 5.54 | | | | | | | |
| 5.62 | | | | | | | |
| 5.83 | | | | | | | |
| 5.86 | | | | | | | |
| 5.88 | | | | | | | |
| 5.101 | | | | | | | |
| 5.108 | | | | | | | |

*Note: mAb 5.56 had a similar binding pattern as that of 3.38 and 5.103 with minor differences and much lower signal.

Example 6

Determination of Anti-Ang-2 Antibody Affinity Using Biacore Analysis

Low Resolution Screen of 27 Purified Monoclonal Antibodies

The label-free surface plasmon resonance (SPR), or Biacore, was utilized to measure the antibody affinity to the antigen. For this purpose, a high-density goat anti-human antibody surface over a CM5 Biacore chip was prepared using routine amine coupling. All the purified mAbs were diluted to approximately 8 µg/ml in HBS-P running buffer containing 100 µg/ml BSA and 10 mg/mL carboxymethyl-dextran. Each mAb was captured on a separate surface using a 42-second contact time, and a 5-minute wash for stabilization of the mAb baseline.

Ang-2 was injected at 90.9 nM over all surfaces for one minute, followed by a 10-minute dissociation. Double-referenced binding data was prepared by subtracting the signal from a control flow cell and subtracting the baseline drift of a buffer injected just prior to the Ang-2 injection. Ang-2 binding data for each mAb were normalized for the amount of mAb captured on each surface, and the normalized, drift-corrected responses for the 27 mAbs were determined. Data were fit globally to a 1:1 interaction model to determine the binding kinetics. The kinetic analysis results of Ang-2 binding at 25° C. are listed in the table below. The mAbs are ranked from highest to lowest affinity.

TABLE 6

Ang-2 low resolution Biacore screen of 27 purified monoclonal antibodies

| Sample | Amt. Captured (RU) | $k_a$ (M$^{-1}$s$^{-1}$) | $k_d$ (s$^{-1}$) | $K_d$ (pM) |
|---|---|---|---|---|
| 5.16 | 157 | $3.6 \times 10^5$ | $1.0 \times 10^{-5}$ * | 27 |
| 5.41 | 152 | $3.6 \times 10^5$ | $1.0 \times 10^{-5}$ * | 28 |
| 5.35 | 138 | $3.4 \times 10^5$ | $1.0 \times 10^{-5}$ * | 29 |
| 3.38 | 143 | $3.4 \times 10^5$ | $1.0 \times 10^{-5}$ * | 30 |
| 5.108 | 66 | $3.2 \times 10^5$ | $1.0 \times 10^{-5}$ * | 31 |
| 3.3 | 125 | $3.0 \times 10^5$ | $1.0 \times 10^{-5}$ * | 33 |

TABLE 6-continued

Ang-2 low resolution Biacore screen of 27 purified monoclonal antibodies

| Sample | Amt. Captured (RU) | $k_a$ (M$^{-1}$s$^{-1}$) | $k_d$ (s$^{-1}$) | $K_d$ (pM) |
|---|---|---|---|---|
| 5.49 | 260 | $3.0 \times 10^5$ | $1.0 \times 10^{-5}$ * | 33 |
| 3.28 | 280 | $2.7 \times 10^5$ | $1.0 \times 10^{-5}$ * | 37 |
| 5.88 | 65 | $2.7 \times 10^5$ | $1.0 \times 10^{-5}$ * | 37 |
| 5.28 | 136 | $2.5 \times 10^5$ | $1.0 \times 10^{-5}$ * | 40 |
| 5.78 | 222 | $2.4 \times 10^5$ | $1.0 \times 10^{-5}$ * | 42 |
| 5.39 | 166 | $2.3 \times 10^5$ | $1.0 \times 10^{-5}$ * | 43 |
| 5.103 | 127 | $2.2 \times 10^5$ | $1.0 \times 10^{-5}$ * | 45 |
| 5.13 | 78 | $2.1 \times 10^5$ | $1.0 \times 10^{-5}$ * | 47 |
| 5.14 | 471 | $2.0 \times 10^5$ | $1.0 \times 10^{-5}$ * | 49 |
| 3.31 | 196 | $1.9 \times 10^5$ | $1.0 \times 10^{-5}$ * | 51 |
| 5.56 | 144 | $1.9 \times 10^5$ | $1.0 \times 10^{-5}$ * | 52 |
| 5.2 | 111 | $1.6 \times 10^5$ | $1.0 \times 10^{-5}$ * | 62 |
| 5.62 | 126 | $1.5 \times 10^5$ | $1.0 \times 10^{-5}$ * | 65 |
| 5.54 | 131 | $1.5 \times 10^5$ | $1.0 \times 10^{-5}$ * | 66 |
| 6.3 | 221 | $1.4 \times 10^5$ | $1.0 \times 10^{-5}$ * | 73 |
| 3.19 | 252 | $9.0 \times 10^4$ | $1.0 \times 10^{-5}$ * | 111 |
| 5.40 | 130 | $7.8 \times 10^4$ | $1.0 \times 10^{-5}$ * | 129 |
| 5.83 | 157 | $6.8 \times 10^4$ | $1.0 \times 10^{-5}$ * | 147 |
| 5.101 | 217 | $1.5 \times 10^5$ | $8.7 \times 10^{-5}$ | 581 |
| 5.86 | 126 | $1.5 \times 10^5$ | $1.1 \times 10^{-4}$ | 744 |
| 5.52 | 114 | $1.3 \times 10^5$ | $1.0 \times 10^{-5}$ * | 750 |

The asterisks next to the $k_d$ results for all mAbs except for mAbs 5.101 and 5.86 indicate that these $k_d$'s were held constant as a best estimate for the order of magnitude characteristic of slow off-rate data. The fitting model for these samples detected no measurable change in the off-rate over the relatively brief dissociation time and therefore required the $k_d$ to be constant in order to fit the on-rate data. The data for those indicated $k_d$'s also fit well in a simulation with the $k_d$ on the order of $10^{-6}$ s$^{-1}$, therefore the interactions may be 10-fold or more stronger than reported above.

Dissociation data is normally measured 4-6 hours for high-resolution kinetic experiments with mAbs having sub-100 pM affinities. The maximum dissociation time that can be measured without drift artifacts from a captured mAb surface is 20 minutes. Almost negligible signal decay is measured over such a relatively short time with high affinity mAbs so the $k_d$ estimate may vary by as much as two orders of magnitude.

Example 7

Determination of Anti-Ang-2 Antibody Affinity Using Biacore Analysis

Ang-2 Medium/High Resolution Screen with Three Purified Monoclonal Antibodies

Purified mAbs 5.16, 5.35, and 5.41 were diluted to approximately 8 μg/ml in 10 mM sodium acetate, pH 5.0. Each diluted mAB was then immobilized on a different flow cell surface (CM5 Biacore chip) using routine amine coupling.

For on-rate data acquisition, eight concentrations (2-fold dilutions) ranging from 90.9-0.71 nM of Ang-2 were randomly injected for 90 seconds in triplicate with several buffer injections interspersed for double referencing, followed by a four minute dissociation. The antibody surfaces were regenerated with two 9-second pulses of 10 mM glycine-HCl, pH 1.5 after each injection cycle.

For off-rate data acquisition, three 90.9 nM Ang-2 samples in HBS-P running buffer containing 100 μg/ml BSA were injected as described above and dissociation data was recorded over eight hours. The sample injections alternated with three blank injection cycles. Regeneration was performed as described above.

The data were globally fit to a 1:1 interaction model with mass transport using CLAMP (David G. Myszka and Thomas Morton (1998) "CLAMP©: a biosensor kinetic data analysis program," TIBS 23, 149-150). The resulting binding constants are shown in Table 7 below.

TABLE 7

Ang-2 medium resolution Biacore screen of 3 purified monoclonal antibodies

| Sample | $R_{max}$ | $k_a$ (M$^{-1}$s$^{-1}$) | $k_d$ (s$^{-1}$) | $K_d$ (pM) |
|---|---|---|---|---|
| 5.16 | 36 | $3.41 \times 10^5$ | $2.77 \times 10^{-6}$ | 8.13 |
| 5.35 | 54 | $5.64 \times 10^5$ | $1.87 \times 10^{-6}$ | 3.31 |
| 5.41 | 44 | $4.69 \times 10^5$ | $8.31 \times 10^{-6}$* | 17.7* |

Significant signal decay was measured over the 8-hour dissociation time. With the eight hour dissociation data, CLAMP was able to more reasonably estimate the $k_d$ for each mAb. Here the $k_d$'s for both 5.16 and 5.35 are on the order of $10^{-6}$ s$^{-1}$.

The cross-reactivity of antibodies to Ang-1 was then investigated by measuring the affinity of the mAbs to Ang-1, as described below in Example 8.

Example 8

Determination of Anti-Ang-1 Antibody Affinity Using Biacore Analysis

The cross-reactivity of antibodies to Ang-1 was further investigated by measuring the affinity of the mAbs to Ang-1. Instead of immobilizing Ang-1, as described in ELISA-based counter-binding (Example 3), Ang-2 mAbs were immobilized to the CM5 Biacore chips, and Ang-1 in solution was injected for the determination of the on-rate and off-rate. Six mAbs, including 3.3.2, 3.31.2, 5.16.3, 5.86.1, 5.88.3, and 3.19.3, were tested in this experiment as described below to determine how strongly they cross-reacted with Ang-1.

Medium Resolution Screen of Six Purified Monoclonal Antibodies

Label-free surface plasmon resonance (SPR), or a Biacore 2000 instrumentation, was utilized to measure antibody affinity to Ang-1. For this purpose, a high-density goat α-human antibody surface over a CM5 Biacore chip was prepared using routine amine coupling. For developmental experiments, purified mAbs (clones 3.19.3, 3.3.2, 5.88.3, 5.86.1, 3.31.2, 5.16.3) were diluted to approximately 2.5-3.5 μg/ml in HBS-P running buffer containing 100 μg/ml BSA. The capture level for each mAb was approximately 150 RU. A 5-minute wash followed each capture cycle to stabilize the mAb baseline.

A single Ang-1 sample diluted to 87.4 nM in the running buffer was injected for one minute over all capture surfaces. No binding was evident for five mAbs, although Ang-1 was found to bind to mAb 3.19.3. This experiment was repeated by increasing the mAb capture levels to well over 500-600 RU and injecting 380 nM Ang-1 for one minute. The mAb 3.19.3 was again found to bind Ang-1.

Because Ang-1 only showed binding activity towards mAb 3.19.3, the affinity of this mAb to both Ang-1 and Ang-2 was determined. Since Ang-1 displayed a slow off-rate during the above developmental experiments, a medium resolution capture experiment would not have recorded sufficient off-rate data to accurately estimate kd. As a result, the binding of Ang-1 and Ang-2 to mAb 3.19.3 was measured under high-resolution Biacore conditions.

Example 9

Determination of mAb 3.19.3 Affinity for Ang-1 and Ang-2 Using High Resolution Biacore Analysis Purified mAb 3.19.3 was diluted to 12.5 μg/ml in 10 mM sodium acetate, pH 4.0. The mAb was then immobilized on flow cells 1-3 (CM5 Biacore chip) using routine amine coupling, leaving flow cell 4 as the reference flow cell.

For on-rate data acquisition, eight concentrations (2-fold dilutions) ranging from 39.8-0.31 nM of Ang-1 (in HBS-P running buffer containing 100 μg/ml BSA) were randomly injected for 90 seconds (100 μL/min. flow rate) in triplicate with several buffer injections interspersed for double referencing, followed by a four minute dissociation. The antibody surfaces were regenerated with a 6-second pulse of 10 mM NaOH after each injection cycle.

For off-rate data acquisition, three 19.9 nM Ang-1 samples were injected as described above and dissociation data was recorded over six hours. The sample injections alternated with three blank injection cycles. Regeneration was performed as described above.

The data were globally fit to a 1:1 interaction model with a term for mass transport included using CLAMP (David G. Myszka and Thomas Morton (1998) "CLAMPED: a biosensor kinetic data analysis program," TIBS 23, 149-150).

Ang-2 High Resolution Biacore Study with Purified mAb 3.19.3

Purified mAb 3.19.3 was diluted to 12.5 μg/ml in 10 mM sodium acetate, pH 4.0. The mAb was then immobilized on flow cells 1-3 (CM5 Biacore chip) using routine amine coupling, leaving flow cell 4 as the reference flow cell.

For on-rate data acquisition, eight concentrations (2-fold dilutions) ranging from 30.0-0.23 nM of Ang-2 (in HBS-P running buffer containing 100 μg/ml BSA) were randomly injected for 90 seconds (100 μL/min. flow rate) in triplicate with several buffer injections interspersed for double referencing, followed by a four minute dissociation. The antibody surfaces were regenerated with a 6-second pulse of 15 mM NaOH after each injection cycle.

For off-rate data acquisition, three 15.0 nM Ang-2 samples were injected as described above and dissociation data were recorded over six hours. The sample injections alternated with three blank injection cycles. Each surface was regenerated with a 6-second pulse of 15 mM NaOH after each long off-rate injection cycle.

The data were globally fit to a 1:1 interaction model with a term for mass transport included using CLAMP (David G. Myszka and Thomas Morton (1998) "CLAMP®: a biosensor kinetic data analysis program," TIBS 23, 149-150).

Results And Discussion: Ang-1 and Ang-2 High Resolution Biacore Study With mAb 3.19.3

Two independent experiments were run with each antigen. The results are shown in Table 8 below:

TABLE 8

High resolution Biacore results of Ang-1 and Ang-2 binding to purified mAb 3.19.3

| Antigen | $k_a$ (M$^{-1}$s$^{-1}$) | $k_d$ (s$^{-1}$) | $K_D$ (pM) |
|---|---|---|---|
| Ang-1 (1$^{st}$) | 1.33 × 10$^5$ | 4.05 × 10$^{-6}$ | 30.4 |
| Ang-1 (2$^{nd}$) | 1.82 × 10$^5$ | 5.51 × 10$^{-6}$ | 30.2 |
| Ang-2 (1$^{st}$) | 1.89 × 10$^5$ | 1.00 × 10$^{-6}$* | 5.3 |
| Ang-2 (2$^{nd}$) | 1.78 × 10$^5$ | 1.00 × 10$^{-6}$* | 5.6 |

The $k_d$'s for Ang-2 in the above table are asterisked because these values were held constant during the 1:1 interaction model fit in CLAMP software. There was no significant dissociation signal recorded for the Ang-2 experiments, so the best off-rate estimate was to hold $k_d$ constant at 1×10$^{-6}$ sec$^{-1}$. The long off-rate data for Ang-2 actually displayed an upward trend over the six hours of data acquisition. This trend was repeated on two different sensor chips with two different instruments after both instruments had been subjected to a "super clean" maintenance protocol. In order to more precisely measure the binding affinity of mAb 3.19.3 for Ang-1 and Ang-2, a further experiment (see Example 10) was run to determine the Kd of mAb 3.19.3 towards these antigens.

Interestingly, mAb 3.19.3 did not bind to Ang-1 in the ELISA-based binding assay (Example 3), when Ang-1 was immobilized on the ELISA plate. The likely explanation for this discrepancy is that when Ang-1 was immobilized on the surface of plastics, a subtle epitope critical for the binding of mAb 3.19.3 was not exposed appropriately. However, when Ang-1 was in the liquid phase, such as in the Biacore experimental conditions, this epitope became accessible to mAb 3.19.3 and binding occurred.

Example 10

Determination of Affinity of mAb 3.19.3 to Human Ang-2 Using High Resolution Kinexa (Kinetic Exclusion Assay)

When affinity of mAb 3.19.3 to human Ang-2 was measured using high resolution Biacore (Example 9), it was found that there was no significant dissociation signal. The long off-rate data for Ang-2 shows an upward trend over the six-hour data acquisition. Because of this, the $K_D$ of mAb 3.19.3 binding to human Ang-2 was determined using KinExA technology, with the goal of obtaining a more reliable Kd value. For this purpose, a KinExA 3000 instrument was utilized. Firstly, 1 mL (~271 μg) of stock Ang-2 (R&D Systems, Inc., Lot #BNO32510A) was buffer exchanged into 1×PBS, pH 7.0 using a 10 mL desalting column (Pierce D-Salt™ polyacrylamide column, 6000 molecular weight cut-off, Lot #GF97965). The concentration of the pooled fractions was determined to be 1.7 μM using the protein concentration determination method described by C. Nick Pace (Pace, et al., *Protein Science, Vol.* 4: 2411-2423, 1995). Secondly, 200 mg of polymethyl methacrylate (PMMA, Lot #206-01) beads were coupled with 450 μL (~122 μg) of stock Ang-2 overnight at 24° C. The beads were then centrifuged and washed once with blocking buffer (1×PBS, 10 mg/ml BSA), centrifuged again, and then incubated in blocking buffer for one hour at 24° C. After blocking, the beads were diluted in approximately 30 mL of HBS buffer (0.01 M Hepes, 0.15 M NaCl, pH 7.4) in a standard KinExA bead reservoir vial and placed on the instrument.

$K_D$-Controlled Titration

Twelve solutions containing a mAb 3.19.3 binding site concentration of 25.3 pM were titrated with increasing concentrations of Ang-2. The buffer-exchanged Ang-2 was used for the sample preparations. Each solution had a total volume of 25 mL and was allowed to equilibrate for 5 days at ~24° C. The titration solutions were prepared using volumetric glassware and the Ang-2 concentrations varied from 5.09 nM to 99.3 fM. The KinExA instrument method used for the analysis of these solutions consisted of a bead packing step in which the PMMA beads were packed into a glass capillary, and the equilibrated solutions were flowed through the bead column at 0.25 mL/min for 6 min (1.5 mL) in duplicate. Subsequently, a fluorescently labeled Cy-5 goat anti-human (Fc specific) polyclonal antibody at 3.4 nM was flowed through the bead pack for 1 min at 0.5 mL/min to label the mAb with free binding sites captured on the beads. The fluorescence emission from the bead pack was measured at 670 nm with excitation at 620 nm. The resulting fluorescence measurements were converted into "% free mAb binding site" versus total antigen concentration using the accompanying KinExA software package (version 1.0.3, Sapidyne, Inc.). The resulting $K_D$-controlled titration curve was fit with the KinExA software to a 1:1 equilibrium isotherm with a drift correction factor included. The value of the $K_D$ that fit the data optimally was 86.4 pM with low and high 95% confidence limits at 64.3 pM and 98.7 pM, respectively. A mAb-controlled titration curve was not performed.

Example 11

Blockage of Ang-2-Induced Tie2 Phosphorylation Ectopically Expressed in HEK293 Cells As discussed above, Tie2 is an endothelial cell specific receptor tyrosine kinase. In vitro experiments with vascular endothelial cells show that Ang-1 induces Tie2 phosphorylation, whereas, Ang-2 inhibits the receptor phosphorylation induced by Ang-1. However, when Tie2 is expressed ectopically, such as in fibroblasts, Ang-2 is also able to induce Tie2 phosphorylation under certain conditions, including but not limited to, prolonged exposure to Angiopoietin-2 or exposure to high concentrations of Angiopoietin-2.

Ang-2 induced Tie2 phosphorylation also occurs when the receptor is expressed in HEK293F cells. The ability of anti-Ang-2 mAbs to block Ang-2 induced Tie2 phosphorylation was examined using HEK293F cells transfected with human Tie2 receptor. Plasmid vector pORK/pBS-SK having a Tie2 cDNA was obtained from the ATCC (Cat. No. 69003, Genbank sequence BC033514). The accuracy of the cDNA was confirmed by nucleotide sequencing. A 3.9 kb fragment containing a 3375 bp cDNA that encodes human Tie2 was removed from the vector by EcoRI digestion. This fragment was subcloned in the proper orientation into a pCR3.1 vector digested with EcoRI following standard procedures. The selected plasmid was amplified and purified by standard protocols.

The Tie2 containing construct obtained by the above procedures was transfected into HEK293F cells by the calcium phosphate transfection method. $1\times10^6$ HEK293F cells were grown in 100 mm tissue culture dishes coated with 1% gelatin at 37° C. with 5% $CO_2$. The cells were fed with fresh media for 2-3 hours before transfection. 10 µg of the plasmid DNA was dissolved in 248 mM calcium phosphate solution. Transfection was performed using standard procedures. Stable transfectants were selected by incubation in 0.5 mg/ml G418. Stable transfectants expressing Tie2 were identified by FACS analysis using mouse anti-Tie2 mAb (R&D Cat. No. MAB313) and a goat anti-mouse IgG-PE conjugate antibody (Caltag, Cat. No. M30004-4) for detection.

To perform the Tie2 phosphorylation assay, HEK 293F/Tie-2 transfectants were grown in 60 mm cell culture dishes at a density of $2\times10^6$ cells/plate with complete medium at 37° C. with 5% $CO_2$ until they reached sub-confluency. The complete medium in each plate was replaced with 2 ml of serum free medium. The cells were incubated for an additional 16 hours. Subsequently, the medium was replaced again with 2 ml of serum-free medium. After an additional 2-hr incubation, the cells were treated with 0.1 mM sodium orthovanadate (Sigma, Cat. No. S 6508) for 20 minutes. The cells were treated with Ang-2 (2 µg/ml) in the presence or absence of mAbs at 100 µg/ml. Treatments were performed in duplicate. A negative control without Ang-2 treatment was included. Cells were rinsed with ice-cold TBS containing vanadate and lysed with 300 µl/plate of cooled NP-40 lysis buffer (50 mM Hepes, pH7.2, supplemented with 0.15M NaCl, 10% glycerol, 10 mM pyrophosphate, 50 mM NaF, 1% NP40, 100 U/ml aprotinin, 1 mM PMSF, 0.1 mM orthovanadate, 10 µM leupeptin and 10 µM pepstatin A), while putting the plates on ice for 10 minutes. The treated cells were scraped from the plates into a microtube pre-chilled on ice.

The cell lysates were sonicated briefly and centrifuged at 12,000×g for 10 minutes at 4° C. in a tabletop microfuge. Supernatants were collected into fresh microtubes, and 1-5 µg of anti-Tie2 mAb (R&D Systems, Inc.) were added to the supernatant, followed by gentle rocking for 2 hours at 4° C. 50 µA of ImmunoPure Immobilized Protein A (PIERCE Cat. No. 20333) was added to the mixture, and incubated for at least 3 hours at 4° C. on a rocking platform. Complexes were collected by centrifugation at 12,000×g for 10 minutes. After carefully removing the supernatant, the complexes were washed twice with the lysis buffer by centrifuging (12,000×g, 4° C.) for 4 minutes. The pellets were re-suspended in 50 µl of 2× electrophoresis sample buffer (Invitrogen, Cat. No. LC-2676) with 1 mM of β-mercaptoethanol or DTT, and boiled for 5 minutes before being centrifuged (12,000×g, 4° C.) for 5 minutes. The supernatants were transferred to fresh tubes.

The samples were loaded into the wells of an SDS-PAGE gel (e.g., 4-20% Tris-Glycine gel, Invitrogen, Cat. No. EC 6025). Electrophoreses was performed in Tris-Glycine buffer system. After electrophoresis, the gel was blotted onto a PVDF membrane (Invitrogen, Cat. No. LC 2005) following a standard protocol. Tyrosine phosphorylation was probed with 4G10 anti-phosphotyrosine antibody at 1 µg/ml (Upstate, Cat. No. 05-321) by incubation for 1 hour at room temperature with shaking, and followed by washing with 1×TBST (TBS with 0.1% of Tween-20) three times. The bound antibodies were detected by incubation with horseradish peroxidase-conjugated goat anti-mouse IgG (Santa Cruz, Cat. No. sc-2302) at 1:10,000 dilution for 1 hour at room temperature, followed by the enhance chemiluminescence reaction using SuperSignal West Dura Extended Duration Substrate system (PIERCE Cat. No. 34075). Subsequently, the blot was stripped with Restore Western Blot Stripping Buffer (PIERCE, Cat. No. 21059) and re-probed with specific antibodies against RTK to verify the quality of sample loading.

It was discovered that when human Tie2 was ectopically expressed in HEK293F cells, autophosphorylation of Tie2 was not detectable. In response to Ang-2 (2 µg/ml) treatment, a significant level of tyrosine phosphorylation was detected by a mAb to phosphorylated tyrosine (4G10) from Tie2 immunoprecipitated by the specific mAb. At a concentration of 100 µg/ml, all the anti-Ang-2 mAbs tested showed obvious inhibition of Tie2 phosphorylation, whereas, the isotype control mAb did not have inhibitory effect (FIG. 1). Monoclonal antibody 5.103.1, which is not shown in FIG. 1, had a similar inhibitory effect.

Figure 2:
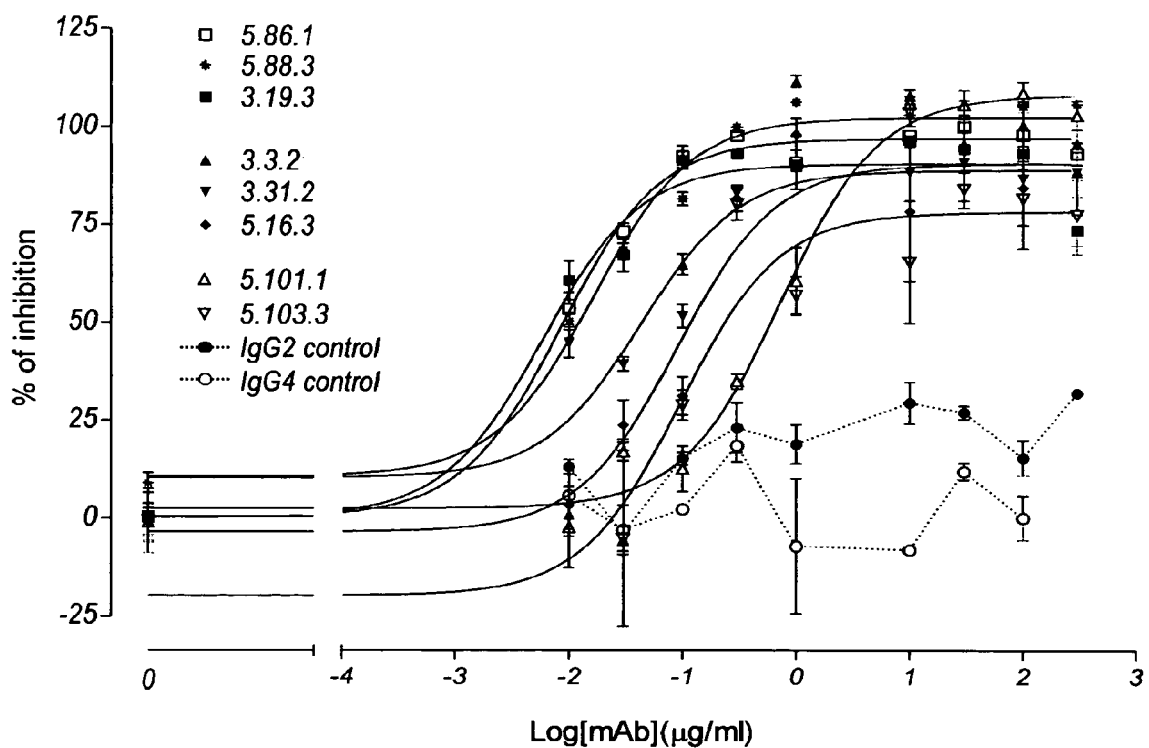
FIG. 2 is a line graph of the dose-response relationship of anti-Ang-2 monoclonal antibodies on the inhibition of Ang-2 induced Tie2 phosphorylation.

To rank the potency of the Ang-2 mAbs to inhibit Ang-2-induced Tie2 phosphorylation in vitro, an ELISA-based quantifiable method to detect Tie2 phosphorylation was established. Briefly, cell lysates were made from HEK293F/Tie2 transfectants that were treated with Ang-2 with the mAbs at various concentrations. Total Tie2 from the lysate was captured in the 96-well ELISA plate that was coated with mouse anti-hTie-2 mAb. The phosphorylated Tie2 was detected using primary antibody 4G10-HRP (purchased from Upstate) and HRP substrate solution. OD at 650 nm was determined by a SpectraMax reader. The concentration-response relationship was found by curve fitting using Graphpad Prism graphic software (non-linear, Sigmoid curve). The maximal inhibition (efficacy) and $IC_{50}$ (potency) were calculated as shown in FIG. 2. The EC50 was calculated as shown in below in Table 9.

TABLE 9

| mAb | EC50 (µg/ml) | 95% CI |
|---|---|---|
| 3.19.3 | 0.006 | 0.004 to 0.009 |
| 5.86.1 | 0.008 | 0.007 to 0.011 |
| 5.88.3 | 0.016 | 0.011 to 0.024 |
| 3.31.2 | 0.043 | 0.029 to 0.064 |
| 3.3.2 | 0.046 | 0.020 to 0.105 |
| 5.16.3 | 0.089 | 0.046 to 0.174 |
| 5.103.3 | 0.095 | 0.046 to 0.199 |
| 5.101.1 | 0.733 | 0.487 to 1.105 |

As reported above, it was found that mAb 3.19.3 cross-reacted with Ang-1. However, the results of initial experiments did not find inhibition of Angiopoietin-1 induced Tie-2 phosphorylation by mAb 3.19.3. It is worthwhile to note that ectopic expression of Tie2 may affect its susceptibility to activation by different ligands, as evidenced by the fact that Ang-2 does not induce Tie2 phosphorylation in HUVECs, whereas, it does induce robust Tie2 phosphorylation when the receptor is ecotopically expressed in HEK293 cells.

In view of these results further experiments were performed to more fully investigate whether mAb 3.19.3 was capable of inhibiting binding of both Ang-1 and Ang-2 to cell-bound Tie2. In addition, inhibition of Angiopoietin-1 induced Tie-2 phosphorylation by mAb 3.19.3 was investigated in more detail as described in Example 12 below.

Example 12 mAb 3.19.3 Inhibits Angiopoietin-1 Binding to TIE-2 and Ang-1 Induced Tie2 Phosphorylation The mAb 3.19.3 cross-reacts with human Ang-1 (Examples 8 and 9). However, initial experiments indicated that mAb 3.19.3 did not inhibit Tie2 phosphorylation induced by Ang-1. The discrepancy may be explained by the following: (1) high concentration of Ang-1, which is far above physiological concentration, may be required to generate robust Tie2 phosphorylation signal; or (2) Ecotopic expression of Tie2 in HEK293 may alter the conformation of Tie2, and thus change its susceptibility to different ligands. To test there hypotheses mAb 3.19.3 was tested in a binding assay where low concentration of Ang-1 or Ang-2 (3 nM) bound to cell surface Tie2. It was found that mAb 3.19.3 inhibited binding of both Ang-1 and Ang-2 in this experiment. Secondly, immortalized endothelial cells (EA.hy926/B3) were used to investigate Ang-1 induced Tie2 phosphorylation. The results of this experiment, as described in more detail below, demonstrate that mAb 3.19.3 inhibits Ang-1 induced Tie2 phosphorylation in a dose-dependent manner.

HEK293F/Tie2 transfectants were allowed to grow until 95% confluent in culture flasks before being harvested. Cell suspension of 4 million cells/mL in FACS Buffer were prepared, and then aliquoted to a 96-well polypropylene plate with 50 ul per well. The mAb 3.19.3 with indicated concentrations were added into the cell suspension. Subsequently, solutions of recombinant human Ang-1 and Ang-2 were added into the cell suspension, followed by incubation at room temperature for 2 hours. Cells were washed by centrifuging the plate at 1,200 rpm for 5 minutes, removing the supernatant by aspirating, and resuspending the cells with 200 ul per well of FACS Buffer. Washing procedures were repeated twice. The cells were then suspended with 100 ul of mouse Anti-6X-Histidine antibody diluted to 2 ug/ml in FACS Buffer, and incubated at room temperature for 30 minutes. After washing, the cells were suspended in 100 ul of PE-conjugated goat anti-mouse-IgG, which was diluted 1:100 in FACS Buffer, for incubation at room temperature for 30 minutes. The volume of the samples were brought to 300 ul with FACS Buffer, and measured with FACS Calibur.

Figure 3:
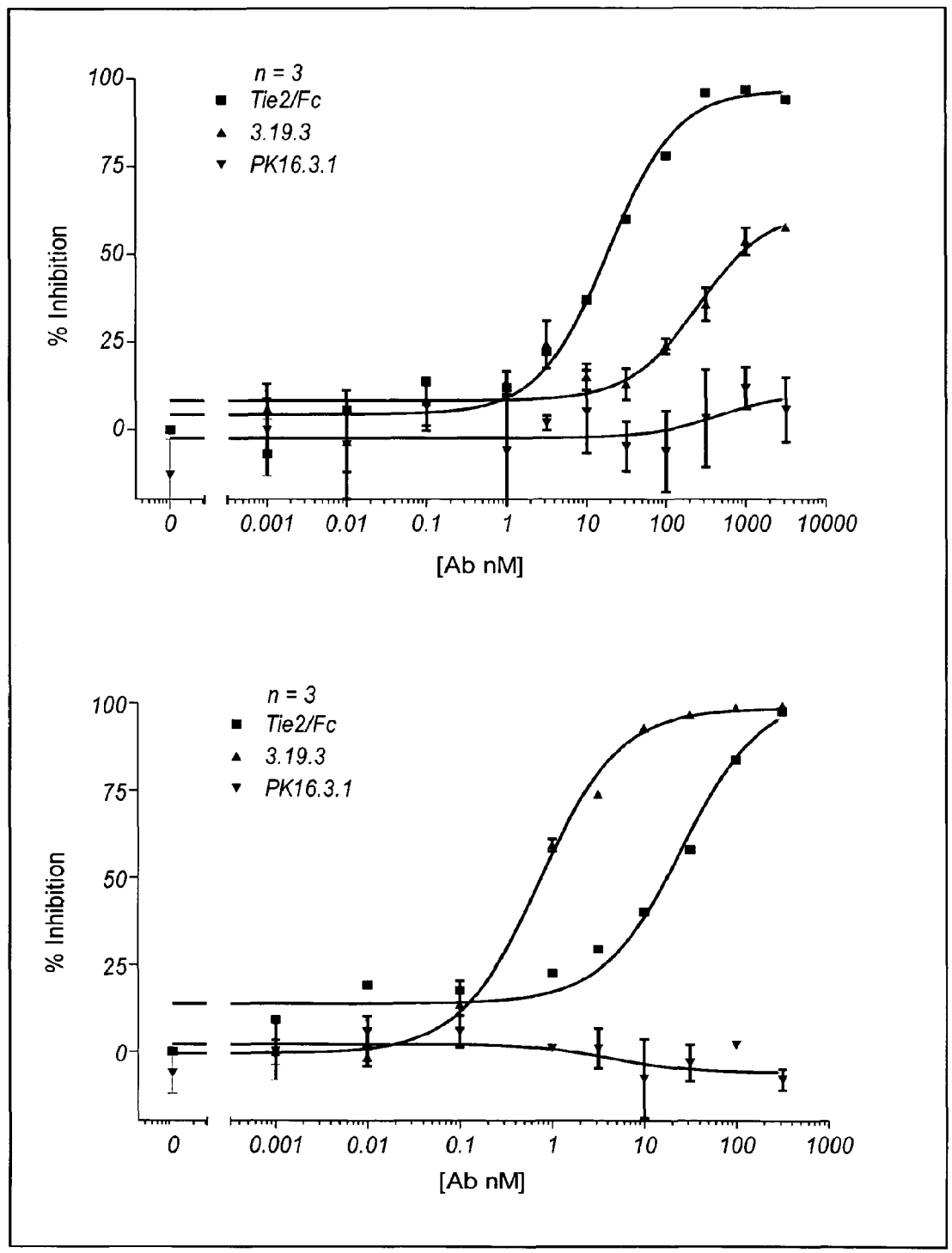
FIG. 3 is a line graph showing inhibition of both Ang-1 (top graph) and Ang-2 (bottom graph) binding to Tie2 in a dose-dependent manner using mAb 3.19.3 or Tie2/Fc.

The results are illustrated in FIG. 3 and summarized in Table 10. As shown, soluble Tie2/Fc dose-dependently inhibited binding of both Ang-1 and Ang-2 by blocking the ligands, whereas, the isotype control mAb, PK16.3.1 had no effect in the binding of either ligand. The mAb 3.19.3 showed concentration dependent inhibition of both Ang-1 and Ang-2. Interestingly, with the potency of Tie2/Fc as a reference, the potency of mAb 3.19.3 to the binding of Ang-2 was higher than that to Ang-1.

TABLE 10

| Inhibition of Ang-1 and Ang-2 binding to Tie2 | | |
|---|---|---|
| | EC50 (nM) | |
| | Ang-1 | Ang-2 |
| Tie2/Fc | 18.73 | 25.70 |
| 3.19.3 | 218.5 | 0.7310 |

These results indicated that mAb 3.19.3 not only bound to human Ang-1, but also blocked its binding to the receptor Tie2. This was further confirmed by the inhibition of Ang-1 induced Tie2 phosphorylation in immortalized endothelial cells as described below.

Figure 4:
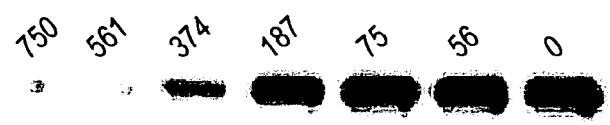
FIG. 4 is a Western blot showing inhibition of Angiopoietin-1 stimulated phosphorylation of Tie-2 on Eahy 926 endothelial cells by mAb 3.19.3. Inhibition of Angiopoietin-1 induced Tie-2 phosphorylation is observed in this system. The antibody concentrations are shown in nM.
Figure 5:
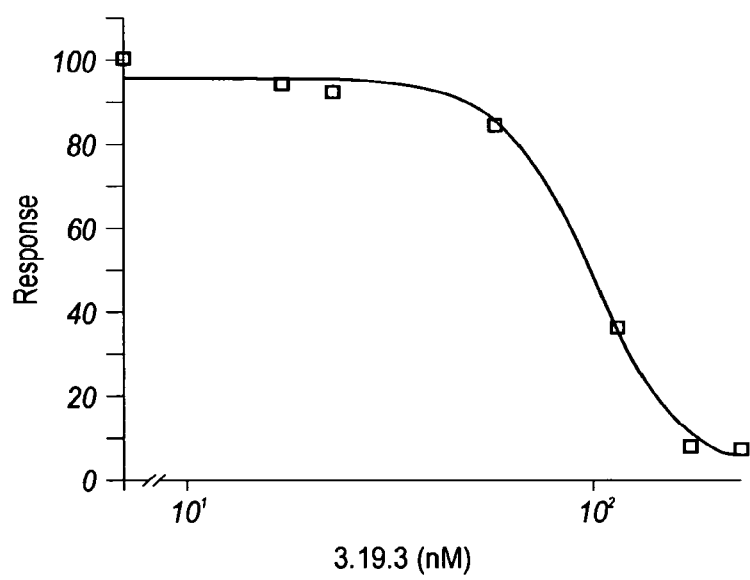
FIG. 5 is a line graph showing inhibition of Angiopoietin-1 stimulated phosphorylation of Tie-2 on Eahy 926 endothelial cells by mAb 3.19.3. The IC50=99 nM. The x axis is the concentration of mAb 3.19.3 and the y axis indicates the response.

The inhibitory activity of the mAb 3.19.3 on Ang-1 induced Tie2 phosphorylation was quantified as follows. The mAb showed an obvious increasing inhibition of Tie-2 phosphorylation with increasing antibody concentration, as shown in FIGS. 4 and 5. A plot of the dose response curve led to the calculation of an IC50 of 99 nM.

Angiopoietin-1 Ligand Stimulated Tie-2 Receptor Phosphorylation Assay

EA.hy926/B3 cells were seeded into 6 well plates using 2.5×105 EA.hy 926 cells/well in 2 ml volume DMEM; HAT; 10% FCS and incubated for 3 days under standard mammalian cell growth conditions.

The growth medium was replaced with 2 mls of DMEM (with no FCS) and the cells serum-starved for a total of 2 hours. Test compounds were diluted in DMEM; 1% FCS to twice the desired final concentration. After 1 hour 40 minutes of the serum starvation, the medium was removed from the cells and replaced with 1 ml of test compound dilutions.

Similarly, non-compound treated controls were also progressed to provide samples that represent 100% ligand stimulation standards.

Incubation was continued for a further 10 minutes after which 100 μl of an 10 mM orthovanadate in DMEM solution was added to each well to obtain a final concentration of 1 mM orthovanadate in each well. The cells were then incubated for the last 10 minutes of the 2 hour serum starvation period.

Once the 2 hour serum starvation period was complete, 1 ml of Angiopoietin-1 (diluted to the appropriate concentration in DMEM and containing 1 mM orthovanadate) was added to each well and incubated at 37° C. for a further 10 minutes.

The 6 well plate(s) were then cooled by placing on an ice cold metal plate (itself kept on ice). The cell medium was removed and the cell layer washed with 5 ml of cold PBS; 1 mM orthovanadate. One ml of ice cold lysis buffer (20 mM Tris pH 7.6, 150 mM NaCl, 50 mM NaF, 0.1% SDS, 1% NP40, 0.5% DOC, 1 mM orthovanadate, 1 mM EDTA, 1 mM PMSF, 30 μl/ml Aprotinin, 10 μg/ml Pepstatin, 10 μg/ml Leupeptin) was added to each well and left on ice for 10-20 minutes. The cells were scraped off the plate using a cell lifter and the whole lysate solution transfer to a 1.5 ml Eppendorf tube and kept on ice. The samples were then spun for 3 minutes at 13000 rpm at 4° C. and all subsequent steps carried out at 4° C.

50 μl of each lysate were kept for the BCA Protein assay (Pierce, Cat. No. 23225) (in low protein binding polypropylene microtiter plates from Greiner). The protein concentration was determined using the standard assay conditions supplied with the kit. A further 800 μl of each sample lysate was transferred to a fresh 2 ml Eppendorf tube in preparation for the immunoprecipitation (IP). 15 μl (3 mg) of anti P-Y (Santa Cruz Cat. No. E2203) were added to the lysates and left to incubate for 2 hours at 4° C. before adding 600 μl of the Magnabind beads (goat anti mouse IgG, Pierce Cat. No. 21354). The Magnabind beads were prepared as follows: The required volume was transferred into 15 ml conical tubes. Tubes were then placed in the presence of a magnetic field and the liquid was removed. Fresh PBS was added using the original volume, and the beads were re-suspended. This process was repeated twice. The lysate-containing solution was then mixed with the beads and the tubes left to rotate overnight at 4° C. on a rotor mixer.

The samples were exposed for about 1 min to the magnet and the liquid carefully removed. 1 ml lysis buffer was added and the tubes rotated for 5 min to wash. The wash steps were repeated twice. The liquid was completely removed and the beads re-suspended in 12 μl of hot (94° C.) 2× Laemmli loading buffer+bME, then left to stand for 15 min at room temperature. The tubes were exposed for 1 min in the magnet, and the liquid which separated from the beads was analyzed on PAGE/SDS gels.

The samples were analyzed using PAGE/SDS gels using 4-12% BisTris NuPAGE/MOPS gels with 15 wells (Novex). The total 12 μl of each immunoprecipitate was loaded per slot. The gels were run at 200 V/120 mA/25 Watts for 55 minutes and then the samples western blotted onto nitrocellulose membrane for 1 hr 30 min at 50 V/250 mA. All blots were then treated with 5% Marvel in PBS-Tween for 1 hour at room temperature and then washed with PBS-Tween Rabbit anti Tie-2 antibody (Santa Cruz Cat. No. C1303) was diluted 1:500 in 0.5% Marvel/PBS-Tween and 12.5 mls added to each blot and left at 4° C. overnight. The blots were then washed with PBS-Tween and goat anti rabbit —POD (Dako Cat. No. P 0448) (1:5000 dilution in 0.5% Marvel/PBS-Tween) added to each blot and left for 1 hour at room temperature. The blots were washed with PBS-Tween and each blot developed for 10 minutes using 12.5 mLs (equal volumes of solution A and B) of Supersignal (PIERCE Cat. No. 34080). The blots were transfer to X-Ray cassette and expose to film (5 sec/15 sec/30 sec/60 sec/150 second exposures). FIG. 4 is a Western blot showing the results of this assay. In this system, inhibition of Angiopoietin-1 stimulated phosphorylation of Tie-2 by mAb 3.19.3 was observed.

The images seen on the film for each sample were then evaluated using the Fluor S BioRad image analyzer system. The pixel density was measured as OD/mm2 and expressed in percentage volume. The percentage volume results were normalized to 1 mg protein/immunoprecipitation using the protein concentration determined using the BCA assay and the lysate volume of each sample used in the immunoprecipitation. The percentage phosphorylation of each sample was calculated against the 100% phosphorylation value of the untreated control sample on each gel with percentage inhibition of each sample being calculated against the 100% phosphorylation value, which itself represents 0% inhibition). FIG. 5 is a graphical representation of these values, and shows that the IC50 for inhibition of Angiopoietin-1 stimulated Tie-2 phosphorylation is 99 nM.

Taken together, these data show that, in this system, the mAb inhibits Angiopoietin-1 induced phosphorylation of Tie-2.

Example 13

Structural Analysis of Ang-2 Antibodies

The variable heavy chains and the variable light chains of the antibodies were sequenced to determine their DNA sequences. The complete sequence information for the anti-Ang-2 antibodies is provided in the sequence listing with nucleotide and amino acid sequences for each gamma and kappa chain combination. The variable heavy sequences were analyzed to determine the VH family, the D-region sequence and the J-region sequence. The sequences were then translated to determine the primary amino acid sequence and compared to the germline VH, D and J-region sequences to assess somatic hypermutations.

Table 11 is a table comparing the antibody heavy chain regions to their cognate germ line heavy chain region. Table 12 is a table comparing the antibody kappa light chain regions to their cognate germ line light chain region.

The variable (V) regions of immunoglobulin chains are encoded by multiple germ line DNA segments, which are joined into functional variable regions ($V_H D J_H$ or $V_K J_K$) during B-cell ontogeny. The molecular and genetic diversity of the antibody response to Ang-2 was studied in detail. These assays revealed several points specific to anti-Ang-2 antibodies.

Analysis of 152 individual antibodies specific to Ang-2 resulted in the determination that the antibodies were derived from 21 different germline VH genes, 112 of them from the VH3 family, with 46 antibodies being derived from the VH3-33 gene segment. Tables 11 and 12 show the results of this analysis.

It should be appreciated that amino acid sequences among the sister clones collected from each hybridoma are identical. For example, the heavy chain and light chain sequences for mAb 3.19.3 are identical to the sequences shown in Tables 11 and 12 for mAbs 3.19 and 3.19.1.

TABLE 11

Heavy chain analysis

| Chain Name | SEQ ID NO: | V | D | J | FR1 | CDR1 FR2 | CDR2 | FR3 | CDR3 | J |
|---|---|---|---|---|---|---|---|---|---|---|
| | 558 | Germline | | | EVQLVESGGGLVK PGGSLRLSCAAS | GFTFSWVRQAPG NAWMSKGLEWVG | RIKSKTDGGTRFTISRDDSKNTLYLQM TDYAAPVKG NSLKTEDTAVYYCTT | | DYGDYGM DV | WGQGTT VTVSSA |
| 4.2 | 141 | VH3-15 | D4-17 | JH6B | EVQLVESGGGLVK PGGSLRLSCAAS | GFTFSWVRQAPG NAWMTKGLEWVG | RIKSKTVGGTRFTISRDDSKNTLYLQM TDYAAPVKG NSLKTEDTAVYYCTT | | DYGDYYN SGYGMDV | WGQGTT VTVSSA |
| | 559 | Germline | | | QVQLVQSGAEVKK PGASVKVSCKAS | GYTFTWVRQAPG GYYMHQGLEWMG | WINPNSGGTNRVTMTRDTSISTAYMEL YAQKFQG SRLRSDDTAVYYCAR | | IAVAGFD Y | WGQGTL VTVSSA |
| 5.103.1 | 503 | VH1-2 | D6-19 | JH4A | QVQLVQSGAEVKK PGASVKVSCKAS | GYTFTWVRQAPG GYYLYQGLEWMG | WIsPNSGGTNRVTMTRDTSISTAYMEL YAQKFQG SRLRSDDTAVYYCAR | | DQVIAVA GPFDY | WAQGTL VTVSSA |
| | 560 | Germline | | | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | DYGGNFD Y | WGQGTL VTVSSA |
| 3.42 | 137 | VH3-33 | D4-23 | JH4B | QVQLVESGGGVVQ PGRSLRLSCAAS | GFTFSWVRQAPG SYGIHKGLEWVA | VIWYDGSSKYRFTISRDNSKNTLYLQM YADSVKG NSLRAEDTAVYYCAR | | ANDYGGN GLFDY | WGQGTL VTVSSA |
| | 561 | Germline | | | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | AFDI | WGQGTM VTVSSA |
| 5.11 | 221 | VH3-33 | -NA- | JH3B | QVQLVESGGGVVQ PGRSLRLPCAAS | GFTFSWVRQAPG SYGMHKGLEWVA | VIWYDGSNKYRFTISRDNSKNTLYLQM YADSVKG NSLRAEDTAVYYCAR | | DKALAFD I | WGQGTM VTVSSA |
| | 562 | Germline | | | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | EL | WGQGTL VTVSSA |
| 5.108 | 513 | VH3-33 | D1-7 | JH5B | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAMYYCAR | | ELAL | WGQGTL VTVSSA |
| 5.108.1 | 513 | VH3-33 | D1-7 | " | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAMYYCAR | | ELAL | WGQGTL VTVSSA |
| | 563 | Germline | | | EVQLVESGGGVVR PGGSLRLSCAAS | GFTFDWVRQAPG DYGMSKGLEWVS | GINWNGGSTGRFTISRDNAKNSLYLQM YADSVKG NSLRAEDTALYHCAR | | QWLWYFD L | WGRGTL VTVSSA |
| 5.19 | 251 | VH3-20 | D6-19 | JH2 | EVQLVESGGGVVR PGGSLRLSCAAS | GFSFDWVRQAPG DYGMSKGLEWVS | GINWNGGRTVRFTISRDSAKNSLYLQM YADSVKG NSLRAEDTALYHCAR | | NKQWLWY FDL | WGRGTL VTVSSA |
| 5.6 | 205 | VH3-20 | D6-19 | " | EVQLVESGGGVVR PGGSLRLSCAAS | GFSFDWVRQAPG DYGMSKGLEWVS | GINWNGGRTVRFTISRDSAKNSLYLQM YADSVKG NSLRAEDTALYHCAR | | NKQWLWY FDL | WGRGTL VTVSSA |
| 5.8 | 211 | VH3-20 | D6-19 | " | EVQLVESGGGVVR PGGSLRLSCAAS | GFTFDWVRQAPG DYGMSKGLEWVS | GINWNGGGTGRFTISRDDAKNSLYLQM YADSMKG NSLRAEDTALYHCAR | | NKQWLWY FDL | WGRGTL VTVSSA |
| 5.35 | 297 | VH3-20 | D6-19 | " | EVQLVESGGGVVR PGGSLRLSCTTS | GFTFDWVRQAPG DYGMSKGLEWVS | GINWNGGSTVRFTISRDSAKNSLYLQM YADSVKG NSLRAEDTALYHCAR | | NKQWLWY FDL | WGRGTL VTVSSA |
| 5.38 | 309 | 20 | 19 | " | EVKLVESGGGMVR PGGSLRLSCAAS | GFTFDWVRQAPG DYGMSKGLEWVS | GINWNGGGTARFTISRDNAKNSLYLQL YADSVKG NSLRAEDTALYHCAR | | NKQWLWY FDL | WGRGTL VTVSSA |
| 5.44 | 329 | VH3-20 | D6-19 | " | EVQLVESGGGVVR TGGSLRLSCAAS | GFSFDWVRQAPG DYGMSKGLEWVS | GINWNGGRTVRFTISRDSAKNSLYLQM YADSVKG NSLRAEDTALYHCAR | | NKQWLWY FDL | WGRGTL VTVSSA |
| 5.35.1 | 297 | 20 | 19 | " | EVQLVESGGGVVR PGGSLRLSCTTS | GFTFDWVRQAPG DYGMSKGLEWVS | GINWNGGSTVRFTISRDSAKNSLYLQM YADSVKG NSLRAEDTALYHCAR | | NKQWLWY FDL | WGRGTL VTVSSA |
| | 564 | Germline | | | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCA | | YGGNSYY YYYGMDV | WGQGTT VTVSSA |
| 3.1 | 7 | VH3-33 | D4-23 | JH6B | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAG | | DYGEYFY YGMDV | WGQGTT VTVSSA |
| 3.18 | 71 | VH3-33 | D4-23 | " | QVQLVESGGGVVQ PGRSLRLSCAAS | GFTFSWVRQAPG SFGMHKGLEWVA | VIWFDGSNKYRFTISRDNSKNTLYLQM YADSVKG NSLRAEDTAVYYCAS | | DYGDYFY YGMDV | WGQGTT VTVSSA |
| 3.39 | 125 | VH3-33 | D4-23 | " | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCA | | DRSYGGN SFYYYYY GMDV | WGQGTT VTVSSA |
| 3.11 | 47 | VH3-33 | D4-23 | " | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAG | | DYGDYFY YGMDV | WGQGTT VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| 3.26 | 93 | 33 | 23 | " | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAG | | | DYGEYFY YGMDV | WGQGTT VTVSSA |
| | 565 | | | Germline | EVQLVESGGVVVQ PGGSLRLSCAAS | GFTFDWVRQAPG DYTMHKGLEWVS | LISWDGGSTYRFTISRDNSKNSLYLQM YADSVKG NSLRTEDTALYYCAK | | | DIAVAGF DY | WGQGTL VTVSSA |
| 5.28 | 277 | VH3-43 | D6-19 | JH4B | EVQLVESGGIVVQ PGGSLRLSCAAS | GFTFDWVRQTPG DYTMHKGLEWVS | LISWDGGSTYRFTISRDNSKNSLYLQM YADSVKG NSLRTEDTALYYCAK | | | DIDIAVA GTGFDH | WGQGTL VTVSSA |
| 5.28.1 | 277 | VH3-43 | D6-19 | " | EVQLVESGGIVVQ PGGSLRLSCAAS | GFTFDWVRQTPG DYTMHKGLEWVS | LISWDGGSTYRFTISRDNSKNSLYLQM YADSVKG NSLRTEDTALYYCAK | | | DIDIAVA GTGFDH | WGQGTL VTVSSA |
| | 566 | | | Germline | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | NWNYFDY | WGQGTL VTVSSA |
| 5.56.1 | 363 | VH3-33 | D1-7 | JH4B | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | EDNWNFY FDY | WGQGTL VTVSSA |
| 5.56 | 363 | VH3-33 | D1-7 | " | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | EDNWNFY FDY | WGQGTL VTVSSA |
| | 567 | | | Germline | QVQLQQWGAGLLK PSETLSLTCAVY | GGSFSWIRQPPG GYYWSKGLEWIG | EINHSGSTNYRVTISVDTSKNQFSLKL NPSLKS SSVTAADTAVYYCAR | | | DYGDFDY | WGQGTL VTVSSA |
| 3.37 | 121 | VH4-34 | D4-17 | JH4B | QVQLQQWGAGLLK PSETLSLTCAVY | GGSFSWIRQPPG GYYWSKGLEWIG | EIYHSGSTNYRVTISVDTSKNQFSLKL NPSLKS SSVTAADTAVYSCAR | | | NDYGDHE GFDY | WGQGTL VTVSSA |
| | 568 | | | Germline | QVQLQESGPGLVK PSETLSLTCTVS | GGSVSWIRQPPG SGGYYKGLEWIG WS | YIYYSGSTNYRVTISVDTSKNQFSLKL NPSLKS SSVTAADTAVYYCAR | | | GYSYGYY FDY | WGQGTL VTVSSA |
| 5.36 | 301 | VH4-61 | D5-5 | JH4B | QVQLQESGPGLVK PSETLSLTCTVS | GGSVSWIRQPPG SGGYYKGLEWIG WS | YINYSRSTNHRVTISVDTSKNQFSLKL NPSLKS SSVTAADTAVYYCAR | | | EGRGDSY GYYFDY | WGQGTL VTVSSA |
| 6.7 | 551 | VH3-61 | D5-5 | " | QVQLQESGPGLVK PSETLSLTCTVS | GGSVSWIRQPPG SGGYYKGLEWIG WS | YIYYSRSTNYRVTISVDTSKNQFSLKL NPSLKS SSVTAADTAVYYCAR | | | EGRGYSY GYYFDY | WGQGTL VTVSSA |
| 5.107 | 511 | VH3-61 | D5-5 | " | QVQLQESGPGLVK PSETLSLTCTVS | GGSVSWIRQPPG SGGYYKGLEWIG WS | YIYYSRSTNYRVTISVDTSKNQFSLKL NPSLKS SSVTAADTAVYYCAR | | | EGRGNSY GYYFDY | WGQGTL VTVSSA |
| | 569 | | | Germline | QVQLVESGGGVVQ PGRSLRLSCAAS | GFTFSWVRQAPG SYGMHKGLEWVA | VISYDGSNKYRFTISRDNSKNTLYLQM YADSVKG NSLRAEDTAVYYCAR | | | WLRYYYY GMDV | WGQGTT VTVSSA |
| 5.111 | 521 | VH3-30 | D5-12 | JH6B | QVQLVESGGDVVQ PGRSLRLSCAAS | GFTFSWVRQAPG SYGMHKGLEWVA | VISYDGSNKYRFTISRDNSKNTLYLQM YADSVKG HLRAEDTAVYYCAR | | | DGGWLRL DYYYYGM DV | WGQGTT VTVSSA |
| | 570 | | | Germline | EVQLVESGGGLVK PGGSLRLSCAAS | GFTFSWVRQAPG NAWMSKGLEWVG | RIKSKTDGGTRFTISRDDSKNTLYLQM TDYAAPVKG NSLKTEDTAVYYCTT | | | YSSGWYW YFDL | WGRGTL VTVSSA |
| 5.45 | 333 | VH3-15 | D6-19 | JH2 | EVQLVESGGGLVK PGGSLRLSCAAS | GFTFSWVRQAPG NAWMSKGLEWVG | RIKSKTDGGTRFTISRDDSKNTLYLQM TDYAAPVKG NSLKTEDTAVYYCTT | | | SYSSGWF YWYFDI | WGRGTP VTVSSA |
| | 571 | | | Germline | EVQLVESGGGLVQ PGGSLRLSCAAS | GFTFSWVRQAPG SYSMNKGLEWVS | YISSSSSTIYRFTISRDNAKNSLYLQM YADSVKG NSLRDEDTAVYYCAR | | | AAAGFDY | WGQGTL VTVSSA |
| 5.43 | 325 | VH3-48 | D6-13 | JH4B | EVQLVESGGGLVQ PGGSLRLSCAAS | GFTFSWVRQAPG TYSMNKGLEWIS | YISRSSRTINRFTVSRDNAKNSLYLQM HADSVKG ISLRDEDTAVYYCAR | | | KAAAGPF DY | WGQGTL VTVASA |
| | 572 | | | Germline | EVQLLESGGGLVQ PGGSLRLSCAAS | GFTFSWVRQAPG SYAMSKGLEWVS | AISGSGGTYRFTISRDNSKNTLYLQM YADSVKG NSLRAEDTAVYYCAK | | | DYGGNFD Y | WGQGTL VTVSSA |
| 5.97 | 491 | VH3-23 | D4-23 | JH4B | EVQLLESGGGLVQ PGGSLRLSCAAS | GFTFSWVRQAPG SYAMSKGLEWVS | GISGSGGNYRFTISRDNSKNTLYLQM HADSVKG NSLRAEDTAVYYCAK | | | DEDYGGN YSDFDY | WGQGTL VTVSSA |
| 6.8 | 553 | VH3-23 | D4-23 | " | EVQLLESGGGLVQ PGGSLRLSCAAS | GFTFSWVRQAPG SYAMSKGLEWVS | AISGSGGSTYRFTISRDNSKNTLYLQM YADSVKG NSLRAEDTAVYYCAK | | | DEDYGGN SDFDY | WGQGTL VTVSSA |
| | 573 | | | Germline | QVQLQQSGPGLVK PSQTLSLTCAIS | GDSVSWIRQSPS SNSAARGLEWLG WN | RTYYRSKWYNRITINPDTSKNQFSLQL DYAVSVKS NSVTPEDTAVYYCA | | | WFYWYFD L | WGRGTL VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| 5.61 | 377 | VH6-1 | D3-9 | JH2 | QVQLQQSGPGLVK PSQTLSLTCAIS | GDSVSWIRQSPS SNSAARGLEWLG WN | MTYYRSKWSNRITINPDTSKNQFSLQL DYAVSLKS | | NSVTPEDTAVYYCAR | GNWFYWY FDL | WGRGTL VTVSSA |
| | 574 | | | Germline | QVQLVESGGGVVQ PGRSLRLSCAAS | GFTFSWVRQAPG SYGMHKGLEWVA | VIWYDGSNKYRFTISRDNSKNTLYLQM YADSVKG | | NSLRAEDTAVYYCAR | TGDY | WGQGTL VTVSSA |
| 5.52 | 347 | VH3-33 | D1-1 | JH4B | QVQLVESGGGVVQ PGRSLRLSCAAS | GFTFSWVRQAPG SYGMHKGLEWVA | VRWYDESNKYRFTISRDNSKNTLYLQM YADSVKG | | NSLRAEDTAVYYCAR | DPFETGT TFDY | WGQGTL VTVSSA |
| 5.52.1 | 351 | VH3-33 | D1-1 | " | QVQLVESGGGVVQ PGRSLRLSCAAS | GFTFSWVRQAPG SYGMHKGLEWVA | VRWYDESNKYRFTISRDNSKNTLYLQM YADSVKG | | NSLRAEDTAVYYCAR | DPFETGT TFDY | WGQGTL VTVSSA |
| 5.53 | 355 | VH3-33 | D1-1 | " | QVQLVESGGGVVQ PGRSLRLSCAAS | GFTFSWVRQAPG DYGMHKGLEWMA | VLWYDESNKYRFTISRDSSKNTLYLQM YADSVKG | | NSLRAEDTAVYYCAR | DPFETGT TFDY | WGQGTL VTVSSA |
| 5.26 | 273 | VH3-33 | D1-1 | " | QVQLVESGGGVVQ PGRSLRLSCAAS | GFTFSWVRQAPG SYGMHKGLEWVA | VIWYDESNKYRFTISRDNSKNTLYLQM YADSVKG | | NSLRAEDTAVYYCAR | DPFETGT TFDY | WGQGTL VTVSSA |
| | 575 | | | Germline | QVQLVESGGGVVQ PGRSLRLSCAAS | GFTFSWVRQAPG SYGMHKGLEWVA | VISYDGSNKYRFTISRDNSKNTLYLQM YADSVKG | | NSLRAEDTAVYYCAR | GYSSGWF DY | WGQGTL VTVSSA |
| 5.20 | 253 | VH3-30 | D6-19 | JH4B | QVQLVESGGGVVQ PGRSLRLSCAAS | GFTFSWVRQAPG TYGMHKGLEWVA | VISYDGSKKYRFTISRDNSKNTLYLQM YADSVKG | | NSLRAEDTALYYCAR | GGYSTGW GPDFDY | WGQGTL VTVSSA |
| | 576 | | | Germline | QVQLVESGGGVVQ PGRSLRLSCAAS | GFTFSWVRQAPG SYGMHKGLEWVA | VIWYDGSNKYRFTISRDNSKNTLYLQM YADSVKG | | NSLRAEDTAVYYCAR | CGGDCYY YYYYGMD V | WGQGTT VTVSSA |
| 3.22 | 89 | VH3-33 | D2-21 | JH6B | QVQLVESGGGVVQ PGRSLRLSCAAS | GFTFSWVRQAPG NYGMHKGLEWVA | VIWYDGSNKYRFTISRDNSRNTLYLQM YADSVKG | | NSLRAEDTAVYYCAR | EGGYCGG DCWVYGM DV | WGQGTT VTVSSA |
| 5.51 | 345 | VH3-33 | D2-21 | " | QVQLVESGGGVVQ PGRSLRLSCAAS | GFTFSWVRQAPG SYGMHKGLEWVA | VIWYDGSNKYRFTISRDNSKNTLYLQM YADSVKG | | NSLRAEDTAVYYCAR | ENCGGDC YQLNYYY YYGMDV | WGQGTT VTVSSA |
| 5.47 | 339 | VH3-33 | D2-21 | " | QVQLVESGGGVVQ PGRSLRLSCAAS | GFTFSWVRQAPG SYGMHKGLEWVA | VIWYDGSNKYRFTISRDNSKNTLYLQM YADSVKG | | NSLRAEDTAVYYCAR | ENCGGDC YQLNYYY YYGMDV | WGQGTT VTVSSA |
| | 577 | | | Germline | QVQLQESGPGLVK PSQTLSLTCTVS | GGSISWIRQHPG SGGYYKGLEWIG WS | YIYYSGSTYYRVTISVDTSKNQFSLKL NPSLKS | | SSVTAADTAVYYCAR | WDFDY | WGQGTL VTVSSA |
| 3.21 | 85 | VH4-31 | D7-27 | JH4B | QVQLQESGPGLVK PSQTLSLTCTVS | GGSISWIRQHPG SGGYFKGLEWIG WS | YIYYSGRTYYRVTISVDASKNQFSLKL NPSLKS | | SSVTAADTAVYHCAR | EGSYWDF DY | WGQGTL VTVSSA |
| | 578 | | | Germline | QVQLQESGPGLVK PSETLSLTCTVS | GGSISWIRQPPG SYYWSKGLEWIG | YIYYSGSTNYRVTISVDTSKNQFSLKL NPSLKS | | SSVTAADTAVYYCAR | P | WGQGTL VTVSSA |
| 5.66 | 389 | VH4-59 | -NA- | JH5B | QVQLQESGPGLVK PSETLSLTCTVS | GGSISWIRQPPG SYYWSKGLEWIG | FIYYSGTTNYRVTISVDTSKNQFSLKL NPSLKS | | SSVTAADTAVYYCAR | AYDP | WGQGTL VTVSSA |
| | 579 | | | Germline | QVQLVESGGGVVQ PGRSLRLSCAAS | GFTFSWVRQAPG SYGMHKGLEWVA | VIWYDGSNKYRFTISRDNSKNTLYLQM YADSVKG | | NSLRAEDTAVYYCAR | NWNYYYY GMDV | WGQGTT VTVSSA |
| 5.73 | 409 | VH3-33 | D1-20 | JH6B | QVQLVESGGGVVQ PGRSLRLSCAAS | GFTFSWVRQAPG SYGMHKGLEWVA | VIWYDGSNKYRFTISRDNSKNTLYLQM YADSVKG | | NSLRAEDTAVYYCAR | GDNWYE GDGMDV | WGQGTT VTVSSA |
| 5.29 | 281 | VH3-33 | D1-20 | " | QVQLVESGGGVVQ PGRSLRLSCAAS | GFTFSWVRQAPG SYGMHKGLEWVA | VIWYDGSNKYRFTISRDNSKNTLYLQM YADSVKG | | NSLRAEDTAVYYCAR | APYDWNS YYGLDV | WGQGTT VTVSSA |
| 5.104 | 507 | VH3-33 | D1-20 | " | QVQLVESGGGVVQ PGRSLRLSCAAS | GFTFSWVRQAPG SYGMHKGLEWVA | VIWYDGSNKYRFTISRDNSKNTLYLQM YADSVKD | | NSLRAEDTAVYYCAR | APYDWNS YYGLDV | WGQGTT VTVSSA |
| | 580 | | | Germline | QVQLVESGGGVVQ PGRSLRLSCAAS | GFTFSWVRQAPG SYGMHKGLEWVA | VISYDGSNKYRFTISRDNSKNTLYLQM YADSVKG | | NSLRAEDTAVYYCAR | YYGSGSY GMDV | WGQGTT VTVSSA |
| 5.21 | 255 | VH3-30 | D3-10 | JH6B | QVQLVESAGGVVQ PGRSLRLSCAAS | GFTFSWVRQAPG IYGMHKGLEWVA | VISYDGSNKYRFTISRDDSKNTLYLQM YADSVKG | | NSLRAEDTAVYYCAR | NYYGSGS PYGMDV | WGQGTT VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| | 581 | Germline | | | QVQLQESGPGLVK PSETLSLTCTVS | GGSVSWIRQPPG SGGYYKGLEWIG WS | | YIYYSGSTNYR NPSLKS | VTISVDTSKNQFSLKL SSVTAADTAVYYCAR | YYGSGYY YYGMDV | WGQGTT VTVSSA |
| 3.2 | 11 | VH4-61 | D3-10 | JH6B | QVQLQESGPGLVK PSETLSLTCTVS | GGSVSWIRQPPG SGGYYKGLEWIG WN | | YIYYSGSTNYR NPSLKS | VTISVDTSKNQFSLKL SSVTAADTAVYYCAR | DQDYYGS GRGYYYY GMDV | WGQGTT VTVSS |
| | 582 | Germline | | | QVQLVQSGAEVKK PGASVKVSCKAS | GYTFTWVRQAPG GYYMHQGLEWMG | | WINPNSGGTNR YAQKFQG | VTMTRDTSISTAYMEL SRLRSDDTAVYYCAR | NWNYFDY | WGQGTL VTVSSA |
| 6.3.1 | 539 | VH1-2 | D1-7 | JH4B | QVQLVQSGAEVKK PGASVKVSCKAS | GYTFTWVPQAPG GYFMHQGLEWMG | | WINPNSGGTNR YAQNFQG | VTMTRDTSISTAYMEL SRLRSDDTPVYYCAR | DPWQNWN SYFDY | WGQGTL VTVSSA |
| | 583 | Germline | | | EVQLVESGGGLVK PGGSLRLSCAAS | GFTFSWVRQAPG NAWMSKGLEWVG | | RIKSKTDGGTRF TDYAAPVKG | TISRDDSKNTLYLQM NSLKTEDTAVYYCT | YGWYFDL | WGRGTL VTVSSA |
| 5.46 | 337 | VH3-15 | D4-17 | JH2 | EVQLVESGGGLVK PGGSLRLSCAAS | GFTFSWVRQAPG NAWMSKGLEWVG | | RIKSKTDGGTRF TDYAAPVKG | TMSRDDSKNTLYLQM NSLKTEDTAVYYCTI | LYGDFWY FDL | WGRGTL VTVSSA |
| 3.9 | 39 | VH3-15 | D4-17 | " | EVQLVESGGGLVK PGGSLRLSCAAS | GFTFSWVRQAPG NAWMSKGLEWVG | | RIKSKTDGGTRF TDYAAPVKG | TMSRDDSKNTLYLQM NSLKTEDTAVYYCTT | EYGDFWY FDF | WGRGTL VTVSSA |
| | 584 | Germline | | | QVQLQESGPGLVK PSETLSLTCTVS | GGSISWIRQPAG SYYWSKGLEWIG | | RIYTSGSTNYR NPSLKS | VTMSVDTSKNQFSLKL SSVTAADTAVYYCAR | WWYFDL | WGRGTL VTVSSA |
| 5.68 | 397 | VH4-4 | D2-21 | JH2 | QVQLQESGPGLVK PSETLSLTCTVS | GGSISWIRQPAG SHYWIKGLEWIG | | RIYSSGSTNYR NPSLKS | VTMSGDTSKNQFSLKL SSVTAADTAVYYCAR | GRWGSWY FDL | WGRGTL VTVSSA |
| | 585 | Germline | | | QVQLVESGGGVVQ PGRSLRLSCAAS | GFTFSWVRQAPG SYGMHKGLEWVA | | VIWYDGSNKYR YADSVKG | FTISRDNSKNTLYLQM NSLRAEDTAVYYCAR | Y | WGQGTL VTVSSA |
| 5.67 | 393 | VH3-33 | -NA- | JH4B | QVQLVESGGGVVQ PGRSLRLSCAAS | GFTFSWVRQAPG SYGMHKGLEWVA | | VIWYDGSNKYR YADSVKG | FTISRDNSKNTLYLQM NSLRAEDTAVYYCAR | ELAY | WGQGTL VTVSSA |
| | 586 | Germline | | | QVQLVQSGAEVKK PGASVKVSCKAS | GYTFTWVRQAPG GYYMHQGLEWMG | | WINPNSGGTNR YAQKFQG | VTMTRDTSISTAYMEL SRLRSDDTAVYYCAR | WYYYYYY GMDV | WGQGTT VTVSSA |
| 5.78.1 | 429 | VH1-2 | D2-2 | JH6B | QVQLVQSGAEVKK PGASVKVSCKAS | GYTFTWVRQAPG GYYMHQGLEWMG | | WINPNSGGTNR YAQKFQG | VTMTRDTSISTAYMEL SRLRSDDTAVYYCAR | DRGWNYA DYYYYGM DV | WGQGTT VTVSSA |
| | 587 | Germline | | | EVQLVESGGGLVK PGGSLRLSCAAS | GFTFSWVRQAPG SYSMNKGLEWVS | | SISSSSSYIYR YADSVKG | FTISRDNAKNSLYLQM NSLRAEDTAVYYCAR | VGAFDY | WGQGTL VTVSSA |
| 4.18 | 187 | VH3-21 | D1-26 | JH4B | EVQLVESGGGLVK PGGSLRLSCAAS | GFTFSWVRQAPG SYRMNKGLEWVS | | SISSSSSHIYR YVDSVKG | FTISRDNAKNSLYLQM NSLRAEDTAVYYCAR | DRGVGAP FDY | WGQGTL VTVSSA |
| 3.40 | 129 | VH3-21 | D1-26 | " | EVQLVESGGGLVK PGGSLRLSCAAS | GFTFSWVRQAPG SYRMNKGLEWVS | | SISSSSSHIYR YVDSVKG | FTISRDNAKNSLYLQM NSLRAEDTAVYYCAR | DRGVGAP FDY | WGQGTL VTVSSA |
| 5.80 | 435 | VH3-21 | D1-26 | " | EVQLVESGGGLVK PGGSLRLSCAAS | GFTFSWVRQAPG SYRMNKGLEWVS | | SISSSGSYIYR YADSVKG | FTISRDNAKNSLYLQM NSLRAEDTAVYYFAR | DRGVGAA FDY | WGQGTL VTVSSA |
| 3.41 | 133 | VH3-21 | D1-26 | " | EVQLVESGGGLVK PGGSLRLSCAAS | GFTFSWVRQAPG SYRMNKGLEWVS | | SISSSSSHIYR YVDSVKG | FTISRDNAKNSLYLQM NSLRAEDTAVYYCAR | DRGVGAP FDY | WGQGTL VTVSSA |
| | 588 | Germline | | | QVQLVESGGGVVQ PGRSLRLSCAAS | GFTFSWVRQAPG SYGMHKGLEWVA | | VIWYDGSNKYR YADSVKG | FTISRDNSKNTLYLQM NSLRAEDTAVYYCAR | YSYFDY | WGQGTL VTVSSA |
| 5.22 | 259 | VH3-33 | D6-6 | JH4B | QVQLVESGGGVVQ PGRSLRLSCAAS | GFTFSWVRQAPG SYGMHKGLEWVA | | VIWYDGSNKYR YADSVKG | FTISRDNSKNTLYLQM NSLRAEDTAVYYCAR | GGPLYSN SFYYFDY | WGQGTL VTVSSA |
| 5.31 | 289 | VH3-33 | D6-6 | " | QVQLVESGGGVVQ PGRSLRLSCAAS | GFTFSWVRQAPG SYGMHKGLEWVA | | IIWFDGSNEYR YADSVKG | FTISRDNSKNTLYLQM NSLRAEDTAVYFCAR | GGPLYSN SFYYFDY | WGQGTL VTVSSA |
| 5.37 | 305 | VH3-33 | D6-6 | " | QVQLVESGGGVVQ PGRSLRLSCAAS | GFTFSWVRQAPG NYGMHKGLEWVA | | VIWYDGSHKYR YADSVKG | FTISRDNSKNSLYLQM NSLRAEDTAVYYCAR | GGPLYSN SFYYFDY | WGQGTL VTVSSA |
| 5.112 | 525 | VH3-33 | D6-6 | " | QVQLVESGGGVVQ PGRSLRLSCAAS | GFTFSWVRQAPG SYGMHKGLEWVA | | ILWYDGSNKYR YADSVKG | FTISRDNSKNTLYLQM NSLRAEDTAVYYCAR | GGPLYTN SFYYFDY | WGQGTL VTVSSA |
| 5.10 | 217 | VH3-33 | D6-6 | " | QVQLVESGGGVVQ PGRSLRLSCAAS | GFTFSWVRQAPD SYGMHKGLEWVA | | VIWYDGSYKYR YADSVKG | FTISRDNSKNTLYLQM NSLRAEDTAVYYCAR | GGPLYSN SFYYFDY | WGQGTL VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| 5.76 | 419 | VH3-33 | D6-6 | " | QVQLVESGGGVVQ PGRSLRLSCVAS | GFTFSWVRQAPG SYGMHKGLEWVA | VIWYDGSNKYRFTISRDNSKNTLYLQM YADSVKG | | NSLRAEDTAVYYCAR | GGPLYSN SFYYFDY | WGQGTL VTVSSA |
| 5.17 | 243 | VH3-33 | D6-6 | " | QVQLVESGGGVVQ PGRSLRLSCAAS | GFTFSWVRQAPG SYGMHKGLEWVT | VIWYDGSNKYRFTISRDSSKNTLYLQM YADSVKG | | NSLRAEDTAVYYCAR | GGPLYSN SFYYFDY | WGQGTL VTVSSA |
| | 589 | Germline | | | QVQLQESGPGLVK PSETLSLTCTVS | GGSISWIRQPAG SYYWSKGLEWIG | RIYTSGSTNYRVTMSVDTSKNQFSLKL NPSLKS | | SSVTAADTAVYYCAR | DDYSYYY YYGMDV | WGQGTT VTVSSA |
| 5.81 | 439 | VH4-4 | D4-11 | JH6B | QVQLQESGPGLVK PSETLSLTCTVS | GGSISWIRQPAG SYYWSKGLEWIG | RIYTSGSTNYRVTMSVDTSKNQFSLKL NPSLKS | | SSVTAADTAVYYCAR | DDYSHSY YYYYGMD V | WGQGTT VTVSSA |
| | 590 | Germline | | | EVQLVESGGGLVK PGGSLRLSCAAS | GTFSWVRQAPG NAWMSKGLEWVG | RIKSKTDGGTRFTISRDDSKNTLYLQM TDYAAPVKG | | NSLKTEDTAVYYCTT | YGGNSYG MDV | WGQGTT VTVSSA |
| 4.5 | 151 | VH3-15 | D4-23 | JH6B | EVQLVESGGGLVK PGGSLRLSCAAS | GTFSWVRQAPG NAWMNKGLEWVG | RIKSKTDGGTRFTISRDDSKNTLYLQM TDYAAPVKG | | NSLKTEDTAVYYCTT | AYGGNSD QEDYGMD V | WGQGTT VTVSSA |
| | 591 | Germline | | | EVQLVESGGGLVQ PGGSLRLSCAAS | GTFSWVRQAPG SYWMSKGLEWVA | NIKQDGSEKYRFTISRDNAKNSLYLQM YVDSVKG | | NSLRAEDTAVYYCAR | GIAVAFD Y | WGQGTL VTVSSA |
| 3.31.1 | 99 | VH3-7 | D6-19 | JH4B | EVQLVESGGGLVQ PGGSLRLSCAAS | GTFSWVRQAPG SYWMSKGLEWVA | NIKQDGSDKYRFTISRDNAKNSLYLRM YVDSVKG | | NSLRAEDTAVFYCAR | DMGSGWF DYFDY | WGQGTL VTVSSA |
| 5.13.1 | 229 | VH3-7 | D6-19 | " | EVQLVESGGGLVQ PGGSLRLSCAAS | GTFSWVRQAPG SYWMSKGLEWVA | NIKQDGSEKYRFTISRDNAKNSLYLQM YVDSVKG | | NSLRAEDTAVYYCAR | DPGIAVA GPFDY | WGQGTL VTVSSA |
| 5.13 | 229 | VH3-7 | D6-19 | " | EVQLVESGGGLVQ PGGSLRLSCAAS | GTFSWVRQAPG SYWMSKGLEWVA | NIKQDGSEKYRFTISRDNAKNSLYLQM YVDSVKG | | NSLRAEDTAVYYCAR | DPGIAVA GPFDY | WGQGTL VTVSSA |
| 5.62 | 381 | VH3-7 | D6-19 | " | EVQLVESGGGLVQ PGGSLRLSCAAS | GTFSWVRQAPG SYWMSKGLEWVA | NIKQDGSEKYRFTISRDNAKNSLYLQM YVDSVKG | | NSLRAEDTAVYYCAR | DPGIAVA GPFDY | WGQGTL VTVSSA |
| 3.28.1 | 97 | VH3-7 | D6-19 | " | EVQLVESGGGLVQ PGGSLRLSCAAS | GTFSWVRQAPG SSWMSKGLEWVA | NIKQDGSDKYRFTISRDNAKNSLYLQM YVDSVKG | | NSLRAEDTAVYYCVR | DKGSGWF DY | WGQGTL VTVSSA |
| 5.41 | 321 | VH3-7 | D6-19 | " | EVQLVESGGGLVQ PGGSLRLSCAAS | GTFSWVRQAPG SYWMSKGLEWVA | NIKEDGSEKYRFTISRDNAKNSLYLQM YVDSVKG | | NSLRAEDTAVFYCAR | DRSSGFF DY | WGQGTL VTVSSA |
| 5.109 | 517 | VH3-7 | D6-19 | " | EVQLVESGGGLVQ PGGSLRLSCAAS | GTFSWVRQAPG SYWMSKGLEWVA | NIKQDGSEQYRFTISRDNAKNSLYLQM SVDSVKG | | NTLRAEDTAVYYCVR | DPGIEVA GPFDY | WGQGTL VTVSSA |
| 3.3 | 15 | VH3-7 | D6-19 | " | EVQLVESGGGLVQ PGGSLRLSCAVS | GTFSWVRQAPG SYWMSKGLEWVA | NIKQDGSEKYRFTISRDNAKNSLYLQM YVDSVKG | | NSLRAEDTAVYYCAR | DQGIAVA GPFDY | WGQGTL VTVSSA |
| 3.3.1 | 19 | VH3-7 | D6-19 | " | EVQLVESGGGLVQ PGGSLRLSCAVS | GTFSWVRQAPG SYWMSKGLEWVA | NIKQDGSEKYRFTISRDNAKNSLYLQM YVDSVKG | | NSLRAEDTAVYYCAR | DQGIAVA GPFDY | WGQGTL VTVSSA |
| 5.41.1 | 321 | VH3-7 | D6-19 | " | EVQLVESGGGLVQ PGGSLRLSCAAS | GTFSWVRQAPG SYWMSKGLEWVA | NIKEDGSEKYRFTISRDNAKNSLYLQM YVDSVKG | | NSLRAEDTAVFYCAR | DRSSGFF DY | WGQGTL VTVSSA |
| 5.62.1 | 381 | VH3-7 | D6-19 | " | EVQLVESGGGLVQ PGGSLRLSCAAS | GTFSWVRQAPG SYWMSKGLEWVA | NIKQDGSEKYRFTISRDNAKNSLYLQM YVDSVKG | | NSLRAEDTAVYYCAR | DPGIAVA GPFDY | WGQGTL VTVSSA |
| 5.83 | 447 | VH3-7 | D6-19 | " | EVQLVESGGGLVQ PGGSLRLSCEAS | GTFSWVRQAPG TYWMTKGLEWVA | NIKQDGSEKYRFTISRDNAKNSLYLQM YVDSVKG | | NSLRAEDTAVYYCAR | DAGMEVA GPFDY | WGQGTL VTVSSA |
| | 592 | Germline | | | EVQLLESGGGLVQ PGGSLRLSCAAS | GTFSWVRQAPG SYAMSKGLEWVS | AISGSGGSTYRFTISRDNSKNTLYLQM YADSVKG | | NSLRAEDTAVYYCAK | QWLVFDY | WGQGTL VTVSSA |
| 5.40.2 | 317 | VH3-23 | D6-19 | JH4B | EVQLLESGGGLVQ PGGSLRLSCAAS | GTFSWVRQAPG SYAMSKGLEWVS | AISGSGYSTYRFTISRDNSKNTLYLQM YADSVKG | | NSLRAEDTAVYYCAK | DLQQWLV PTVFDY | WGQGTL VTVSSA |
| | 593 | Germline | | | QVQLQESGPGLVK PSETLSLTCTVS | GGSISWIRQPPG SYYWSKGLEWIG | YIYYSGSTNYRVTISVDTSKNQFSLKL NPSLKS | | SSVTAADTAVYYCAR | QWLDY | WGQGTL VTVSSA |
| 5.15 | 235 | VH4-59 | D6-19 | JH4B | QVQLQESGPGLVK PSETLSLTCTVS | GGSISWIRQPPG GYYWSKGLEWIG | YIYYSGSTNYRVTISVDTSKNQFSLKL NPSLKS | | SSVTAADTAVYYCAR | DRQWLDY | WGQGTL VTVSSA |
| | 594 | Germline | | | QVQLQESGPGLVK PSETLSLTCTVS | GGSISWIRQPPG SYYWSKGLEWIG | YIYYSGSTNYRVTISVDTSKNQFSLKL NPSLKS | | SSVTAADTAVYYCAR | AFDI | WGQGTM VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| 3.13 | 55 | VH4-59 | -NA- | JH3B | QVQLQESGPGLVK PSETLSLTCTVS | GGSISWIRQPPG NYYWSKGLEWIG | YIYYSGSTNYRVTISVDTSKNQFSLKL NPSLKS SSVTAADTAVYYCAR | | | DRADAFD I | WGQGTM VTVSSA |
| 3.7 | 31 | VH4-59 | " | " | QVQLQESGPGLVK PSETLSLTCTVS | GGSISWIRQPPG NYYWSKGLEWIG | YIYYSGSTNYRVTISVDTSKNQFSLKL NPSLKS SSVTAADTAVYYCAR | | | DRADAFD I | WGQGTM VTVSSA |
| 3.12 | 51 | VH4-59 | " | " | QVQLQESGPGLVK PSETLSLTCTVS | GGSISWIRQPPG NYYWSKGLEWIG | YIYYSGSTNYRVTISVDTSKNQFSLKL NPSLKS SSVTAADTAVYYCAR | | | DRADAFD I | WGQGTM VTVSSA |
| 3.33 | 111 | VH4-59 | " | " | QVQLQESGPGLVK PSETLSLTCTVS | GDSISWIRQPPG NYYWSKGLEWIG | YIYYSGSTNYRVTISVDTSKNQFSLKL NPSLKS SSVTAADTAVYYCAR | | | ERGDAFD I | WGQGRV VTVSSA |
| 4.16 | 183 | VH4-59 | " | " | QVQLQESGPGLVK PSETLSLTCTVS | GGSISWIRQPPG NYYWSKGLEWIG | YIYYSGSTNYRVTISVDTSKNQFSLKL NPSLKS SSVTAADTAVYYCAR | | | DRADAFD I | WGQGTM VTVSSA |
| 3.35 | 119 | VH4-59 | " | " | QVQLQESGPGLVK PSETLSLTCTVS | GDSISWIRQPPG NYYWSKGLEWIG | YIYYSGSTNYRVTISVDTSKNQLSLKL NPSLKS SSVTAADTAVYYCAR | | | ERGDAFD I | WGQGRV VTVSSA |
| 3.32 | 107 | VH4-59 | " | " | QVQLQESGPGLVK PSETLSLTCTVS | GGSISWIRQPPG NYYWSKGLEWIG | YIYYSGSTNYRVTISVDTSKNQFSLKL NPSLKS SSVTAADTAVYYCAR | | | DRADAFD I | WGQGTM VTVSSA |
|  | 595 | Germline |  |  | QVQLVESGGGLVK PGGSLRLSCAAS | GFTFSWIRQAPG DYYMSKGLEWVS | YISSSGSTIYRFTISRDNAKNSLYLQM YADSVKG NSLRAEDTAVYYCAR | | | GAFDI | WGQGTM VTVSSA |
| 5.90 | 475 | VH3-11 | D3-16 | JH3B | QVQLVESGGGLVK PGGSLRLSCAAS | GFTFSWIRQAPG DYYMSKGLEWVS | YISSSGSSKNRITISRDNAKNSLYLQM YADSVKG NSLRAEDTAVYYCAR | | | ERGDAFD I | WGQGTM VTVSSA |
|  | 596 | Germline |  |  | QVQLQESGPGLVK PSETLSLTCTVS | GGSISWIRQPAG SYYWSKGLEWIG | RIYTSGSTNYRVTMSVDTSKNQFSLKL NPSLKS SSVTAADTAVYYCAR | | | YNWNYWY FDL | WGRGTL VTVSSA |
| 5.18 | 247 | VH4-4 | D1-20 | JH2 | QVQLQESGPGLVK PSETLSLTCTVS | GGSISWIRQPAG SYYWSKGLEWIG | RIYTSGFTNYRVTMSVDTSKNQFSLKL NPSLKS SSVTAADTAVYYCAR | | | YNWNYWY FDL | WGRGIL VTVSSA |
|  | 597 | Germline |  |  | QVQLVQSGAEVKK PGASVKVSCKAS | GYTFTWVRQAPG GYYMHQGLEWMG | WINPNSGGTNRVTMTRDTSISTAYMEL YAQKFQG SRLRSDDTAVYYCAR | | | IAVAGFD Y | WGQGTL VTVSSA |
| 5.54.1 | 357 | VH1-2 | D6-19 | JH4B | QVQLVQSGAEVKK PGASVKVSCKAS | GYTFTWVRQAPG GYYMHQGLEWMG | WINPNSGGTNRVTMTRDTSISTAYMEL YAQKFQG SRLRSDDTAVYYCAR | | | DGGSIAV AGHFEY | WGQGTL VTVSSA |
| 5.14.1 | 233 | VH1-2 | D6-19 | " | QVQLVQSGAEVKK PGASVKVSCKAS | GYTFTWVRQAPG GYYMYQGLEWMG | WINPNSGGTNRVTMTRDTSISTAYMEL YAQKFQG SRLRSDDTAVYYCAR | | | DQGITVA GPFDY | WGQGSL VTVSSA |
| 5.101.1 | 497 | VH1-2 | D6-19 | " | QVQLVQSGAEVKK PGASVKVSCKAS | GYTFTWVPQAPG GYYMHQGLEWMG | WINPNSGGTNRVTMTRDTSISTAYMEL YAQKFQG RLRSDDTAVYYCAR | | | DGGSIPV SGHFDY | WGQGTL VTVSSA |
| 5.83.1 | 449 | VH1-2 | D6-19 | " | QVQLVQSGAEVKK PGASVKVSCKAS | GYTFTWVRQAPG GYYMHQGLEWMG | WINPNSGGTNRVTMTRDTSISTAYMEL YAQKFQG SRLRSDDTAVYYCAR | | | DGGSIAV AGHFDY | WGQGTL VTVSSA |
|  | 598 | Germline |  |  | EVQLVESGGGLIQ PGGSLRLSCAAS | GFTVSWVRQAPG SNYMSKGLEWVS | VIYSGGSTYYRFTISRDNSKNTLYLQM ADSVKG NSLRAEDTAVYYCA | | | YSSGWYY GMDV | WGQGTT VTVSSA |
| 6.9 | 555 | VH3-53 | D6-19 | JH6B | EVQLVESGGGLIQ SGGSLRLSCAAS | GFTVSWVRQAPG SKYMSKGLEWVS | VIYSGGFTYYRFTVSRDNSKNTLYLQM ADSVKG NSLGAEDTAVYYCAT | | | YSSGWHY YGMDV | WGQGTT VTVSSA |
|  | 599 | Germline |  |  | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | GDLLLRY GRL | GPRDHG HRLLS |
| 3.10 | 43 | VH3-33 | D4-17 | JH6B | QVQLVESGGGVVQ PGRSLRLSCAAS | GFTFSWVRQAPG SYGMHKGLEWVA | VIRYDGSNKYRFTISRDNSKNTLNLQM YADSVKG NSLRAEDTAVYYCAR | | | DRDGDYP LLLLGMD V | WGQGTT VTVSSA |
| 4.13 | 171 | VH3-33 | D4-17 | " | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAA | | | DYGDSDY YYYYGMD V | WGQGTT VTVSSA |
|  | 600 | Germline |  |  | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | DIVATIN YYYGMDV | WGQGTT VTVSSA |
| 5.2 | 195 | VH3-33 | D5-12 | JH6B | QVQLVESGGGVVQ PGRSLRLSCAAS | GFTFSWVRQAPG SYGMHKGLEWVA | VIWFDGFNKYRFTISRDNSKNTLYLQM YADSVKG NSLRAEDTAVYHCAR | | | DRGYSGY DHYYGMD V | WGQGTT VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| 5.12 | 225 | VH3-33 | D5-12 | " | QVQLVESGGGVVQ PGRSLRLSCAAS | GFTFSWVRQAPG SYGMHKGLEWVA | VIWYDGGNKYRFTISRDNSKNTLYLQM YTDSVKG | NSLRAEDTAVYYCAR | DEDIVAT INYYYGM DV | WGQGTT VTVSSA |
| | 601 | | | Germline | EVQLVESGGGLVQ PGGSLRLSCAAS | GFTFSWVRQAPG SYWMSKGLEWVA | NIKQDGSEKYRFTISRDNAKNSLYLQM YVDSVKG | NSLRAEDTAVYYCAR | DIWYFDL | WGRGTL VTVSSA |
| 5.4 | 201 | VH3-7 | D3-22 | JH2 | EVQLVESGGDLVQ PGGSLRLSCAAS | GFTFSWVRQAPG SYWMSKGLEWVA | NIKQDGSEKYRFTISRDNAKNSLYLQM FDSVKG | NSLRAEDTAVYYCAR | DIRWYFD L | WGRGTL VTVSSA |
| | 602 | | | Germline | EVQLVESGGGLVQ PGGSLRLSCAAS | GFTFSWVRQAPG SYWMSKGLEWVA | NIKQDGSEKYRFTISRDNAKNSLYLQM YVDSVKG | NSLRAEDTAVYYCAR | WYFDL | WGRGTL VTVSSA |
| 5.91 | 479 | VH3-7 | -NA- | JH2 | EVQLVESGGGLVQ PGGSLRLSCAAS | GFTFSWVRQAPG SYWMSKGLEWVA | NIKQDGSEKYRFTISRDNAKNSLYLQM YVDSVKG | NSLRAEDTAVYYCAR | DSWWYFD L | WGRGTL VTVSSA |
| | 603 | | | Germline | EVQLVESGGGLVQ PGGSLRLSCAAS | GFTFSWVRQAPG SYWMSKGLEWVA | NIKQDGSEKYRFTISRDNAKNSLYLQM YVDSVKG | NSLRAEDTAVYYCAR | AAAFDY | WGQGTL VTVSSA |
| 5.88 | 461 | VH3-7 | D6-13 | JH4B | EVQMVESGGGLVQ PGGSLRLSCAAS | GFTLRWVRQAPG SYWMSKGLEWVA | NIKEDGSEKYRFTISRDNAENSLFLQM HVDSVKG | SSLRAEDTAVYYCAR | DMEASAG LFDY | WGQGTL VTVSSA |
| 5.88.1 | 465 | VH3-7 | D6-13 | " | EVQMVESGGGLVQ PGGSLRLSCAAS | GFTLRWVRQAPG SYWMSKGLEWVA | NIKEDGSEKYRFTISRDNAENSLFLQM HVDSVKG | SSLRAEDTAVYYCAR | DMEASAG LFDY | WGQGTL VTVSSA |
| | 604 | | | Germline | QVQLVESGGGVVQ PGRSLRLSCAAS | GFTFSWVRQAPG SYGMHKGLEWVA | VIWYDGSNKYRFTISRDNSKNTLYLQM YADSVKG | NSLRAEDTAVYYCA | YSNYYFD Y | WGQGTL VTVSSA |
| 5.89 | 473 | VH3-33 | D4-11 | JH4B | QVQLVESGGGVVQ PGRSLRLSCAAS | GFTFRWVRQAPG SYGMHKGLEWVA | VIWYDGSYKNRFTISRDNSKNTLYLQM YGDSVKG | NSLRAEDTAVYYCAR | DYSNYEE YFDY | WGQGTL VTVSSA |
| | 605 | | | Germline | QITLKESGPTLVK PTQTLTLTCTFS | GFSLSWIRQPPG TSGVGKALEWLA VG | LIYWNDDKRYRLTITKDTSKNQVVLTM SPSLKS | TNMDPVDTATYYCAH | RSSSWFD Y | WGQGTL VTVSSA |
| 5.115 | 529 | VH2-5 | D6-13 | JH4B | QITLKESGPTLVK PTQTLTLTCTLS | GFSLSWIRQPPG ISGVGKALEWLA VG | FIYWNDDKRYRLTITKDTSKNQVVLTM SPSLKS | TNMDPVDTATYYCAH | RPDSSSW DFDY | WGQGTL VTVSSA |
| | 606 | | | Germline | EVQLVESGGGLVK PGGSLRLSCAAS | GFTFSWVRQAPG SYSMNKGLEWVS | SISSSSSYIYRFTISRDNAKNSLYLQM YADSVKG | NSLRAEDTAVYYCAR | GIAFDY | WGQGTL VTVSSA |
| 5.64 | 385 | VH3-21 | D2-2 | JH4B | EVQLVESGGGLVK PGGSLRLSCAAS | GFTFNWVRQAPG SYRMNKGLEWVS | SITSSSHYIYRFTISRDNAKNSLYLQM YADSVKG | NSLRAEDTAVYYCAR | DRGIAAP FDY | WGQGTL VTVSSA |
| | 607 | | | Germline | QVQLVQSGAEVKK PGASVKVSCKAS | GYTFTWVRQAPG GYYMHQGLEWMG | WINPNSGGTNRVTMTRDTSISTAYMEL YAQKFQG | SRLRSDDTAVYYCAR | GIAAAGF DY | WGQGTL VTVSSA |
| 5.39.1 | 313 | VH1-2 | D6-13 | JH4B | QVQLVQSGAEVTK PGASVKVSCKAS | GYTFTWVRQAPG AYHMYQGLEWMG | WINPNSGGTNRVTMTRDTSISTAYMEL YAQKFQG | SRLRSDDSPVYYCAR | DQGIAAA GPFDY | WGQGTL VTVSSA |
| 5.16.1 | 239 | VH1-2 | D6-13 | " | QVQLVQSGAEVKK PGASVKVSCKAS | GYTFTWVRQAPG GFYMYQGLEWMG | WINPNSSGTNRVTMTRDTSISTAYMEL HAQKFQG | SRLRSDDTAVYYCAR | DQDIATA GPFDY | WGQGTL VTVSSA |
| 5.86.1 | 453 | VH1-2 | D6-13 | " | QVQLVQSGAEVKK PGASVKVSCKAS | GYTFTWVRQAPG GYHMYQGLEWLG | WINPNSGGTNRVTMTRDTSISTAYMEL YAQKFQG | SRLRSDDTAVYYCVR | DQGIAAA GPFDY | WCQGTL VTVSSA |
| | 608 | | | Germline | QVQLQESGPGLVK PSETLSLTCTVS | GGSISWIRQPAG SYYWSKGLEWIG | RIYTSGSTNYRVTMSVDTSKNQFSLKL NPSLKS | SSVTAADTAVYYCAR | GITFDP | WGQGTL VTVSSA |
| 5.79 | 433 | VH4-4 | D1-20 | JH5B | QVQLQESGPGLVK PSETLSLTCTVS | GGSISWIRQPAG SYYWSKGLEWIG | RIYTSGSTNYRVTMSVDTSKNQFSLKL NPSLKS | SSVTAADTAVYYCAR | GITGYGG FDP | WGQGTL VTVSSA |
| 5.23 | 263 | VH4-4 | D1-20 | " | QVQLQESGPGLVK PSETLSLTCTVS | GDSINWIRQPAG SYYWSKGLEWIG | RIYTSGSTNYRVTMSVDTSKNQFSLKL NPSLKS | SSVTAADTAVYYCAR | GITGYGG FDP | WGQGTL VTVSSA |
| | 609 | | | Germline | QVQLVESGGGVVQ PGRSLRLSCAAS | GFTFSWVRQAPG SYGMHKGLEWVA | VIWYDGSNKYRFTISRDNSKNTLYLQM YADSVKG | NSLRAEDTAVYYCG | GMDV | WGQGTT VTVSSA |
| 5.87 | 457 | VH3-33 | D3-16 | JH6B | QVQLVESGGGVVQ PGRSLRLSCAAS | GFTFSWVRQAPG SYGMHKGLEWVA | VIWYDGSNKYRFTISRDNSKNTLYLQM YADSVKG | NSLRAEDTAVYYCAG | GATAMDV | CGQGST GTVSSA |
| | 610 | | | Germline | EVQLVQSGAEVKK PGESLKISCKGS | GYSFTWVRQMPG SYWIGKGLEWMG | IIYPGDSDTRQVTISADKSISTAYLQW YSPSFQG | SSLKASDTAMYYCAR | NWNFDI | WGQGTM VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| 3.6 | 27 | VH5-51 | D1-7 | JH3B | EVQLVQSGAEVKK PGESLKISCKGS | GYSFSWVRQMPG NYWIAKGLEWMG | IIYPGDSDTRQVTISADKSISTAYLQW SSLKASDTAMYYCAR | | | HENWN FFDTFDI | WGQGTM VTVSSA |
| | 611 | | | Germline | EVQLVESGGGLVK PGGSLRLSCAAS | GFTFSWVRQAPG SYSMNKGLEWVS | SISSSSSYIYRFTISRDNAKNSLYLQM YADSVKG NSLRAEDTAVYYCAR | | | IFGVVNW YFDL | WGRGTL VTVSSA |
| 4.6 | 155 | VH3-21 | D3-3 | JH2 | EVQLVESGGGLVK PGGSLRLSCAAS | GFTFSWVRQAPG SYSMNKGLEWVS | SISSSSSYIYRFTISRDNAKNSLYLQM YADSVKG NSLRAEDTAVYYCAR | | | DGAIFGV VNWYFDL | WGRGTL VTVSSA |
| 5.94 | 487 | VH3-21 | D3-3 | " | EVQLVESGGGLFK PGGSLRLSCAAS | GFTFSWVRQAPG SYSMNKGLEWVS | SISSSSSYIYRFTISRDNAKNSLYLQM YADSVKG NSLRAEDTAVYYCAR | | | DGAIFGV VNWYFDL | WGRGTL VTVSSA |
| 5.58 | 367 | VH3-21 | D3-3 | " | EVQLVESGGGLVK PGGSLRLSCAAS | GFTFSWVRQAPG SYSMNKGLEWVS | SISSSSSYIYRFTISRDNAKNSLYLQM YADSVKG NSLRAEDTAVYYCAR | | | DGAIFGV VNWYFDL | WGRGTL VTVSSA |
| 4.9 | 163 | VH3-21 | D3-3 | " | EVQLVESGGGLVK PGGSLRLSCAAS | GFTFSWVRQAPG SYSMNKGLEWVS | SISSSSSYIYRFTISRDNAKNSLYLQM YADSVKG NSLRAEDTAVYYCAR | | | DGAIFGV VNWYFDL | WGRGTL VTVSSA |
| 5.70 | 399 | VH3-21 | D3-3 | " | EVQLVESGGGLVK PGGSLRLSCAAS | GFTFSWVRQAPG SYSMNKGLEWVS | SISSSSSYIYRFTISRDNAKNSLYLQM YADSVKG NSLRAEDTAVYYCAR | | | DGAIFGV VNWYFDL | WGRGTL VTVSSA |
| 4.15 | 179 | VH3-21 | D3-3 | " | EVQLVESGGGLVK PGGSLRLSCAAS | GFTFSWVRQAPG SYSMNKGLEWVS | SISSSSSYIYRFTISRDNAKNSLYLQM YADSVKG NSLRAEDTAVYYCAR | | | DGAIFGV VNWYFDL | WGRGTL VTVSSA |
| 4.8 | 159 | VH3-21 | D3-3 | " | EVQLVESGGGLVK PGGSLRLSCAAS | GFTFSWVRQAPG SYSMNKGLEWVS | SISSSSSYIYRFTISRDNAKNSLYLQM YADSVKG NSLRAEDTAVYYCAR | | | DGAIFGV VNWYFDL | WGRGTL VTVSSA |
| 4.7 | 157 | VH3-21 | D3-3 | " | EVQLVESGGGLVK PGGSLRLSCAAS | GFTFSWVRQAPG SYSMNKGLEWVS | SISSSSSYIYRFTISRDNAKNSLYLQM YADSVKG NSLRAEDTAVYYCAR | | | DGAIFGV VNWYFDL | WGRGTL VTVSSA |
| | 612 | | | Germline | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | QNYDFWS GYGMDV | WGQGTT VTVSSA |
| 4.11 | 167 | VH3-33 | D3-3-D3-3 | JH6B | QVQLVESGGGVVQ PGRSLRLSCAAS | GFTFSWVRQAPG SYGMYKGLEWVA | VIWYDGSNKYRFTISRDNSKNTLYLQM YADSVKG NSLRAEDTAVYYCAR | | | DFFQNYD FWSGSPV GYGMDV | WGQGTT VTVSSA |
| | 613 | | | Germline | QVQLVQSGAEVKK PGASVKVSCKAS | GYTFTWVRQAPG SYGISQGLEWMG | WISAYNGNTNRVTMTTDTSTSTAYMEL YAQKLQG RSLRSDDTAVYYCAR | | | VGADY | WGQGTL VTVSSA |
| 6.6 | 547 | VH1-18 | D1-26 | JH4B | LVQSGAEVKKPGA SVKVSCKAS | GYTFTWVRQAPG SYGISQGLEWMG | WISAYNGNTNRVTMTTDTSTSTAYMEL YAQKLQD RSLRSDDTAVYYCAR | | | GVGAKDY | WGQGTL VTVSSA |
| 3.34 | 115 | VH1-18 | D1-26 | " | QVQLVQSGAEVKK PGASVKVSCKAS | GYTFTWVRQAPG SYGISQGLEWMG | WISTYNDNTNRVTMTTDTSTSTAYMEL YAQKLQG RSLRSDDTAVYYCAR | | | GVGATDY | WGQGTL VTVSSA |
| 5.30 | 285 | VH1-18 | D1-26 | " | QVQLVQSGAEVKK PGASVKVSCKAS | GYTFTWVRQAPG SYGISQGLEWMG | WISAHNGNTNRVTMTTDTSTSTAYMEL YAQKLQG RSLRSDDTAVYYCAR | | | GVGSKDY | WGQGTL VTVSSA |
| | 614 | | | Germline | EVQLVESGGGLVK PGGSLRLSCAAS | GFTFSWVRQAPG NAWMSKGLEWVG | RIKSKTDGGTRFTISRDDSKNTLYLQM TDYAAPVKG NSLKTEDTAVYYCT | | | SSGWYYY YYGMDV | WGQGTT VTVSSA |
| 5.55 | 361 | VH3-15 | D6-19 | JH6B | EVQLVESGGGLVK PGGSLRLSCAAS | GFTFSWVRQAPG NAWMSKGLEWVG | RIKSKTDGGTRFTISRDDSKNTLYLQM TDYAAPVKG NSLKTEDTAVYYCTI | | | GSSGWYE AYYYYGM DV | WGQGTT VTVSSA |
| 5.7 | 209 | VH3-15 | D6-19 | " | EVQLVESGGGLVK PGGSLRLSCAAS | GFTFSWVRQAPG NAWMSKGLEWVG | RIKSKTDGGTRFTISRDDSKYTLYLQM TDYAAPVKG NSLKTEDTAVYYCTI | | | GSSGWYE AYYYYGM DV | WGQGTT VTVSSA |
| 5.5 | 203 | VH3-15 | D6-19 | " | EVQLVESGGGLVK PGGSLRLSCAAS | GFTFSWVRQAPG NAWMSKGLEWVG | RIKSKTDGGTRFTISRDDSKYTLYLQM TDYAAPVKG NSLKTEDTAVYYCTI | | | GSSGWYE AYYYYGM DV | WGQGTT VTVSSA |
| | 615 | | | Germline | QVQLVESGGGVVQ PGRSLRLSCAAS | GFTFSWVRQAPG SYGMHKGLEWVA | VISYDGSNKYRFTISRDNSKNTLYLQM YADSVKG NSLRAEDTAVYYCAR | | | DFWSNWF DP | WGQGTL VTVSSA |
| 3.19 | 75 | VH3-30 | D3-3 | JH5B | QVQLVESGGGVVQ PGRSLRLSCAAS | GFTFTWGRQAPG NYGMHKGLEWVA | VISHDGNNKYRFTISRDNSKNTLYLQM YVDSVKG NSLRAEDTAVYYCAR | | | EGIDFWS GLNWFDP | WGQGTL VTVSSA |
| 3.19.1 | 75 | VH3-30 | D3-3 | " | QVQLVESGGGVVQ PGRSLRLSCAAS | GFTFTWGRQAPG NYGMHKGLEWVA | VISHDGNNKYRFTISRDNSKNTLYLQM YVDSVKG NSLRAEDTAVYYCAR | | | EGIDFWS GLNWFDP | WGQGTL VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| | 616 | Germline | | | EVQLVESGGGLVK PGGSLRLSCAAS | GFTFSWVRQAPG NAWMSKGLEWVG | RIKSKTDGGTRFTISRDDSKNTLYLQM TDYAAPVKG NSLKTEDTAVYYCT | | | YGDAFDI | WGQGTM VTVSSA |
| 5.72 | 405 | VH3-15 | D4-17 | JH3B | EVQLVESGGGLVK PGGSLRLSCAAS | GFTFSWVRQAPG NAWMSKGLEWVG | RIKSKTDGGTRFTISRDDSKNTLYLQM TDYAAPVKG NSLKTEDTAVYYCTN | | | YYGDFYA FDI | WGQGTM VTVSSA |
| 3.14 | 59 | VH3-15 | D4-17 | " | EVQLVESGGGLVK PGGSLRLSCAAS | GFTFSWVRQAPG NAWMSKGLEWVG | RIKSKTDGGTRFTISRDDSKNTLYLQM TDYAAPVKG NSLKTEDTAVYYCII | | | FYGDFDA FDI- | WGQGTM VTVSSA |
| 3.17 | 67 | VH3-15 | D4-17 | " | EVQLVESGGGLVK PGGSLRLSCAAS | GFTFSWVRQAPG NAWMHKGLDWVG | RIKSKTDGGTRFTISRDDSENTLYLQM ADYAAPVKG NSLKTEDTAVYYCTN | | | DYGDFYA FDI | WGQGTM VTVSSA |
| | 617 | Germline | | | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | GYCSGGY GMDV | WGQGTT VTVSSA |
| 5.82 | 443 | VH3-33 | D2-15 | JH6B | QVQLVESGGGVVQ PGRSLRLSCAAS | GFTFSWVRQAPG SYGMHKGLEWVA | IIWFDGSNKYRFTISRDNSKNTLYLQM YADSVKG VSLRAEDTAVYYCAR | | | KGYCSGG RCVYGMD V | WGQGTT VTVSSA |
| 5.59 | 371 | VH3-33 | D2-15 | " | QVQLVESGGGVVQ PGRSLRLSCAAS | GFTFSWVRQAPG SYGMHKGLEWVA | IIWYDGSNKYRFTISRDNSKNTLHLQM YADSVKG NSLRAEDTAVYYCAR | | | KGYCSGG SCVYGMD V | WGQGTT VTVSSA |
| 5.92 | 481 | VH3-33 | D2-15 | " | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | KGYCSGG RCVYGMD V | WGQGTT VTVSSA |
| | 618 | Germline | | | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | RYFDWDY | WGQGTL VTVSSA |
| 6.5 | 545 | VH3-33 | D3-9 | JH4B | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | GPLRYFD WPSDY | WGQGTL VTVSSA |
| 6.2 | 535 | VH3-33 | D3-9 | " | QVQLVESGGGVVQ PGRSLRLSCAAS | GFTFSWVRQAPG SYGMHKGLEWVS | LIWYAGSNKYRFTISRDNSKNTLYLQM YADSVKG NSLRAEDTAVYYCAR | | | GPLRYFD WPSDY | WGQGTL VTVSSA |
| 3.8 | 35 | VH3-33 | D3-9 | " | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | GPLRYFD WPPDY | WGQGTL VTVSSA |
| | 619 | Germline | | | QVQLVQSGAEVKK PGASVKVSCKAS | GYTFTWVRQAPG SYGISQGLEWMG | WISAYNGNTNRVTMTTDTSTSTAYMEL YAQKLQG RSLRSDDTAVYYCAR | | | YSSFDY | WGQGTL VTVSSA |
| 5.74 | 413 | VH1-18 | D6-19 | JH4B | QVQLVQSGAEVKK PGASVKVSCKAS | GYTFTWVRQAPG SYCISRGLEWMG | WICSYNGNTNRVTMTTDTSTTTAYMEL CAQKLQG RGLRSDDTAVYYCAR | | | ESLYSSG WFDY | WGQGTL VTVSSA |
| | 620 | Germline | | | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | DFWSNWF DP | WGQGTL VTVSSA |
| 5.71 | 401 | VH3-33 | D3-3 | JH5B | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | EGLDFWS DFYNWFD P | WGQGTL VTVSSA |
| | 621 | Germline | | | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | | WGQGTL VTVSSA |
| 4.14 | 175 | VH3-33 | -NA- | JH5B | QVQLVESGGGVVQ PGRSLRLSCAAS | GFTFSWVRQAPG SYGMHKGLEWVA | VIWYDGSNKYRFTISRDNSKNTLYLQM YADSVKG NSLRAEDTAVYYCAR | | | ELAS | WGQGTL VTVSSA |
| 6.1 | 533 | VH3-33 | " | " | QVLLVESGGGVVQ PGRSLRLSCAAS | GFTFSWVRQAPG SYGMHKGLEWVA | VIWFDGSKKYRFTISRDNSKNSLYLQM YADSVKG NSLRAEDTAVYYCAR | | | ELEL | WGLGTL VTVSSA |
| | 622 | Germline | | | QVQLQESGPGLVK PSETLSLTCTVS | GGSISWIRQPPG SYYWSKGLEWIG | YIYYSGSTNYRVTISVDTSKNQFSLKL NPSLKS SSVTAADTAVYYCA | | | TGDY | WGQGTL VTVSSA |
| 5.106 | 509 | VH4-59 | D7-27 | JH4B | QVQLQESGPGLVK PSETLSLTCTVS | GGSISWIRQPPG SYYWSKGLEWIG | YIYYSGSTNFRVTSVDTSKNQFSLNL NPSLKS RSVTAADTAVYYCAR | | | GTGASDY | WGQGTL VTVSSA |
| 5.48 | 341 | VH4-59 | D7-27 | " | QVQLQESAPGLVK PSETLSLTCTVS | GGSISWIRQPPG SYYWSKGLEWIG | YISYSGSTNYRVTSVDTSKNQFSLKL NPSLKS SSVTAADTAVYYCTR | | | GTGASDY | WGQGTL VTVSSA |
| | 623 | Germline | | | QVQLVESGGGLVK PGGSLRLSCAAS | GFTFSWIRQAPG DYYMSKGLEWVS | YISSSGSTIYRFTISRDNAKNSLYLQM YADSVKG NSLRAEDTAVYYCAR | | | AFDI | WGQGTM VTVSSA |

TABLE 11-continued

Heavy chain analysis

| Chain Name | SEQ ID NO: | V | D | J | FR1 | CDR1 | FR2 | CDR2 | FR3 | CDR3 | J |
|---|---|---|---|---|---|---|---|---|---|---|---|
| 5.102 | 501 | VH3-11 | -NA- | JH3B | QVQLVESGGGLVKPGGSLRLSCAAS | GFTFSWIRQAPGDYYMSKGLEWVS | YISSSGSTIYRFTISRDNAKNSLYLQMYADSVKG | NSLRAEDTAVYYCAR | ERGDAFDI | WGQGTMVTVSSA |
| 5.24 | 267 | VH3-11 | " | " | QVRLVESGGGLVKPGGSLRLSCAAS | GFTFSWIRQAPGDYYMSKGLEWAS | YISSSGYSIYRFTISRDNAKNSLYLQMYADSVKG | NSLRAEDTAVYYCAR | ERGDAFDI | WGQGTMVTVSSA |
|  | 624 |  | Germline |  | EVQLVESGGGLVKPGGSLRLSCAAS | GFTFSWVRQAPGNAWMSKGLEWVG | RIKSKTDGGTRFTISRDDSKNTLYLQMTDYAAPVKG | NSLKTEDTAVYYCT | YGDYYFDY | WGQGTLVTVSSA |
| 5.1 | 191 | VH3-15 | D4-17 | JH4B | EVQLVESGGGLVKPGGSLRLSCAAS | GFTFSWVRQAPGNAWMSKGLEWVG | RIKSKTDGGTRFTISRDDSKNTLYLQMTDYAAPVKG | NSLKIEDTAVYYCTI | TYGDYPYFDC | WGQGTLVTVSSA |
| 5.33 | 293 | VH3-15 | D4-17 | " | EVQLVESGGGLVKPGGSLRLSCAAS | GFTFSWVRQAPGNTWMSKGLEWVG | RIKSKTDGGTRFTISRDDSKNTLCLQLTDYAAPVKG | NSLKTEDTAVYYCSA | GYGDYPYFDF | WGQGTLVTVSSA |
|  | 625 |  | Germline |  | QVQLQESGPGLVKPSETLSLTCTVS | GGSISWIRQPPGSYYWSKGLEWIG | YIYYSGSTNYRVTISVDTSKNQFSLKLNPSLKS | SSVTAADTAVYYCAR | FDY | WGQGTLVTVSSA |
| 4.3 | 145 | VH4-59 | -NA- | JH4B | QVQLQESGPGLVKPSETLSLTCTVS | GGSINWIRQPPGNYYWSKGLEWIG | YIYYSGSTNYRVTISVDTSKNQFSLKLNPSLKS | SSVTAADTAVYYCAR | ERGDSFDY | WGQGTLVTVSSA |
|  | 626 |  | Germline |  | QVQLVESGGGVVQPGRSLRLSCAAS | GFTFSWVRQAPGSYGMHKGLEWVA | VISYDGSNKYRFTISRDNSKNTLYLQMYADSVKG | NSLRAEDTAVYYCAR | QLWDY | WGQGTLVTVSSA |
| 5.60 | 373 | VH3-30 | D5-5 | JH4B | QVQLVESGGGVVQPGRSLRLSCAAS | GFTFSWVRQAPGGYDIHKGLEWVA | VISYDGSNKYRFTISRDNSKNTLYLQMYADSVKG | NSLRAEDTAVYYCAR | ERQLWLIDY | WGQGTLVTVSSA |
|  | 627 |  | Germline |  | QVQLVESGGGVVQPGRSLRLSCAAS | GFTFSWVRQAPGSYGMHKGLEWVA | VISYDGSNKYRFTISRDNSKNTLYLQMYADSVKG | NSLRAEDTAVYYCAR | GIAVAYGMDV | WGQGTTVTVSSA |
| 5.75 | 417 | VH3-30 | D6-19 | JH6B | QVQLVESGGGVVQPGRSLRLSCAAS | GFTFSWVRQAPGGYGMHKGLEWVA | VISYDGSNKYRFTISRDNSKNTLYLQMYADSVKG | NSLRAEDTAVYYCAR | DRGIAVAGYYGMDV | WGQGNTVTVSSA |

TABLE 12

Light chain analysis

| Chain Name | SEQ ID NO: | V | J | FR1 | CDR1 | FR2 | CDR2 | FR3 | CDR3 | J |
|---|---|---|---|---|---|---|---|---|---|---|
|  | 628 |  | Germline | EIVLTQSPGTLSLSPGERATLSC | RASQSVSSSYLA | WYQQKPGQAPRLLIY | GASSRAT | GIPDRFSGSGSGTDFTLTISRLEPEDFAVYYC | QQYGSSPWT | FGQGTKVEIKR |
| 5.77 | 423 | A27 | JK1 | EVVLTQSPGTLSLSPGDRATLSC | RASQSVSSSYLA | WYNQKPGQAPRLLIF | GASSRAT | GIPDRFSGSGSGTDFTLTISRLEPEDFAVYYC | LQYGSSPWT | FGQGTKVEIKR |
|  | 629 |  | Germline | DIQMTQSPSSLSASVGDRVTITC | QASQDISNYLN | WYQQKPGKAPKLLIY | DASNLET | GVPSRFSGSGSGTDFTFTISSLQPEDIATYYC | QQYDN | FGQGTKLEIKR |
| 5.61 | 379 | O18 | JK2 | DIQMTQSPSSLSASVGDRVTITC | QASQDISNYLN | WYQQKPGKAPKLLIY | DASNLET | GVPSRFSGSGSGTDFTFTISRLQPEDIATYYC | QQYDNLCS | FGQGTKLEIKR |
|  | 630 |  | Germline | DIQMTQSPSSVSASVGDRVTITC | RASQGISSWLA | WYQQKPGKAPKLLIY | AASSLQS | GVPSRFSGSGSGTDFTLTISSLQPEDFATYYC | QQANSFPWT | FGQGTKVEIKR |
| 5.3 | 199 | L5 | JK1 | DIQMTQSPSSVSASVGDRVTITC | RASQGIRSWLA | WYQQKPGKAASSLQSAPKLLIY | AASSLQS | GVPSRFSGSGSGTDFTLTISSLQPEDFATYYC | QQANSFPWT | FGQGTKVEIKR |
| 3.2 | 13 | L5 | JK1 | DIQMTQSPSSVSASVGDRVTITC | RASQGISSWLA | WYQQKPGKAPKLLIY | AASSLQS | GVPSRFSGSGSGTDFTLTISSLQPEDFATYYC | QQAYSFRT | FGQGTKVEIKR |
| 5.34 | 295 | L5 | JK1 | DIQMTQSPSSVSASVGDRVTITC | RASQGISSWLA | WYQQKPGKAPKLLIY | AASSLQS | GVPSRFSGSGSGTDFTLTISSLQPEDFATYYC | QQANSFPWT | FGQGTKVEIKR |
| 3.22 | 91 | L5 | JK1 | DIQMTQSPFSVSASVGDRVTITC | RASQGISNWLA | WYQQKPGKAPKLLIY | TASSLQN | GVPSRFSGSGSGTDFTLTISSLQPEDFATYYC | QQINSFPWT | FGQGTKVEIKR |
| 5.73 | 411 | L5 | JK1 | DIQMTQSPSSVSASVGDRVTITC | RASQGISRWLA | WYQQKPGKAPKLLIY | VASSLQS | GVPSRFSGSGSGTDFTLTISSLQPEDFATYYC | QQANSFPRT | FGQGTKVEIKR |

TABLE 12-continued

Light chain analysis

| Chain Name | SEQ ID NO: | V | J | FR1 | CDR1 | FR2 | CDR2 | FR3 | CDR3 | J |
|---|---|---|---|---|---|---|---|---|---|---|
| 5.1 | 193 | L5 | JK1 | DIQMTQSPSSVS ASVGDRVTITC | RASQGIRSWLA | WYQQKPGK APKLLIY | AASSLQS | GVPSRFSGSGSGTDFT LTISSLQPEDFATYYC | QQANSFPWT | FGQGTKVEIKR |
| 3.9 | 41 | L5 | JK1 | DIQMTQSPSSVS ASVGDRVTITC | RASQGISSWLA | WYQQKPGK APNLLIY | AASSLQS | GVPSRFSGSGSGTDFI LTISSLQPEDFATYYC | QQNSFPRT | FGQGTKVEIKR |
| 5.81 | 441 | L5 | JK1 | DIQMTQSPSSVS ASVGDRVTITC | RASQGISSWLA | WYQQKPGK APKLLIY | AASSLQS | GVPSRFSGSGSGTDFT LTISSLQPEDFATYYC | QQANSFPRT | FGQGTKVEIKR |
|  | 631 |  | Germline | ETTLTQSPAFMS ATPGDKVNISC | KASQDIDDDMN | WYQQKPGE AAIFIIQ | EATTLVP | GIPPRFSGSGYGTDFT LTINNIESEDAAYYFC | LQHDNFPLT | FGGGTKVEIKR |
| 5.24 | 269 | B2 | JK4 | ETTLTQSPAFMS ATPGDKVNISC | KASQDIDDDMN | WYQQKPGE VAIFIIQ | EATTLVP | GIPPRFSGSGYGTDFT LTINNIESEDAAYYFC | LQHDNFPLT | FGGGTKVEIKR |
|  | 632 |  | Germline | DIQMTQSPSSLS ASVGDRVTITC | RASQGISNYLA | WYQQKPGK VPKLLIY | AASTLQS | GVPSRFSGSGSGTDFT LTISSLQPEDVATYYC | QKYNSAPFT | FGPGTKVDIKR |
| 5.56.1 | 365 | A20 | JK3 | DIQMTQSPSSLS ASVGDRVTITC | RASQGISYYLA | WYQQKPGK VPKLLIY | AASTLQS | GVPSRFSGSGSGTDFT LTISSLQPEDVATYYC | QKYNSAPFT | FGPGTKVDIKR |
|  | 633 |  | Germline | EIVMTQSPATLS VSPGERATLSC | RASQSVSSNLA | WYQQKPGQ APRLLIY | GASTRAT | GIPARFSGSGSGTEFT LTISSLQSEDFAVYYC | QQYNNWPLT | FGGGTKVEIKR |
| 5.6 | 207 | L2 | JK4 | EIVMTQSPATLS VSPGERATLSC | RASQSVSSNLA | WYQQKPGQ APRLLIY | GASTRAT | GIPARFSGSGSGTELT LTISSLQSEDFAVYYC | QQYNNWPLT | FGGGTKVEIKR |
| 5.44 | 331 | L2 | JK4 | EIVMTQSPATLS VSPGERATLSC | RASQSISSNLA | WYQQKPGQ APRLLIY | GASTRAT | GIPARFSGSGSGTEFT LTISSLQPEDFAVYYC | QQYNNWPLT | FGRGTKVEIKR |
| 5.38 | 311 | L2 | JK4 | EIVMTQSPATLS VSPGERVTLSC | RASQSVSGNLA | WYQQKPGQ APRLLIY | GASTRAT | GIPARFSGSGSGTEFT LTISSLQSEDFAVYYC | QHYNNWPLT | FGGGTKVEIKR |
| 5.35 | 299 | L2 | JK4 | EIVMTQSPATLS VSPGERATLSC | RASQSVSSNLA | WYQQKPGQ APRLLIY | GASTRAT | GIPARFSGSGSGTEFT LTISSLQSEDFAVYYC | EQYNNWPLT | FGGGTKVEIKR |
| 5.8 | 213 | L2 | JK4 | EIVMTQSPATLS VSLGERATLSC | RASQSVRSNLA | WYQQKPGQ APRLLIY | GASTRAT | GIPARFSGSGSGTELT LTISSLQSEDFAVYYC | HQYNNWPLT | FGGGTKVEIKR |
| 5.35.1 | 299 | L2 | JK4 | EIVMTQSPATLS VSPGERATLSC | RASQSVSSNLA | WYQQKPGQ APRLLIY | GASTRAT | GIPARFSGSGSGTEFT LTISSLQSEDFAVYYC | EQYNNWPLT | FGGGTKVEIKR |
|  | 634 |  | Germline | DIQMTQSPSSLS ASVGDRVTITC | RASQGIRNDLG | WYQQKPGK APKRLIY | AASSLQS | GVPSRFSGSGSGTEFT LTISSLQPEDFATYYC | LQHNSYPFT | FGPGTKVDIKR |
| 4.13 | 173 | A30 | JK3 | DIQMTQSPSSLS ASVGDRVTITC | RASQGIRDDLG | WYQQKPGK APKRLTY | AASSLQS | GVPSRFSGSGSGTEFT LTISSLQPEDFATYYC | LQYNSYPFT | FGPGTKVDIKR |
|  | 635 |  | Germline | EIVMTQSPATLS VSPGERATLSC | RASQSVSSNLA | WYQQKPGQ APRLLIY | GASTRAT | GIPARFSGSGSGTEFT LTISSLQSEDFAVYYC | QQYNNWPFT | FGPGTKVDIKR |
| 5.28.1 | 279 | L2 | JK3 | EIVMTQSPATLS VSPGERATLSC | RASQSVTSNLA | WYQQKPGQ APRLLIY | GALIRAT | GIPARFSGSGSGTEFT LTISSLQSEDFAVYYC | QQYNNWPFT | FGPGTKVDIKR |
| 5.28 | 279 | L2 | JK3 | EIVMTQSPATLS VSPGERATLSC | RASQSVTSNLA | WYQQKPGQ APRLLIY | GALIRAT | GIPARFSGSGSGTEFT LTISSLQSEDFAVYYC | QQYNNWPFT | FGPGTKVDIKR |
|  | 636 |  | Germline | DIQMTQSPSSLS ASVGDRVTITC | RASQGIRNDLG | WYQQKPGK APKRLIY | AASSLQS | GVPSRFSGSGSGTEFT LTISSLQPEDFATYYC | LQHNSYP | FGQGTKLEIKR |
| 4.4 | 149 | A30 | JK2 | DIQMTQSPSSLS ASVGDRVTITC | RASQGIRNDLG | WYQQKPGK APKRLIY | AASSLQS | GVPSRFSGSRSGTEFT LTISSLQPEDFATYYC | LQHNSYPPS | FGQGTKLEIKR |
| 3.33 | 113 | A30 | JK2 | DIQMTQSPSSLS ASVGDRVTITC | RASQGIRNDLG | WYQQKPGK APKRLIY | AASSLQS | GVPSRFSGSRSGTEFT LTISSLQPEDFATYYC | LQHNSYPPS | FGQGTKLEIKR |
| 3.39 | 127 | A30 | JK2 | DIQMTQSPSSLS ASVGDRVTITC | RASQGIRNDLG | WYQQKPGK APKRLIY | AASSLQS | GVPSRFSGSRSGTEFT LTISSLQPEDFATYYC | LQHNSYPPS | FGQGTKLEIKR |
|  | 637 |  | Germline | DIQMTQSPSSLS ASVGDRVTITC | RASQGIRNDLG | WYQQKPGK APKRLIY | AASSLQS | GVPSRFSGSGSGTEFT LTISSLQPEDFATYYC | LQHNSYPRT | FGQGTKVEIKR |
| 3.26 | 95 | A30 | JK1 | DIQMTQSPSSLS ASVGDRVTITC | RASQGIRNDLG | WYQQKPGK APKRLIY | AASSLQS | GVPSRFSGSGSGTDFT LTISSLQPEDFATYYC | LQHNNYPRT | FGQGTKVEIKR |

TABLE 12-continued

Light chain analysis

| Chain Name | SEQ ID NO: | V | J | FR1 | CDR1 | FR2 | CDR2 | FR3 | CDR3 | J |
|---|---|---|---|---|---|---|---|---|---|---|
| 3.11 | 49 | A30 | JK1 | DIQMTQSPSSLS TSVGDRVTITC | RASQGIRNDLG | WYQQKPGK APKRLIY | AASSLQS | GVPSRFSGSGSGTEFT LTISSLRPEDFATYYC | LQLNSYPRT | FGQGTKVEIKR |
| 3.1 | 9 | A30 | JK1 | DIQMTQSPSSLS ASVGDRVTITC | RASQGIRNDLG | WYQQKPGK APKRLIY | AASSLQS | GVPSRFSGSGSGTEFT LTISSLQPEDFATYYC | LQHNSYPRT | FGQGTKVEIKR |
| 4.15 | 181 | A30 | JK1 | DIQMTQSPSSLS ASVGDRVTITC | RASQGIRNDLG | WYQQKPGK APKRLIY | AASSLQS | GVPSRFSGSGSGTEFT LTISSLQPEDFATYYC | LQHNSYPPT | FGQGTKVEIKR |
| 3.18 | 73 | A30 | JK1 | DIQMTQSPSSLS ASVGDRVTITC | RASQGIRNDLG | WYQQKPGK APKRLIY | AASSLQS | GVPSRFSGSGSGTEFT LTISSLQPEDFATYYC | LQYNSYPRT | FGQGTKVEIKR |
|  | 638 |  | Germline | EIVMTQSPATLS VSPGERATLSC | RASQSVSSNLA | WYQQKPGQ APRLLIY | GASTRAT | GIPARFSGSGSGTEFT LTISSLQSEDFAVYYC | QQYNNWPRT | FGQGTKVEIKR |
| 5.16.1 | 241 | L2 | JK1 | EIVMTQSPATLS VSPGERATLSC | RASQSVSSNLA | WYQQKPGQ APRLLIF | GASTRAT | GIPARFSGSGSGTEFT LTISSLQSEDFAVYYC | QQYNNWWT | FGRGTKVEIKR |
| 5.40.2 | 319 | L2 | JK1 | EIVMTQSPATLS VSPGERATLSC | RASQSVSSNLV | WYQQKPGQ APRLLIY | DSSTRAT | GIPVRFSGSGSGTEFT LTISSLQSEDFAVYYC | QQYNHWWT | FGQGTKVEIKR |
| 5.41.1 | 323 | L2 | JK1 | EIVMTQSPATLS VSPGERATLSC | RASQSVSSNLA | WYQQKPGQ APRFLIY | GASTRAT | GIPARFSGSGSGTEFT LTISSLQSEDFAVYYC | QQYNHWWT | FGQGTKVEIKR |
| 6.4 | 543 | L2 | JK1 | EIVMTQSPATLS VSPGERATLSC | RASQSLISNLA | WYQQKPGQ APRQLLF | GASTRAT | GIPARFSGSGSGTEFT LTISSLQSEDFAVYYC | HQYNNWWT | FGQGTKVEIKR |
| 5.103.1 | 505 | L2 | JK1 | ETVMTQSPATLS VSPGERVTLSC | RASQSVISSLA | WYQQKPGQ APRLLIY | GASTRAT | GIPARFSGSGSGTEFT LTISSLQSEDFAVYYC | QQYNNWWT | FGQGTKVEIKR |
| 5.54.1 | 359 | L2 | JK1 | EIVMTQSPATLS VSPGERATLSC | RASQSLISNLA | WYQQKPGQ APRLLIF | GASTRAT | GIPARFSGSGSGTEFT LTISSLQSEDFAVYYC | HQYNNWWT | FGQGTKVEIKR |
| 5.13 | 231 | L2 | JK1 | EIVMTQSPATLS VSPGERATLSC | RASQSVSSNLA | WYQQKPGQ APRLLIY | GASTRAT | GIPARFSGSGSGTEFT LTISSLQSEDFAVYYC | QQYNHWWT | FGQGTKVEIKR |
| 3.31.1 | 101 | L2 | JK1 | EVVMTQSPATLS VSPGERATLSC | RASQSVGSNLA | WYQQKPGQ APRLLIY | GASTRAT | GIPARFSGSGSGTEFT LTISSLQSEDFAVYCC | QQYNHWWT | FGQGTKVEIKR |
| 5.88.1 | 467 | L2 | JK1 | EIVMTQSPATLS VSPGERATLSC | RASQSISSNLA | WYQQKPGQ APRLLIY | GASTRAT | GIPARFSGSGSGTEFT LTISSLQSEDFAVYYC | QQYNYWWT | FGQGTKVEIKR |
| 3.3 | 17 | L2 | JK1 | EIVMTQSPATLS VSPGERATLSC | RASQTVSSDLA | WYQQKPGQ APRLLIY | GASIRAT | GIPARFSGSGSGTEFT LTISSLQSEDFAVYSC | QQYYNWWT | FGQGTKVEIKR |
| 5.62 | 383 | L2 | JK1 | EIVMTQSPATLS VSPGERATLSC | RASQSVSSNLA | WYQQKPGQ APRLLIY | GAFTRAT | GIPARFSGSGSGTEFT LTISSLQSEDFAVYYC | QQYNHWWT | FGQGTKVGIKR |
| 5.101 | 499 | L2 | JK1 | EIVMTQSPATLS VSPGERATLSC | RASQSLISNLA | WYQQKPGQ APRLLIF | GASTRAT | GIPARFSGSGSGTEFT LTISSLQSEDFAVYYC | HQYNNWWT | FGQGTKVEIKR |
| 5.52 | 349 | L2 | JK1 | EIVMTQSPATLA VSPGERATLSC | RARQSVSSNLA | WYQQKPGQ APRLLIY | GASTMAT | GFPARFSGRGSGTEFT LTISSLQSEDFAVYYC | QQYNNWWT | FGQGTKVEIKR |
| 5.16 | 241 | L2 | JK1 | EIVMTQSPATLS VSPGERATLSC | RASQSVSSNLA | WYQQKPGQ APRLLIF | GASTRAT | GIPARFSGSGSGTEFT LTISSLQSEDFAVYYC | QQYNNWWT | FGRGTKVEIKR |
| 5.39 | 315 | L2 | JK1 | EIVMTQSPATLS VSPGDRATLSC | RASQSVSSNFA | WYQQKPGQ APRLLIY | GSSTRAT | GIPARFSGSGSGTEFT LTISSLQSEDFAVYYC | QQYHYWWT | FGQGTKVEFKR |
| 3.6 | 29 | L2 | JK1 | EIVMTQSPATLS VSPGERATLSC | RASQSISSNLA | WFQQKPGQ APRLLIY | GASTRAT | GIPARFSGSGSGTEFT LTISSLQSEDFAVYYC | QQYNNWPRT | FGQGTTVEIKR |
| 5.39.1 | 315 | L2 | JK1 | EIVMTQSPATLS VSPGDRATLSC | RASQSVSSNFA | WYQQKPGQ APRLLIY | GSSTRAT | GIPARFSGSGSGTEFT LTISSLQSEDFAVYYC | QQYHYWWT | FGQGTKVEFKR |
| 5.15 | 237 | L2 | JK1 | EIVMTQSPATLS VSPGERATLSC | RASQTVISNLA | WYQQKPGQ APRLLIY | GASTRAT | GIPARFSGSGSGTEFT LTISSLQSEDFALYYC | QQYNNWWT | FGQGTKVEIKR |
| 5.83.1 | 451 | L2 | JK1 | EIVMTQSPATLS VSPGERATLSC | RASQSLISNLA | WYQQKPGQ APRLLIF | GASTRAT | GIPARFSGSGSGTEFT LTISSLQSEDFAVYYC | HQYNNWWT | FGQGTKVEIKR |
| 5.41 | 323 | L2 | JK1 | EIVMTQSPATLS VSPGERATLSC | RASQSVSSNLA | WYQQKPGQ APRFLIY | GASTRAT | GIPARFSGSGSGTEFT LTISSLQSEDFAVYYC | QQYNHWWT | FGQGTKVEIKR |

TABLE 12-continued

Light chain analysis

| Chain Name | SEQ ID NO: | V | J | FR1 | CDR1 | FR2 | CDR2 | FR3 | CDR3 | J |
|---|---|---|---|---|---|---|---|---|---|---|
| 5.62.1 | 383 | L2 | JK1 | EIVMTQSPATLSVSPGERATLSC | RASQSVSSNLA | WYQQKPGQAPRLLIY | GAFTRAT | GIPARFSGSGSGTEFTLTISSLQSEDFAVYYC | QQYNHWWT | FGQGTKVGIKR |
| 5.64 | 387 | L2 | JK1 | EIVMTQSPATLSVSPGERATLSC | RASQSVSSNLA | WYQQKPGQAPRLLIY | GASTRAT | GIPARFSGSGSGTEFTLTISSLQSEDFAVYYC | QQYNNWWT | FGQGTKVEIKR |
| 5.101.1 | 499 | L2 | JK1 | EIVMTQSPATLSVSPGERATLSC | RASQSLISNLA | WYQQKPGQAPRLLIF | GASTRAT | GIPARFSGSGSGTEFTLTISSLQSEDFAVYYC | HQYNNWWT | FGQGTKVEIKR |
| 5.103 | 505 | L2 | JK1 | ETVMTQSPATLSVSPGERVTLSC | RASQSVISSLA | WYQQKPGQAPRLLIY | GASTRAT | GIPARFSGSGSGTEFTLTISSLQSEDFAVYYC | QQYNNWWT | FGQGTKVEIKR |
| 5.54 | 359 | L2 | JK1 | EIVMTQSPATLSVSPGERATLSC | RASQSLISNLA | WYQQKPGQAPRLLIF | GASTRAT | GIPARFSGSGSGTEFTLTISSLQSEDFAIYYC | HQYNNWWT | FGQGTKVEIKR |
| 5.13.1 | 231 | L2 | JK1 | EIVMTQSPATLSVSPGERATLSC | RASQSVSSNLA | WYQQKPGQAPRLLIY | GASTRAT | GIPARFSGSGSGTEFTLTISSLQSEDFAVYYC | QQYNHWWT | FGQGTKVEIKR |
| 5.109 | 519 | L2 | JK1 | EIVMTQSPATLSVSPGERATLSC | RASQSVSSYLA | WYQQKPGQAPRLLIY | GAFTRAT | GIPARFRGSGSGPEFTLTISSLQSEDFAVYYC | QQYSHWWT | FGQGTKVEIKR |
| 5.108.1 | 515 | L2 | JK1 | EIVMTQSPATLSVSPGERATLSC | RASQSVSSYLA | WYQQKPGQAPRLLIY | GAFTRAT | GIPARFRGSGSGPEFTLTISSLQSEDFAVYYC | QQYSHWWT | FGQGTKVEIKR |
| 3.3.1 | 21 | L2 | JK1 | EIVMTQSPATLSVSPGERATLSC | RASQTVSSDLA | WYQQKPGQAPRLLIY | GASIRAT | GIPARFSGSGSGTEFTLTISSLQSEDFAVYSC | QQYYNWWT | FGQGTKVEIKR |
|  | 639 |  | Germline | DIVMTQSPLSLPVTPGEPASISC | RSSQSLLHSNGYNYLD | WYLQKPGQLGSNRASSPQLLIY |  | GVPDRFSGSGSGTDFTLKISRVEAEDVGVYYC | MQALQTPIT | FGQGTRLEIKR |
| 5.92 | 483 | A3 | JK5 | DIVMTQSPLSLPVTPGEPASISC | RSSQSLLYSNGYNYLD | WYLQKPGQLGSNRASSPQVLIY |  | GVPDRFSGSGSGTDFTLKISRVEAEDVGVYYC | MQALQTPIT | FGQGTRLEIKR |
| 5.82 | 445 | A3 | JK5 | DIVMTQSPLSLPVTPGEPASISC | RSSQSLLHSNGYNYLD | WYLQKPGQLGSNRASSPLLIY |  | GVPDRFSGSGSGTDFTLKISRVEAEDVGVYYC | MQALQTPIT | FGQGTRLEIKR |
|  | 640 |  | Germline | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPPLT | FGQGTKVEIKR |
| 3.41 | 135 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPLT | FGGGTNVEIKR |
| 3.40 | 131 | A1 | JK4 | DVVMTQSPLSLPVTLGQPASISC | RSSQSLVYSDGNTYLN | WFQQRPGQKDSNWDSSPRRLIY |  | GVPDRFSGSGSGTDFTLKISRVEAEDVGVYYC | MQGTHWPLT | FGGGTNVEIKR |
| 3.13 | 57 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPPLT | FGGGTKVEIKR |
| 3.12 | 53 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPPLT | FGGGTKVEIKR |
| 3.32 | 109 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPPLT | FGGGTKVEIKR |
| 4.18 | 189 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPLT | FGGGTNVEIKR |
| 4.16 | 185 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPPLT | FGGGTKVEIKR |
| 3.7 | 33 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPPLT | FGGGTKVEIKR |
| 4.14 | 177 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPPLT | FGGGTKVEIKR |
| 3.15 | 63 | A1 | JK4 | DVVMTQSPLSLPVTLGQPASISC | RSSQSLVYSDGNTYLN | WFQQRPGQKVSNWDSSPRRLIY |  | GVPDRFSGSGSGTDFTLKISRVEAEDVGVYYC | MQGTHWPPLT | FGGGTKVEIKR |
|  | 641 |  | Germline | DIVMTQSPLSLPVTPGEPASISC | RSSQSLLHSNGYNYLD | WYLQKPGQLGSNRASSPQLLIY |  | GVPDRFSGSGSGTDFTLKISRVEAEDVGVYYC | MQALQTPLT | FGGGTKVEIKR |
| 3.10 | 45 | A3 | JK4 | DIVMTQSPLSLPVTPGEPASISC | RSSQSLLHSNGYNYLD | WYLQKPGQLGSNRASSPQLLIY |  | GVPDRFSGSGSGTDSTLKISRVEAEDVGVYYC | MQALQTPLT | FGGGTKVEIKR |

TABLE 12-continued

Light chain analysis

| Chain Name | SEQ ID NO: | V | J | FR1 | CDR1 | FR2 | CDR2 | FR3 | CDR3 | J |
|---|---|---|---|---|---|---|---|---|---|---|
| 3.37 | 123 | A3 | JK4 | DIVMTQSPLSLP VTPGEPASISC | RSSQSLLHSDG YNYLD | WYLQKPGQ SPQLLIY | LGSNRAS | GVPDRFSGSGSCTDFT LKISRVEAEDVGIYYC | MQALQTPHF | FGGGTKVEIKR |
| | 642 | | Germline | DIVMTQSPDSLA VSLGERATINC | KSSQSVLYSSN NKNYLA | WYQQKPGQ PPKLLIY | WASTRES | GVPDRFSGSGSGTDFT LTISSLQAEDVAVYYC | QQYYSTPIT | FGGGTRLEIKR |
| 5.78 | 427 | B3 | JK5 | DIVMTQSPDSLA VSLGERATINC | KSSQSVLYSSN NQNFLA | WYQQKPGQ PPKLLIY | WASTRES | GVPDRFSGSGSGTDFT LTISSLQAEDVAVYYC | HQYYSTPIT | FGGGTRLEIKR |
| 5.90 | 477 | B3 | JK5 | DIVMTQSPDSLA VSLGEKATINC | KSSQSVIYSSN NQNFLA | WYQHKPGQ PPKLLIY | WASTRES | GVPDRFSGSGSGTDFT LTISSLQAEDVAVYYC | HQYYSTPIT | FGGGTRLEIKR |
| 5.78.1 | 431 | B3 | JK5 | DIVMTQSPDSLA VSLGERATINC | KSSQSVLYSSN NQNFLA | WYQQKPGQ PPKLLIY | WASTRES | GVPDRFSGSGSGTDFT LTISSLQAEDVAVYYC | HQYYSTPIT | FGGGTRLEIKR |
| | 643 | | Germline | DVVMTQSPLSLP VTLGQPASISC | RSSQSLVYSDG NTYLN | WFQQRPGQ SPRRLIY | KVSNWDS | GVPDRFSGSGSGTDFT LKISRVEAEDVGVYYC | MQGTHW | FGGGTKLEIKR |
| 4.3 | 147 | A1 | JK2 | DVVMTQSPLSLP VTLGQPASISC | RSSRSLVYSDG NTYLN | WFQQRPGQ SPRRLIY | KVSNWDS | GVPDRFSGSGSGTDFT LKISRVEAADVGVYYC | MQGTHWPCS | FGGGTKLEIKR |
| | 644 | | Germline | DIVMTQSPDSLA VSLGERATINC | KSSQSVLYSSN NKNYLA | WYQQKPGQ PPKLLIY | WASTRES | GVPDRFSGSGSGTDFT LTISSLQAEDVAVYYC | QQYYSTT | FGGGTKVEIKR |
| 5.43 | 327 | B3 | JK4 | DIVMTQSPDSLA VSLGERATINC | KSSQSVLYSSN NKNYLA | WYQQKPGQ PPKLLIY | WSSTRES | GVPDRFSGSGSGTDFT LTISSLQAEDVAVYYC | QQYYSTPLT | FGGGTKVEIKR |
| | 645 | | Germline | DVVMTQSPLSLP VTLGQPASISC | RSSQSLVYSDG NTYLN | WFQQRPGQ SPRRLIY | KVSNWDS | GVPDRFSGSGSGTDFT LKISRVEAEDVGVYYC | MQGTHWPPT | FGGGTKVEIKR |
| 3.20 | 83 | A1 | JK1 | DVVMTQSPLSLP VTLGQPASISC | RSSQSLVYSDG NTYLN | WFQQRPGQ SPRRLIY | KVSKWDS | GVPDRFSGSGSGTDFT LKISRVEAEDVGVYYC | MQGTHWPPT | FGGGTKVEIKR |
| | 646 | | Germline | DIVMTQSPLSLP VTPGEPASISC | RSSQSLLHSNG YNYLD | WYLQKPGQ SPQLLIY | LGSNRAS | GVPDRFSGSGSGTDFT LKISRVEAEDVGVYYC | MQALQWT | FGGGTKVEIKR |
| 5.9 | 647 | A3 | JK1 | DIVMTQSPLSLP VTPGEPASISC | RSSQSLLHSNG YNYLD | WYLQKPGQ SPQLLIY | LGSNRAS | GVPDRFSGSGSGTDFT LKISRVEAEDVGVYYC | MQALQTPWT | FGGGTKVEIKR |
| 4.11 | 169 | A3 | JK1 | DIVMTQSPLSLP VTPGEPASISC | RSSQSLLYSNG YNYLD | WYLQKPGQ SPQLLIY | LGSNRAS | GVPDRFGGSGSGTDFT LKISRVEAEDVGVYYC | MQALQTPWT | FGGGTKVEIKR |
| | 648 | | Germline | DIQMTQSPSSLS ASVGDRVTITC | RASQSISSYLN | WYQQKPGK APKLLIY | AASSLQS | GVPSRFSGSGSGTDFT LTISSLQPEDFATYYC | QQSYSTT | FGGGTKVEIKR |
| 5.115 | 531 | O12 | JK4 | DIEMTQSPSSLS ASVGDRVTITC | RASQNISSYLN | WYQQKPGK APKLLIY | AASSLQS | GVPSRFSGSGSGTDFT LTISSLQPEDFATYYC | QQSYSSPLT | FGGGTKVEIKR |
| 5.66 | 391 | O12 | JK4 | DIQMTQSPSSLS ASVGDRVTITC | RASQSISSYFN | WYQQKPGK APKLLIY | AASSLQS | GVPSRFSGSGSGTDFT LTISSLQPEDFATYYC | QQSYSTPLT | FGGGTKVEIKR |
| 5.72 | 407 | O12 | JK4 | DIQMTQSPSSLS ASVGDRVTITC | RASQTISSYLN | WYQQKPGK APKLLIY | AASSLQS | GVPSRFSGSGSGTDFT LTISSLQPEDFATYYC | QQTYSKSLT | FGGGTKVEIKR |
| 5.114 | 527 | O12 | JK4 | DIEMTQSPSSLS ASVGDRVTITC | RASQNISSYLN | WYQQKPGK APKLLIY | AASSLQS | GVPSRFSGSGSGTDFT LTISSLQPEDFATYYC | QQSYSSPLT | FGGGTKVEIKR |
| 4.5 | 153 | O12 | JK4 | DIQMTQSPSSLS ASVGDRVTITC | RASQSISIYLN | WYQQKPGK APKLLIY | AASSLQS | GVPSRFSGSGSGTDFT LTISSLQPEDFATYYC | QQSYSTPLT | FGGGTKVEIKR |
| | 649 | | Germline | DIVMTQSPDSLA VSLGERATINC | KSSQSVLYSSN NKNYLA | WYQQKPGQ PPKLLIY | WASTRES | GVPDRFSGSGSGTDFT LTISSLQAEDVAVYYC | QQYYST | FGGGTKLEIKR |
| 3.42 | 139 | B3 | JK2 | DIVMTQSPDSLA VSLGERATINC | RSSQSILFSSN NKNYLA | WYQQKPGQ PPKLLLY | WASTRES | GVPARFSGSGSGTDFT LTISSLQAEDVAVYYC | QQYYSTPCS | FGGGTRLEIKR |
| 5.60 | 375 | B3 | JK2 | DIVMTQSPDSLA VSLGERATINC | KSSQSVLYSSN NKNYLV | WYQQKPGQ PPKLLIY | WASTRES | GVPDRFSGSGSGTDFT LTISSLQAEDVAVYYC | QQYYNTPCS | FGGGTKLEIKR |
| | 650 | | Germline | EIVLTQSPGTLS LSPGERATLSC | RASQSVSSSYL A | WYQQKPGQ APRLLIY | GASSRAT | GIPDRFSGSGSGTDFT LTISRLEPEDFAVYYC | QQYGIT | FGGGTRLEIKR |
| 5.58 | 369 | A27 | JK5 | EIVLTQSPGTLS LSPGERATLSC | RASQSVSSSYL A | WYQQKAGQ APRLLIY | GASSRAT | GIPDRFSGSGSGTDFT LTISRLEPEDFAVYYC | QQYGWSSIT | FGGGTRLEIKR |

TABLE 12-continued

Light chain analysis

| Chain Name | SEQ ID NO: | V | J | FR1 | CDR1 | FR2 | CDR2 | FR3 | CDR3 | J |
|---|---|---|---|---|---|---|---|---|---|---|
| 3.19.1 | 77 | A27 | JK5 | EIVLTQSPGTLS LSPGERATLSC | RASQSITGSYL A | WYQQKPGQ APRLLIC | GASSWAT | GIPDRFSGSGSGTDFT LTISRLEPEDFAVYYC | QQYSSSPIT | FGQGTRLEIKR |
|  | 651 | Germline |  | DIQMTQSPSSLS ASVGDRVTITC | RASQGISNYLA | WFQQKPGK APKSLIY | AASSLQS | GVPSRFSGSGSGTDFT LTISSLQPEDFATYYC | QQYNSYPLT | FGGGTKVEIKR |
| 3.16 | 65 | L1 | JK4 | DIQMTQSPSSLS ASVGDRVTITC | RASQGISSYLA | WFQQKPGK APKSLIY | AASSLQS | GVPSKFSGSGSGTDFT LTISSLQPEDFATYYC | QQYNSYPLT | FGGGTKVEIKR |
| 5.67 | 395 | L1 | JK4 | DIQMTQSPSSLS ASVGDRVTITC | RASQGISNYLA | WFQQKPGK APESLIY | AASSLQT | GVPSKFSGNGSGTDFT LTISSLQPEDFATYYC | QQYNSYPLT | FGGGTKVEIKR |
|  | 652 | Germline |  | DIQMTQSPSSLS ASVGDRVTITC | RASQSISSYLN | WYQQKPGK APKLLIY | AASSLQS | GVPSRFSGSGSGTDFT LTISSLQPEDFATYYC | QQYSTPFT | FGPGTKVDIKR |
| 5.86 | 455 | O12 | JK3 | DIRMTQSPSSLS ASVGDRVTITC | RASQRISTYLN | WYQQKPGK APKFLIY | AASSLQS | GVPSRFSGSGSGTDFT LTISSLQPEDFATYYC | QQSYTTPFT | FGPGTKVDIKR |
| 5.71 | 403 | O12 | JK3 | DIQMTQSPSSLS ASVGDRVTITC | RASQSISNYLN | WYQQKPGK APKLLIF | TASSLQS | GVPSRFSGSGSGTDFT LTISSLQPEDFATYFC | QQSYSTPFT | FGPGTKVGIKR |
| 5.25 | 271 | O12 | JK3 | DIRMTQSPSSLS ASVGDRVTITC | RASQRISSYLN | WFQQKPGK APKFLIY | AASSLQS | GVPSRFSGSGSGTDFT LTISSLQPEDFATYYC | QQSYSTPFT | FGPGTKVDIKR |
| 5.74 | 415 | O12 | JK3 | DIRMTQSPSSLS ASVGDRVTITC | RASQRISTYLN | WYQQKPGK APKFLIY | AASSLQS | GVPSRFSGSGSGTDFT LTISSLQPEDFATYYC | QQSYTTPFT | FGPGTKVDIKR |
| 3.14 | 61 | O12 | JK3 | DIQMTQSPSSLS ASVGDRVTITC | RASQSISSYLN | WYQQKPGK APKLLIY | AASSLQS | GVPSRFSGSGSGTDFT LTISSLQAEDFATYYC | QQSLT | FGPGTKVDIKR |
| 5.111 | 523 | O12 | JK3 | DIQMTQSPSSLS ASVGDRVTFTC | RASQSIITFLN | WFQHKPGK APKLLFY | GASSLES | GVPSRFSGSGSGTNFT LTISSLQPEDFATYYC | QQSYSDPFT | FGPGTKVDIKR |
| 5.87 | 459 | O12 | JK3 | DIRMTQSPSSLS ASVGDRVTITC | RASQGIRTYLN | WYQQKPGK APKLLIY | AASSLQS | GVPSRFSGSGSGTDFT LTISSLQPEDFATYYC | QQNYTTPFT | FGPGTKVDIKR |
| 4.2 | 143 | O12 | JK3 | DIQMTQSPSSLS ASVGDRVTITC | RASQSISFYLN | WYQQKPGK APKLLIY | AASSLQS | GVPSRFSGSGSGTDFT LTISSLQPEDFATYYC | QQSYSSPFT | FGPGTKVDIKR |
| 5.86.1 | 455 | O12 | JK3 | DIRMTQSPSSLS ASVGDRVTITC | RASQRISTYLN | WYQQKPGK APKFLIY | AASSLQS | GVPSRFSGSGSGTDFT LTISSLQPEDFATYYC | QQSYTTPFT | FGPGTKVDIKR |
| 3.17 | 69 | O12 | JK3 | DIQMTQSPSSLS ASVGDRITITC | RARQSISSYLN | WYQQKPGK APKLLIY | AASSLQS | GVPSRFSGSGSGTDFT LTISSLQPEDFATYFC | QQSYSTPFT | FGPGAKVDIKR |
| 5.11 | 223 | O12 | JK3 | DIQMTQSPSSLS ASVGDRVTITC | RASQSISNYLN | WYQQKPGK APKLLIY | AASSLQS | GVPSRFSGSGSGTDFT LTISSLQPEDFATYYC | QQSYSIPFT | FGPGTKVDIKR |
| 5.45 | 335 | O12 | JK3 | DIQMTQSPSSLS ASVGDRVTITC | RASQSISSYLN | WYQQKPGK APELLIY | AASSLQS | GVPSRFSGSGSGTDFT LTISSLQPEDFATYYC | QQSYINPFT | FGPGTKVDIKR |
| 5.12 | 227 | O12 | JK3 | DIQMTQSPSSLS ASVGDRVTITC | RASQSISNYLN | WYQQKPGK APKLLIY | AASSLQS | GVPSRFSGSGSGTDFT LTISSLQPEDFATYYC | QQSYSIPFT | FGPGTKVDIKR |
|  | 653 | Germline |  | EIVLTQSPGTLS LSPGERATLSC | RASQSVSSSYL A | WYQQKPGQ APRLLIY | GASSRAT | GIPDRFSGSGSGTDFT LTISRLEPEDFAVYYC | QQYGSST | FGGGTKVEIKR |
| 6.2 | 537 | A27 | JK4 | EIVLTQSPGTLS LSPGERATLSC | RASQSFSSSYL A | WFQQKPGQ APRLLIY | GASNRAT | GIPDRFSGSGSGTDFT LTISRLEPEDFAVYYC | HHFGTSPLT | FGGGTKVEIKR |
|  | 654 | Germline |  | DIQMTQSPSSLS ASVGDRVTITC | QASQDISNYLN | WYQQKPGK APKLLIY | DASNLET | GVPSRFSGSGSGTDFT FTISSLQPEDIATYYC | QQYDNLPIT | FGQGTRLEIKR |
| 5.23 | 265 | O18 | JK5 | DIQMTQSPSSLS ASVGDRVTITC | QASQDISNYLN | WYQQKPGK APNLLIY | DASNLET | GVPSRFSGSGSGTDFT FTISSLQPEDIATYYC | QQYNLPIT | FGQGTRLEIKR |
| 5.17 | 245 | O18 | JK5 | DIQMTQSPSSLS TSVGDRVTITC | QASQDIRNYLN | WYQQKPGK APKLLIH | DASNLET | GVPSRFSGNGSGTDFS FTITSLQPEDIATYYC | QQYANLPIT | FGQGTRLEIKR |
| 5.29 | 283 | O18 | JK5 | DIQMTQSPSSLS ASVGDRVTITC | QASQDIRNYLN | WYQQKPGK APKLLIY | DASNLET | GVPSRFSGSGSGTDFT FTISSLQPEDIATYYC | QQYDNLPIT | FGQGTRLEIKR |
| 5.76 | 421 | O18 | JK5 | DIQMTQSPSSLS ASVGDRVTITC | QASQDIRNYLN | WYQQKPGT APKLLIY | DASNLET | GVPSRFSGSGSGTDFT FTISSLQPEDIATYYC | QQYDNLPIT | FGQGTRLEIKR |

TABLE 12-continued

Light chain analysis

| Chain Name | SEQ ID NO: | V | J | FR1 | CDR1 | FR2 | CDR2 | FR3 | CDR3 | J |
|---|---|---|---|---|---|---|---|---|---|---|
| 5.10 | 219 | O18 | JK5 | DIQMTQSPSSLSASVGDRVTITC | QASQDIRNYLN | WYQQKPGKAPKLLIY | DASNLET | GVPSRFSGSGSGTDFTFTISSLQPEDIATYYC | QQYDNLPIT | FGQGARLEIKR |
| 5.22 | 261 | O18 | JK5 | DIRMTQSPSSLSASVGDSVTITC | QASQDIRNYLN | WYQQKPGKAPKLLIY | DASNLET | GVPSRFSGSGSGTDFTFTISSLQPEDIATYYC | QQYDNLPIT | FGQGTRLEIKR |
| 5.37 | 307 | O18 | JK5 | DIQMTQSPSSLSASVGDRVTITC | QASQDIRNYLN | WYQQKPGKAPKLLIY | DASNLET | GVPSRFSGSGSGTDFTFTISSLQPEDIATYYC | QQYDNLPIT | FGQGTRLEIKR |
| 5.31 | 291 | O18 | JK5 | DIQMTQSPSSLSASVGDRVTITC | QASQDIRNYLN | WYQQKPGKAPKLLIY | DASNLET | GVPSRFSGSGSGTDFTFTISSLQPEDIATYYC | QQYDNLPIT | FGQGTRLEIKR |
|  | 655 |  | Germline | DIQMTQSPSSLSASVGDRVTITC | RASQGISNYLA | WFQQKPGKAPKSLIY | AASSLQS | GVPSRFSGSGSGTDFTLTISSLQPEDFATYYC | QQYNSYT | FGPGTKVDIKR |
| 3.34 | 117 | L1 | JK3 | DIQMTQSPSSLSASVGDRVSIIC | RASQGISNYLA | WFQQKPGKAPKSLIY | AASSLQS | GVPSKFSGSGSGTDFTLTISSLQPEDFATYYC | QQYNSYPST | FGPGTKVDIKR |
| 5.99 | 495 | L1 | JK3 | DIQMTQSPSSLSASVGDRVTITC | RASQDISNYLA | WFQQKPGKAPKSLIY | AASSLQS | GVPSQFSGSGSGTDFTLTISSLQPEDFATYYC | QQYNNYPFT | FGPGTKVDVKR |
|  | 656 |  | Germline | DIQMTQSPSSLSASVGDRVTITC | RASQSISSYLN | WYQQKPGKAPKLLIY | AASSLQS | GVPSRFSGSGSGTDFTLTISSLQPEDFATYYC | QQSYSTP | FGQGTKLEIKR |
| 6.3.1 | 541 | O12 | JK2 | DIQMTQSPSSLSASVGDRVTITC | RASQSIRSYLN | WYQQKPGKAPKVLIY | AASSLQS | GVPSRFSGSGSGTDFTLTISSLQPEDFATYYC | QQSYSTLCS | FGQGTKLEIKR |
| 5.97 | 493 | O12 | JK2 | DIQMTQSPSSLSASVGTRVTITC | RASQSIRSYLN | WYQQKPGKAPKLLIY | AASSLQR | GVPSRFSGSGSGTDFTLTISSLQAEDFATYYC S | QQYTTPLC | FGQGTRLEIKR |
| 5.27 | 275 | O12 | JK2 | DIQMTQSPSSLSASVGDRVTITC | RASQSISSYLN | WYQQKPGKAPKILIY | AASSLQS | GVPSRFSGSGSGTDFTLTISSLQPEDFATYYC CS | QQSCSTPPE | FGQGTKLEIKR |
| 5.21 | 257 | O12 | JK2 | DIQMTQSPSSLSASVGDRVTITC | RASQSISSYLN | WYQQKPGKAPKLLIY | AASSLQS | GVPSRFSGSRSGTDFTLTISSLQPEDFATYYC | QQSYSVPCS | FGQGTKLEIKR |
| 6.3 | 657 | O12 | JK2 | DIQMTQSPSSLSASVGDRVTITC | RASQSIRSYLN | WYQQKPGKAPKVLIY | AASSLQS | GVPSRFSGSGSGTDFTLTISSLQPEDFATYYC | QQSYSTLCS | FGQGTKLEIKR |
| 5.93 | 485 | O12 | JK2 | DIQMTQSPSSLSASVGDRVTITC | RASQSISSYLN | WYQQKPGKAPKVLIY | GASSLQS | GVPSRFSGSGSGTDFTLTISSLQPEDFATYYC | QQSYSTLCS | FGQGTKLEIKR |
|  | 658 |  | Germline | DIQMTQSPSSVSASVGDRVTITC | RASQGISSWLA | WYQQKPGKAPKLLIY | AASSLQS | GVPSRFSGSGSGTDFTLTISSLQPEDFATYYC | QQANSFPLT | FGGGTKVEIKR |
| 5.95 | 489 | L5 | JK4 | DIQMTQSPSSVSASVGDRVTITC | RASQGISSWLA | WYQQKPGKAPKLLIF | AASSLQS | GVPSRFSGSGSGTDFTLTISSLQPEDFATYYC | QQANSFPLT | FGGGTKVEIKR |
| 5.52.1 | 353 | L5 | JK4 | DIQMTQSPSSVSASVGDRVTITC | RASQGISSWLA | WYQQKPGKAPKLLIY | AVSSLES | GVPSRFSGSGSGTDFTLTISSLQPEDFATYYC | QQALT | FGGGTKVEIKR |
|  | 659 |  | Germline | EIVLTQSPGTLSLSPGERATLSC | RASQSVSSSYLA | WYQQKPGQAPRLLIY | GASSRAT | GIPDRFSGSGSGTDFTLTISRLEPEDFAVYYC | QQYGSSPFT | FGPGTKVDIKR |
| 3.8 | 37 | A27 | JK3 | EIVLTQSPGTLSLSPGERATLSC | RASQSVSSSYLA | WYQQKPGQAPRLLIY | GASNRAT | GIPDRFSASGSGTDFTLTISRLEPEDFAVYYC | QQFGTSPFT | FGPGTKVDIKR |
| 3.21 | 87 | A27 | JK3 | EIVLTQSPGTLSLSPGERATLSC | RASQSVSSSYLA | WYQQKPGQAPRLLIY | GTSSRAT | GIPDRFSGSGSGTDFTLTISRLEPEDFAVYYC | QQYGSSLFT | FGPGTKVDIKR |
|  | 660 |  | Germline | DIQMTQSPSSLSASVGDRVTITC | QASQDISNYLN | WYQQKPGKAPKLLIY | DASNLET | GVPSRFSGSGSGTDFTFTISSLQPEDIATYYC | QQYDNLT | FGGGTKVEIKR |
| 5.18 | 249 | O18 | JK4 | DIQMTQSPSSLSASVGDRVTITC | QASQDITNYLN | WYQKKPGKAPKVLIY | DASNLET | GVPSRFSGSGSGTGFTFTISSLQPEDIATYYC | QQYDHIPLT | FGGGTKVEIKR |
| 5.48 | 343 | O18 | JK4 | DIQMTQSPSSLSASVGDRVTITC | QASQDITNYLN | WYQQKPGKAPKLLIY | DASNLET | GVPSRFSGSGSGTDFTFTISSLQPEDIATYFC | QQYDNLPLT | FGGGTKVEIKR |
|  | 661 |  | Germline | DIQMTQSPSSLSASVGDRVTITC | RASQSISSYLN | WYQQKPGKAPKLLIY | AASSLQS | GVPSRFSGSGSGTDFTLTISSLQPEDFATYYC | QQSYSTPT | FGQGTKVEIKR |
| 5.36 | 303 | O12 | JK1 | DIQMTQSPSSLSASVGDRVTITC | RASQSISSYLN | WYQQKPGKAPKLLIY | GASSLQS | GVPSRFSGSGSGTDFTLTISSLQPEDFATYYC | QQSYSIPRT | FGQGTKVEIKR |

TABLE 12-continued

Light chain analysis

| Chain Name | SEQ ID NO: V | J | FR1 | CDR1 | FR2 | CDR2 | FR3 | CDR3 | J |
|---|---|---|---|---|---|---|---|---|---|
| | 662 | Germline | DIQMTQSPSSLS ASVGDRVTITC | RASQGISNYLA | WFQQKPGK APKSLIY | AASSLQS | GVPSRFSGSGSGTDFT LTISSLQPEDFATYYC | QQYNSYPRT | FGQGTKVEIKR |
| 5.80 | 437 L1 | JK1 | DIQMTQSPSSLS ASVGDRVTITC | RASQDISNYLA | WFQQKPGK APKSLIY | AASSLQS | GVPSKFSGSGSGTDFT LTISSLQPEDFATYYC | QQYNSYPRT | FGQGTKVEIKR |
| 6.10 | 557 L1 | JK1 | DIQMTQSPSSLS ASVGDRVTITC | RASQDISNYLA | WFQQKPGK APKSLIY | AVSSLQS | GVPSKFSGSGSGTDFT LTISSLQPEDFATYYC | QQYNSYPRT | FGQGTKVEIKR |
| 4.9 | 165 L1 | JK1 | DIQMTQSPSSLS ASVGDRVTITC | RASQGISNYLA | WFQQKPGK APKSLIY | AASSLQS | GVPSKFSGSGSGTDFT LTISSLQPEDFATYYC | QQYNSYPST | FGQGTKVEIKR |
| 4.8 | 161 L1 | JK1 | DIQMTQSPSSLS ASVGDRVTITC | RASQGISNYLA | WFQQKPGK APKSLIY | AASSLQS | GVPSKFSGSGSGTDFT LTISSLQPEDFATYYC | QQYNSYPST | FGQGTKVEIKR |
| 5.30 | 287 L1 | JK1 | DIQMTQSPSSLS ASVGDRVTITC | RASQDISNYLA | WFQQKPGK APKSLIY | AASSLQS | GVPSKFSGSGSGTDFT LTISSLQPEDFATYYC | QQYNSYPRT | FGQGTKVEIKR |
| 6.6 | 549 L1 | JK1 | DIQMTQSPSSLS ASVGDRVTITC | RASQGISNYLA | WFQQKPGK APKSLIY | AASSLES | GVPSKFSGSGSGTDFN LTISSLQPEDFATYYC | QQYNSYPRT | FGQGTKVESKR |

Example 14

Determination of Canonical Classes of Antibodies

Chothia, et al. have described antibody structure in terms of "canonical classes" for the hypervariable regions of each immunoglobulin chain (*J Mol Biol.* 1987 Aug. 20; 196(4): 901-17). The atomic structures of the Fab and VL fragments of a variety of immunoglobulins were analyzed to determine the relationship between their amino acid sequences and the three-dimensional structures of their antigen binding sites. Chothia, et al. found that there were relatively few residues that, through their packing, hydrogen bonding or the ability to assume unusual phi, psi or omega conformations, were primarily responsible for the main-chain conformations of the hypervariable regions. These residues were found to occur at sites within the hypervariable regions and in the conserved beta-sheet framework. By examining sequences of immunoglobulins having unknown structure, Chothia, et al. show that many immunoglobuins have hypervariable regions that are similar in size to one of the known structures and additionally contained identical residues at the sites responsible for the observed conformation.

Their discovery implied that these hypervariable regions have conformations close to those in the known structures. For five of the hypervariable regions, the repertoire of conformations appeared to be limited to a relatively small number of discrete structural classes. These commonly occurring main-chain conformations of the hypervariable regions were termed "canonical structures." Further work by Chothia, et al. (*Nature* 1989 Dec. 21-28; 342(6252):877-83) and others (Martin, et al. *J Mol Biol.* 1996 Nov. 15; 263(5):800-15) confirmed that there is a small repertoire of main-chain conformations for at least five of the six hypervariable regions of antibodies.

The CDRs of each antibody described above were analyzed to determine their canonical class. As is known, canonical classes have only been assigned for CDR1 and CDR2 of the antibody heavy chain, along with CDR1, CDR2 and CDR3 of the antibody light chain. The table below (Table 13) summarizes the results of the analysis. The Canonical Class data is in the form of *HCDR1-HCDR2-LCDR1-LCDR2-LCDR3, wherein "HCDR" refers to the heavy chain CDR and "LCDR" refers to the light chain CDR. Thus, for example, a canonical class of 1-3-2-1-5 refers to an antibody that has a HCDR1 that falls into canonical class 1, a HCDR2 that falls into canonical class 3, a LCDR1 that falls into canonical class 2, a LCDR2 that falls into canonical class 1, and a LCDR3 that falls into canonical class 5.

Assignments were made to a particular canonical class where there was 70% or greater identity of the amino acids in the antibody with the amino acids defined for each canonical class. Where there was less than 70% identity, the canonical class assignment is marked with an asterisk ("*") to indicate that the best estimate of the proper canonical class was made, based on the length of each CDR and the totality of the data. Where there was no matching canonical class with the same CDR length, the canonical class assignment is marked with a "Y." The amino acids defined for each antibody can be found, for example, in the articles by Chothia, et al. referred to above. Table 13 reports the canonical class data for each of the Ang-2 antibodies.

TABLE 13

Canonical classes of antibodies against Ang-2

| Antibody | Canonical Class |
|---|---|
| 5.18 | 1-1-2-1-1 |
| 5.81 | 1-1-2-1-1 |
| 5.66 | 1-1-2-1-1 |
| 5.48 | 1-1-2-1-1 |
| 5.23 | 1-1-2-1-1 |
| 3.33 | 1-1-2-1-1 |
| 5.15 | 1-1-2-1-3* |
| 4.3 | 1-1-4-1-1 |
| 3.12 | 1-1-4-1-5* |
| 4.16 | 1-1-4-1-5* |
| 3.13 | 1-1-4-1-5* |
| 3.7 | 1-1-4-1-5* |
| 3.32 | 1-1-4-1-5* |
| 3.37 | 1-1-4-1-Y |
| 5.30 | 1-2-2-1-1 |
| 3.6 | 1-2-2-1-1 |
| 6.6 | 1-2-2-1-1 |
| 3.34 | 1-2*-2-1-1 |

TABLE 13-continued

Canonical classes of antibodies against Ang-2

| Antibody | Canonical Class |
|---|---|
| 5.74 | 1-2*-2-1-1 |
| 5.38 | 1-3-2-1-1 |
| 5.28.1 | 1-3-2-1-1 |
| 5.6 | 1-3-2-1-1 |
| 5.44 | 1-3-2-1-1 |
| 5.28 | 1-3-2-1-1 |
| 5.86.1 | 1-3-2-1-1 |
| 5.35.1 | 1-3-2-1-1 |
| 5.35 | 1-3-2-1-1 |
| 5.8 | 1-3-2-1-1 |
| 5.22 | 1-3-2-1-1 |
| 4.15 | 1-3-2-1-1 |
| 5.67 | 1-3-2-1-1 |
| 5.87 | 1-3-2-1-1 |
| 5.10 | 1-3-2-1-1 |
| 5.71 | 1-3-2-1-1 |
| 5.21 | 1-3-2-1-1 |
| 5.80 | 1-3-2-1-1 |
| 3.18 | 1-3-2-1-1 |
| 3.11 | 1-3-2-1-1 |
| 3.26 | 1-3-2-1-1 |
| 5.31 | 1-3-2-1-1 |
| 5.76 | 1-3-2-1-1 |
| 4.9 | 1-3-2-1-1 |
| 5.17 | 1-3-2-1-1 |
| 3.39 | 1-3-2-1-1 |
| 5.37 | 1-3-2-1-1 |
| 3.22 | 1-3-2-1-1 |
| 5.29 | 1-3-2-1-1 |
| 5.73 | 1-3-2-1-1 |
| 5.12 | 1-3-2-1-1 |
| 3.1 | 1-3-2-1-1 |
| 5.11 | 1-3-2-1-1 |
| 4.8 | 1-3-2-1-1 |
| 5.24 | 1-3-2-1-1 |
| 6.3.1 | 1-3-2-1-1* |
| 5.56.1 | 1-3-2-1-1* |
| 5.111 | 1-3-2-1*-1 |
| 4.13 | 1-3-2-1*-1 |
| 5.52 | 1-3*-2-1-3* |
| 5.16.1 | 1-3-2-1-3* |
| 5.39.1 | 1-3-2-1-3* |
| 5.103.1 | 1-3-2-1-3* |
| 5.101.1 | 1-3-2-1-3* |
| 5.54.1 | 1-3-2-1-3* |
| 5.83.1 | 1-3-2-1-3* |
| 5.62 | 1-3-2-1-3* |
| 5.88.1 | 1-3-2-1-3* |
| 5.40.2 | 1-3-2-1-3* |
| 5.109 | 1-3-2-1-3* |
| 5.64 | 1-3-2-1-3* |
| 5.13 | 1-3-2-1-3* |
| 3.3 | 1-3-2-1-3* |
| 5.41 | 1-3-2-1-3* |
| 3.3.1 | 1-3-2-1-3* |
| 3.31.1 | 1-3-2-1-3* |
| 5.41.1 | 1-3-2-1-3* |
| 5.62.1 | 1-3-2-1-3* |
| 5.108.1 | 1-3-2-1-3* |
| 5.13.1 | 1-3-2-1-3* |
| 5.97 | 1-3-2-1-5* |
| 5.52.1 | 1-3-2-1-Y |
| 5.78.1 | 1-3-3-1-1 |
| 5.60 | 1-3-3-1-1 |
| 5.43 | 1-3-3-1-1 |
| 5.90 | 1-3-3-1*-1 |
| 3.42 | 1-3-3-1*-1 |
| 4.11 | 1-3-4-1-1 |
| 3.40 | 1-3-4-1-1 |
| 5.82 | 1-3-4-1-1 |
| 4.18 | 1-3-4-1-1 |
| 3.41 | 1-3-4-1-1 |
| 5.92 | 1-3-4-1-1 |
| 3.10 | 1-3-4*-1-1 |
| 4.14 | 1-3-4-1-5* |
| 3.19.1 | 1-3-8*-1-1 |
| 6.2 | 1-3-8*-1-1 |
| 3.8 | 1-3-8*-1-1 |
| 5.58 | 1-3-8-1-1* |
| 4.5 | 1-4*-2-1-1 |
| 5.1 | 1-4*-2-1-1 |
| 4.2 | 1-4*-2-1-1 |
| 3.9 | 1-4*-2-1-1 |
| 5.45 | 1-4*-2-1-1 |
| 3.17 | 1-4*-2-1-1 |
| 5.72 | 1-4*-2-1-1* |
| 3.14 | 1-4*-2-1-Y |
| 5.115 | 3-1-2-1-1 |
| 5.36 | 3-1*-2-1-1 |
| 3.2 | 3-1-2-1-3* |
| 3.21 | 3-1-8-1-1* |
| 5.61 | 3-Y-2-1-3* |

Table 14 is an analysis of the number of antibodies per class. The number of antibodies having the particular canonical class designated in the left column is shown in the right column.

TABLE 14

Number of anti-Ang-2 antibodies in each canonical class

| H1-H2-L1-L2-L3 | Number of mAbs |
|---|---|
| 1-1-2-1-1 | 6 |
| 1-1-2-1-3* | 1 |
| 1-1-4-1-1 | 1 |
| 1-1-4-1-5* | 5 |
| 1-1-4-1-Y | 1 |
| 1-2-2-1-1 | 5 |
| 1-3-2-1-1 | 38 |
| 1-3-2-1-3* | 21 |
| 1-3-2-1-5* | 1 |
| 1-3-2-1-Y | 1 |
| 1-3-3-1-1 | 5 |
| 1-3-4-1-1 | 7 |
| 1-3-4-1-5* | 1 |
| 1-3-8*-1-1 | 4 |
| 1-4*-2-1-1 | 7 |
| 1-4*-2-1-Y | 1 |
| 3-1-2-1-1 | 2 |
| 3-1-2-1-3* | 1 |
| 3-1-8-1-1* | 1 |
| 3-Y-2-1-3* | 1 |

Notes:
1. Those with * means assignment has been given to the best matching class, although there are some violations at the defining positions.
2. Y means there is no matching canonical class with the same CDR length.

Example 15

Epitope Mapping of Ang-2 Antibodies

The binding domain of 27 antibodies neutralizing the activity of Ang-2 was analyzed.

Recombinant Human Ang-2 was purchased from R&D systems (623-AN). Goat anti-human Ang-2 polyclonal antibodies (R&D systems AF623) were selected for their ability to recognize rhAng-2 in direct ELISA and Western blots. The polyclonal antibodies were biotinylated for detection with HRP conjugated—Streptavidin All restriction enzymes were supplied by New England Biolabs and were used according to the manufacture's instructions. All plasmids DNA were purified using spin mini columns (Invitrogen, Carlsbad, Calif.). Oligonucleotide primers used for cloning and site directed mutagenesis were synthesized by Qiagen Operon.

Antibodies: 27 hybridoma derived human anti Ang-2 antibodies were selected based on their ability to inhibit binding of rhAng-2 to its receptor. The antibodies are listed below in Table 15.

TABLE 15

| | Hybridoma code | OD650 in inibition assay |
|---|---|---|
| 1 | x5.56 | 0.0863 |
| 2 | x3.38 | 0.0792 |
| 3 | x3.19 | 0.0633 |
| 4 | x3.28* | 0.0588 |
| 5 | x3.3 | 0.0558 |
| 6 | x3.31* | 0.0516 |
| 7 | x5.88* | 0.0874 |
| 8 | x5.49* | 0.0856 |
| 9 | x5.101 | 0.0824 |
| 10 | x5.41* | 0.0776 |
| 11 | x5.108* | 0.0688 |
| 12 | x5.62 | 0.0650 |
| 13 | x5.39 | 0.0519 |
| 14 | x5.16* | 0.0500 |
| 15 | x5.83 | 0.0484 |
| 16 | x5.54 | 0.0440 |
| 17 | x5.14 | 0.0430 |
| 18 | x5.86 | 0.0419 |
| 19 | x5.78 | 0.0984 |
| 20 | x5.103* | 0.1013 |
| 21 | x5.28 | 0.0821 |
| 22 | x5.40 | 0.0691 |
| 23 | x5.35* | 0.0663 |
| 24 | x6.3 | 0.0617 |
| 25 | x5.13 | 0.0744 |
| 26 | x5.2 | 0.0690 |
| 27 | x5.52 | 0.0627 |

Epitope Characterization of the 27 Neutralizing Anti-Ang-2 Antibodies
Dot Blots

RhAng-2 (R&D systems) was spotted on nitrocellulose membrane in its native or reduced form, using Bio-Dot Microfiltration unit. All human monoclonal antibodies (MAbs) raised against human Ang-2 had bound to non-reduced Ang-2, but not to reduced form, indicating that all mAbs recognize conformational epitopes, which are apparently destroyed upon reduction of the protein.

Cloning and Expression of Ang1 and Ang-2 Proteins

To better understand the structural basis for interaction of mAbs with Ang-2, a set of chimeric Ang1/Ang-2 molecules were used. This approach takes advantage of the fact that members of the angiogenic family are structurally related. Although Ang-2 and Ang1 show only 60% homology in their protein sequence, both share the same modular structure composed of an amino terminal coiled-coil domain and a carboxyl terminal fibrinogen like-domain.

Cloning of Human Ang-1 and Ang-2

Two alternatively spliced forms of human Ang-2 cDNAs were amplified from human umbilical vein endothelial cell line (HUVEC). PCR amplification of HUVEC cDNA using Ang-2 specific primers reveled both the full length Ang-2 (1491 bp) and a 1330 base pain variant Ang-$2_{443}$ (Injune et al., (2000) *JBC* 275: 18550). Ang-$2_{443}$ is a variant generated by alternative splicing of exon B and missing part of the coiled-coil domain (amino-acids 96-148). Both Ang-2 cDNAs were cloned into pCR3.1 expression vector and expressed in 293F cells as shown in FIG. 6. Human Ang-1 cDNA was obtained by RT-PCR using total RNA extracted from human breast cell line MDA-MB-231. A 1.5 Kb cDNA was cloned into pCR3.1 expression vector and expression was detected in the supernatant of transiently transfected 293F cells.

ELISA

Binding of the 27 mAbs to supernatants generated from transient transfection of Ang-2 and Ang1 cDNAs was tested using antibody capture ELISA. Ang-2, Ang-$2_{443}$ and Ang-1 were bound to an ELISA plate coated with goat polyclonal antibodies against human Ang-2 or Ang-1 (respectively). The binding of the top 27 human monoclonal antibodies was detected with a HRP-conjugated goat anti-human antibody, followed by colorimetric horseradish peroxidase substrate (Enhanced K-Blue TMB substrate Neogen Corporation). The absorbance of each well of the ELISA plates was measured at 450 nm on a microplate autoreader.

Transfection of 293F Cells 293F human embryonic kidney cells were maintained in 10% fetal bovine serum in Dulbecco's modified eagles medium supplemented with penicillin and streptomycin. 293F cells were transiently transfected using Calcium phosphate. At 72 hours, the medium was harvested and filtered for ELISA and Western Blot analysis.

All 27 antibodies were shown to bind specifically Ang-2/Ang-$2_{443}$ antigens. No cross reactivity was detected with human Ang-1. Amino acids 96-148 in the coiled-coil domain of Ang-2, which are missing in the Ang-$2_{443}$ protein sequence, were excluded as the binding domain for each of the 27 antibodies.

Construction of Ang-1/Ang-2 Chimeric Molecules

Restriction cleavage sites common in human Ang-1 and Ang-2 genes were used for construction of In-frame fusion Angiopoietin chimeric proteins.

Four constructs were made: Human Ang-1/2 BsmI, Ang-2/1 BsmO, Ang-1/2SspI and Ang-2/1 SspI. All proteins were expressed and secreted in detectable levels measured by ELISA assay using polyclonal antibodies against human Ang-1 and Ang-2.

The Amino acid joining points are at the following positions:

BsmI—117(Ang-2)/119(Ang-1)
SspI—353(Ang-2)/354(Ang-1)

The difference of one amino acid is due to the presence of 497 residues in the human Ang-1 compared to 496 residues in the human Ang-2. All constructs were expressed in 293F cells, and detected by goat anti-human polyclonal antibodies against Ang-1 and Ang-2. The top 27 antibodies were tested for their ability to bind chimeric Ang-1/2 molecules. All 27 antibodies showed a similar pattern of binding to the Ang-1/2BsmI construct only. The results of these experiments indicate that the binding domain for all antibodies is between residues 117-496, most likely in the fibrinogen binding domain, where the epitope is disrupted in the Sspl fusion Ang proteins around amino acid 353.

Construction of Mouse/Human Ang-2 Chimeric Molecules

Since Ang-2 shares ~55% amino acid identity with Ang-1, it was difficult to find a common restriction site to be used for cloning of chimeric molecules. Mouse and human Ang-2 are more similar, having about 85% sequence homology. Mouse Ang-2 cDNA cloned in the pCMCsport expression vector was purchased from Invitrogen. The 27 selected antibodies were tested for their immunoreactivity with recombinant mouse Ang-2. Six out of the 27 cross reacted with mouse Ang-2 with 100% of their immunoreactivity on human Ang-2, indicating that the murine antigen retains most of the immunoreactivity of human Ang-2 (Data are summarized in Table 16).

The human-Mouse chimeric system was chosen for epitope mapping based on the findings that most antibodies bind specifically to the human Ang-2 antigen and do not cross react with mouse Ang-2. Various cDNA constructs of Ang-2 were generated and cloned into a mammalian expression vector.

Constructs of Mouse/human Ang-2 were made using the common StuI restriction site, located in the fibrinogen-binding domain, with the amino acid joining point at residue 311. All mAbs specific to the human Ang-2 were able to bind to the Mouse/Human Ang-2 StuI, indicating that the binding domain is in the fibrinogen-binding domain between residues 311-496. In order to narrow down the binding domain, a new construct was prepared in which the human fragment StuI-TfiI replaced the mouse sequence in the mouse Ang-2 cDNA. (FIG. 9).

All antibodies specific to human Ang-2 showed a positive ELISA signal, with 15-100% of their immunoreactivity on human Ang-2. The binding domain of two antibodies with a unique VH gene usage 5.35.1 (VH3-20) and 5.28.1 (VH3-43) as shown in Table 17, was mapped to a region between amino-acids 310-400.

Antibodies that cross reacted with mouse Ang-2 were expected to show 100% reactivity and could not be mapped using Mouse/human chimeric constructs.

Site Directed Mutagenesis

In order to define the important residues involved in the binding site of different antibodies, a few residues of Human Ang-2 were mutated, and screened against the entire panel of antibodies for binding by ELISA assay.

Because direct binding detected by ELISA is insensitive to small and moderate differences in affinity, large changes in binding observed after substitution of single amino acid probably identify key sites that interact with the antibody. In addition, polyclonal antibodies against human Ang-2 maintain 100% reactivity with each construct, indicating that the mutagenesis procedure did not introduce any broad structural changes across the Ang-2 molecule. Two independent changes of Val to Met in position 345 (V345M) and His to Gln at position 375 (H375Q) were ignored by all 27 antibodies, indicating that these residues are not reactive, or that the changes in the conformational epitopes require more than single amino acid substitution. Changing of two residues at positions 365 and 367 dramatically changed the binding of single antibody, Mab 5.35.1. Sequence analysis of 5.35.1 showed the unique usage of VH3-20 and unique CDR3 on both the heavy and light chains. All fusion points of Ang-2 chimeric molecules and point mutations are highlighted in FIG. 8. FIG. 9 is an amino acid sequence comparison of mouse Ang-1 (SEQ ID NO: 5), human Ang-1 (SEQ ID NO: 2), mouse Ang-2 (SEQ ID NO: 4), and human Ang-2 (SEQ ID NO: 3). The arrowhead shows the cleavage site for hydrophobic leader sequences. The arrows define the limits of the coiled-coil and fibrinogen like domains. The solid circles show the conserved cysteine residues (image taken from Maisonpierre et al., 1997, *Science* 277:55).

Binding data to all Ang-2 molecules is summarized below in Table 16:

TABLE 16

| Clone | Bin | binding domain | Human Ang-2-443 | Mouse CX | M/H BsmI | M/H StuI 310-496 | Stu-TfiI 310-400 | V345M | N365Q367 | H375Q |
|---|---|---|---|---|---|---|---|---|---|---|
| 5.39.1 | 1 | Fib. Like Domain | 100% | No | 100% | 100% | 25% | 100% | 100% | 100% |
| 5.16.1* | 1 | Fib. Like Domain | 100% | No | 100% | 100% | 30% | 100% | 100% | 100% |
| 5.86.1 | 1 | Fib. Like Domain | 100% | No | 100% | 100% | 23% | 100% | 100% | 100% |
| 5.54.1 | 1 | Fib. Like Domain | 100% | No | 100% | 100% | 77% | 100% | 100% | 100% |
| 5.14.1 | 1 | Fib. Like Domain | 100% | No | 100% | 100% | 31% | 100% | 100% | 100% |
| 5.83.1 | 1 | Fib. Like Domain | 100% | No | 100% | 100% | 86% | 100% | 100% | 100% |
| 5.101.1 | 1 | Fib. Like Domain | 100% | No | 100% | 100% | 28% | 100% | 100% | 100% |
| 6.3.1 | 7 | Fib. Like Domain | 100% | No | 100% | 100% | 27% | 100% | 100% | 100% |
| 5.103.1* | 2 | Fib. Like Domain | 100% | No | 100% | 100% | 40% | 100% | 100% | 100% |
| 5.78.1 | 5 | Fib. Like Domain | 100% | Yes | 100% | 100% | 100% | 100% | 100% | 100% |
| 5.35.1* | 8 | Fib. Like Domain | 100% | No | 100% | 100% | 100% | 100% | 15% | 100% |
| 5.40.2* | 8 | Fib. Like Domain | 100% | No | 100% | 100% | 65% | 100% | 100% | 100% |
| 3.19.1 | 6 | Fib. Like Domain | 100% | Yes | 100% | 100% | 100% | 100% | 100% | 100% |
| 5.108.1* | 1 | Fib. Like Domain | 100% | No | 100% | 100% | 36% | 100% | 100% | 100% |
| 5.52.1 | | Fib. Like Domain | 100% | Yes | 100% | 100% | 100% | 100% | 100% | 100% |
| 5.56.1 | 3 | Fib. Like Domain | 100% | Yes | 100% | 100% | 100% | 100% | 100% | 100% |
| 5.2 | | Fib. Like Domain | 100% | Yes | 100% | 100% | 100% | 100% | 100% | 100% |
| 5.28.1 | 4 | Fib. Like Domain | 100% | No | 100% | 100% | 100% | 100% | 100% | 100% |
| 5.41.1* | 1 | Fib. Like Domain | 100% | No | 100% | 100% | 30% | 100% | 100% | 100% |
| 5.13.1 | | Fib. Like Domain | 100% | No | 100% | 100% | 27% | 100% | 100% | 100% |
| 3.3.1 | 1 | Fib. Like Domain | 100% | No | 100% | 100% | 15% | 100% | 100% | 100% |
| 3.31.1* | 1 | Fib. Like Domain | 100% | No | 100% | 100% | 15% | 100% | 100% | 100% |
| 5.62.1 | 1 | Fib. Like Domain | 100% | No | 100% | 100% | 30% | 100% | 100% | 100% |
| 3.28.1* | 1 | Fib. Like Domain | 100% | No | 100% | 100% | 31% | 100% | 100% | 100% |
| 5.88.1* | 1 | Fib. Like Domain | 100% | No | 100% | 100% | 20% | 100% | 100% | 100% |
| 3.38 | | Fib. Like Domain | 100% | Yes | 100% | 100% | ND | 100% | 100% | 100% |
| 5.49* | | Fib. Like Domain | 100% | No | 100% | 100% | 35% | 100% | 100% | 100% |

Data are presented as percent binding compared to human Ang-2.

TABLE 17

Sequence analysis and cross reactivity with mouse Ang-2.

| Hybridoma code | OD650 in inibition assay | Mouse Ang-2 XR | Bin | VH | DH | JH | VK | JK |
|---|---|---|---|---|---|---|---|---|
| x5.56 | 0.0863 | Yes | 3 | VH3-33 | D1-7 | JH4b | A20 | JK3 |
| x3.38 | 0.0792 | Yes | 2 | | | | | |

TABLE 17-continued Sequence analysis and cross reactivity with mouse Ang-2.

| Hybridoma code | OD650 in inibition assay | Mouse Ang-2 XR | Bin | VH | DH | JH | VK | JK |
|---|---|---|---|---|---|---|---|---|
| x3.19 | 0.0633 | Yes | 6 | VH3-30 | D3-3 | JH5b | A27 | JK5 |
| x3.28* | 0.0588 | No | 1 | VH3-7 | D6-19 | JH4b | L2 | JK1 |
| x3.3 | 0.0558 | No | 1 | VH3-7 | D6-19 | JH4b | L2 | JK1 |
| x3.31* | 0.0516 | No | 1 | VH3-7 | D6-19 | JH4b | L2 | JK1 |
| x5.88* | 0.0874 | No | 1 | VH3-7 | D6-19 | JH4b | L2 | JK1 |
| x5.49* | 0.0856 | No | 1 | | | | | |
| x5.101 | 0.0824 | No | 1 | VH1-2 | D6-19 | JH4b | L2 | JK1 |
| x5.41* | 0.0776 | No | 1 | VH3-7 | D6-19 | JH4b | L2 | JK1 |
| x5.108* | 0.0688 | No | 1 | VH3-33 | D1-7 | JH5b | L2 | JK1 |
| x5.62 | 0.0650 | No | 1 | VH3-7 | D6-19 | JH4b | L2 | JK1 |
| x5.39 | 0.0519 | No | 1 | VH1-2 | D6-13 | JH4b | L2 | JK1 |
| x5.16* | 0.0500 | No | 1 | VH1-2 | D6-13 | JH4b | L2 | JK1 |
| x5.83 | 0.0484 | No | 1 | VH1-2 | D6-19 | JH4b | L2 | JK1 |
| x5.54 | 0.0440 | No | 1 | VH1-2 | D6-19 | JH4b | L2 | JK1 |
| x5.14 | 0.0430 | No | 1 | VH1-2 | D6-19 | JH4b | | |
| x5.86 | 0.0419 | No | 1 | VH1-2 | D6-13 | JH4b | O12 | JK3 |
| x5.78 | 0.0984 | Yes | 5 | VH1-2 | D2-2 | JH6b | B3 | JK5 |
| x5.103* | 0.1013 | No | 2 | VH1-2 | D6-19 | JH4a | L2 | JK1 |
| x5.28 | 0.0821 | No | 4 | VH3-43 | D6-19 | JH4b | L2 | JK3 |
| x5.40 | 0.0691 | No | 8 | VH3-23 | D6-19 | JH4B | L2 | JK1 |
| x5.35* | 0.0663 | No | 8 | VH3-20 | D6-19 | JH2 | L2 | JK4 |
| x6.3 | 0.0617 | No | 7 | VH1-2 | D1-7 | JH4b | O12 | JK2 |
| x5.13 | 0.0744 | No | | VH3-7 | D6-19 | JH4b | L2 | JK1 |
| x5.2 | 0.0690 | Yes | | VH3-33 | D5-12 | JH6b | | |
| x5.52 | 0.0627 | Yes | | VH3-33 | D1-1 | JH4b | L5 | JK4 |

The sequence analysis of IgH and IgL sequences was accomplished using sequence analysis software tools, and by alignment of VH genes to a germ line database. The software also evaluates D elements, reading frame, N region insertion, P nucleotide addition, nucleotide loss and CDR3 length. Analysis of 27 individual antibodies specific to CR64 yielded only 7 germline VH genes, 10 of them from the same VH1 family. Selection of neutralizing antibodies showed that antibodies expressing same Ig $V_H$ and in some cases same $V_H DJ_H$ rearrangements and that pairs of H and L chain were conserved. This finding suggests that, for any given epitope, only a few members of the germ line repertoire are used to form the corresponding paratope, and for each antigenic epitope a limited number of L- and H-chain genes can pair to form a specific paratope.

Recurrent usage of similar $V_H$, $V_K$ and complementary determining region (CDR) structures by different monoclonal antibodies is linked to the fact that all Ang-2 neutralizing activity is restricted to the fibrinogen like domain, and is in agreement with work published by Procopio et al (1999, JBC 274: 30196), showing that the effect of Ang-2 on Tie2 is linked to the Fibrinogen-like domain. The epitope mapping data indicates that the monoclonal antibodies bind Ang-2 through a broad interface that includes most of the fibrinogen like domain.

Example 16

Determination of Cross-Reactivity with Mouse Ang-2

The cross-reactivity of the anti-human Ang-2 mAbs to mouse Ang-2 was tested by ELISA. For this purpose, a mouse Ang-2 expression vector was constructed, and eukaryotic cells were transfected transiently to produce mouse Ang-2.

The mouse Angiopoietin-2 (mAng-2) expression construct was obtained from Research Genetics, a distributor of the I.M.A.G.E consortium (see world wide web at image.lln-l.gov). Mouse Ang-2 cDNA (GenBank Accession No. BC027216, IMAGE: 3494566) was derived from the library NCI_CGAP_Lu29, which is a lung tumor library. The cDNA was cloned into the pCMV-SPORT6 expression vector (Invitrogen Carlsbad, Calif.) through SalI(5') and NotI(3') sites and contained the full length mouse Ang-2 (mAng-2) open reading frame of 496 amino acids, as well as the 5' and 3' untranslated flanking regions for a total of 2471 base pairs.

Ten µg of the above mAng-2 plasmid was transfected into HEK293F cells using the calcium phosphate method. Approximately, $1 \times 10^6$ HEK293F cells were seeded on a 10 cm tissue culture plate on the previous day. The medium was changed after 5 hours or overnight transfection and the cells were grown for another 2-3 days before the supernatants containing the secreted mAng-2 protein were collected. The expression of mAng-2 was confirmed by ELISA using a polyclonal antibody obtained from R&D Systems (catalog No. AF623).

96-well Nunc Immplates were coated with conditioned-medium collected from HEK293F/mouse Ang-2 transfectants, 100 µl in each well. The plates were incubated at 4° C. overnight, followed by washing four times using Phosphate Buffer Saline with a Skan Washer 300 station (SKATRON). The wells were blocked by 100 µl of ABX-block buffer (0.5% BSA, 0.1% Tween, 0.01% Thimerosal in PBS) for 1 hour. Anti-Ang-2 mAbs with appropriate concentrations and diluted in the blocking buffer were added into the wells with a volume of 100 µl/well, and incubated at room temperature for at least 1 hour. The mAbs and each of their dilutes were tested in duplicate. After washing twice, the bound mAbs were detected by goat anti-human Fc-HPPO-conjugated antibody (Caltag, Code H10507) at 1/1,000 dilution at room temperature for an hour. To set up the detecting chromagenic reaction, 100 µl of TMB substrate (TMB-microwell, BioFX, Cat. No. TMSK-1000-01) was added after washing the wells three times using PBS. The plates were incubated for 30 minutes before 650 stop solution (100 µl/well, BioFX, Cat.

No. BSTP-0100-01) was added to terminate the reaction. The light absorbance at 650 nm was determined by a Spectramax Plus reader.

Figure 10:
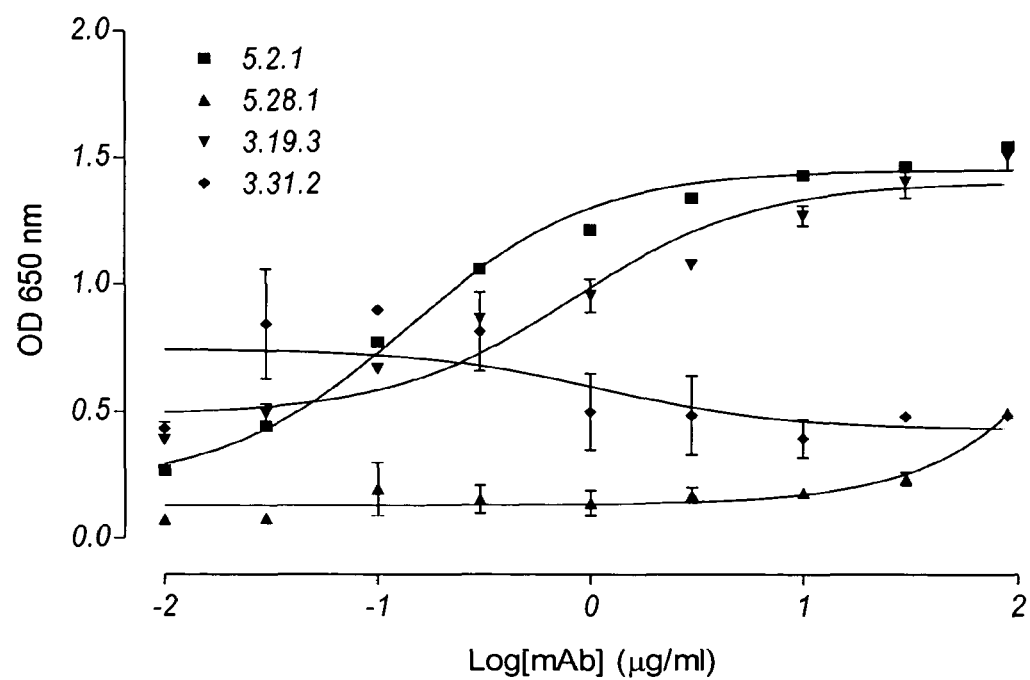
FIG. 10 is a line graph demonstrating mouse cross-reactivity in a dose-response relationship. Monoclonal antibody clones 5.2.1, 5.28.1, 3.19.3, and 3.31.2 are shown.

The top 27 neutralizing mAbs were tested in this assay. The light absorbance demonstrated that monoclonal antibodies 3.19.3, 3.38, 5.2.1, 5.52.1, 5.56.1, and 5.78.1 were capable of binding to mouse Ang-2 under the experimental conditions. For confirmation, each binding antibody was titered by ELISA. The mean OD 650 nm (±S.D.) values were plotted against Log concentration of mAbs (μg/ml) is shown in FIG. 10. The clones 5.2.1, 5.28.1, 3.19.3 and 3.31.2 are shown in the figure. Monoclonal antibodies 5.2.1 and 3.19.3 bound mouse Ang-2 in a dose-dependent manner, reaching saturation at about 10 μg/ml (FIG. 10). The binding curves of these two mAbs were typical Sigmoidal dose-response relationship curves. Dose-dependency and saturation was not observed in the antibody concentration range tested, except for clones 5.2.1 and 3.19.3. Based on this result, it appears that only mAbs 5.2.1 and 3.19.3 have cross-reactivity to mouse Ang-2.

Example 17

Inhibition of Murine Ang-2 Binding to Human Tie2

The monoclonal antibody 3.19.3 was selected for further testing of its ability to inhibit the binding of mouse Ang-2 to human Tie2. For this purpose, an ELISA plate was coated with 4 μg/ml of hTie2/Fc (R&D Systems, Inc.) at 100 μl/well, and the wells were blocked as routine at 4° C. overnight. The recombinant mouse Ang-2 (mAng-2) in the culture supernatant of the 293T/mAng-2 transfectants described above was employed. 100 μl of mAng-2 containing supernatant with mAb 3.19.3 at various concentrations was added into the pre-coated wells, and incubated at room temperature for 1 hr.

Figure 11:
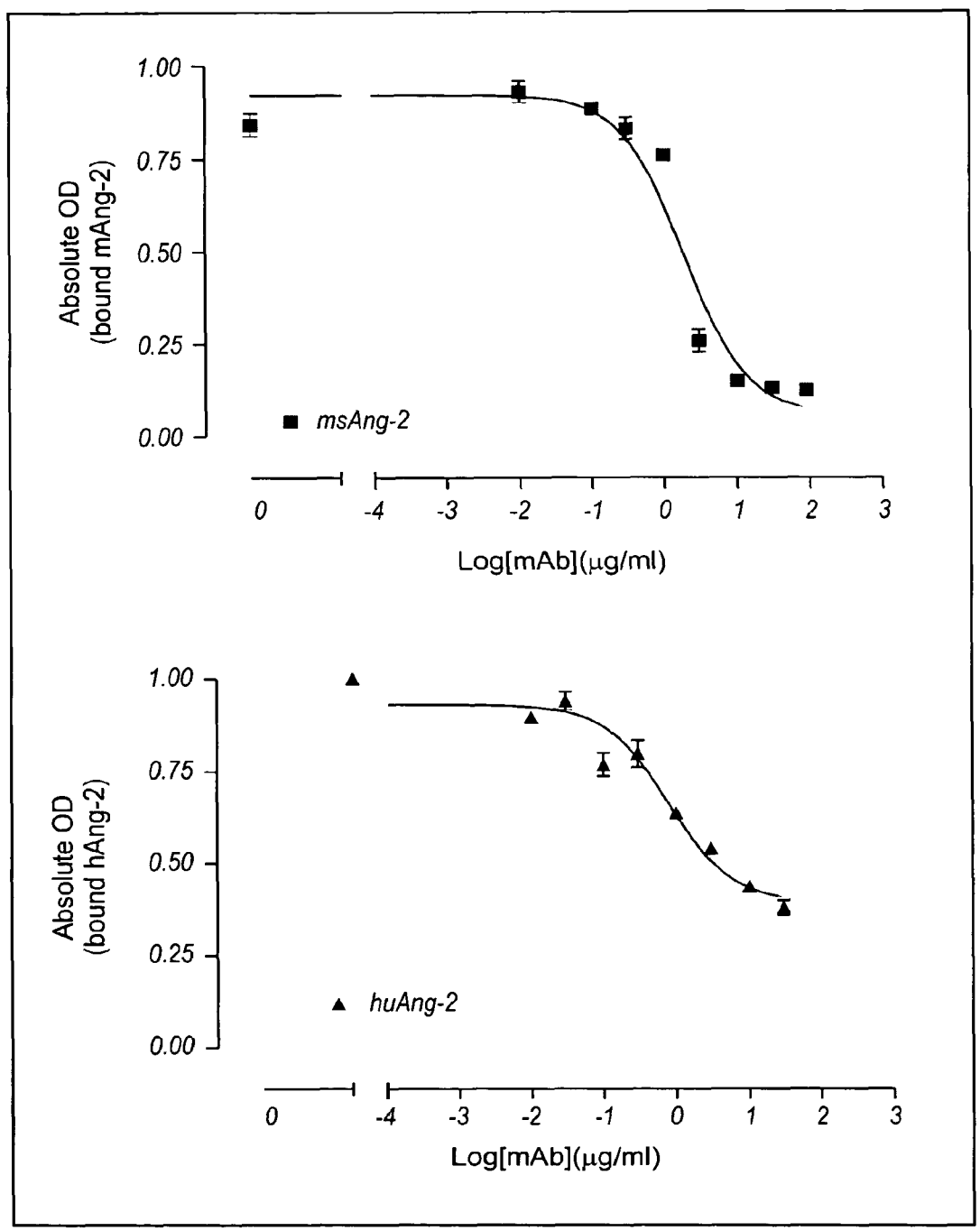
FIG. 11 is a line graph showing inhibition of both human (black triangles) and mouse (black squares) Ang-2 binding to human Tie2 in a dose-dependent manner using mAb 3.19.3.

As a control, recombinant human Ang-2 (R&D Systems, Inc.) mixed with the antibody was also included. Each concentration of the mAb was tested in triplicate. The bound mouse and human Ang-2 were detected using a goat anti-human Ang-2 polyclonal antibody (Santa Cruz Biotechnology, Santa Cruz, Calif.) that cross-react with mouse Ang-2, coupled with a secondary rabbit anti-goat IgG-HRP. OD650 was determined 30 min after the HRP substrate was added. It was discovered that mAb 3.19.3 inhibited binding of both human and mouse Ang-2 to human Tie2 in a dose-dependent manner (FIG. 11).

Example 18

Determination of Cross-Reactivity with Monkey Vasculature

Because Ang-2 is specifically expressed in angiogenic endothelial cells, these cells from monkeys were immunohistochemically stained with anti-Ang-2 antibodies as a way to indirectly determine whether each antibody cross-reacted with monkey Ang-2.

The top 10 neutralizing mAbs selected as described in Example 4 (Table 4) were examined in this experiment using endothelial cell-rich ovarian tissue from monkeys. Completely dried 6 μm frozen monkey (*Cynomolgus macaque*) ovary tissue sections were fixed with 4° C. acetone for 5 minutes. After washing the slides three times with PBS, the endogenous peroxidase of the tissues was blocked with 0.3% of $H_2O_2$ for 10 minutes. Subsequently, the tissues were washed with PBS and blocked with 10 μg/ml goat anti-human IgG Fab for 15 minutes. The tissue sections were washed again with PBS followed by treatment with 10% normal goat serum for 10 minutes. After draining the serum, each of the anti-Ang-2 mAbs (10 μg/ml) were applied to the sections and incubated for 2 hours. The bound Ang-2 mAbs were detected with 10 μg/ml mouse anti-human IgG for 15 minutes followed by incubation with peroxidase conjugated goat anti-mouse IgG for 30 minutes. Staining was performed using AEC-substrate system (DAKO, Cat. No. 3464) under microscopic observation for optimal result.

All 10 mAbs were found to stain the angiogenic vascular endothelial cells among the ovary tissue; whereas, the isotype control mAbs did not stain. This demonstrated that the 10 mAbs from Table 4 would cross react with monkey Ang-2.

Example 19 mAb 3.19.3 Inhibits In Vivo Angiogenesis in Matrigel Plug Assay

To evaluate the in vivo anti-angiogenic potential of anti-Ang-2 monoclonal antibodies, a Matrigel plug angiogenesis assay was conducted. MCF-7 cells were found to produce Ang-2 when cultured in vitro, or implanted in an immunodeficient mouse as a xenograft. When MCF-7 was incorporated into Matrigel and implanted subcutaneously into nude mice, robust vascular in growth into the gel was found. To establish the Matrigel plug model, 6-8 week old female BALB/c/nu/nu mice, with body weights ranging from 18 to 20 g (Charles River Laboratories, Wilmington, Mass.) were employed. A total of 0.5 mL of Matrigel containing $2\times10^6$ MCF-7 cells, with or without Ang-2 antibodies, or control agents (including Matrigel alone, Tie2/Fc, IgG2 and IgG4 isotype controls, and anti-VEGF mAb), were subcutaneously injected into the right flank of the nude mice. Five mice were used for each test group. All the mAbs tested were adjusted to a concentration of 100 μg/ml.

After seven days, Matrigel plugs were harvested and scored for blood vessel density. For this purpose, cervical dislocation of mice under deep anesthesia was performed. The Matrigel plugs were exposed through removal of the covering skin flap. The Matrigel plugs were then removed and digital images were then recorded. The Matrigel plugs were resected carefully and cut into two parts. One part was snap frozen in TissueTek and the other fixed in buffered formalin. Both parts were then embedded in paraffin for sectioning. Three 5 to 7 μm thick sections from each mouse were cut and stained with hematoxylin and eosin. The sections were then examined under a phase contrast microscope. Representative photomicrographs were recorded [two frames (100× and 400×)] and endothelial cell and blood vessel infiltration was recorded.

Figure 12A:
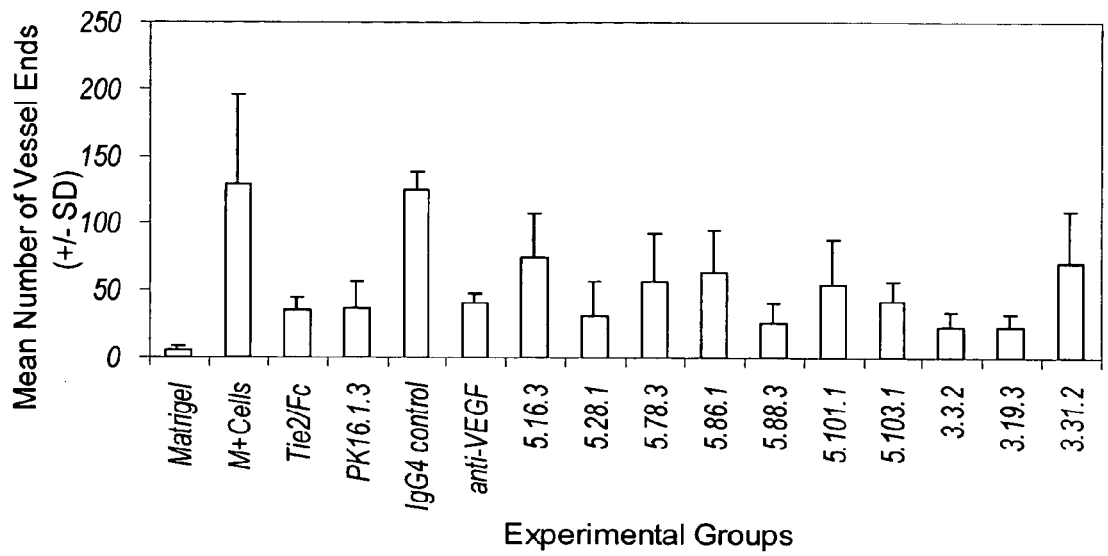
FIGS. 12A and 12B are bar graph analyses of the effect of antibodies on MCF-7 cell-induced angiogenesis.
Figure 12B:
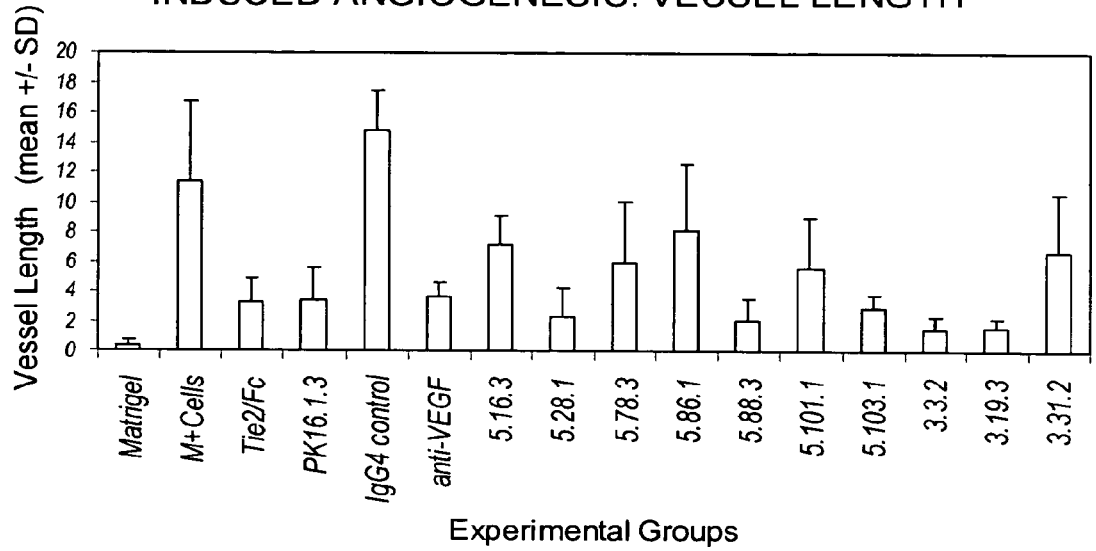

The frozen Matrigel plugs were sectioned (10 μm sections) in a Cryocut microtome. Two independent sections per mouse were made and used for staining. Sections were blocked with BSA (0.1%) and then treated with monoclonal antibody reactive to mouse. CD31 conjugated to Phycoerythin (dilutions as recommended by the manufacturer). After thorough washings, sections were mounted under anti-fading reagent (Vecta Shield) and observed under a UV microscope using a red filter. Representative Digital images were captured (two images at 100× and 200× magnification). Nuclei were counterstained with DAPI. Immunofluorescence images of CD31 staining were analyzed by a Skeletinization program. Data were processed to provide mean vessel density, node and length for each group. The results can be found in FIGS. 12A and 12B, which show the effect of anti-Ang-2 antibodies on the number of blood vessels ends (FIG. 12A) and blood vessel length (FIG. 12B).

This experiment demonstrated that, in comparison with Matrigel alone, MCF-7 cells that were incorporated in the Matrigel were able to induce a significant level of angiogenesis. The induced angiogenesis could be inhibited by a positive control anti-VEGF antibody. The angiogenesis was also significantly inhibited by soluble recombinant Tie2/Fc protein, suggesting that Ang-2 produced by MCF-7 cells plays a role in the angiogenesis in this model. By binding to any Ang-2, the Tie2/Fc would effectively reduce the level of Ang-2 that is exposed to the MCF-7 cells.

It is not clear how the IgG2 isotype negative control antibody, PK16.1.3, impacted angiogenesis, although this antibody was also found to occasionally interfere with tumor growth in some xenograft models (data not shown). The IgG4 isotype control antibody did not have any effect on the angiogenesis in this model. As seen in FIGS. 12A and 12B, clones 5.88.3, 3.3.2, 3.19.3 and 5.28.1 significantly inhibited angiogenesis (P<0.05, t-test performed by VasculoGen), while others had lesser effects.

It is well established that Ang-2 is expressed by endothelial cells in the tumor, and thus has been considered as a autocrine angiogenic factor. However, Ang-2 has also been found to be expressed by many types of tumor cells in vitro and in vivo. Except 3.19.3, the mAbs tested here do not cross-react with mouse Ang-2. In this in vivo model, the mAbs only neutralized human Ang-2 produced by the MCF-7 cell, but not the mouse Ang-2. The inhibitory effect of these mAbs suggests that tumor expressed Ang-2 can be a paracrine angiogenesis factor. The overall anti-angiogenic activity of the mAb was partially attributable to the neutralization of the tumor Ang-2, in addition to neutralization of vascular endothelium expressed Ang-2.

Example 20

Determination of the Therapeutic Efficacy of mAb 3.19.3 in A431 Preventional Xenograft Model Anti-Ang-2 mAb clone 3.19.3 not only bound to mouse Ang-2, but also inhibited binding of mouse Ang-2 to human Tie2. The anti-tumor activity of this monoclonal antibody was tested in a mouse xenograft model of human skin epidermoid carcinoma by using the A431 cell line.

A431 cells were cultured in flasks as routine until the cells reached sub-confluence. Immunodeficient 6-8 week old female mice (Balb/c/nu/nu) were employed for model development. The A431 cells were harvested and suspended in Matrigel. A cell suspension containing $5\times10^6$ cells was injected intradermally into the flank of the mice. The mice were randomized into different groups, each containing 11 mice. On the same day, the mice were injected intraperitoneally with 0.5 mg of mAb 3.19.3, or isotype control antibody, and twice per week thereafter. The dimensions of each tumor were measured twice per week. The volume of the tumor was calculated as: Volume=Length×Width)$^2$×0.5 (cm$^3$).

Figure 13:
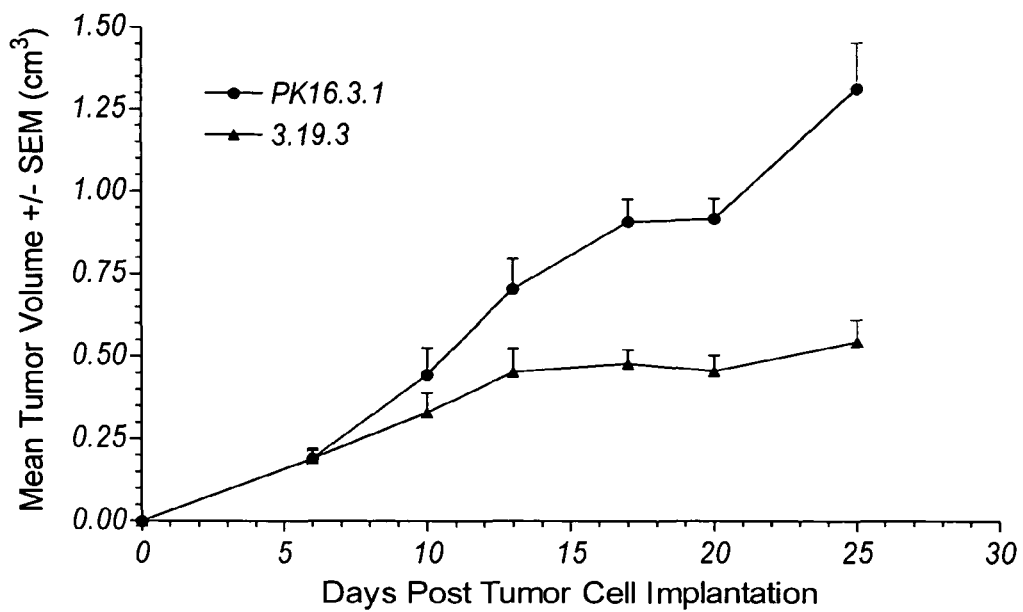
FIG. 13 is a line graph showing the anti-tumor effect of the anti-Ang-2 monoclonal antibody clone 3.19.3, as tested in a mouse xenograft model of human skin epidermoid carcinoma using the A431 cell line. The x axis indicates the number of days post tumor cell implantation and the y axis indicates the mean tumor volume+/−SEM in cm$^3$. The Solid black triangles represent the post implantation tumor volume measurements of mice injected with anti-Ang-2 monoclonal antibody clone 3.19.3; the solid black circles represent the post implantation tumor volume measurements of mice injected with an isotype control antibody PK16.3.1.

As illustrated in FIG. 13, mAb 3.19.3 significantly delayed A431 xenograft tumor growth. The average tumor volume of the isotype control group reached about 1.5 cm$^3$ at the end of the experiment, whereas the growth rate of the treated group significantly slowed after Day 10, and was about 0.5 cm$^3$ at the end. At Day 23, the volume ration of T/C (Treatment/Control) is 1/3, indicating a 66% inhibition of the growth.

The results suggest that at the dosage used in this experiment, by binding to mouse Ang-2 and blocking the binding of this ligand to its receptor Tie2, mAb 3.16.3 was able to significantly delay the growth of A431 xenograft in nude mice. It is likely that the anti-tumor effect of the monoclonal antibody is due to inhibiting angiogenesis in the host, as demonstrated by the Matrigel plug assays. Using the Microvessel Density (MVD) in the tumor as a pharmacodynamic marker, the mechanism of action with respect to anti-angiogenesis is further demonstrated in Example 22.

The mechanism of action of mAb 3.19.3 may not be limited to its blockage of Ang-2/Tie2 association and consequent signaling. As indicated in Example 7, this mAb is also found to bind to Ang-1 and block binding of Ang-1 to Tie2. Interestingly, the mAb also blocks Ang-1-induced Tie2 phosphorylation. It is known that Ang-1 is involved in vessel maturation. When comparing the potency of mAb 3.19.3 for its inhibition in the binding of Ang-1 versus Ang-2 to Tie2 (Example 12), it is apparent that mAb 3.19.3 is predominantly an Ang-2 antagonist. Without being bound to any particular theory, it is possible that dual blockage of signaling from Ang-2 and Ang-1 impairs angiogenesis and consequently tumor growth.

Example 21 mAb 3.19.3 Inhibits Tumor Growth in Established Xenograft Models

Ang-2 is upregulated by angiogenic endothelial cells, and is correlated to progression of many types of tumor. It is reasonable to postulate that a monoclonal antibody that blocks binding of Ang-2/Tie2 association will be able to inhibit angiogenesis, and therefore, inhibit the tumor growth. In this experiment, the therapeutic efficacy of an anti-Ang-2 mAb was demonstrated. Since mAb 3.19.3 cross-reacts and neutralizes mouse Ang-2/Tie2 signaling, this mAb was chosen to demonstrate the in vivo efficacy of inhibiting tumor growth.

Figure 14A:
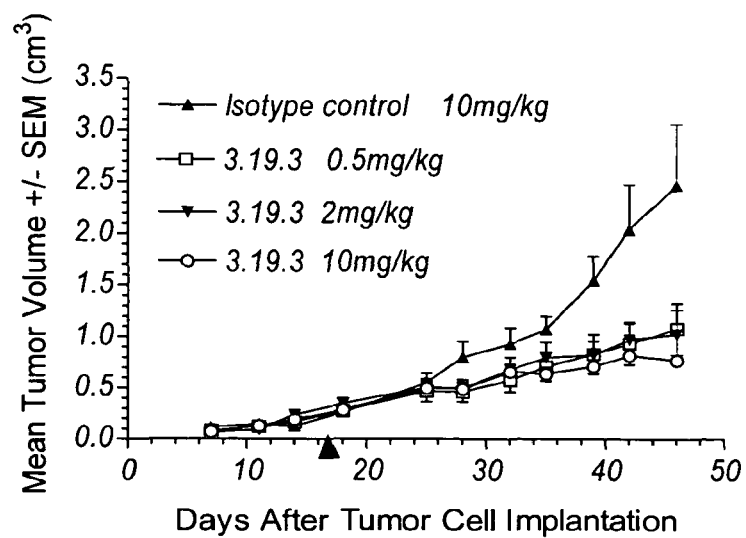
FIG. 14A is a line graph showing prevention of tumor growth in the human colon adenocarcinoma LoVo xenograft model with tumor size indicated for mice treated with 0.5, 2, and 10 mg/kg or isotype control indicated. The x axis indicates the number of days post tumor cell implantation and the y axis indicates the mean tumor volume+/−SEM in cm$^3$.

To test whether anti-Ang-2 mAb 3.19.3 also inhibits established tumor, and tumors other than A-431, the human colon adenocarcinoma LoVo xenograft model was employed. Doses of Mab 3.19.3 at 0.5, 2, and 10 mg/kg were administered twice per week intraperitoneally. The treatments did not start until the tumors were established with an average volume of 0.2 cm$^3$. On these established tumors, mAb 3.19.3 also demonstrated an inhibitory effect in comparison with the isotype control. FIG. 14A shows that 79% inhibition at 0.5 and 2 mg/kg (p values are 0.022 and 0.027, respectively) was achieved, and 75% inhibition on tumor growth were found (p=0.006) at 10 mg/kg.

Figure 14B:
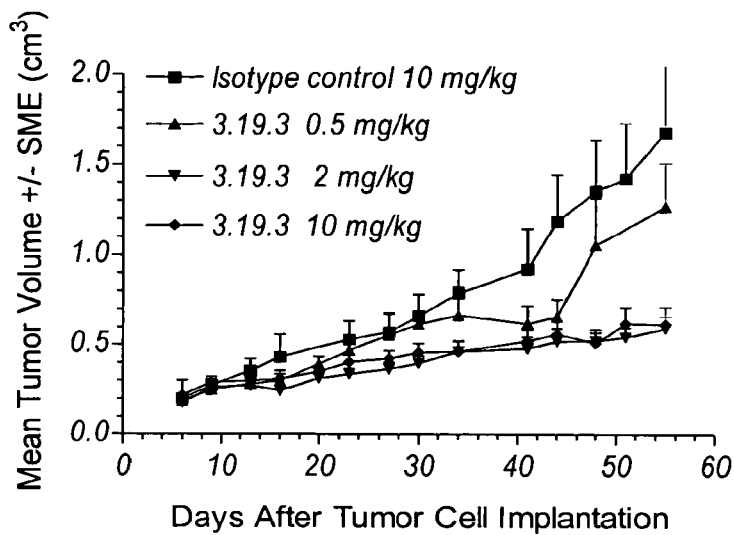
FIG. 14B is a line graph showing tumor growth inhibitory effect of the mAb in a human colon adenocarcinoma SW480 xenograft model.

The tumor growth inhibitory effect was reproduced in an additional xenograft model, human colon adenocarcinoma SW480, which was allowed to grow to an average volume of 0.2 cm$^3$. Although at 0.5 mg/kg the mAb 3.19.3 was not found to have a significant effect, at both 2 and 10 mg/kg, the mAb inhibited tumor growth by 60% (p=0.003 and 0.006 respectively) at Day 53 after tumor implantation (FIG. 14B).

In summary of the above results, anti-Ang-2 mAb 3.19.3 significantly inhibited tumor growth in the three models tested. Interestingly, both LoVo and SW480 express human Ang-2. However, two other mAbs that have no mouse Ang-2 cross-reactivity did not show significant inhibitory activity on tumor growth (data not shown), despite the fact that human Ang-2 was expressed by the tumor cells. These results imply that an antagonist of the host Ang-2 is required to block angiogenesis and tumor growth.

As discussed above, Mab 3.19.3 cross-reacts with Ang-1. However, the potency of mAb 3.19.3 on Ang-1/Tie2 association was far lower than that on Ang-2/Tie2 association (Example 12). For this reason, it is reasonable to conclude that the therapeutic efficacy seen in these models is predominantly due to Ang-2 antagonism. However, blockage of Ang-1 in vivo in the models could not be completely excluded. During the entire course of the experiments, no obvious toxicity effect, such as weight loss or bleeding, was observed.

Example 22

In Vivo Efficacy of mAb 3.19.3 in Additional Tumor Xenograft Models

The anti-tumor activity of the 3.19.3 monoclonal antibody was tested in mouse xenograft models of human cancer by using 9 different tumor cell lines.

Figure 15A:
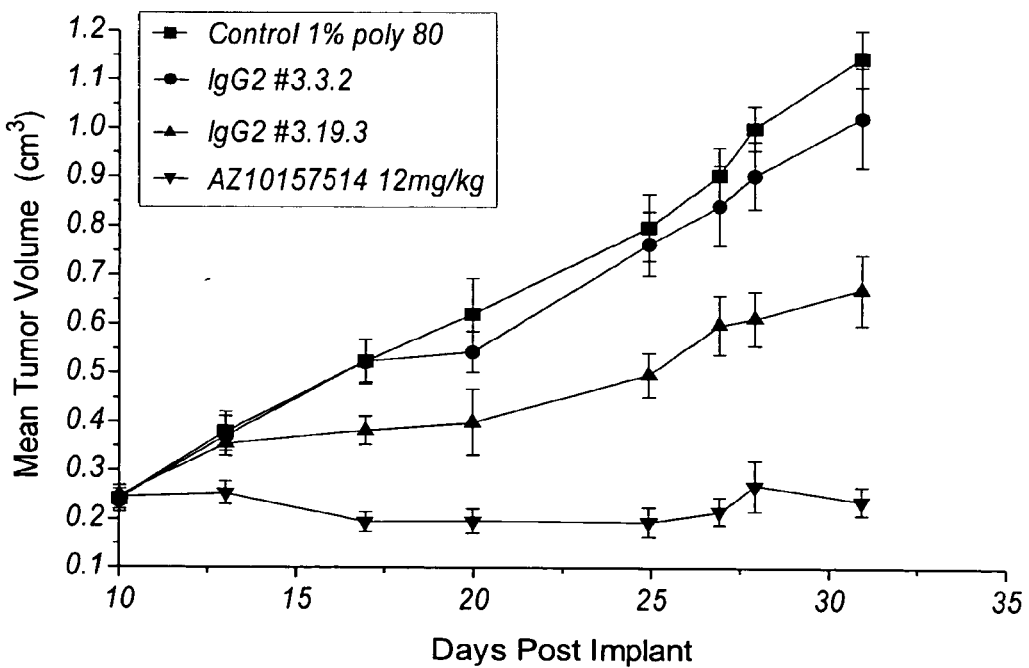
FIG. 15A is a line graph showing prevention of tumor growth in the HT29 xenograft model. The x axis indicates the number of days post tumor cell implantation, and the y axis indicates the mean tumor volume+/−SEM in cm3.
Figure 15B:
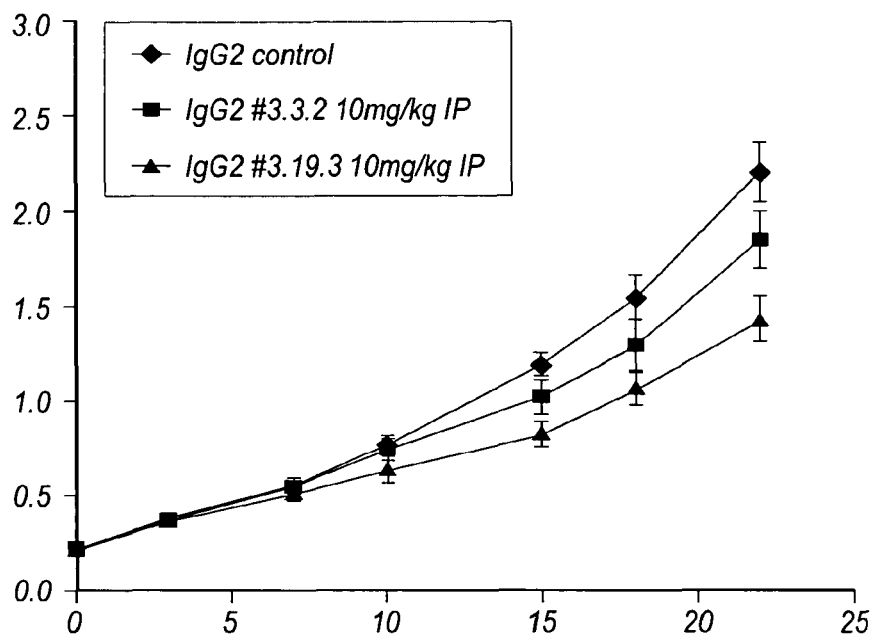
FIG. 15B is a line graph showing prevention of tumor growth in the Calu-6 xenograft model with tumor size indicated for mice treated with 10 mg/kg of mAb clone 3.3.2 or 3.19.3 or with isotype control antibody.

Colon adenocarcinoma (Lovo, SW480, Colo205, HT29, HCT116), epidermoid carcinoma (A431), lung carcinoma (Calu-6) and breast adenocarcinoma (MCF7, MDA-MB-231) cells were cultured in flasks as routine until the cells reached sub-confluence. Immunodeficient 7-10 week old female mice were employed for model development. The cells were harvested, suspended in Matrigel, and then injected subcutaneously into each mouse. The mice were then randomized into cohorts containing 10-12 mice. The mice were injected intraperitoneally with 0.5 mg of mAb 3.19.3, or isotype control antibody, and twice per week thereafter. For all experiments, isotype control antibody treatment was included. The dimensions of each tumor were measured twice per week. The volume of the tumor was calculated as: Volume=Length×(Width)$^2$×0.5 (cm$^3$). Graphical comparisons of tumor growth inhibition is shown for HT29 (FIG. 15A) and Calu6 (FIG. 15B) xenografts.

As seen in Table 16, mAb 3.19.3 showed significant activity in all 7 xenograft subcutaneous models tested and both orthotopic models with non-optimized dose and schedule.

TABLE 18

Summary of in vivo efficacy of mAb 3.19.3

| SubQ Xenografts | % Inhibition 2 mg/kg twice weekly | % Inhibition 10 mg/kg twice weekly |
|---|---|---|
| Tumor models | | |
| Colo205 | 35 | 46 |
| A431 | 43 | 66 |
| HT29 | N.D. | 54 |
| Calu6 | N.D | 38 |
| HCT116 | N.D | 33 |
| Orthotopic models | | |
| MCF7 | 35* | 74 |
| MDA-MB-231 | 50 | 58 |

Figure 15C:
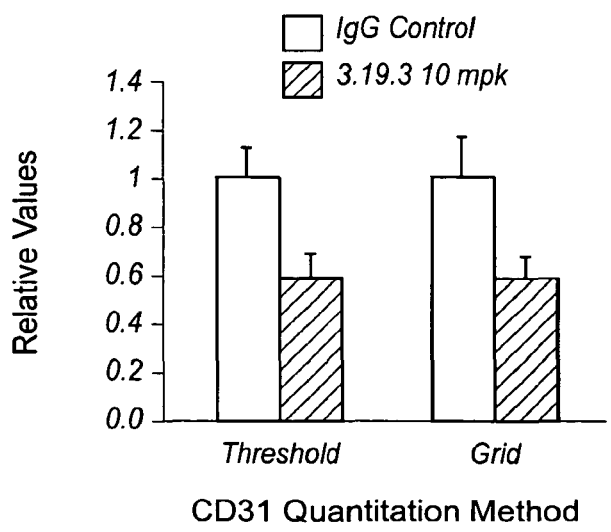
FIG. 15C is a bar graph indicating the density of CD31+ staining in tumors from MDA-MB-231 tumor-bearing mice treated with either IgG control or 10 mg/kg 3.19.3 mAb. Results from both threshold and manual grid counting methods are shown.

P < 0.05 in all cases
*Growth inhibition not statistically significant.
N.D.—not determined The MDA-MB-231 tumor tissue was analyzed via CD31+ vessel staining density. CD31 staining density was measured by threshold and by manual grid counting methods. Eleven tumors per group and at least 20 images per tumor were analyzed. As seen in FIG. 15C, treatment of mice with 3.19.3 antibody decreased the density of CD31 staining by 40% compared to a control IgG antibody. This was statistically significant with both counting methods, threshold (p<0.015) and manual grid counting (p<0.00004) by 1-tailed T-test. Similar CD31+ vessel counts were made on ex-vivo tissue for the Colo205 and HCT116 xenografts. These samples also exhibited a similar significant reduction in CD31+ vessels.

Example 23

Uses of Anti-Ang-2 Antibodies for the Treatment of Angiogenesis Related Diseases To determine the in vivo effects of anti-Ang-1 and anti-Ang-2 antibody treatment in human patients with various solid tumors, human patients are dosed periodically with an effective amount of anti-Ang-1 and anti-Ang-2 antibody. At periodic times during the treatment, the human patients are monitored to determine whether tumor growth is inhibited. Following treatment, it is found that patients undergoing treatment with the anti-Ang-1 and anti-Ang-2 antibody in comparison to patients that are not treated have relative improvements in one or more of the following including but not limited to smaller tumors, delayed time to progression or longer time of survival.

Example 24

Use of Anti-Ang-2 Antibodies as a Diagnostic Agent

Detection of Ang-2 Antigen in a Sample

An Enzyme-Linked Immunosorbent Assay (ELISA) for the detection of Ang-1 or Ang-2 antigen in a sample may be developed. In the assay, wells of a microtiter plate, such as a 96-well microtiter plate or a 384-well microtiter plate, are adsorbed for several hours with a first fully human monoclonal antibody directed against Ang-1 and Ang-2. The immobilized antibody serves as a capture antibody for any of the antigen that may be present in a test sample. The wells are rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample may be, for example, a serum sample from a subject suspected of having levels of circulating antigen considered to be diagnostic of a pathology.

After rinsing away the test sample or standard, the wells are treated with a second fully human monoclonal anti-Ang-1 and anti-Ang-2 antibody that is labeled by conjugation with biotin. A monoclonal or mouse or other species origin might also be used. The labeled anti-Ang-1 and anti-Ang-2 antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

This ELISA assay provides a highly specific and very sensitive assay for the detection of the Ang-1 and Ang-2 antigen in a test sample.

Determination of Ang-2 Antigen Concentration in Patients

A sandwich ELISA is developed to quantify Ang-1 and Ang-2 levels in human serum. The two fully human monoclonal anti-Ang-2 antibodies from the sandwich ELISA, recognizes different epitopes on the Ang-2 molecule. Alternatively, monoclonal antibodies of mouse or other species origin may be used. The ELISA could be but is not necessarily performed as follows: 50 µL of capture anti-Ang-2 antibody in coating buffer (0.1 M NaHCO$_3$, pH 9.6) at a concentration of 2 µg/mL is coated on ELISA plates (Fisher). After incubation at 4° C. overnight, the plates are treated with 200 µL of blocking buffer (0.5% BSA, 0.1% Tween 20, 0.01% Thimerosal in PBS) for 1 hour at 25° C. The plates are washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 µL/well of biotinylated detection anti-Ang-2 antibody for 1 hour at 25° C. After washing, the plates are incubated with HRP-Streptavidin for 15 minutes, washed as before, and then treated with 100 µL/well of o-phenylenediamine in $H_2O_2$ (Sigma developing solution) for color generation. The reaction is stopped with 50 µL/well of $H_2SO_4$ (2M) and analyzed using an ELISA plate reader at 492 nm. Concentration of Ang-2 antigen in serum samples is calculated by comparison to dilutions of purified Ang-2 antigen using a four parameter curve fitting program.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method of treating Angiopoietin-2 induced angiogenesis, comprising administering to an animal in need thereof a therapeutically effective dose of a monoclonal antibody that binds Angiopoietin-2 (Ang-2), wherein the animal in need suffers from an angiogenesis-related disease, and wherein the antibody is selected from the group consisting of:

a) an antibody comprising the heavy chain CDR1, CDR2 and CDR3 of SEQ ID NO:79, and the light chain CDR1, CDR2 and CDR3 of SEQ ID NO: 81; and b) an antibody comprising a variable heavy chain sequence with 90% identity to SEQ ID NO:79 and a variable light chain sequence with 90% identity to SEQ ID NO:81, wherein angiogenesis is inhibited.

2. The method of claim 1, wherein said animal is human.

3. The method of claim 1, wherein said monoclonal antibody is antibody 3.19.3 (ATCC Accession Number PTA-7260).

4. The method of claim 1, wherein the monoclonal antibody is provided in association with a pharmaceutically acceptable carrier.

* * * * *

```
                          SEQUENCE LISTING

<160> NUMBER OF SEQ ID NOS: 662

<210> SEQ ID NO 1
<211> LENGTH: 496
<212> TYPE: PRT
<213> ORGANISM: Artificial Sequence
<220> FEATURE:
<223> OTHER INFORMATION: Artificially created chimeric human/mouse
      polypeptide sequence

<400> SEQUENCE: 1

Met Trp Gln Ile Ile Phe Leu Thr Phe Gly Trp Asp Leu Val Leu Ala
 1               5                  10                  15

Ser Ala Tyr Ser Asn Phe Arg Lys Ser Val Asp Ser Thr Gly Arg Arg
            20                  25                  30

Gln Tyr Gln Val Gln Asn Gly Pro Cys Ser Tyr Thr Phe Leu Leu Pro
        35                  40                  45

Glu Thr Asp Ser Cys Arg Ser Ser Ser Pro Tyr Met Ser Asn Ala
    50                  55                  60

Val Gln Arg Asp Ala Pro Leu Asp Tyr Asp Asp Ser Val Gln Arg Leu
 65                  70                  75                  80

Gln Val Leu Glu Asn Ile Leu Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Val Val Gln Asn Gln Thr Ala Val Met Ile Glu Ile Gly
        115                 120                 125

Thr Ser Leu Leu Asn Gln Thr Ala Ala Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Gln His Ser Ile Ser Thr Asn Lys Leu Glu Lys Gln Ile Leu Asp
                165                 170                 175

Gln Thr Ser Glu Ile Asn Lys Leu Gln Asn Lys Asn Ser Phe Leu Glu
            180                 185                 190

Gln Lys Val Leu Asp Met Glu Gly Lys His Ser Glu Gln Leu Gln Ser
        195                 200                 205

Met Lys Glu Gln Lys Asp Glu Leu Gln Val Leu Val Ser Lys Gln Ser
    210                 215                 220

Ser Val Ile Asp Glu Leu Glu Lys Lys Leu Val Thr Ala Thr Val Asn
225                 230                 235                 240
```

-continued

```
Asn Ser Leu Leu Gln Lys Gln Gln His Asp Leu Met Glu Thr Val Asn
            245                 250                 255

Ser Leu Leu Thr Met Met Ser Ser Pro Asn Ser Lys Ser Ser Val Ala
        260                 265                 270

Ile Arg Lys Glu Glu Gln Thr Thr Phe Arg Asp Cys Ala Glu Ile Phe
            275                 280                 285

Lys Ser Gly Leu Thr Thr Ser Gly Ile Tyr Thr Leu Thr Phe Pro Asn
        290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
            325                 330                 335

Arg Thr Trp Lys Glu Tyr Lys Val Gly Phe Gly Asn Pro Ser Gly Glu
        340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
        370                 375                 380

Ser Leu Tyr Glu His Phe Tyr Leu Ser Ser Glu Glu Leu Asn Tyr Arg
385                 390                 395                 400

Ile His Leu Thr Gly Leu Thr Gly Thr Ala Ala Lys Ile Ser Ser Ile
            405                 410                 415

Ser Gln Pro Gly Ser Asp Phe Ser Thr Lys Asp Ser Asp Asn Asp Lys
        420                 425                 430

Cys Ile Cys Lys Cys Ser Gln Met Leu Ser Gly Gly Trp Trp Phe Asp
            435                 440                 445

Ala Cys Gly Pro Ser Asn Leu Asn Gly Gln Tyr Tyr Pro Gln Lys Gln
        450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
            485                 490                 495
```

<210> SEQ ID NO 2
<211> LENGTH: 497
<212> TYPE: PRT
<213> ORGANISM: Homo sapiens

<400> SEQUENCE: 2

```
Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
            85                  90                  95

Leu Gln Lys Leu Glu Asn Tyr Ile Val Glu Asn Met Lys Ser Glu Met
        100                 105                 110

Ala Gln Ile Gln Gln Asn Ala Val Gln Asn His Thr Ala Thr Met Leu
            115                 120                 125
```

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Lys Glu Asn Leu Gln Gly Leu Val Thr
210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Val Leu Leu Lys
            260                 265                 270

Gly Gly Lys Arg Glu Glu Lys Pro Phe Arg Asp Cys Ala Asp Val
        275                 280                 285

Tyr Gln Ala Gly Phe Asn Lys Ser Gly Ile Tyr Thr Ile Tyr Ile Asn
290                 295                 300

Asn Met Pro Glu Pro Lys Lys Val Phe Cys Asn Met Asp Val Asn Gly
305                 310                 315                 320

Gly Gly Trp Thr Val Ile Gln His Arg Glu Asp Gly Ser Leu Asp Phe
                325                 330                 335

Gln Arg Gly Trp Lys Glu Tyr Lys Met Gly Phe Gly Asn Pro Ser Gly
            340                 345                 350

Glu Tyr Trp Leu Gly Asn Glu Phe Ile Phe Ala Ile Thr Ser Gln Arg
        355                 360                 365

Gln Tyr Met Leu Arg Ile Glu Leu Met Asp Trp Glu Gly Asn Arg Ala
    370                 375                 380

Tyr Ser Gln Tyr Asp Arg Phe His Ile Gly Asn Glu Lys Gln Asn Tyr
385                 390                 395                 400

Arg Leu Tyr Leu Lys Gly His Thr Gly Thr Ala Gly Lys Gln Ser Ser
                405                 410                 415

Leu Ile Leu His Gly Ala Asp Phe Ser Thr Lys Asp Ala Asp Asn Asp
            420                 425                 430

Asn Cys Met Cys Lys Cys Ala Leu Met Leu Thr Gly Gly Trp Trp Phe
        435                 440                 445

Asp Ala Cys Gly Pro Ser Asn Leu Asn Gly Met Phe Tyr Thr Ala Gly
450                 455                 460

Gln Asn His Gly Lys Leu Asn Gly Ile Lys Trp His Tyr Phe Lys Gly
465                 470                 475                 480

Pro Ser Tyr Ser Leu Arg Ser Thr Thr Met Met Ile Arg Pro Leu Asp
                485                 490                 495

Phe

<210> SEQ ID NO 3
<211> LENGTH: 496
<212> TYPE: PRT
<213> ORGANISM: Homo sapiens

<400> SEQUENCE: 3

-continued

```
Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
             20                  25                  30

Gln Tyr Gln Val Gln His Gly Ser Cys Ser Tyr Thr Phe Leu Leu Pro
             35                  40                  45

Glu Met Asp Asn Cys Arg Ser Ser Ser Pro Tyr Val Ser Asn Ala
 50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
             85                  90                  95

Leu Glu Asn Tyr Ile Gln Asp Asn Met Lys Lys Glu Met Val Glu Ile
             100                 105                 110

Gln Gln Asn Ala Val Gln Asn Gln Thr Ala Val Met Ile Glu Ile Gly
             115                 120                 125

Thr Asn Leu Leu Asn Gln Thr Ala Glu Gln Thr Arg Lys Leu Thr Asp
 130                 135                 140

Val Glu Ala Gln Val Leu Asn Gln Thr Thr Arg Leu Glu Leu Gln Leu
 145                 150                 155                 160

Leu Glu His Ser Leu Ser Thr Asn Lys Leu Glu Lys Gln Ile Leu Asp
             165                 170                 175

Gln Thr Ser Glu Ile Asn Lys Leu Gln Asp Lys Asn Ser Phe Leu Glu
             180                 185                 190

Lys Lys Val Leu Ala Met Glu Asp Lys His Ile Ile Gln Leu Gln Ser
             195                 200                 205

Ile Lys Glu Glu Lys Asp Gln Leu Gln Val Leu Val Ser Lys Gln Asn
 210                 215                 220

Ser Ile Ile Glu Glu Leu Glu Lys Lys Ile Val Thr Ala Thr Val Asn
 225                 230                 235                 240

Asn Ser Val Leu Gln Lys Gln His Asp Leu Met Glu Thr Val Asn
             245                 250                 255

Asn Leu Leu Thr Met Met Ser Thr Ser Asn Ser Ala Lys Asp Pro Thr
             260                 265                 270

Val Ala Lys Glu Glu Gln Ile Ser Phe Arg Asp Cys Ala Glu Val Phe
 275                 280                 285

Lys Ser Gly His Thr Thr Asn Gly Ile Tyr Thr Leu Thr Phe Pro Asn
 290                 295                 300

Ser Thr Glu Glu Ile Lys Ala Tyr Cys Asp Met Glu Ala Gly Gly Gly
 305                 310                 315                 320

Gly Trp Thr Ile Ile Gln Arg Arg Glu Asp Gly Ser Val Asp Phe Gln
             325                 330                 335

Arg Thr Trp Lys Glu Tyr Lys Val Gly Phe Gly Asn Pro Ser Gly Glu
             340                 345                 350

Tyr Trp Leu Gly Asn Glu Phe Val Ser Gln Leu Thr Asn Gln Gln Arg
             355                 360                 365

Tyr Val Leu Lys Ile His Leu Lys Asp Trp Glu Gly Asn Glu Ala Tyr
 370                 375                 380

Ser Leu Tyr Glu His Phe Tyr Leu Ser Ser Glu Glu Leu Asn Tyr Arg
 385                 390                 395                 400

Ile His Leu Lys Gly Leu Thr Gly Thr Ala Gly Lys Ile Ser Ser Ile
             405                 410                 415
```

```
Ser Gln Pro Gly Asn Asp Phe Ser Thr Lys Asp Gly Asp Asn Asp Lys
                420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 4
<211> LENGTH: 496
<212> TYPE: PRT
<213> ORGANISM: Mus musculus

<400> SEQUENCE: 4

Met Trp Gln Ile Ile Phe Leu Thr Phe Gly Trp Asp Leu Val Leu Ala
 1               5                  10                  15

Ser Ala Tyr Ser Asn Phe Arg Lys Ser Val Asp Ser Thr Gly Arg Arg
                20                  25                  30

Gln Tyr Gln Val Gln Asn Gly Pro Cys Ser Tyr Thr Phe Leu Leu Pro
            35                  40                  45

Glu Thr Asp Ser Cys Arg Ser Ser Ser Pro Tyr Met Ser Asn Ala
    50                  55                  60

Val Gln Arg Asp Ala Pro Leu Asp Tyr Asp Asp Ser Val Gln Arg Leu
65                  70                  75                  80

Gln Val Leu Glu Asn Ile Leu Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Val Val Gln Asn Gln Thr Ala Val Met Ile Glu Ile Gly
            115                 120                 125

Thr Ser Leu Leu Asn Gln Thr Ala Ala Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Gln His Ser Ile Ser Thr Asn Lys Leu Glu Lys Gln Ile Leu Asp
                165                 170                 175

Gln Thr Ser Glu Ile Asn Lys Leu Gln Asn Lys Asn Ser Phe Leu Glu
            180                 185                 190

Gln Lys Val Leu Asp Met Glu Gly Lys His Ser Glu Gln Leu Gln Ser
        195                 200                 205

Met Lys Glu Gln Lys Asp Glu Leu Gln Val Leu Val Ser Lys Gln Ser
    210                 215                 220

Ser Val Ile Asp Glu Leu Glu Lys Lys Leu Val Thr Ala Thr Val Asn
225                 230                 235                 240

Asn Ser Leu Leu Gln Lys Gln His Asp Leu Met Glu Thr Val Asn
                245                 250                 255

Ser Leu Leu Thr Met Met Ser Ser Pro Asn Ser Lys Ser Val Ala
            260                 265                 270

Ile Arg Lys Glu Glu Gln Thr Thr Phe Arg Asp Cys Ala Glu Ile Phe
    275                 280                 285

Lys Ser Gly Leu Thr Thr Ser Gly Ile Tyr Thr Leu Phe Pro Asn
                290                 295                 300
```

```
Ser Thr Glu Glu Ile Lys Ala Tyr Cys Asp Met Asp Val Gly Gly Gly
305                 310                 315                 320

Gly Trp Thr Val Ile Gln His Arg Glu Asp Gly Ser Val Asp Phe Gln
                325                 330                 335

Arg Thr Trp Lys Glu Tyr Lys Glu Gly Phe Gly Asn Pro Leu Gly Glu
            340                 345                 350

Tyr Trp Leu Gly Asn Glu Phe Val Ser Gln Leu Thr Gly Gln His Arg
        355                 360                 365

Tyr Val Leu Lys Ile Gln Leu Lys Asp Trp Glu Gly Asn Glu Ala His
    370                 375                 380

Ser Leu Tyr Asp His Phe Tyr Leu Ala Gly Glu Ser Asn Tyr Arg
385                 390                 395                 400

Ile His Leu Thr Gly Leu Thr Gly Thr Ala Ala Lys Ile Ser Ser Ile
                405                 410                 415

Ser Gln Pro Gly Ser Asp Phe Ser Thr Lys Asp Ser Asp Asn Asp Lys
                420                 425                 430

Cys Ile Cys Lys Cys Ser Gln Met Leu Ser Gly Gly Trp Trp Phe Asp
            435                 440                 445

Ala Cys Gly Pro Ser Asn Leu Asn Gly Gln Tyr Tyr Pro Gln Lys Gln
        450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 5
<211> LENGTH: 498
<212> TYPE: PRT
<213> ORGANISM: Mus musculus

<400> SEQUENCE: 5

Met Thr Val Phe Leu Ser Phe Ala Phe Phe Ala Ala Ile Leu Thr His
1               5                   10                  15

Ile Gly Cys Ser Asn Gln Arg Arg Asn Pro Glu Asn Gly Gly Arg Arg
                20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Ala Thr Glu Gln Tyr Asn Thr
        50                  55                  60

Asn Ala Leu Gln Arg Asp Ala Pro His Val Glu Pro Asp Phe Ser Val
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
```

|     |     |     |     |     |     |     |     |     |     |     |     |
| --- | --- | --- | --- | --- | --- | --- | --- | --- | --- | --- | --- |
|     |     |     | 180 |     |     | 185 |     |     | 190 |     |     |
| Leu | Leu | Glu | His | Lys | Ile | Leu | Glu | Met | Glu | Gly | Lys | His | Lys | Glu | Glu |
|     |     |     | 195 |     |     | 200 |     |     | 205 |     |     |

Leu Leu Glu His Lys Ile Leu Glu Met Glu Gly Lys His Lys Glu Glu
                    195                 200                 205

Leu Asp Thr Leu Lys Glu Glu Lys Glu Asn Leu Gln Gly Leu Val Ser
        210                 215                 220

Arg Gln Thr Phe Ile Ile Gln Glu Leu Glu Lys Gln Leu Ser Arg Ala
225                 230                 235                 240

Thr Asn Asn Ser Ile Leu Gln Lys Gln Gln Leu Glu Leu Met Asp
                245                 250                 255

Thr Val His Asn Leu Val Ser Leu Cys Thr Lys Glu Gly Val Leu Leu
        260                 265                 270

Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Phe
        290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
        450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 6
<211> LENGTH: 366
<212> TYPE: DNA
<213> ORGANISM: Homo sapiens

<400> SEQUENCE: 6

```
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gggggactac     300
```

```
ggtgagtact tctactacgg tatggacgtc tggggccaag ggaccacggt caccgtctcc    360
tcagcc                                                                366
```

<210> SEQ ID NO 7
<211> LENGTH: 122
<212> TYPE: PRT
<213> ORGANISM: Homo sapiens

<400> SEQUENCE: 7

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Asp Tyr Gly Glu Tyr Phe Tyr Tyr Gly Met Asp Val Trp Gly
            100                 105                 110

Gln Gly Thr Thr Val Thr Val Ser Ser Ala
        115                 120
```

<210> SEQ ID NO 8
<211> LENGTH: 324
<212> TYPE: DNA
<213> ORGANISM: Homo sapiens

<400> SEQUENCE: 8

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctcggac gttcggccaa   300
gggaccaagg tggaaatcaa acga                                          324
```

<210> SEQ ID NO 9
<211> LENGTH: 108
<212> TYPE: PRT
<213> ORGANISM: Homo sapiens

<400> SEQUENCE: 9

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Tyr Cys Leu Gln His Asn Ser Tyr Pro Arg
                85                  90                  95
Thr Phe Gly Gln Gly Thr Lys Val Glu Ile Lys Arg
            100                 105
```

<210> SEQ ID NO 10
<211> LENGTH: 386
<212> TYPE: DNA
<213> ORGANISM: Homo sapiens

<400> SEQUENCE: 10

```
caggtgcagc tgcaggagtc gggcccagga ctggtgaagc cttcggagac cctgtccctc      60
acctgcactg tctctggtgg ctccgtcagc agtggtggtt actactggaa ctggatccgg     120
cagcccccag ggaagggact ggagtggatt ggatatatct attacagtgg gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcgagagat     300
caggattact atggttcggg gagggctac tactactacg gtatggacgt ctggggccaa     360
gggaccacgg tcaccgtctc ctcagc                                         386
```

<210> SEQ ID NO 11
<211> LENGTH: 128
<212> TYPE: PRT
<213> ORGANISM: Homo sapiens

<400> SEQUENCE: 11

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Val Ser Ser Gly
             20                  25                  30
Gly Tyr Tyr Trp Asn Trp Ile Arg Gln Pro Pro Gly Lys Gly Leu Glu
         35                  40                  45
Trp Ile Gly Tyr Ile Tyr Tyr Ser Gly Ser Thr Asn Tyr Asn Pro Ser
 50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
             85                  90                  95
Cys Ala Arg Asp Gln Asp Tyr Tyr Gly Ser Gly Arg Gly Tyr Tyr Tyr
            100                 105                 110
Tyr Gly Met Asp Val Trp Gly Gln Gly Thr Thr Val Thr Val Ser Ser
            115                 120                 125
```

<210> SEQ ID NO 12
<211> LENGTH: 322
<212> TYPE: DNA
<213> ORGANISM: Homo sapiens

<400> SEQUENCE: 12

```
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gcttacagtt ccggacgtt cggccaaggg     300
accaaggtgg aaatcaaacg aa                                             322
```

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Phe Arg Thr
                85                  90                  95

Phe Gly Gln Gly Thr Lys Val Glu Ile Lys Arg
            100                 105

<210> SEQ ID NO 14
<211> LENGTH: 366
<212> TYPE: DNA
<213> ORGANISM: Homo sapiens

<400> SEQUENCE: 14
gaggtgcagc tggtggagtc tgggggaggc ttggtccagc ctggggggtc cctgagactc      60
tcctgtgcag tctctggatt cacctttagt agctattgga tgagctgggt ccgccaggct     120
ccagggaagg gctggagtg gtggccaac ataaagcaag atggaagtga aaatactat        180 gtggactctg tgaagggccg attcaccatc tccagagaca acgccaagaa ctcactgtat     240
ctgcaaatga acagcctgag agccgaggac acggctgtgt attactgtgc gagagatcaa     300
ggtatagcag tggctgggcc ctttgactac tggggccagg gaaccctggt caccgtctcc     360
tcagcc                                                                 366

<210> SEQ ID NO 15
<211> LENGTH: 122
<212> TYPE: PRT
<213> ORGANISM: Homo sapiens

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Ile Ala Val Ala Gly Pro Phe Asp Tyr Trp Gly 100                 105                 110
Gln Gly Thr Leu Val Thr Val Ser Ser Ala
        115                 120

<210> SEQ ID NO 16
<211> LENGTH: 322
<212> TYPE: DNA
<213> ORGANISM: Homo sapiens

<400> SEQUENCE: 16
gaaatagtga tgacgcagtc tccagccacc ctgtctgtgt ctccagggga aagagccacc     60
ctctcctgca gggccagtca gactgttagc agcgacttag cctggtacca gcagaaacct    120
ggccaggctc ccaggctcct catctatgga gcatccatta gggccactgg tatcccagcc    180
aggttcagtg gcagtgggtc tgggacagag ttcactctca ccatcagcag cctgcagtct    240
gaagattttg cagtttattc ctgtcagcag tattataact ggtggacgtt cggccaaggg    300
accaaggtgg aaatcaaacg aa                                              322

<210> SEQ ID NO 17
<211> LENGTH: 107
<212> TYPE: PRT
<213> ORGANISM: Homo sapiens

<400> SEQUENCE: 17

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Thr Val Ser Ser Asp
            20                  25                  30

Leu Ala Trp Tyr Gln Gln Lys Pro Gly Gln Ala Pro Arg Leu Leu Ile
        35                  40                  45

Tyr Gly Ala Ser Ile Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Tyr Asn Trp Trp Thr
                85                  90                  95

Phe Gly Gln Gly Thr Lys Val Glu Ile Lys Arg
            100                 105

<210> SEQ ID NO 18
<211> LENGTH: 366
<212> TYPE: DNA
<213> ORGANISM: Homo sapiens

<400> SEQUENCE: 18
gaggtgcagc tggtggagtc tgggggaggc ttggtccagc ctggggggtc cctgagactc     60
tcctgtgcag tctctggatt caccttttagt agctattgga tgagctgggt ccgccaggct    120
ccagggaagg ggctggagtg ggtggccaac ataaagcaag atggaagtga aaatactat     180 gtggactctg tgaagggccg attcaccatc tccagagaca acgccaagaa ctcactgtat    240
ctgcaaatga acagcctgag agccgaggac acggctgtgt attactgtgc gagagatcaa    300
ggtatagcag tggctgggcc ctttgactac tggggccagg gaaccctggt caccgtctcc    360
tcagcc                                                                366

<210> SEQ ID NO 19
<211> LENGTH: 122

```
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Ile Ala Val Ala Gly Pro Phe Asp Tyr Trp Gly
            100                 105                 110

Gln Gly Thr Leu Val Thr Val Ser Ser Ala
        115                 120

<210> SEQ ID NO 20
<211> LENGTH: 322
<212> TYPE: DNA
<213> ORGANISM: Homo sapiens

<400> SEQUENCE: 20
gaaatagtga tgacgcagtc tccagccacc ctgtctgtgt ctccagggga aagagccacc    60
ctctcctgca gggccagtca gactgttagc agcgacttag cctggtacca gcagaaacct   120
ggccaggctc ccaggctcct catctatgga gcatccatta gggccactgg tatcccagcc   180
aggttcagtg gcagtgggtc tgggacagag ttcactctca ccatcagcag cctgcagtct   240
gaagattttg cagtttattc ctgtcagcag tattataact ggtggacgtt cggccaaggg   300
accaaggtgg aaatcaaacg aa                                            322

<210> SEQ ID NO 21
<211> LENGTH: 107
<212> TYPE: PRT
<213> ORGANISM: Homo sapiens

<400> SEQUENCE: 21

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Thr Val Ser Ser Asp
            20                  25                  30

Leu Ala Trp Tyr Gln Gln Lys Pro Gly Gln Ala Pro Arg Leu Leu Ile
        35                  40                  45

Tyr Gly Ala Ser Ile Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Tyr Asn Trp Trp Thr
                85                  90                  95

Phe Gly Gln Gly Thr Lys Val Glu Ile Lys Arg
            100                 105
```

<210> SEQ ID NO 22
<211> LENGTH: 366
<212> TYPE: DNA
<213> ORGANISM: Homo sapiens

<400> SEQUENCE: 22

```
gaggtgcagc tggtggagtc tgggggaggc ttggtccagc ctggggggtc cctgagactc      60
tcctgtgcag tctctggatt cacctttagt agctattgga tgagctgggt ccgccaggct     120
ccagggaagg ggctggagtg ggtggccaac ataaagcaag atggaagtga aaatactat     180 gtggactctg tgaagggccg attcaccatc tccagagaca acgccaagaa ctcactgtat     240
ctgcaaatga acagcctgag agccgaggac acggctgtgt attactgtgc gagagatcaa     300
ggtatagcag tggctgggcc ctttgactac tggggccagg gaaccctggt caccgtctcc     360
tcagcc                                                                366
```

<210> SEQ ID NO 23
<211> LENGTH: 122
<212> TYPE: PRT
<213> ORGANISM: Homo sapiens

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Ile Ala Val Ala Gly Pro Phe Asp Tyr Trp Gly
            100                 105                 110

Gln Gly Thr Leu Val Thr Val Ser Ser Ala
        115                 120

<210> SEQ ID NO 24
<211> LENGTH: 322
<212> TYPE: DNA
<213> ORGANISM: Homo sapiens

<400> SEQUENCE: 24

```
gaaatagtga tgacgcagtc tccagccacc ctgtctgtgt ctccagggga aagagccacc      60
ctctcctgca gggccagtca gactgttagc agcgacttag cctggtacca gcagaaacct     120
ggccaggctc ccaggctcct catctatgga gcatccatta gggccactgg tatcccagcc     180
aggttcagtg gcagtgggtc tgggacagag ttcactctca ccatcagcag cctgcagtct     240
gaagattttg cagtttattc ctgtcagcag tattataact ggtggacgtt cggccaaggg     300
accaaggtgg aaatcaaacg aa                                              322
```

<210> SEQ ID NO 25
<211> LENGTH: 107
<212> TYPE: PRT
<213> ORGANISM: Homo sapiens

<400> SEQUENCE: 25

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Ser Ser Asp
                20                  25                  30

Leu Ala Trp Tyr Gln Gln Lys Pro Gly Gln Ala Pro Arg Leu Leu Ile
            35                  40                  45

Tyr Gly Ala Ser Ile Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Tyr Asn Trp Trp Thr
                85                  90                  95

Phe Gly Gln Gly Thr Lys Val Glu Ile Lys Arg
            100                 105

<210> SEQ ID NO 26
<211> LENGTH: 366
<212> TYPE: DNA
<213> ORGANISM: Homo sapiens

<400> SEQUENCE: 26
gaggtgcagc tggtgcagtc tggagcagag gtgaaaaagc ccggggagtc tctgaagatc      60
tcctgtaagg gttctggata cagcttttcc aactactgga tcgcctgggt gcgccagatg     120
cccgggaaag gcctggagtg gatggggatc atctatcctg gtgactctga taccagatac     180
agcccgtcct tccaaggcca ggtcaccatc tcagccgaca gtccatcag taccgcctac      240
ctgcagtgga gcagcctgaa ggcctcggac accgccatgt attactgtgc gagacatgag     300
aactggaact ttttgatac ttttgatatc tggggccaag ggacaatggt caccgtctct     360
tcagcc                                                               366

<210> SEQ ID NO 27
<211> LENGTH: 122
<212> TYPE: PRT
<213> ORGANISM: Homo sapiens

<400> SEQUENCE: 27

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Asn Trp Asn Phe Phe Asp Thr Phe Asp Ile Trp Gly
            100                 105                 110

Gln Gly Thr Met Val Thr Val Ser Ser Ala
        115                 120

<210> SEQ ID NO 28

<211> LENGTH: 324
<212> TYPE: DNA
<213> ORGANISM: Homo sapiens

<400> SEQUENCE: 28

```
gaaatagtga tgacgcagtc tccagccacc ctgtctgtgt ctccagggga aagagccacc    60
ctctcctgca gggccagtca gagtattagc agcaacttag cctggttcca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctcggac gttcggccaa   300
gggaccacgg tggagatcaa acga                                          324
```

<210> SEQ ID NO 29
<211> LENGTH: 108
<212> TYPE: PRT
<213> ORGANISM: Homo sapiens

<400> SEQUENCE: 29

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Thr Val Glu Ile Lys Arg
            100                 105

<210> SEQ ID NO 30
<211> LENGTH: 351
<212> TYPE: DNA
<213> ORGANISM: Homo sapiens

<400> SEQUENCE: 30

```
caggtgcagc tgcaggagtc gggcccagga ctggtgaagc cttcggagac cctgtccctc    60
acctgcactg tctctggtgg ctccatcagt aattactact ggagctggat ccggcagccc   120
ccagggaagg gactggagtg gattggatat atctattaca gtgggagcac caactacaac   180
ccctccctca gagtcgagt caccatatca gtagacacgt ccaagaacca gttctccctg   240
aaactgagct ctgtgaccgc tgcggacacg gccgtgtatt actgtgcgag agaccgggct   300
gatgctttg atatctgggg ccaagggaca atggtcaccg tctcttcagc c             351
```

<210> SEQ ID NO 31
<211> LENGTH: 117
<212> TYPE: PRT
<213> ORGANISM: Homo sapiens

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr

```
              20                  25                  30
Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Arg Ala Asp Ala Phe Asp Ile Trp Gly Gln Gly Thr Met Val
             100                 105                 110

Thr Val Ser Ser Ala
             115

<210> SEQ ID NO 32
<211> LENGTH: 342
<212> TYPE: DNA
<213> ORGANISM: Homo sapiens

<400> SEQUENCE: 32
gatgttgtga tgactcagtc tccactctcc ctgcccgtca cccttggaca gccggcctcc     60
atctcctgca ggtctagtca aagcctcgtt tacagtgatg gaaacaccta cttgaattgg    120
tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
ccgctcactt tcggcggagg gaccaaggtg gagatcaaac ga                       342

<210> SEQ ID NO 33
<211> LENGTH: 114
<212> TYPE: PRT
<213> ORGANISM: Homo sapiens

<400> SEQUENCE: 33

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Trp Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Leu Thr Phe Gly Gly Gly Thr Lys Val Glu Ile
             100                 105                 110

Lys Arg

<210> SEQ ID NO 34
<211> LENGTH: 366
<212> TYPE: DNA
<213> ORGANISM: Homo sapiens

<400> SEQUENCE: 34
```

```
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctaag agccgaggac acggctgtgt attactgtgc gagaggggga   300
ttacgatatt ttgactggcc ccctgactac tggggccagg gaaccctggt caccgtctcc   360
tcagcc                                                              366
```

<210> SEQ ID NO 35
<211> LENGTH: 122
<212> TYPE: PRT
<213> ORGANISM: Homo sapiens

<400> SEQUENCE: 35

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Arg Tyr Phe Asp Trp Pro Pro Asp Tyr Trp Gly
            100                 105                 110

Gln Gly Thr Leu Val Thr Val Ser Ser Ala
        115                 120

<210> SEQ ID NO 36
<211> LENGTH: 327
<212> TYPE: DNA
<213> ORGANISM: Homo sapiens

<400> SEQUENCE: 36

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca cagggccac tggcatccca    180 gacaggttca gtgccagtgg gtctgggaca gacttcactc tcaccatcag cagactggag   240
cctgaagatt ttgcagtgta ttactgtcag cagtttggta cctcaccatt cactttcggc   300
cctgggacca agtggatat caaacga                                        327
```

<210> SEQ ID NO 37
<211> LENGTH: 109
<212> TYPE: PRT
<213> ORGANISM: Homo sapiens

<400> SEQUENCE: 37

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

```
Tyr Leu Ala Trp Tyr Gln Gln Lys Pro Gly Gln Ala Pro Arg Leu Leu
         35                  40                  45

Ile Tyr Gly Ala Ser Asn Arg Ala Thr Gly Ile Pro Asp Arg Phe Ser
 50                  55                  60

Ala Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Thr Ser Pro
                 85                  90                  95

Phe Thr Phe Gly Pro Gly Thr Lys Val Asp Ile Lys Arg
            100                 105
```

<210> SEQ ID NO 38
<211> LENGTH: 366
<212> TYPE: DNA
<213> ORGANISM: Homo sapiens

<400> SEQUENCE: 38

```
gaggtgcagc tggtggagtc tgggggaggc ttggtaaagc ctggggggtc ccttagactc      60
tcctgtgcag cctctggatt cactttcagt aacgcctgga tgagctgggt ccgccaggct     120
ccagggaagg ggctggagtg ggttggccgt attaaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacac ccgtgtatta ctgtaccacg     300
gaatacggtg acttttggta cttcgatttc tggggccgtg caccctggtc actgtctcc      360 tcagcc                                                                366
```

<210> SEQ ID NO 39
<211> LENGTH: 122
<212> TYPE: PRT
<213> ORGANISM: Homo sapiens

<400> SEQUENCE: 39

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Glu Tyr Gly Asp Phe Trp Tyr Phe Asp Phe Trp Gly
            100                 105                 110

Arg Gly Thr Leu Val Thr Val Ser Ser Ala
            115                 120
```

<210> SEQ ID NO 40
<211> LENGTH: 324
<212> TYPE: DNA
<213> ORGANISM: Homo sapiens

<400> SEQUENCE: 40

```
gacatccaga tgacccagtc tccatcttcc gtgtctgcat ctgtaggaga cagagtcacc      60
```

```
atcacttgtc gggcgagtca gggtattagc agctggttag cctggtatca gcagaaacca    120
gggaaagccc ctaacctcct gatctatgct gcatccagtt tgcaaagtgg ggtcccatca    180
aggttcagcg gcagtggatc tgggacagat ttcattctca ccatcagcag cctgcagcct    240
gaagattttg caacttacta ttgtcaacag tctaacagtt ccctcggac gttcggccaa     300 gggaccaagg tggaaatcaa acga                                           324
```

<210> SEQ ID NO 41
<211> LENGTH: 108
<212> TYPE: PRT
<213> ORGANISM: Homo sapiens

<400> SEQUENCE: 41

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Ile Leu Thr Ile Ser Ser Leu Gln Pro
65                  70                  75                  80

Glu Asp Phe Ala Thr Tyr Tyr Cys Gln Gln Ser Asn Ser Phe Pro Arg
                85                  90                  95

Thr Phe Gly Gln Gly Thr Lys Val Glu Ile Lys Arg
            100                 105

<210> SEQ ID NO 42
<211> LENGTH: 374
<212> TYPE: DNA
<213> ORGANISM: Homo sapiens

<400> SEQUENCE: 42

```
caggtgcagc tggtggagtc tgggggaggc gtggtccagc ctgggaggtc cctgagactc    60
tcctgtgcag cgtctggatt caccttcagt agttatggca tgcactgggt ccgccaggct    120
ccaggcaagg ggctggagtg ggtggcagtt ataaggtatg atggaagtaa taaatactat    180
gcagactccg tgaagggccg attcaccatc tccagagaca attccaagaa cacgctgaat    240
ctgcaaatga acagcctgag agccgaggac acggctgtgt attactgtgc gagagatcgg    300
gacggtgact atcctctgct actactgggt atggacgtct ggggccaagg gaccacggtc    360
accgtctcct cagc                                                      374
```

<210> SEQ ID NO 43
<211> LENGTH: 125
<212> TYPE: PRT
<213> ORGANISM: Homo sapiens

<400> SEQUENCE: 43

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Arg Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Ala Glu Asp Thr Ala Val Tyr Tyr Cys
                85                  90                  95

Ala Arg Asp Arg Asp Gly Asp Tyr Pro Leu Leu Leu Gly Met Asp
                100                 105                 110

Val Trp Gly Gln Gly Thr Thr Val Thr Val Ser Ser Ala
                115                 120                 125

<210> SEQ ID NO 44
<211> LENGTH: 339
<212> TYPE: DNA
<213> ORGANISM: Homo sapiens

<400> SEQUENCE: 44
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattctac actgaaaatc   240
agcagagtgg aggctgagga tgttggggtt tattactgca tgcaagctct acaaactcct   300
ctcactttcg gcggagggac caaggtggag atcaaacga                          339

<210> SEQ ID NO 45
<211> LENGTH: 113
<212> TYPE: PRT
<213> ORGANISM: Homo sapiens

<400> SEQUENCE: 45

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Ser Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
                100                 105                 110

Arg

<210> SEQ ID NO 46
<211> LENGTH: 366
<212> TYPE: DNA
<213> ORGANISM: Homo sapiens

<400> SEQUENCE: 46
gtcaggtgca gctggtggag tctgggggag gcgtggtcca gcctggggagg tccctgagac    60 tctcctgtgc agcgtctgga ttcaccttca gtagctatgg catgcactgg gtccgccagg   120
ctccaggcaa ggggctggag tgggtggcag ttatatggta tgatggaagt aataaatact   180

```
atgcagactc cgtgaagggc cgattcacca tctccagaga caattccaag aacacgctgt      240
atctgcaaat gaacagcctg agagccgagg acacggctgt gtattactgt gcgggggact      300
acggtgacta cttctactac ggtatggacg tctggggcca agggaccacg gtcaccgtct      360
cctcag                                                                 366
```

<210> SEQ ID NO 47
<211> LENGTH: 122
<212> TYPE: PRT
<213> ORGANISM: Homo sapiens

<400> SEQUENCE: 47

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Asp Tyr Gly Asp Tyr Phe Tyr Tyr Gly Met Asp Val Trp Gly
            100                 105                 110

Gln Gly Thr Thr Val Thr Val Ser Ala
        115                 120
```

<210> SEQ ID NO 48
<211> LENGTH: 324
<212> TYPE: DNA
<213> ORGANISM: Homo sapiens

<400> SEQUENCE: 48

```
gacatccaga tgacccagtc tccatcctcc ctgtctacat ctgtaggaga cagagtcacc       60
atcacttgcc gggcaagtca gggcattaga aatgatttag ctggtatca gcagaaacca      120 gggaaagccc ctaagcgcct gatctatgct gcatccagtt tgcaaagtgg ggtcccatca      180
aggttcagcg gcagtggatc tgggacagaa ttcactctca caatcagcag cctgcggcct      240
gaagattttg caacttatta ctgtctacag cttaatagtt accctcggac gttcggccaa      300
gggaccaagg tggaaatcaa acga                                             324
```

<210> SEQ ID NO 49
<211> LENGTH: 108
<212> TYPE: PRT
<213> ORGANISM: Homo sapiens

<400> SEQUENCE: 49

```
Asp Ile Gln Met Thr Gln Ser Pro Ser Ser Leu Ser Thr Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
```

```
                    50                  55                  60

Ser Gly Ser Gly Thr Glu Phe Thr Leu Thr Ile Ser Ser Leu Arg Pro
 65                  70                  75                  80

Glu Asp Phe Ala Thr Tyr Tyr Cys Leu Gln Leu Asn Ser Tyr Pro Arg
                    85                  90                  95

Thr Phe Gly Gln Gly Thr Lys Val Glu Ile Lys Arg
                100                 105

<210> SEQ ID NO 50
<211> LENGTH: 351
<212> TYPE: DNA
<213> ORGANISM: Homo sapiens

<400> SEQUENCE: 50
caggtgcagc tgcaggagtc gggcccagga ctggtgaagc cttcggagac cctgtccctc      60
acctgcactg tctctggtgg ctccatcagt aattactact ggagctggat ccggcagccc     120
ccagggaagg gactggagtg gattggatat atctattaca gtgggagcac caactacaac     180
ccctccctca agagtcgagt caccatatca gtagacacgt ccaagaacca gttctccctg     240
aaactgagct ctgtgaccgc tgcggacacg gccgtgtatt actgtgcgag agaccgggct     300
gatgcttttg atatctgggg ccaagggaca atggtcaccg tctcttcagc c              351

<210> SEQ ID NO 51
<211> LENGTH: 117
<212> TYPE: PRT
<213> ORGANISM: Homo sapiens

<400> SEQUENCE: 51

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Asn Tyr
                 20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Arg Ala Asp Ala Phe Asp Ile Trp Gly Gln Gly Thr Met Val
                100                 105                 110

Thr Val Ser Ser Ala
        115

<210> SEQ ID NO 52
<211> LENGTH: 342
<212> TYPE: DNA
<213> ORGANISM: Homo sapiens

<400> SEQUENCE: 52
gatgttgtga tgactcagtc tccactctcc ctgcccgtca cccttggaca gccggcctcc      60
atctcctgca ggtctagtca agcctcgtt acagtgatg aaacacctta cttgaattgg      120
tttcagcaga ggccaggcca atctccaagg cgcctaattt ataaggtttc taactgggac     180
tctggggtcc cagacagatt cagcggcagt gggtcaggca ctgatttcac actgaaaatc     240
```
agcagggtgg aggctgagga tgttggggtt tattactgca tgcaaggtac acactggcct    300
ccgctcactt tcggcggagg gaccaaggtg gagatcaaac ga                       342

<210> SEQ ID NO 53
<211> LENGTH: 114
<212> TYPE: PRT
<213> ORGANISM: Homo sapiens

<400> SEQUENCE: 53

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
            100                 105                 110

Lys Arg

<210> SEQ ID NO 54
<211> LENGTH: 351
<212> TYPE: DNA
<213> ORGANISM: Homo sapiens

<400> SEQUENCE: 54
caggtgcagc tgcaggagtc gggcccagga ctggtgaagc cttcggagac cctgtccctc    60
acctgcactg tctctggtgg ctccatcagt aattactact ggagctggat ccggcagccc    120
ccagggaagg gactggagtg gattggatat atctattaca gtgggagcac caactacaac    180
ccctccctca agagtcgagt caccatatca gtagacacgt ccaagaacca gttctccctg    240
aaactgagct ctgtgaccgc tgcggacacg gccgtgtatt actgtgcgag agaccgggct    300
gatgcttttg atatctgggg ccaagggaca atggtcaccg tctcttcagc c             351

<210> SEQ ID NO 55
<211> LENGTH: 117
<212> TYPE: PRT
<213> ORGANISM: Homo sapiens

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala

```
                    85                  90                  95
Arg Asp Arg Ala Asp Ala Phe Asp Ile Trp Gly Gln Gly Thr Met Val
            100                 105                 110
Thr Val Ser Ser Ala
        115

<210> SEQ ID NO 56
<211> LENGTH: 342
<212> TYPE: DNA
<213> ORGANISM: Homo sapiens

<400> SEQUENCE: 56
gatgttgtga tgactcagtc tccactctcc ctgcccgtca cccttggaca gccggcctcc      60
atctcctgca ggtctagtca aagcctcgtt tacagtgatg aaacaccta cttgaattgg     120 tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
ccgctcactt tcggcggagg gaccaaggtg gagatcaaac ga                       342

<210> SEQ ID NO 57
<211> LENGTH: 114
<212> TYPE: PRT
<213> ORGANISM: Homo sapiens

<400> SEQUENCE: 57

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
            100                 105                 110

Lys Arg

<210> SEQ ID NO 58
<211> LENGTH: 366
<212> TYPE: DNA
<213> ORGANISM: Homo sapiens

<400> SEQUENCE: 58
gaggtgcagc tggtggagtc tgggggaggc ttggtaaagc ctggggggtc ccttagactc      60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ttgtatcatt    300
ttctacggtg actttgatgc ttttgatatc tggggccaag ggacaatggt caccgtctct    360
``` tcagcc                                                                                366

<210> SEQ ID NO 59
<211> LENGTH: 122
<212> TYPE: PRT
<213> ORGANISM: Homo sapiens

<400> SEQUENCE: 59

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ile Ile Phe Tyr Gly Asp Phe Asp Ala Phe Asp Ile Trp Gly
            100                 105                 110

Gln Gly Thr Met Val Thr Val Ser Ser Ala
        115                 120

<210> SEQ ID NO 60
<211> LENGTH: 313
<212> TYPE: DNA
<213> ORGANISM: Homo sapiens

<400> SEQUENCE: 60
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccatca       180
aggttcagtg gcagtggatc tgggacagat ttcactctca ccatcagcag tctgcaagct       240
gaagattttg caacttacta ctgtcaacag agtttaactt tcggccctgg gaccaaagtg       300
gatatcaaac gaa                                                         313

<210> SEQ ID NO 61
<211> LENGTH: 104
<212> TYPE: PRT
<213> ORGANISM: Homo sapiens

<400> SEQUENCE: 61

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Leu Thr Phe Gly Pro
                85                  90                  95

```
Gly Thr Lys Val Asp Ile Lys Arg
            100

<210> SEQ ID NO 62
<211> LENGTH: 342
<212> TYPE: DNA
<213> ORGANISM: Homo sapiens

<400> SEQUENCE: 62
gatgttgtga tgactcagtc tccactctcc ctgcccgtca cccttggaca gccggcctcc      60
atctcctgca ggtctagtca aagcctcgtt tacagtgatg aaacacccta cttgaattgg     120
tttcagcaga ggccaggcca atctccaagg cgcctaattt ataaggtttc taactgggac     180
tctggggtcc cagacagatt cagcggcagt gggtcaggca ctgatttcac actgaaaatc     240
agcagggtgg aggctgagga tgttggggtt tattactgca tgcaaggtac acactggcct     300
ccgctcactt tcggcggagg gaccaaggtg gagatcaaac ga                        342

<210> SEQ ID NO 63
<211> LENGTH: 114
<212> TYPE: PRT
<213> ORGANISM: Homo sapiens

<400> SEQUENCE: 63

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Trp Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Leu Thr Phe Gly Gly Gly Thr Lys Val Glu Ile
            100                 105                 110

Lys Arg

<210> SEQ ID NO 64
<211> LENGTH: 324
<212> TYPE: DNA
<213> ORGANISM: Homo sapiens

<400> SEQUENCE: 64
gacatccaaa tgacccagtc tccatcctca ctgtctgcat ctgtaggaga cagagtcacc      60
atcacttgtc gggcgagtca gggcattagc agttatttag cctggtttca gcagaaacca     120
gggaaagccc ctaagtccct gatctatgct gcatccagtt tgcaaagtgg ggtcccatca     180
aagttcagcg gcagtggatc tgggacagat ttcactctca ccatcagcag cctgcagcct     240
gaagattttg caacttatta ctgccaacag tataatagtt accctctcac tttcggcgga     300
gggaccaagg tggagatcaa acga                                            324

<210> SEQ ID NO 65
<211> LENGTH: 108
<212> TYPE: PRT
```

<213> ORGANISM: Homo sapiens

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 66
<211> LENGTH: 366
<212> TYPE: DNA
<213> ORGANISM: Homo sapiens

<400> SEQUENCE: 66
gaggtgcaac tggtggagtc tgggggaggc ttggtaaagc ctggggggtc ccttagactc      60
tcctgtgcag cctctggatt cactttcagt aacgcctgga tgcactgggt ccgccaggct     120
ccagggaagg ggctggactg ggttggccgt attaaaagca aaactgatgg tgggacagca     180
gactacgctg cacccgtgaa aggcagattc accatctcaa gagatgattc agaaaacacg     240
ctgtatctgc aaatgaacag cctgaaaacc gaggacacag ccgtgtatta ctgtaccaat     300
gactacggtg acttctatgc ttttgatatc tggggccaag ggacaatggt caccgtctct     360
tcagcc                                                                366

<210> SEQ ID NO 67
<211> LENGTH: 122
<212> TYPE: PRT
<213> ORGANISM: Homo sapiens

<400> SEQUENCE: 67

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Asp Trp Val
        35                  40                  45

Gly Arg Ile Lys Ser Lys Thr Asp Gly Gly Thr Ala Asp Tyr Ala Ala
    50                  55                  60

Pro Val Lys Gly Arg Phe Thr Ile Ser Arg Asp Asp Ser Glu Asn Thr
65                  70                  75                  80

Leu Tyr Leu Gln Met Asn Ser Leu Lys Thr Glu Asp Thr Ala Val Tyr
                85                  90                  95

Tyr Cys Thr Asn Asp Tyr Gly Asp Phe Tyr Ala Phe Asp Ile Trp Gly
            100                 105                 110

Gln Gly Thr Met Val Thr Val Ser Ser Ala
        115                 120

<210> SEQ ID NO 68
<211> LENGTH: 324
<212> TYPE: DNA
<213> ORGANISM: Homo sapiens

<400> SEQUENCE: 68

```
gacatccaga tgacccagtc tccatcctcc ctgtctgcat ctgtaggaga cagaatcacc    60
atcacttgcc gggcaaggca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttactt ctgtcaacag agttacagta ccccattcac tttcggccct   300
ggggccaaag tggatatcaa acga                                          324
```

<210> SEQ ID NO 69
<211> LENGTH: 108
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
1               5                   10                  15
Asp Arg Ile Thr Ile Thr Cys Arg Ala Arg Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Phe Cys Gln Gln Ser Tyr Ser Thr Pro Phe
                85                  90                  95
Thr Phe Gly Pro Gly Ala Lys Val Asp Ile Lys Arg
            100                 105

<210> SEQ ID NO 70
<211> LENGTH: 366
<212> TYPE: DNA
<213> ORGANISM: Homo sapiens

<400> SEQUENCE: 70

```
caggtgcagc tggtggagtc tgggggaggc gtggtccagc ctgggaggtc cctgagactc    60
tcctgtgcag cgtctggatt caccttcagt agctttggca tgcactgggt ccgccaggct   120
ccaggcaagg ggctggagtg ggtggcagtt atatggtttg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagtgactac   300
ggtgactact ctactacggg tatggacgtc tggggccaag gaccacggt caccgtctcc   360
tcagcc                                                              366
```

<210> SEQ ID NO 71
<211> LENGTH: 122
<212> TYPE: PRT
<213> ORGANISM: Homo sapiens

<400> SEQUENCE: 71

```
Gln Val Gln Leu Val Glu Ser Gly Gly Gly Val Val Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Tyr Tyr Ala Asp Ser Val
        50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Tyr Gly Asp Tyr Phe Tyr Tyr Gly Met Asp Val Trp Gly
            100                 105                 110

Gln Gly Thr Thr Val Thr Val Ser Ser Ala
            115                 120
```

```
<210> SEQ ID NO 72
<211> LENGTH: 324
<212> TYPE: DNA
<213> ORGANISM: Homo sapiens

<400> SEQUENCE: 72
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
agattcagcg gcagtggatc tgggacagaa ttcactctca caatcagcag cctgcagcct    240
gaagattttg caacttatta ctgtctacag tataatagtt accctcggac gttcggccaa    300
gggaccaagg tggaaatcaa acga                                           324
```

```
<210> SEQ ID NO 73
<211> LENGTH: 108
<212> TYPE: PRT
<213> ORGANISM: Homo sapiens

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Arg
                85                  90                  95

Thr Phe Gly Gln Gly Thr Lys Val Glu Ile Lys Arg
            100                 105
```

```
<210> SEQ ID NO 74
<211> LENGTH: 372
<212> TYPE: DNA
<213> ORGANISM: Homo sapiens
```

<400> SEQUENCE: 74

```
caggtgcagc tggtggagtc tgggggaggc gtggtccagc ctgggaggtc cctgagactc      60
tcctgtgcag cctctggatt caccttcact aactatggca tgcactgggg ccgccaggct     120
ccaggcaagg gctggagtg gtggcagtt atatcacatg atggaaataa taagtattat     180
gtagactccg tgaagggccg attcaccatc tccagagaca attccaagaa cacgctgtat     240
ctgcaaatga acagcctgag agctgaggac acggctgtgt attactgtgc gagagaggga     300
atcgattttt ggagtggcct caactggttc gacccctggg gccagggaac cctggtcacc     360
gtctcctcag cc                                                        372
```

<210> SEQ ID NO 75
<211> LENGTH: 124
<212> TYPE: PRT
<213> ORGANISM: Homo sapiens

<400> SEQUENCE: 75

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Thr Asn Tyr
            20                  25                  30
Gly Met His Trp Gly Arg Gln Ala Pro Gly Lys Gly Leu Glu Trp Val
        35                  40                  45
Ala Val Ile Ser His Asp Gly Asn Asn Lys Tyr Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Gly Ile Asp Phe Trp Ser Gly Leu Asn Trp Phe Asp Pro
            100                 105                 110
Trp Gly Gln Gly Thr Leu Val Thr Val Ser Ser Ala
        115                 120

<210> SEQ ID NO 76
<211> LENGTH: 327
<212> TYPE: DNA
<213> ORGANISM: Homo sapiens

<400> SEQUENCE: 76

```
gaaattgtgt tgacgcagtc tccaggcacc ctgtctttgt ctccagggga aagagccact      60
ctctcctgca gggccagtca gagtattacc ggcagctact tagcctggta ccagcagaaa     120
cctggccagg ctcccagact cctcatctgt ggtgcatcca gctgggccac tggcatccca     180
gacaggttca gtggcagtgg gtctgggaca gacttcactc tcaccatcag tagactggag     240
cctgaagatt ttgcagtgta ttactgtcag cagtatagta gttcaccgat caccttcggc     300
caagggacac gactggagat taaacga                                        327
```

<210> SEQ ID NO 77
<211> LENGTH: 109
<212> TYPE: PRT
<213> ORGANISM: Homo sapiens

<400> SEQUENCE: 77

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Ala Pro Arg Leu Leu
        35                  40                  45

Ile Cys Gly Ala Ser Ser Trp Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Pro
                85                  90                  95

Ile Thr Phe Gly Gln Gly Thr Arg Leu Glu Ile Lys Arg
                100                 105

<210> SEQ ID NO 78
<211> LENGTH: 372
<212> TYPE: DNA
<213> ORGANISM: Homo sapiens

<400> SEQUENCE: 78
caggtgcagc tggtggagtc tgggggaggc gtggtccagc ctggagggtc cctgagactc     60
tcctgtgcag cctctggatt caccttcact aactatggca tgcactgggg ccgccaggct    120
ccaggcaagg ggctggagtg ggtggcagtt atatcacatg atggaaataa taagtattat    180
gtagactccg tgaagggccg attcaccatc tccagagaca attccaagaa cacgctgtat    240
ctgcaaatga acagcctgag agctgaggac acggctgtgt attactgtgc gagagaggga    300
atcgattttt ggagtggcct caactggttc gacccctggg gccagggaac cctggtcacc    360
gtctcctcag cc                                                        372

<210> SEQ ID NO 79
<211> LENGTH: 124
<212> TYPE: PRT
<213> ORGANISM: Homo sapiens

<400> SEQUENCE: 79

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Met His Trp Gly Arg Gln Ala Pro Gly Lys Gly Leu Glu Trp Val
        35                  40                  45

Ala Val Ile Ser His Asp Gly Asn Asn Lys Tyr Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Asp Phe Trp Ser Gly Leu Asn Trp Phe Asp Pro
            100                 105                 110

Trp Gly Gln Gly Thr Leu Val Thr Val Ser Ser Ala
        115                 120

<210> SEQ ID NO 80
<211> LENGTH: 327
<212> TYPE: DNA
<213> ORGANISM: Homo sapiens

<400> SEQUENCE: 80

```
gaaattgtgt tgacgcagtc tccaggcacc ctgtctttgt ctccagggga aagagccact    60
ctctcctgca gggccagtca gagtattacc ggcagctact tagcctggta ccagcagaaa   120
cctggccagg ctcccagact cctcatctgt ggtgcatcca gctgggccac tggcatccca   180
gacaggttca gtggcagtgg gtctgggaca gacttcactc tcaccatcag tagactggag   240
cctgaagatt ttgcagtgta ttactgtcag cagtatagta gttcaccgat caccttcggc   300
caagggacac gactggagat taaacga                                       327
```

<210> SEQ ID NO 81
<211> LENGTH: 109
<212> TYPE: PRT
<213> ORGANISM: Homo sapiens

<400> SEQUENCE: 81

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Cys Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg
            100                 105
```

<210> SEQ ID NO 82
<211> LENGTH: 339
<212> TYPE: DNA
<213> ORGANISM: Homo sapiens

<400> SEQUENCE: 82

```
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggcca atctccaagg cgcctaattt ataaggtttc aagtgggac   180 tctggggtcc cagacagatt cagcggcagt gggtcaggca ctgatttcac actgaaaatc   240
agcagggtgg aggctgagga tgttggggtt tattactgca tgcaaggtac acactggcct   300
ccgacgttcg gccaagggac caaggtggaa atcaaacga                          339
```

<210> SEQ ID NO 83
<211> LENGTH: 113
<212> TYPE: PRT
<213> ORGANISM: Homo sapiens

<400> SEQUENCE: 83

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45
```

Pro Arg Arg Leu Ile Tyr Lys Val Ser Lys Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Thr Phe Gly Gln Gly Thr Lys Val Glu Ile Lys
             100                 105                 110

Arg

<210> SEQ ID NO 84
<211> LENGTH: 360
<212> TYPE: DNA
<213> ORGANISM: Homo sapiens

<400> SEQUENCE: 84
caggtgcagc tgcaggagtc gggcccagga ctggtgaagc cttcacagac cctgtccctc     60
acctgcactg tctctggtgg ctccatcagt agtggtggtt acttctggag ctggatccgc    120
cagcacccag ggaagggcct ggagtggatt gggtacatct attacagtgg agaacctac     180 tacaacccgt ccctcaagag tcgagttacc atatcagtag acgcgtctaa gaaccagttc    240
tccctgaagc tgagctctgt gactgccgcg gacacggccg tgtatcactg tgcgagagag    300
gggtcgtact gggactttga ctactggggc cagggaaccc tggtcaccgt ctcctcagcc    360

<210> SEQ ID NO 85
<211> LENGTH: 120
<212> TYPE: PRT
<213> ORGANISM: Homo sapiens

<400> SEQUENCE: 85

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Phe Trp Ser Trp Ile Arg Gln His Pro Gly Lys Gly Leu Glu
         35                  40                  45

Trp Ile Gly Tyr Ile Tyr Tyr Ser Gly Arg Thr Tyr Tyr Asn Pro Ser
 50                  55                  60

Leu Lys Ser Arg Val Thr Ile Ser Val Asp Ala Ser Lys Asn Gln Phe
 65                  70                  75                  80

Ser Leu Lys Leu Ser Ser Val Thr Ala Ala Asp Thr Ala Val Tyr His
                 85                  90                  95

Cys Ala Arg Glu Gly Ser Tyr Trp Asp Phe Asp Tyr Trp Gly Gln Gly
             100                 105                 110

Thr Leu Val Thr Val Ser Ser Ala
         115                 120

<210> SEQ ID NO 86
<211> LENGTH: 327
<212> TYPE: DNA
<213> ORGANISM: Homo sapiens

<400> SEQUENCE: 86
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtacatcca gcagggccac tggcatccca    180

```
gacaggttca gtggcagtgg gtctgggaca gacttcactc tcaccatcag cagactggag    240
cctgaagatt ttgcagtgta ttactgtcag cagtatggta gctcactatt cactttcggc    300
cctgggacca agtggatat caaacga                                         327
```

<210> SEQ ID NO 87
<211> LENGTH: 109
<212> TYPE: PRT
<213> ORGANISM: Homo sapiens

<400> SEQUENCE: 87

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser
             20                  25                  30

Tyr Leu Ala Trp Tyr Gln Gln Lys Pro Gly Gln Ala Pro Arg Leu Leu
         35                  40                  45

Ile Tyr Gly Thr Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Leu
                 85                  90                  95

Phe Thr Phe Gly Pro Gly Thr Lys Val Asp Ile Lys Arg
            100                 105
```

<210> SEQ ID NO 88
<211> LENGTH: 378
<212> TYPE: DNA
<213> ORGANISM: Homo sapiens

<400> SEQUENCE: 88

```
caggtgcagc tggtggagtc tggggggaggc gtggtccagc ctgggaggtc cctgagactc    60
tcctgtgcag cgtctggatt caccttcagt aactatggca tgcactgggt ccgtcaggct    120
ccaggcaagg gctggagtg gtggcagtt atatggtatg atggaagtaa taaatactat    180
gcagactccg tgaagggccg attcaccatc tccagagaca attccaggaa cacgctgtat    240
ctgcaaatga acagcctgag agccgaggac acggctgtgt attactgtgc gagagagggg    300
gggtattgtg gtggtgactg ctgggtttac ggtatggacg tctggggcca agggaccacg    360
gtcaccgtct cctcagcc                                                  378
```

<210> SEQ ID NO 89
<211> LENGTH: 126
<212> TYPE: PRT
<213> ORGANISM: Homo sapiens

<400> SEQUENCE: 89

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Arg Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Glu Gly Gly Tyr Cys Gly Gly Asp Cys Trp Val Tyr Gly Met
                100                 105                 110

Asp Val Trp Gly Gln Gly Thr Thr Val Thr Val Ser Ser Ala
            115                 120                 125

<210> SEQ ID NO 90
<211> LENGTH: 324
<212> TYPE: DNA
<213> ORGANISM: Homo sapiens

<400> SEQUENCE: 90
gacatccaga tgacccagtc tccatttccc gtgtctgcat ctgtaggaga cagagtcacc    60
atcacttgtc gggcgagtca gggtattagc aactggttag cctggtatca gcagaaacca   120
gggaaagccc ctaaactcct gatctatact gcatccagtt tgcaaaatgg ggtcccatca   180
aggttcagcg gcagtggatc tgggacagat ttcactctca ccatcagcag cctgcagcct   240
gaagattttg caacttacta ttgtcaacag attaacagtt tcccgtggac gttcggccaa   300
gggaccaagg tggaaatcaa acga                                          324

<210> SEQ ID NO 91
<211> LENGTH: 108
<212> TYPE: PRT
<213> ORGANISM: Homo sapiens

<400> SEQUENCE: 91

Asp Ile Gln Met Thr Gln Ser Pro Phe Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Thr Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Asn Ser Phe Pro Trp
                85                  90                  95

Thr Phe Gly Gln Gly Thr Lys Val Glu Ile Lys Arg
            100                 105

<210> SEQ ID NO 92
<211> LENGTH: 366
<212> TYPE: DNA
<213> ORGANISM: Homo sapiens

<400> SEQUENCE: 92
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc ggggactac   300 ggtgagtact ctactacgg tatggacgtc tggggccaag gaccacggt caccgtctcc   360
```

```
tcagcc                                                                  366
```

<210> SEQ ID NO 93
<211> LENGTH: 122
<212> TYPE: PRT
<213> ORGANISM: Homo sapiens

<400> SEQUENCE: 93

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Gly Asp Tyr Gly Glu Tyr Phe Tyr Tyr Gly Met Asp Val Trp Gly
                100                 105                 110

Gln Gly Thr Thr Val Thr Val Ser Ser Ala
            115                 120
```

<210> SEQ ID NO 94
<211> LENGTH: 324
<212> TYPE: DNA
<213> ORGANISM: Homo sapiens

<400> SEQUENCE: 94

```
gacatccaga tgacccagtc tccatcctcc ctgtctgcat ctgtaggaga cagagtcacc     60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagat ttcactctca caatcagcag cctgcagcct   240
gaagattttg caacttatta ctgtttacag cataataatt accctcggac gttcggccaa   300
gggaccaagg tggaaatcaa acga                                           324
```

<210> SEQ ID NO 95
<211> LENGTH: 108
<212> TYPE: PRT
<213> ORGANISM: Homo sapiens

<400> SEQUENCE: 95

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Leu Gln His Asn Asn Tyr Pro Arg
```

```
                        85                  90                  95
Thr Phe Gly Gln Gly Thr Lys Val Glu Ile Lys Arg
                100                 105

<210> SEQ ID NO 96
<211> LENGTH: 357
<212> TYPE: DNA
<213> ORGANISM: Homo sapiens

<400> SEQUENCE: 96
gaggtgcagc tggtggagtc tgggggaggc ttggtccagc ctggggggtc cctgagactc    60
tcctgtgcag cctctggatt cacctttagt agctcttgga tgagctgggt ccgccaggct   120
ccagggaagg ggctggagtg ggtggccaac ataaagcaag atggaagtga caaatactat   180
gtggactctg tgaagggccg attcaccatc tccagagaca cgccaagaa ctcactgtat   240 ctgcaaatga acagcctgag agccgaggac acggctgtgt attactgtgt gagagataag   300
ggcagtggct ggtttgacta ctggggccag ggaaccctgg tcaccgtctc ctcagcc      357

<210> SEQ ID NO 97
<211> LENGTH: 119
<212> TYPE: PRT
<213> ORGANISM: Homo sapiens

<400> SEQUENCE: 97

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Asp Lys Tyr Tyr Val Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Val Arg Asp Lys Gly Ser Gly Trp Phe Asp Tyr Trp Gly Gln Gly Thr
            100                 105                 110

Leu Val Thr Val Ser Ser Ala
        115

<210> SEQ ID NO 98
<211> LENGTH: 357
<212> TYPE: DNA
<213> ORGANISM: Homo sapiens

<400> SEQUENCE: 98
gaggtgcagc tggtggagtc tgggggaggc ttggtccagc ctggggggtc cctgagactc    60
tcctgtgcag cctctggatt cacctttagt agctattgga tgagctgggt ccgccaggct   120
ccagggaagg ggctggagtg ggtggccaac ataaagcaag atggaagtga caaatactat   180
gtggactctg tgaagggccg attcaccatc tccagagaca cgccaagaa ctcactgtat   240 ctgcgaatga acagcctgag agccgaggac acggctgtgt tttactgtgc gagagatatg   300
ggcagtggct ggtttgacta ctggggccag ggaaccctgg tcaccgtctc ctcagcc      357

<210> SEQ ID NO 99
```

<211> LENGTH: 119
<212> TYPE: PRT
<213> ORGANISM: Homo sapiens

<400> SEQUENCE: 99

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Asp Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Arg Met Asn Ser Leu Arg Ala Glu Asp Thr Ala Val Phe Tyr Cys
                 85                  90                  95

Ala Arg Asp Met Gly Ser Gly Trp Phe Asp Tyr Trp Gly Gln Gly Thr
            100                 105                 110

Leu Val Thr Val Ser Ser Ala
        115
```

<210> SEQ ID NO 100
<211> LENGTH: 321
<212> TYPE: DNA
<213> ORGANISM: Homo sapiens

<400> SEQUENCE: 100

```
gaagtagtga tgacgcagtc tccagccacc ctgtctgtgt ctccagggga aagagccacc    60
ctctcctgca gggccagtca gagtgttggc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttattg ctgtcagcag tataatcact ggtggacgtt cggccaaggg   300
accaaggtgg aaatcaaacg a                                             321
```

<210> SEQ ID NO 101
<211> LENGTH: 107
<212> TYPE: PRT
<213> ORGANISM: Homo sapiens

<400> SEQUENCE: 101

```
Glu Val Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Gly Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Cys Cys Gln Gln Tyr Asn His Trp Trp Thr
                 85                  90                  95

Phe Gly Gln Gly Thr Lys Val Glu Ile Lys Arg
            100                 105
```

<210> SEQ ID NO 102
<211> LENGTH: 357
<212> TYPE: DNA
<213> ORGANISM: Homo sapiens

<400> SEQUENCE: 102

```
gaggtgcagc tggtggagtc tgggggaggc ttggtccagc ctggggggtc cctgagactc      60
tcctgtgcag cctctggatt cacctttagt agctattgga tgagctgggt ccgccaggct     120
ccagggaagg ggctggagtg ggtggccaac ataaagcaag atggaagtga caaatactat     180
gtggactctg tgaagggccg attcaccatc tccagagaca acgccaagaa ctcactgtat     240
ctgcgaatga acagcctgag agccgaggac acggctgtgt tttactgtgc gagagatatg     300
ggcagtggct ggtttgacta ctggggccag ggaaccctgg tcaccgtctc ctcagcc       357
```

<210> SEQ ID NO 103
<211> LENGTH: 119
<212> TYPE: PRT
<213> ORGANISM: Homo sapiens

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Arg Met Asn Ser Leu Arg Ala Glu Asp Thr Ala Val Phe Tyr Cys
                85                  90                  95

Ala Arg Asp Met Gly Ser Gly Trp Phe Asp Tyr Trp Gly Gln Gly Thr
            100                 105                 110

Leu Val Thr Val Ser Ser Ala
        115

<210> SEQ ID NO 104
<211> LENGTH: 321
<212> TYPE: DNA
<213> ORGANISM: Homo sapiens

<400> SEQUENCE: 104

```
gaagtagtga tgacgcagtc tccagccacc ctgtctgtgt ctccagggga aagagccacc      60
ctctcctgca gggccagtca gagtgttggc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttattg ctgtcagcag tataatcact ggtggacgtt cggccaaggg     300
accaaggtgg aaatcaaacg a                                                321
```

<210> SEQ ID NO 105
<211> LENGTH: 107
<212> TYPE: PRT
<213> ORGANISM: Homo sapiens

<400> SEQUENCE: 105

```
Glu Val Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Cys Cys Gln Gln Tyr Asn His Trp Trp Thr
                85                  90                  95

Phe Gly Gln Gly Thr Lys Val Glu Ile Lys Arg
            100                 105
```

<210> SEQ ID NO 106
<211> LENGTH: 351
<212> TYPE: DNA
<213> ORGANISM: Homo sapiens

<400> SEQUENCE: 106

```
caggtgcagc tgcaggagtc gggcccagga ctggtgaagc cttcggagac cctgtccctc    60
acctgcactg tctctggtgg ctccatcagt aattactact ggagctggat ccggcagccc   120
ccagggaagg gactggagtg gattggatat atctattaca gtgggagcac caactacaac   180
ccctccctca gagtcgagt caccatatca gtagacacgt ccaagaacca gttctccctg   240
aaactgagct ctgtgaccgc tgcggacacg gccgtgtatt actgtgcgag agaccgggct   300
gatgcttttg atatctgggg ccaagggaca atggtcaccg tctcttcagc c           351
```

<210> SEQ ID NO 107
<211> LENGTH: 117
<212> TYPE: PRT
<213> ORGANISM: Homo sapiens

<400> SEQUENCE: 107

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Ala Asp Ala Phe Asp Ile Trp Gly Gln Gly Thr Met Val
            100                 105                 110

Thr Val Ser Ser Ala
            115
```

<210> SEQ ID NO 108
<211> LENGTH: 342
<212> TYPE: DNA
<213> ORGANISM: Homo sapiens -continued

<400> SEQUENCE: 108

```
gatgttgtga tgactcagtc tccactctcc ctgcccgtca cccttggaca gccggcctcc    60
atctcctgca ggtctagtca aagcctcgtt tacagtgatg gaaacaccta cttgaattgg   120
tttcagcaga ggccaggcca atctccaagg cgcctaattt ataaggtttc taactgggac   180
tctggggtcc cagacagatt cagcggcagt gggtcaggca ctgatttcac actgaaaatc   240
agcagggtgg aggctgagga tgttggggtt tattactgca tgcaaggtac acactggcct   300
ccgctcactt tcggcggagg gaccaaggtg gagatcaaac ga                      342
```

<210> SEQ ID NO 109
<211> LENGTH: 114
<212> TYPE: PRT
<213> ORGANISM: Homo sapiens

<400> SEQUENCE: 109

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
            100                 105                 110

Lys Arg
```

<210> SEQ ID NO 110
<211> LENGTH: 351
<212> TYPE: DNA
<213> ORGANISM: Homo sapiens

<400> SEQUENCE: 110

```
caggtgcagc tgcaggagtc gggcccagga ctggtgaagc cttcggaaac cctgtccctc    60
acctgcactg tctctggtga ctccatcagt aattactact ggagctggat ccggcagccc   120
ccagggaagg gactggagtg gattgggtat atctattaca gtgggagcac caactacaat   180
ccctccctca agagtcgagt caccatatca gtagacacgt ccaagaacca gttctccctg   240
aagctgagct ctgtgaccgc tgcggacacg gccgtgtatt actgtgcgag agagaggggt   300
gatgcttttg atatctgggg ccaagggaga gtggtcaccg tctcttcagc c             351
```

<210> SEQ ID NO 111
<211> LENGTH: 117
<212> TYPE: PRT
<213> ORGANISM: Homo sapiens

<400> SEQUENCE: 111

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Asn Tyr
            20                  25                  30
```

```
Tyr Trp Ser Trp Ile Arg Gln Pro Pro Gly Lys Gly Leu Glu Trp Ile
            35                  40                  45
Gly Tyr Ile Tyr Tyr Ser Gly Ser Thr Asn Tyr Asn Pro Ser Leu Lys
 50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                85                  90                  95
Arg Glu Arg Gly Asp Ala Phe Asp Ile Trp Gly Gln Gly Arg Val Val
            100                 105                 110
Thr Val Ser Ser Ala
            115

<210> SEQ ID NO 112
<211> LENGTH: 324
<212> TYPE: DNA
<213> ORGANISM: Homo sapiens

<400> SEQUENCE: 112
gacatccaga tgacccagtc tccatcctcc ctgtctgcat ctgtaggaga cagagtcacc      60
atcacttgcc gggcaagtca gggcatcaga aatgatttag gctggtatca gcagaaacca     120
gggaaagccc ctaagcgcct gatctatgct gcatccagtt tgcaaagtgg ggtcccatca     180
aggttcagcg gcagtagatc tgggacagaa ttcactctca caatcagcag cctgcagcct     240
gaagattttg caacttatta ctgtctccag cataatagtt accctcccag ttttggccag     300
gggaccaagc tggagatcaa acga                                            324

<210> SEQ ID NO 113
<211> LENGTH: 108
<212> TYPE: PRT
<213> ORGANISM: Homo sapiens

<400> SEQUENCE: 113

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
            35                  40                  45
Tyr Ala Ala Ser Ser Leu Gln Ser Gly Val Pro Ser Arg Phe Ser Gly
 50                  55                  60
Ser Arg Ser Gly Thr Glu Phe Thr Leu Thr Ile Ser Ser Leu Gln Pro
 65                  70                  75                  80
Glu Asp Phe Ala Thr Tyr Tyr Cys Leu Gln His Asn Ser Tyr Pro Pro
                85                  90                  95
Ser Phe Gly Gln Gly Thr Lys Leu Glu Ile Lys Arg
            100                 105

<210> SEQ ID NO 114
<211> LENGTH: 351
<212> TYPE: DNA
<213> ORGANISM: Homo sapiens

<400> SEQUENCE: 114
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
```

```
cctggacaag ggcttgagtg gatgggatgg atcagcactt acaatgataa cacaaactat    180
gcacagaagc tccagggcag agtcaccatg accacagaca catccacgag cacagcctac    240
atggagctga ggagcctgag atctgacgac acggccgtgt attactgtgc gaggggagtg    300
ggagctacgg actactgggg ccagggaacc ctggtcaccg tctcctcagc c              351
```

<210> SEQ ID NO 115
<211> LENGTH: 117
<212> TYPE: PRT
<213> ORGANISM: Homo sapiens

<400> SEQUENCE: 115

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Thr Tyr Asn Asp Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Val Gly Ala Thr Asp Tyr Trp Gly Gln Gly Thr Leu Val
            100                 105                 110

Thr Val Ser Ser Ala
        115

<210> SEQ ID NO 116
<211> LENGTH: 324
<212> TYPE: DNA
<213> ORGANISM: Homo sapiens

<400> SEQUENCE: 116

```
gacatccaga tgacccagtc tccatcctca ctgtctgcat ctgtaggaga cagagtctcc    60
atcatttgtc gggcgagtca gggcattagc aattatttag cctggtttca gcagaaacca    120
gggaaagccc ctaagtccct gatctatgct gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatagtt acccatcaac tttcggccct    300
gggaccaaag tggatatcaa acga                                            324
```

<210> SEQ ID NO 117
<211> LENGTH: 108
<212> TYPE: PRT
<213> ORGANISM: Homo sapiens

<400> SEQUENCE: 117

Asp Ile Gln Met Thr Gln Ser Pro Ser Ser Leu Ser Ala Ser Val Gly
 1               5                  10                  15

Asp Arg Val Ser Ile Ile Cys Arg Ala Ser Gln Gly Ile Ser Asn Tyr
             20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Lys Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Ser
                85                  90                  95

Thr Phe Gly Pro Gly Thr Lys Val Asp Ile Lys Arg
            100                 105
```

```
<210> SEQ ID NO 118
<211> LENGTH: 351
<212> TYPE: DNA
<213> ORGANISM: Homo sapiens

<400> SEQUENCE: 118
caggtgcagc tgcaggagtc gggcccagga ctggtgaagc cttcggaaac cctgtccctc      60
acctgcactg tctctggtga ctccatcagt aattactact ggagctggat ccggcagccc     120
ccagggaagg gactggagtg gattgggtat atctattaca gtgggagcac caactacaat     180
ccctccctca agagtcgagt caccatatca gtagacacgt ccaagaacca gctctccctg     240
aagctgagct ctgtgaccgc tgcggacacg gccgtgtatt actgtgcgag agagaggggt     300
gatgcttttg atatctgggg ccaagggaga gtggtcaccg tctcttcagc c              351

<210> SEQ ID NO 119
<211> LENGTH: 117
<212> TYPE: PRT
<213> ORGANISM: Homo sapiens

<400> SEQUENCE: 119

Gln Val Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Ser Asn Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Leu Ser Leu
 65                  70                  75                  80

Lys Leu Ser Ser Val Thr Ala Ala Asp Thr Ala Val Tyr Tyr Cys Ala
                85                  90                  95

Arg Glu Arg Gly Asp Ala Phe Asp Ile Trp Gly Gln Gly Arg Val Val
            100                 105                 110

Thr Val Ser Ser Ala
        115

<210> SEQ ID NO 120
<211> LENGTH: 360
<212> TYPE: DNA
<213> ORGANISM: Homo sapiens

<400> SEQUENCE: 120
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atctatcata gtggaagcac caactacaac     180
ccgtccctca agagtcgagt caccatatca gtagacacgt ccaagaacca gttctccctg     240
```

```
aagctgagct ctgtgaccgc cgcggacacg gctgtgtatt cctgtgcgag aaatgactac    300
ggtgaccacg aaggctttga ctactggggc cagggaaccc tggtcaccgt ctcctcagcc    360
```

<210> SEQ ID NO 121
<211> LENGTH: 120
<212> TYPE: PRT
<213> ORGANISM: Homo sapiens

<400> SEQUENCE: 121

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Tyr His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Ser Cys Ala
                85                  90                  95

Arg Asn Asp Tyr Gly Asp His Glu Gly Phe Asp Tyr Trp Gly Gln Gly
            100                 105                 110

Thr Leu Val Thr Val Ser Ser Ala
        115                 120

<210> SEQ ID NO 122
<211> LENGTH: 337
<212> TYPE: DNA
<213> ORGANISM: Homo sapiens

<400> SEQUENCE: 122

```
gatattgtga tgactcagtc tccactctcc ctgcccgtca cccctggaga gccggcctcc    60
atctcctgca ggtctagtca gagcctcctg catagtgatg gatacaacta tttggattgg   120
tacctgcaga agccagggca gtctccacag ctcctgatct atttgggttc taatcgggcc   180
tccggggtcc ctgacaggtt cagtggcagt ggatcatgca cagattttac actgaaaatc   240
agcagagtgg aggctgagga tgttgggatt tattactgca tgcaagctct acaaactcct   300
cactttcggc ggagggacca aggtggagat caaacga                            337
```

<210> SEQ ID NO 123
<211> LENGTH: 112
<212> TYPE: PRT
<213> ORGANISM: Homo sapiens

<400> SEQUENCE: 123

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Cys Thr Asp Phe Thr Leu Lys Ile
65                  70                  75                  80

Ser Arg Val Glu Ala Glu Asp Val Gly Ile Tyr Tyr Cys Met Gln Ala
            85                  90                  95

Leu Gln Thr Pro His Phe Arg Arg Asp Gln Gly Gly Asp Gln Thr
       100                 105                 110

<210> SEQ ID NO 124
<211> LENGTH: 383
<212> TYPE: DNA
<213> ORGANISM: Homo sapiens

<400> SEQUENCE: 124
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatcgg     300
agctacggtg gtaactcctt ctactactac tactacggta tggacgtctg gggccaaggg     360
accacggtca ccgtctcctc agc                                             383

<210> SEQ ID NO 125
<211> LENGTH: 128
<212> TYPE: PRT
<213> ORGANISM: Homo sapiens

<400> SEQUENCE: 125

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Gly Gly Asn Ser Phe Tyr Tyr Tyr Tyr Tyr
            100                 105                 110

Gly Met Asp Val Trp Gly Gln Gly Thr Thr Val Thr Val Ser Ser Ala
        115                 120                 125

<210> SEQ ID NO 126
<211> LENGTH: 324
<212> TYPE: DNA
<213> ORGANISM: Homo sapiens

<400> SEQUENCE: 126
gacatccaga tgacccagtc tccatcctcc ctgtctgcat ctgtaggaga cagagtcacc      60
atcacttgcc gggcaagtca gggcatcaga aatgatttag ctggtatca gcagaaacca     120 gggaaagccc ctaagcgcct gatctatgct gcatccagtt tgcaaagtgg ggtcccatca     180
aggttcagcg gcagtagatc tgggacagaa ttcactctca caatcagcag cctgcagcct     240
gaagattttg caacttatta ctgtctccag cataatagtt accctcccag ttttggccag     300
gggaccaagc tggagatcaa acga                                            324

<210> SEQ ID NO 127
<211> LENGTH: 108
<212> TYPE: PRT
<213> ORGANISM: Homo sapiens

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Ser Phe Gly Gln Gly Thr Lys Leu Glu Ile Lys Arg
            100                 105

<210> SEQ ID NO 128
<211> LENGTH: 360
<212> TYPE: DNA
<213> ORGANISM: Homo sapiens

<400> SEQUENCE: 128
gaggtgcaac tggtggagtc tgggggaggc ctggtcaagc ctgggggtc cctgagactc      60 tcctgtgcag cctctggatt caccttcagt agctatagaa tgaactgggt ccgccaggct     120
ccagggaagg gctggagtg gtctcatcc attagtagta gtagtagtca catatactac      180
gtagactcag tgaagggccg attcaccatc tccagagaca cgccaagaa ttcactgtat     240 ctgcaaatga acagcctgag agccgaggac acggctgtgt attactgtgc gagagatcga    300
ggagtgggag ctccctttga ctactggggc cagggaaccc tggtcaccgt ctcctcagcc    360

<210> SEQ ID NO 129
<211> LENGTH: 120
<212> TYPE: PRT
<213> ORGANISM: Homo sapiens

<400> SEQUENCE: 129

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser His Ile Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Ala Pro Phe Asp Tyr Trp Gly Gln Gly
            100                 105                 110

Thr Leu Val Thr Val Ser Ser Ala
        115                 120

<210> SEQ ID NO 130
<211> LENGTH: 339
<212> TYPE: DNA
<213> ORGANISM: Homo sapiens

<400> SEQUENCE: 130
gatgttgtga tgactcagtc tccactctcc ctgcccgtca cccttggaca gccggcctcc    60
atctcctgca ggtctagtca aagcctcgta tacagtgatg aaacaccta cttgaattgg    120 tttcagcaga ggccaggcca atctccaagg cgcctaattt ataaggattc taactgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
ctcactttcg gcggagggac caacgtggag atcaaacga                          339

<210> SEQ ID NO 131
<211> LENGTH: 113
<212> TYPE: PRT
<213> ORGANISM: Homo sapiens

<400> SEQUENCE: 131

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Asp Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Asn Val Glu Ile Lys
            100                 105                 110

Arg

<210> SEQ ID NO 132
<211> LENGTH: 360
<212> TYPE: DNA
<213> ORGANISM: Homo sapiens

<400> SEQUENCE: 132
gaggtgcaac tggtggagtc tgggggaggc ctggtcaagc ctgggggtc cctgagactc     60 tcctgtgcag cctctggatt caccttcagt agctatagaa tgaactgggt ccgccaggct    120
ccagggaagg ggctggagtg ggtctcatcc attagtagta gtagtagtca catatactac    180
gtagactcag tgaagggccg attcaccatc tccagagaca acgccaagaa ttcactgtat    240
ctgcaaatga acagcctgag agccgaggac acggctgtgt attactgtgc gagagatcga    300
ggagtgggag ctccctttga ctactggggc cagggaaccc tggtcaccgt ctcctcagcc    360

<210> SEQ ID NO 133
<211> LENGTH: 120
<212> TYPE: PRT
<213> ORGANISM: Homo sapiens

<400> SEQUENCE: 133

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser His Ile Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Ala Pro Phe Asp Tyr Trp Gly Gln Gly
            100                 105                 110

Thr Leu Val Thr Val Ser Ser Ala
        115                 120

<210> SEQ ID NO 134
<211> LENGTH: 339
<212> TYPE: DNA
<213> ORGANISM: Homo sapiens

<400> SEQUENCE: 134
gatgttgtga tgactcagtc tccactctcc ctgcccgtca cccttggaca gccggcctcc      60
atctcctgca ggtctagtca agcctcgta tacagtgatg gaaacaccta cttgaattgg     120
tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
ctcactttcg gcggagggac caacgtggag atcaaacga                           339

<210> SEQ ID NO 135
<211> LENGTH: 113
<212> TYPE: PRT
<213> ORGANISM: Homo sapiens

<400> SEQUENCE: 135

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Asn Val Glu Ile Lys
            100                 105                 110

Arg

<210> SEQ ID NO 136
<211> LENGTH: 366
<212> TYPE: DNA
<213> ORGANISM: Homo sapiens

<400> SEQUENCE: 136

```
caggtgcagc tggtggagtc tgggggaggc gtggtccagc ctggagggtc cctgagactc    60
tcctgtgcag cgtctggatt caccttcagt agctatggca tacactgggt ccgccaggct   120
ccaggcaagg ggctggagtg gtggcagtt atttggtatg atggaagtag taaatactat   180
gcagactccg tgaagggccg attcaccatc tccagagaca attccaagaa cacgctgtat   240
ctgcaaatga acagcctgag agccgaggac acggctgtgt attactgtgc gagagcgaat   300
gactacggtg gtaacgggct ttttgactac tggggccagg gaaccctggt caccgtctcc   360
tcagcc                                                              366
```

<210> SEQ ID NO 137
<211> LENGTH: 122
<212> TYPE: PRT
<213> ORGANISM: Homo sapiens

<400> SEQUENCE: 137

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Asp Tyr Gly Gly Asn Gly Leu Phe Asp Tyr Trp Gly
           100                 105                 110

Gln Gly Thr Leu Val Thr Val Ser Ser Ala
           115                 120
```

<210> SEQ ID NO 138
<211> LENGTH: 342
<212> TYPE: DNA
<213> ORGANISM: Homo sapiens

<400> SEQUENCE: 138

```
gacatcgtga tgacccagtc tccagactcc ctggctgtgt ctctgggcga gagggccacc    60
atcaactgca ggtccagcca gagtatttta ttcagctcca acaataagaa ctacttagct   120
tggtaccagc agaaaccagg gcagcctcct aagttgctcc tttactgggc atctacccgg   180
gaatccgggg tccctgcccg attcagtggc agcgggtctg ggacagattt cactctcacc   240
atcagcagcc tgcaggctga agatgtggca gtttattact gtcagcaata ttatagtact   300
ccgtgcagtt ttggccaggg gaccaggctg gagatcaaac ga                      342
```

<210> SEQ ID NO 139
<211> LENGTH: 114
<212> TYPE: PRT
<213> ORGANISM: Homo sapiens

<400> SEQUENCE: 139

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Ala Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Cys Ser Phe Gly Gln Gly Thr Arg Leu Glu Ile
            100                 105                 110

Lys Arg

<210> SEQ ID NO 140
<211> LENGTH: 377
<212> TYPE: DNA
<213> ORGANISM: Homo sapiens

<400> SEQUENCE: 140
gaggtgcagc tggtggagtc tgggggaggc ttggtaaagc ctgggggtc ccttagactc      60
tcctgtgcag cctctggatt cactttcagt aacgcctgga tgacctgggt ccgccaggct    120
ccagggaagg gctggagtg ggttggccgt attaaaagca aaactgttgg tgggacaaca     180
gactacgctg cacccgtgaa aggcagattc accatctcaa gagatgattc aaaaaacacg    240
ctgtatctgc aaatgaacag tctgaaaacc gaggacacag ccgtgtatta ctgtaccaca    300
gactacggtg actactataa ctccggctac ggtatggacg tctggggcca agggaccacg    360
gtcaccgtct cctcagc                                                    377

<210> SEQ ID NO 141
<211> LENGTH: 126
<212> TYPE: PRT
<213> ORGANISM: Homo sapiens

<400> SEQUENCE: 141

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Ile Lys Ser Lys Thr Val Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Tyr Gly Asp Tyr Tyr Asn Ser Gly Tyr Gly Met
            100                 105                 110

Asp Val Trp Gly Gln Gly Thr Thr Val Thr Val Ser Ser Ala
        115                 120                 125

<210> SEQ ID NO 142
<211> LENGTH: 325
<212> TYPE: DNA
<213> ORGANISM: Homo sapiens

<400> SEQUENCE: 142

```
gacatccaga tgacccagtc tccatcctcc ctgtctgcat ctgtaggaga cagagtcacc      60
atcacttgcc gggcaagtca gagcattagc ttctatttaa attggtatca gcagaaacca     120
gggaaagccc ctaaactcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagtt ccccattcac tttcggccct     300
gggaccaaag tggatatcaa acgaa                                            325
```

<210> SEQ ID NO 143
<211> LENGTH: 108
<212> TYPE: PRT
<213> ORGANISM: Homo sapiens

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Phe Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Phe
                85                  90                  95

Thr Phe Gly Pro Gly Thr Lys Val Asp Ile Lys Arg
            100                 105

<210> SEQ ID NO 144
<211> LENGTH: 351
<212> TYPE: DNA
<213> ORGANISM: Homo sapiens

<400> SEQUENCE: 144

```
caggtgcagc tgcaggagtc gggcccagga ctggtgaagc cttcggagac cctgtccctc      60
acctgcactg tctctggtgg ctccatcaat aattactact ggagctggat ccggcagccc     120
ccagggaagg gactggagtg gattggttat atctattaca gtgggagcac caactacaac     180
ccctccctca gagtcgagt caccatatca gtagacacgt ccaagaacca gttctccctg     240
aagctgagct ctgtgaccgc tgcggacacg gccgtgtatt actgtgcgag agagaggggt     300
gactcctttg actactgggg ccagggaacc ctggtcaccg tctcctcagc c             351
```

<210> SEQ ID NO 145
<211> LENGTH: 117
<212> TYPE: PRT
<213> ORGANISM: Homo sapiens

<400> SEQUENCE: 145

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Asn Asn Tyr
            20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
             85                  90                  95

Arg Glu Arg Gly Asp Ser Phe Asp Tyr Trp Gly Gln Gly Thr Leu Val
            100                 105                 110

Thr Val Ser Ser Ala
            115

<210> SEQ ID NO 146
<211> LENGTH: 339
<212> TYPE: DNA
<213> ORGANISM: Homo sapiens

<400> SEQUENCE: 146
gatgttgtga tgactcagtc tccactctcc ctgcccgtca cccttggaca gccggcctcc      60
atctcctgca ggtctagtcg aagcctcgta tacagtgatg aaacaccta cttgaattgg     120 tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgcgga tgttggggtt tattactgca tgcaaggtac acactggccg    300
tgcagttttg gccaggggac caagctggag atcaaacga                           339

<210> SEQ ID NO 147
<211> LENGTH: 113
<212> TYPE: PRT
<213> ORGANISM: Homo sapiens

<400> SEQUENCE: 147

Asp Val Val Met Thr Gln Ser Pro Leu Ser Leu Pro Val Thr Leu Gly
 1               5                  10                  15

Gln Pro Ala Ser Ile Ser Cys Arg Ser Ser Arg Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Ala Asp Val Gly Val Tyr Tyr Cys Met Gln Gly
             85                  90                  95

Thr His Trp Pro Cys Ser Phe Gly Gln Gly Thr Lys Leu Glu Ile Lys
            100                 105                 110

Arg

<210> SEQ ID NO 148
<211> LENGTH: 324
<212> TYPE: DNA
<213> ORGANISM: Homo sapiens
```

<400> SEQUENCE: 148

```
gacatccaga tgacccagtc tccatcctcc ctgtctgcat ctgtaggaga cagagtcacc    60
atcacttgcc gggcaagtca gggcatcaga aatgatttag gctggtatca gcagaaacca   120
gggaaagccc ctaagcgcct gatctatgct gcatccagtt tgcaaagtgg ggtcccatca   180
aggttcagcg gcagtagatc tgggacagaa ttcactctca caatcagcag cctgcagcct   240
gaagattttg caacttatta ctgtctccag cataatagtt accctcccag ttttggccag   300
gggaccaagc tggagatcaa acga                                           324
```

<210> SEQ ID NO 149
<211> LENGTH: 108
<212> TYPE: PRT
<213> ORGANISM: Homo sapiens

<400> SEQUENCE: 149

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Arg Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Pro
                 85                  90                  95

Ser Phe Gly Gln Gly Thr Lys Leu Glu Ile Lys Arg
            100                 105
```

<210> SEQ ID NO 150
<211> LENGTH: 381
<212> TYPE: DNA
<213> ORGANISM: Homo sapiens

<400> SEQUENCE: 150

```
gaggtgcagc tggtggagtc tgggggaggc ttggtaaagc ctgggggtc ccttagactc    60
tcctgtgcag cctctggatt cactttcagt aacgcctgga tgaactgggt ccgccaggct   120
ccagggaagg gctggagtg gttggccgt attaaaagca aaactgatgg tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtaccaca   300
gcctacggtg gtaactccga tcaggaggac tacggtatgg acgtctgggg ccaagggacc   360
acggtcaccg tctcctcagc c                                              381
```

<210> SEQ ID NO 151
<211> LENGTH: 127
<212> TYPE: PRT
<213> ORGANISM: Homo sapiens

<400> SEQUENCE: 151

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30
```

Trp Met Asn Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Ala Tyr Gly Gly Asn Ser Asp Gln Glu Asp Tyr Gly
                100                 105                 110

Met Asp Val Trp Gly Gln Gly Thr Thr Val Thr Val Ser Ser Ala
            115                 120                 125

<210> SEQ ID NO 152
<211> LENGTH: 325
<212> TYPE: DNA
<213> ORGANISM: Homo sapiens

<400> SEQUENCE: 152

```
gacatccaga tgacccagtc tccatcctcc ctgtctgcat ctgtaggaga cagagtcacc      60
atcacttgcc gggcaagtca gagcattagc atctatttaa attggtatca gcagagacca     120
gggaaagccc ctaagctcct gatctatgct gcatccagtt tgcaaagtgg ggtcccatca     180
aggttcagtg gcagtggatc tgggacagac ttcactctca ccatcagcag tctgcaacct     240
gaagattttg caacttacta ctgtcaacag agttacagta ccccgctcac tttcggcgga     300
gggaccaagg tggagatcaa acgaa                                           325
```

<210> SEQ ID NO 153
<211> LENGTH: 108
<212> TYPE: PRT
<213> ORGANISM: Homo sapiens

<400> SEQUENCE: 153

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ile Tyr
             20                  25                  30

Leu Asn Trp Tyr Gln Gln Arg Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg
            100                 105

<210> SEQ ID NO 154
<211> LENGTH: 372
<212> TYPE: DNA
<213> ORGANISM: Homo sapiens

<400> SEQUENCE: 154

```
gaggtgcagt tggtggagtc tgggggaggc ctggtcaagc ctgggggtc cctgagactc       60 tcctgtgcag cctctggatt caccttcagt agctatagca tgaactgggt ccgccaggct     120
```

```
ccagggaagg ggctggagtg gtctcatcc attagtagta gtagtagtta tatatattac        180
gcagactcag tgaagggccg attcaccatc tccagagaca acgccaagaa ctccctgtat        240
ctgcaaatga acagcctgag agccgaggac acggctgtgt attactgtgc gagagatggg        300
gcgatttttg gagtggttaa ctggtacttc gatctctggg gccgtggcac cctggtcact        360
gtctcctcag cc                                                           372
```

<210> SEQ ID NO 155
<211> LENGTH: 124
<212> TYPE: PRT
<213> ORGANISM: Homo sapiens

<400> SEQUENCE: 155

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ile Phe Gly Val Val Asn Trp Tyr Phe Asp Leu
            100                 105                 110

Trp Gly Arg Gly Thr Leu Val Thr Val Ser Ser Ala
        115                 120
```

<210> SEQ ID NO 156
<211> LENGTH: 372
<212> TYPE: DNA
<213> ORGANISM: Homo sapiens

<400> SEQUENCE: 156

```
gaggtgcagt tggtggagtc tgggggaggc ctggtcaagc ctggggggtc cctgagactc         60
tcctgtgcag cctctggatt caccttcagt agctatagca tgaactgggt ccgccaggct        120
ccagggaagg ggctggagtg gtctcatcc attagtagta gtagtagtta tatatattac        180
gcagactcag tgaagggccg attcaccatc tccagagaca acgccaagaa ctccctgtat        240
ctgcaaatga acagcctgag agccgaggac acggctgtgt attactgtgc gagagatggg        300
gcgatttttg gagtggttaa ctggtacttc gatctctggg gccgtggcac cctggtcact        360
gtctcctcag cc                                                           372
```

<210> SEQ ID NO 157
<211> LENGTH: 124
<212> TYPE: PRT
<213> ORGANISM: Homo sapiens

<400> SEQUENCE: 157

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
```

```
                    35                  40                  45
Ser Ser Ile Ser Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Gly Ala Ile Phe Gly Val Val Asn Trp Tyr Phe Asp Leu
                100                 105                 110
Trp Gly Arg Gly Thr Leu Val Thr Val Ser Ser Ala
            115                 120
```

<210> SEQ ID NO 158
<211> LENGTH: 372
<212> TYPE: DNA
<213> ORGANISM: Homo sapiens

<400> SEQUENCE: 158

```
gaggtgcagt tggtggagtc tgggggaggc ctggtcaagc ctggggggtc cctgagactc      60
tcctgtgcag cctctggatt caccttcagt agctatagca tgaactgggt ccgccaggct     120
ccagggaagg ggctggagtg ggtctcatcc attagtagta gtagtagtta tatatattac     180
gcagactcag tgaagggccg attcaccatc tccagagaca acgccaagaa ctccctgtat     240
ctgcaaatga acagcctgag agccgaggac acggctgtgt attactgtgc gagagatggg     300
gcgattttg gagtggttaa ctggtacttc gatctctggg gccgtggcac cctggtcact     360
gtctcctcag cc                                                         372
```

<210> SEQ ID NO 159
<211> LENGTH: 124
<212> TYPE: PRT
<213> ORGANISM: Homo sapiens

<400> SEQUENCE: 159

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Ser Met Asn Trp Val Arg Gln Ala Pro Gly Lys Gly Leu Glu Trp Val
        35                  40                  45
Ser Ser Ile Ser Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Gly Ala Ile Phe Gly Val Val Asn Trp Tyr Phe Asp Leu
                100                 105                 110
Trp Gly Arg Gly Thr Leu Val Thr Val Ser Ser Ala
            115                 120
```

<210> SEQ ID NO 160
<211> LENGTH: 324
<212> TYPE: DNA
<213> ORGANISM: Homo sapiens

<400> SEQUENCE: 160

```
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aagttcagcg gcagtggatc tgggacagac ttcactctca ccatcagcag cctgcagcct   240
gaagattttg caacttatta ctgccaacag tataatagtt acccttcgac gttcggccaa   300
gggaccaagg tggaaatcaa acga                                          324
```

<210> SEQ ID NO 161
<211> LENGTH: 108
<212> TYPE: PRT
<213> ORGANISM: Homo sapiens

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ser
                85                  90                  95

Thr Phe Gly Gln Gly Thr Lys Val Glu Ile Lys Arg
            100                 105

<210> SEQ ID NO 162
<211> LENGTH: 372
<212> TYPE: DNA
<213> ORGANISM: Homo sapiens

<400> SEQUENCE: 162

```
gaggtgcagt tggtggagtc tgggggaggc ctggtcaagc ctggggggtc cctgagactc    60
tcctgtgcag cctctggatt caccttcagt agctatagca tgaactgggt ccgccaggct   120
ccagggaagg ggctggagtg ggtctcatcc attagtagta gtagtagtta tatatattac   180
gcagactcag tgaagggccg attcaccatc tccagagaca acgccaagaa ctccctgtat   240
ctgcaaatga acagcctgag agccgaggac acggctgtgt attactgtgc gagagatggg   300 gcgattttg gagtggttaa ctggtacttc gatctctggg gccgtggcac cctggtcact   360
gtctcctcag cc                                                       372
```

<210> SEQ ID NO 163
<211> LENGTH: 124
<212> TYPE: PRT
<213> ORGANISM: Homo sapiens

<400> SEQUENCE: 163

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

```
Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ala Ile Phe Gly Val Val Asn Trp Tyr Phe Asp Leu
            100                 105                 110

Trp Gly Arg Gly Thr Leu Val Thr Val Ser Ser Ala
            115                 120
```

<210> SEQ ID NO 164
<211> LENGTH: 324
<212> TYPE: DNA
<213> ORGANISM: Homo sapiens

<400> SEQUENCE: 164

```
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aagttcagcg gcagtggatc tgggacagac ttcactctca ccatcagcag cctgcagcct   240
gaagattttg caacttatta ctgccaacag tataatagtt acccttcgac gttcggccaa   300
gggaccaagg tggaaatcaa acga                                          324
```

<210> SEQ ID NO 165
<211> LENGTH: 108
<212> TYPE: PRT
<213> ORGANISM: Homo sapiens

<400> SEQUENCE: 165

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ser
                85                  90                  95

Thr Phe Gly Gln Gly Thr Lys Val Glu Ile Lys Arg
            100                 105
```

<210> SEQ ID NO 166
<211> LENGTH: 389
<212> TYPE: DNA
<213> ORGANISM: Homo sapiens

<400> SEQUENCE: 166

```
caggtgcagc tggtggagtc tgggggaggc gtggtccagc ctggagggtc cctgagactc    60
tcctgtgcag cgtctggatt caccttcagt agctatggca tgtactgggt ccgccaggct   120
ccaggcaagg ggctggagtg ggtggcagtt atatggtatg atggaagtaa taaatactat   180
```

```
gcagactccg tgaagggccg attcaccatc tccagagaca attccaagaa cacgctgtat    240
ctgcaaatga acagcctgag agccgaggac acggctgtgt attactgtgc gagagatttc    300
ttccaaaatt acgatttttg gagtggttcc cccgttgggt acggtatgga cgtctggggc    360
caagggacca cggtcaccgt ctcctcagc                                      389
```

<210> SEQ ID NO 167
<211> LENGTH: 130
<212> TYPE: PRT
<213> ORGANISM: Homo sapiens

<400> SEQUENCE: 167

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Phe Gln Asn Tyr Asp Phe Trp Ser Gly Ser Pro Val
            100                 105                 110

Gly Tyr Gly Met Asp Val Trp Gly Gln Gly Thr Thr Val Thr Val Ser
        115                 120                 125

Ser Ala
    130
```

<210> SEQ ID NO 168
<211> LENGTH: 339
<212> TYPE: DNA
<213> ORGANISM: Homo sapiens

<400> SEQUENCE: 168

```
gatattgtga tgactcagtc tccactctcc ctgcccgtca cccctggaga gccggcctcc    60
atctcctgca ggtctagtca gagcctcctg tatagtaatg gatacaacta tttggattgg    120
tacctgcaga agccagggca gtctccacag ctcctgatct atttgggttc taatcgggcc    180
tccggggtcc ctgacaggtt cggtggcagt ggatcaggca cagattttac actgaaaatc    240
agcagagtgg aggctgagga tgttggggtt tattactgca tgcaagctct acaaactccg    300
tggacgttcg gccaagggac caaggtggaa atcaaacga                           339
```

<210> SEQ ID NO 169
<211> LENGTH: 113
<212> TYPE: PRT
<213> ORGANISM: Homo sapiens

<400> SEQUENCE: 169

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45
```

Pro Gln Leu Leu Ile Tyr Leu Gly Ser Asn Arg Ala Ser Gly Val Pro
    50                  55                  60

Asp Arg Phe Gly Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg

<210> SEQ ID NO 170
<211> LENGTH: 375
<212> TYPE: DNA
<213> ORGANISM: Homo sapiens

<400> SEQUENCE: 170
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc ggccgactac   300
ggtgactctg attactacta ctactacggt atggacgtct ggggccaagg gaccacggtc   360
accgtctcct cagcc                                                    375

<210> SEQ ID NO 171
<211> LENGTH: 125
<212> TYPE: PRT
<213> ORGANISM: Homo sapiens

<400> SEQUENCE: 171

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Ala Asp Tyr Gly Asp Ser Asp Tyr Tyr Tyr Tyr Gly Met Asp
            100                 105                 110

Val Trp Gly Gln Gly Thr Thr Val Thr Val Ser Ser Ala
        115                 120                 125

<210> SEQ ID NO 172
<211> LENGTH: 324
<212> TYPE: DNA
<213> ORGANISM: Homo sapiens

<400> SEQUENCE: 172
gacatccaga tgacccagtc tccatcctcc ctgtctgcat ctgtaggaga cagagtcacc    60

```
atcacttgcc gggcaagtca gggcattaga gatgatttag gctggtttca gcagaaacca    120
gggaaagccc ctaagcgcct gacctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag tataatagtt acccattcac tttcggccct    300
gggaccaaag tggatatcaa acga                                          324
```

<210> SEQ ID NO 173
<211> LENGTH: 108
<212> TYPE: PRT
<213> ORGANISM: Homo sapiens

<400> SEQUENCE: 173

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Phe Gln Gln Lys Pro Gly Lys Ala Pro Lys Arg Leu Thr
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Phe
                85                  90                  95

Thr Phe Gly Pro Gly Thr Lys Val Asp Ile Lys Arg
            100                 105
```

<210> SEQ ID NO 174
<211> LENGTH: 342
<212> TYPE: DNA
<213> ORGANISM: Homo sapiens

<400> SEQUENCE: 174

```
caggtgcagc tggtggagtc tgggggaggc gtggtccagc ctgggaggtc cctgagactc    60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagaattg    300
gcctcgtggg gccagggaac cctggtcacc gtctcctcag cc                       342
```

<210> SEQ ID NO 175
<211> LENGTH: 114
<212> TYPE: PRT
<213> ORGANISM: Homo sapiens

<400> SEQUENCE: 175

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Leu Ala Ser Trp Gly Gln Gly Thr Leu Val Thr Val Ser
        100                 105                 110

Ser Ala

<210> SEQ ID NO 176
<211> LENGTH: 343
<212> TYPE: DNA
<213> ORGANISM: Homo sapiens

<400> SEQUENCE: 176

```
gatgttgtga tgactcagtc tccactctcc ctgcccgtca cccttggaca gccggcctcc      60
atctcctgca ggtctagtca aagcctcgtt tacagtgatg aaacaccta cttgaattgg     120 tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
ccgctcactt tcggcggagg gaccaaggtg gagatcaaac gaa                       343
```

<210> SEQ ID NO 177
<211> LENGTH: 114
<212> TYPE: PRT
<213> ORGANISM: Homo sapiens

<400> SEQUENCE: 177

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
            100                 105                 110

Lys Arg

<210> SEQ ID NO 178
<211> LENGTH: 372
<212> TYPE: DNA
<213> ORGANISM: Homo sapiens

<400> SEQUENCE: 178

```
gaggtgcagt tggtggagtc tgggggaggc ctggtcaagc ctgggggtc cctgagactc       60 tcctgtgcag cctctggatt caccttcagt agctatagca tgaactgggt ccgccaggct    120
ccagggaagg gctggagtg gtctcatcc attagtagta gtagtagtta tatatattac     180
gcagactcag tgaagggccg attcaccatc tccagagaca acgccaagaa ctccctgtat    240
ctgcaaatga acagcctgag agccgaggac acggctgtgt attactgtgc gagagatggg    300
```

```
gcgattttg gagtggttaa ctggtacttc gatctctggg gccgtggcac cctggtcact    360
gtctcctcag cc                                                       372
```

<210> SEQ ID NO 179
<211> LENGTH: 124
<212> TYPE: PRT
<213> ORGANISM: Homo sapiens
<400> SEQUENCE: 179

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Tyr Cys
                85                  90                  95

Ala Arg Asp Gly Ala Ile Phe Gly Val Val Asn Trp Tyr Phe Asp Leu
            100                 105                 110

Trp Gly Arg Gly Thr Leu Val Thr Val Ser Ser Ala
        115                 120
```

<210> SEQ ID NO 180
<211> LENGTH: 324
<212> TYPE: DNA
<213> ORGANISM: Homo sapiens
<400> SEQUENCE: 180

```
gacatccaga tgacccagtc tccatcctcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctccgac gttcggccaa   300
gggaccaagg tggaaatcaa acga                                          324
```

<210> SEQ ID NO 181
<211> LENGTH: 108
<212> TYPE: PRT
<213> ORGANISM: Homo sapiens
<400> SEQUENCE: 181

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
 65                 70                  75                  80
```

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys Arg
            100                 105

<210> SEQ ID NO 182
<211> LENGTH: 351
<212> TYPE: DNA
<213> ORGANISM: Homo sapiens

<400> SEQUENCE: 182
caggtgcagc tgcaggagtc gggcccagga ctggtgaagc cttcggagac cctgtccctc      60
acctgcactg tctctggtgg ctccatcagt aattactact ggagctggat ccggcagccc    120
ccagggaagg gactgagtg gattggatat atctattaca gtgggagcac caactacaac     180
ccctccctca agagtcgagt caccatatca gtagacacgt ccaagaacca gttctccctg    240
aaactgagct ctgtgaccgc tgcggacacg gccgtgtatt actgtgcgag agaccgggct    300
gatgcttttg atatctgggg ccaagggaca atggtcaccg tctcttcagc c             351

<210> SEQ ID NO 183
<211> LENGTH: 117
<212> TYPE: PRT
<213> ORGANISM: Homo sapiens

<400> SEQUENCE: 183

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Asn Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Arg Ala Asp Ala Phe Asp Ile Trp Gly Gln Gly Thr Met Val
            100                 105                 110

Thr Val Ser Ser Ala
        115

<210> SEQ ID NO 184
<211> LENGTH: 342
<212> TYPE: DNA
<213> ORGANISM: Homo sapiens

<400> SEQUENCE: 184
gatgttgtga tgactcagtc tccactctcc ctgcccgtca cccttggaca gccggcctcc     60
atctcctgca ggtctagtca aagcctcgtt tacagtgatg gaaacaccta cttgaattgg    120
tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
ccgctcactt tcggcggagg gaccaaggtg gagatcaaac ga                       342

<210> SEQ ID NO 185
<211> LENGTH: 114
<212> TYPE: PRT
<213> ORGANISM: Homo sapiens

<400> SEQUENCE: 185

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
            100                 105                 110

Lys Arg

<210> SEQ ID NO 186
<211> LENGTH: 360
<212> TYPE: DNA
<213> ORGANISM: Homo sapiens

<400> SEQUENCE: 186
gaggtgcaac tggtggagtc tgggggaggc ctggtcaagc ctgggggtc cctgagactc       60 tcctgtgcag cctctggatt caccttcagt agctatagaa tgaactgggt ccgccaggct     120
ccagggaagg gctggagtg gtctcatcc attagtagta gtagtagtca catatactac      180
gtagactcag tgaagggccg attcaccatc tccagagaca acgccaagaa ttcactgtat    240
ctgcaaatga acagcctgag agccgaggac acggctgtgt attactgtgc gagagatcga    300
ggagtgggag ctccctttga ctactgggc cagggaaccc tggtcaccgt ctcctcagcc    360

<210> SEQ ID NO 187
<211> LENGTH: 120
<212> TYPE: PRT
<213> ORGANISM: Homo sapiens

<400> SEQUENCE: 187

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser His Ile Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Ala Pro Phe Asp Tyr Trp Gly Gln Gly
            100                 105                 110

Thr Leu Val Thr Val Ser Ser Ala
        115                 120

<210> SEQ ID NO 188
<211> LENGTH: 339
<212> TYPE: DNA
<213> ORGANISM: Homo sapiens

<400> SEQUENCE: 188
gatgttgtga tgactcagtc tccactctcc ctgcccgtca cccttggaca gccggcctcc       60
atctcctgca ggtctagtca aagcctcgta tacagtgatg aaacaccta cttgaattgg      120 tttcagcaga ggccaggcca atctccaagg cgcctaattt ataaggtttc taactgggac      180
tctggggtcc cagacagatt cagcggcagt gggtcaggca ctgatttcac actgaaaatc      240
agcagggtgg aggctgagga tgttggggtt tattactgca tgcaaggtac acactggcct      300
ctcactttcg gcggagggac caacgtggag atcaaacga                             339

<210> SEQ ID NO 189
<211> LENGTH: 113
<212> TYPE: PRT
<213> ORGANISM: Homo sapiens

<400> SEQUENCE: 189

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Asn Val Glu Ile Lys
            100                 105                 110

Arg

<210> SEQ ID NO 190
<211> LENGTH: 365
<212> TYPE: DNA
<213> ORGANISM: Homo sapiens

<400> SEQUENCE: 190
gaggtgcagc tggtggagtc tgggggaggc ttggtaaagc ctggggggtc ccttagactc       60
tcctgtgcag cctctggatt cactttcagt aacgcctgga tgagctgggt ccgccaggct      120
ccagggaagg ggctggagtg ggttggccgt attaaaagca aaactgatgg tgggacaaca      180
gactacgctg cacccgtgaa aggcagattc accatctcaa gagatgattc aaaaaacacg      240
ctgtatctgc aaatgaacag cctgaaaatc gaggacacag ccgtgtatta ctgtaccata      300
acctacggtg actacccta ctttgactgc tggggccagg gaaccctggt caccgtctcc      360
tcagc                                                                  365

<210> SEQ ID NO 191

```
<211> LENGTH: 122
<212> TYPE: PRT
<213> ORGANISM: Homo sapiens

<400> SEQUENCE: 191
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Lys | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asn | Ala |
| | | | 20 | | | | | 25 | | | | | 30 | | |
| Trp | Met | Ser | Trp | Val | Arg | Gln | Ala | Pro | Gly | Lys | Gly | Leu | Glu | Trp | Val |
| | | 35 | | | | | 40 | | | | | 45 | | | |
| Gly | Arg | Ile | Lys | Ser | Lys | Thr | Asp | Gly | Gly | Thr | Thr | Asp | Tyr | Ala | Ala |
| | 50 | | | | | 55 | | | | | 60 | | | | |
| Pro | Val | Lys | Gly | Arg | Phe | Thr | Ile | Ser | Arg | Asp | Asp | Ser | Lys | Asn | Thr |
| 65 | | | | | 70 | | | | | 75 | | | | | 80 |
| Leu | Tyr | Leu | Gln | Met | Asn | Ser | Leu | Lys | Ile | Glu | Asp | Thr | Ala | Val | Tyr |
| | | | | 85 | | | | | 90 | | | | | 95 | |
| Tyr | Cys | Thr | Ile | Thr | Tyr | Gly | Asp | Tyr | Pro | Tyr | Phe | Asp | Cys | Trp | Gly |
| | | | 100 | | | | | 105 | | | | | 110 | | |
| Gln | Gly | Thr | Leu | Val | Thr | Val | Ser | Ser | Ala | | | | | | |
| | | 115 | | | | | 120 | | | | | | | | |

```
<210> SEQ ID NO 192
<211> LENGTH: 324
<212> TYPE: DNA
<213> ORGANISM: Homo sapiens

<400> SEQUENCE: 192
gacatccaga tgacccagtc tccatcttcc gtgtctgcat ctgtaggaga cagagtcacc    60
atcacttgtc gggcgagtca gggtattcgc agctggttag cctggtatca gcagaaacca   120
gggaaagccc ctaaactcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccgtggac gttcggccaa   300
gggaccaagg tggaaatcaa acga                                          324

<210> SEQ ID NO 193
<211> LENGTH: 108
<212> TYPE: PRT
<213> ORGANISM: Homo sapiens

<400> SEQUENCE: 193
```

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Val | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Gly | Ile | Arg | Ser | Trp |
| | | | 20 | | | | | 25 | | | | | 30 | | |
| Leu | Ala | Trp | Tyr | Gln | Gln | Lys | Pro | Gly | Lys | Ala | Pro | Lys | Leu | Leu | Ile |
| | | 35 | | | | | 40 | | | | | 45 | | | |
| Tyr | Ala | Ala | Ser | Ser | Leu | Gln | Ser | Gly | Val | Pro | Ser | Arg | Phe | Ser | Gly |
| | 50 | | | | | 55 | | | | | 60 | | | | |
| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | Ala | Asn | Ser | Phe | Pro | Trp |
| | | | | 85 | | | | | 90 | | | | | 95 | |
| Thr | Phe | Gly | Gln | Gly | Thr | Lys | Val | Glu | Ile | Lys | Arg | | | | |
| | | | 100 | | | | | 105 | | | | | | | |

<210> SEQ ID NO 194
<211> LENGTH: 375
<212> TYPE: DNA
<213> ORGANISM: Homo sapiens

<400> SEQUENCE: 194
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagtt atatggtttg atggatttaa taaatactat     180
gcagactccg tgaagggccg attcaccatc tccagagaca attccaagaa cacgctgtat     240
ctgcaaatga acagcctgag agccgaggac acggctgtgt atcactgtgc gagagatcgg     300
ggatatagtg gctacgatca ctactacggt atggacgtct ggggccaagg gaccacggtc     360
accgtctcct cagct                                                      375

<210> SEQ ID NO 195
<211> LENGTH: 125
<212> TYPE: PRT
<213> ORGANISM: Homo sapiens

<400> SEQUENCE: 195

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Phe Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
            85                  90                  95

Ala Arg Asp Arg Gly Tyr Ser Gly Tyr Asp His Tyr Tyr Gly Met Asp
        100                 105                 110

Val Trp Gly Gln Gly Thr Thr Val Thr Val Ser Ser Ala
        115                 120                 125

<210> SEQ ID NO 196
<211> LENGTH: 375
<212> TYPE: DNA
<213> ORGANISM: Homo sapiens

<400> SEQUENCE: 196
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagtt atatggtttg atggatttaa taaatactat     180
gcagactccg tgaagggccg attcaccatc tccagagaca attccaagaa cacgctgtat     240
ctgcaaatga acagcctgag agccgaggac acggctgtgt atcactgtgc gagagatcgg     300
ggatatagtg gctacgatca ctactacggt atggacgtct ggggccaagg gaccacggtc     360
accgtctcct cagct                                                      375

<210> SEQ ID NO 197
<211> LENGTH: 125

<212> TYPE: PRT
<213> ORGANISM: Homo sapiens

<400> SEQUENCE: 197

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Phe Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Arg Asp Arg Gly Tyr Ser Gly Tyr Asp His Tyr Tyr Gly Met Asp
            100                 105                 110

Val Trp Gly Gln Gly Thr Thr Val Thr Val Ser Ser Ala
        115                 120                 125
```

<210> SEQ ID NO 198
<211> LENGTH: 324
<212> TYPE: DNA
<213> ORGANISM: Homo sapiens

<400> SEQUENCE: 198

```
gacatccaga tgacccagtc tccatcttcc gtgtctgcat ctgtaggaga cagagtcacc    60
atcacttgtc gggcgagtca gggtattcgc agctggttag cctggtatca gcagaaacca   120
gggaaagccc ctaaactcct gatctatgct gcatccagtt tgcaaagtgg ggtcccatca   180
aggttcagcg gcagtggatc tgggacagat tcactctcac ccatcagcag cctgcagcct   240
gaagattttg caacttacta ttgtcaacag gctaacagtt tcccgtggac gttcggccaa   300
gggaccaagg tggaaatcaa acga                                          324
```

<210> SEQ ID NO 199
<211> LENGTH: 108
<212> TYPE: PRT
<213> ORGANISM: Homo sapiens

<400> SEQUENCE: 199

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Arg Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys Arg
            100                 105
```

<210> SEQ ID NO 200
<211> LENGTH: 354
<212> TYPE: DNA
<213> ORGANISM: Homo sapiens

<400> SEQUENCE: 200
gaggtgcagc tggtggagtc tgggggagac ttggtccagc ctggggggtc cctgagactc 60
tcctgtgcag cctctggatt cacctttagt agctattgga tgagctgggt ccgccaggct 120
ccagggaagg ggctggagtg gtggccaac ataaagcaag atggaagtga aaattctat 180 gtggactctg tgaagggccg attcaccatc tccagagaca acgccaagaa ctcactgtat 240
ctgcaaatga acagcctgag agccgaggac acggctgtgt attactgtgc gagagatatc 300
aggtggtact cgatctctg gggccgtggc accctggtca ctgtctcctc agct 354

<210> SEQ ID NO 201
<211> LENGTH: 118
<212> TYPE: PRT
<213> ORGANISM: Homo sapiens

<400> SEQUENCE: 201

Glu Val Gln Leu Val Glu Ser Gly Gly Asp Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Arg Trp Tyr Phe Asp Leu Trp Gly Arg Gly Thr Leu
            100                 105                 110

Val Thr Val Ser Ser Ala
        115

<210> SEQ ID NO 202
<211> LENGTH: 383
<212> TYPE: DNA
<213> ORGANISM: Homo sapiens

<400> SEQUENCE: 202
gaggtgcagc tggtggagtc tgggggaggc ttggtaaagc ctggggggtc ccttagactc 60
tcctgtgcag cctctggatt cactttcagt aacgcctgga tgagctgggt ccgccaggct 120
ccagggaagg gactagaatg ggttggccgt attaaaagca aaactgatgg tgggacaaca 180
gactacgctg cacccgtgaa aggcagattc accatctcaa gagatgattc aaaatacacg 240
ctgtatctgc aaatgaacag cctgaaaacc gaggacacag ccgtgtatta ctgtaccata 300
ggtagcagtg gctggtacga ggcctactac tattacggta tggacgtctg ggccaaggg 360 accacggtca ccgtctcctc agc 383

<210> SEQ ID NO 203
<211> LENGTH: 128
<212> TYPE: PRT
<213> ORGANISM: Homo sapiens

<400> SEQUENCE: 203

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Ala |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Arg | Ile | Lys | Ser | Lys | Thr | Asp | Gly | Gly | Thr | Thr | Asp | Tyr | Ala | Ala |
|---|---|---|---|---|---|---|---|---|---|---|---|---|---|---|---|
| | 50 | | | | | 55 | | | | | 60 | | | | |

| Pro | Val | Lys | Gly | Arg | Phe | Thr | Ile | Ser | Arg | Asp | Asp | Ser | Lys | Tyr | Thr |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Thr | Ile | Gly | Ser | Ser | Gly | Trp | Tyr | Glu | Ala | Tyr | Tyr | Tyr |
|---|---|---|---|---|---|---|---|---|---|---|---|---|---|---|
| | | | 100 | | | | | 105 | | | | | 110 | |

| Gly | Met | Asp | Val | Trp | Gly | Gln | Gly | Thr | Thr | Val | Thr | Val | Ser | Ser | Ala |
|---|---|---|---|---|---|---|---|---|---|---|---|---|---|---|---|
| | | 115 | | | | | 120 | | | | | 125 | | | |

<210> SEQ ID NO 204
<211> LENGTH: 360
<212> TYPE: DNA
<213> ORGANISM: Homo sapiens

<400> SEQUENCE: 204

```
gaggtgcagc tggtggagtc tgggggaggt gtggtacggc ctggggggtc cctgagactc    60
tcctgtgcag cctctggatt cagctttgat gattatggca tgagctgggt ccgccaagct   120
ccagggaagg ggctggagtg ggtctctggt attaattgga atggtggtag acagtttat   180
gcagactctg tgaagggccg attcaccatc tccagagaca cgccaagaa ctccctgtat   240
ctgcaaatga acagtctgag agccgaggac acggccttgt atcactgtgc gagaaataag   300
cagtggctct ggtacttcga tctctggggc cgtggcaccc tggtcactgt ctcctcagct   360
```

<210> SEQ ID NO 205
<211> LENGTH: 120
<212> TYPE: PRT
<213> ORGANISM: Homo sapiens

<400> SEQUENCE: 205

| Glu | Val | Gln | Leu | Val | Glu | Ser | Gly | Gly | Gly | Val | Val | Arg | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Ser | Phe | Asp | Asp | Tyr |
|---|---|---|---|---|---|---|---|---|---|---|---|---|---|---|---|
| | | | 20 | | | | | 25 | | | | | 30 | | |

| Gly | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Gly | Ile | Asn | Trp | Asn | Gly | Gly | Arg | Thr | Val | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Ser | Ala | Lys | Asn | Ser | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Leu | Tyr | His | Cys |
|---|---|---|---|---|---|---|---|---|---|---|---|---|---|---|---|
| | | | | 85 | | | | | 90 | | | | | 95 | |

| Ala | Arg | Asn | Lys | Gln | Trp | Leu | Trp | Tyr | Phe | Asp | Leu | Trp | Gly | Arg | Gly |
|---|---|---|---|---|---|---|---|---|---|---|---|---|---|---|---|
| | | | 100 | | | | | 105 | | | | | 110 | | |

| Thr | Leu | Val | Thr | Val | Ser | Ser | Ala |
|---|---|---|---|---|---|---|---|
| | | | 115 | | | | 120 |

```
<210> SEQ ID NO 206
<211> LENGTH: 325
<212> TYPE: DNA
<213> ORGANISM: Homo sapiens

<400> SEQUENCE: 206
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ctcactctca ccatcagcag cctgcagtct   240
gaagattttg cagtttatta ctgtcagcag tataataact ggcctctcac tttcggcggt   300
gggaccaagg tggagatcaa acgaa                                         325

<210> SEQ ID NO 207
<211> LENGTH: 108
<212> TYPE: PRT
<213> ORGANISM: Homo sapiens

<400> SEQUENCE: 207

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Leu Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys Arg
            100                 105

<210> SEQ ID NO 208
<211> LENGTH: 383
<212> TYPE: DNA
<213> ORGANISM: Homo sapiens

<400> SEQUENCE: 208
gaggtgcagc tggtggagtc tgggggaggc ttggtaaagc ctgggggggtc ccttagactc    60 tcctgtgcag cctctggatt cactttcagt aacgcctgga tgagctgggt ccgccaggct   120
ccagggaagg gactagaatg ggttggccgt attaaaagca aaactgatgg tgggacaaca   180
gactacgctg cacccgtgaa aggcagattc accatctcaa gagatgattc aaaatacacg   240
ctgtatctgc aaatgaacag cctgaaaacc gaggacacag ccgtgtatta ctgtaccata   300
ggtagcagtg gctggtacga ggcctactac tattacggta tggacgtctg gggccaaggg   360
accacggtca ccgtctcctc agc                                           383

<210> SEQ ID NO 209
<211> LENGTH: 128
<212> TYPE: PRT
<213> ORGANISM: Homo sapiens

<400> SEQUENCE: 209

Glu Val Gln Leu Val Glu Ser Gly Gly Gly Leu Val Lys Pro Gly Gly
```

```
                  1               5                  10                 15
              Ser Leu Arg Leu Ser Cys Ala Ala Ser Gly Phe Thr Phe Ser Asn Ala
                              20                  25                  30

Trp Met Ser Trp Val Arg Gln Ala Pro Gly Lys Gly Leu Glu Trp Val
                              35                  40                  45

Gly Arg Ile Lys Ser Lys Thr Asp Gly Gly Thr Thr Asp Tyr Ala Ala
                              50                  55                  60

Pro Val Lys Gly Arg Phe Thr Ile Ser Arg Asp Asp Ser Lys Tyr Thr
               65                  70                  75                  80

Leu Tyr Leu Gln Met Asn Ser Leu Lys Thr Glu Asp Thr Ala Val Tyr
                                  85                  90                  95

Tyr Cys Thr Ile Gly Ser Ser Gly Trp Tyr Glu Ala Tyr Tyr Tyr Tyr
                                  100                 105                 110

Gly Met Asp Val Trp Gly Gln Gly Thr Thr Val Thr Val Ser Ser Ala
                                  115                 120                 125
```

<210> SEQ ID NO 210
<211> LENGTH: 360
<212> TYPE: DNA
<213> ORGANISM: Homo sapiens

<400> SEQUENCE: 210

```
gaggtgcaac tggtggagtc tgggggaggt gtggtacggc ctgggggtc cctgagactc      60 tcctgtgcag cctctggatt cacctttgat gattatggca tgagctgggt ccgccaagct    120
ccagggaagg gctggagtg gtctctggt attaattgga atggtggtgg cacaggttat      180
gcagactcta tgaagggccg attcaccatc tccagagacg acgccaagaa ctccctgtat    240
ctgcaaatga acagtctgag agccgaggac acggccttgt atcactgtgc gagaaataag    300
cagtggctct ggtacttcga tctctggggc cgtggcaccc tggtcactgt ctcctcagct    360
```

<210> SEQ ID NO 211
<211> LENGTH: 120
<212> TYPE: PRT
<213> ORGANISM: Homo sapiens

<400> SEQUENCE: 211

```
              Glu Val Gln Leu Val Glu Ser Gly Gly Gly Val Val Arg Pro Gly Gly
               1               5                  10                  15

Ser Leu Arg Leu Ser Cys Ala Ala Ser Gly Phe Thr Phe Asp Asp Tyr
                              20                  25                  30

Gly Met Ser Trp Val Arg Gln Ala Pro Gly Lys Gly Leu Glu Trp Val
                              35                  40                  45

Ser Gly Ile Asn Trp Asn Gly Gly Thr Gly Tyr Ala Asp Ser Met
                              50                  55                  60

Lys Gly Arg Phe Thr Ile Ser Arg Asp Asp Ala Lys Asn Ser Leu Tyr
               65                  70                  75                  80

Leu Gln Met Asn Ser Leu Arg Ala Glu Asp Thr Ala Leu Tyr His Cys
                                  85                  90                  95

Ala Arg Asn Lys Gln Trp Leu Trp Tyr Phe Asp Leu Trp Gly Arg Gly
                                  100                 105                 110

Thr Leu Val Thr Val Ser Ser Ala
                                  115                 120
```

<210> SEQ ID NO 212
<211> LENGTH: 324
<212> TYPE: DNA

<213> ORGANISM: Homo sapiens

<400> SEQUENCE: 212

```
gaaatcgtga tgacgcagtc tccagccacc ctgtctgtgt ctctagggga aagagccacc    60
ctctcctgca gggccagtca gagtgttcgc agcaacttag cctggtacca gcagaaacct   120
ggccaggctc ccaggctcct catctatggt gcatccacca gggccactgg tatcccagcc   180
aggttcagtg gcagtgggtc tgggacagag ctcactctca ccatcagcag cctgcagtct   240
gaagattttg cagtttatta ctgtcaccag tacaataact ggcctctcac tttcggcggt   300
gggaccaagg tggagatcaa acga                                          324
```

<210> SEQ ID NO 213
<211> LENGTH: 108
<212> TYPE: PRT
<213> ORGANISM: Homo sapiens

<400> SEQUENCE: 213

```
Glu Ile Val Met Thr Gln Ser Pro Ala Thr Leu Ser Val Ser Leu Gly
 1               5                  10                  15
Glu Arg Ala Thr Leu Ser Cys Arg Ala Ser Gln Ser Val Arg Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Leu Thr Leu Thr Ile Ser Ser Leu Gln Ser
65                  70                  75                  80
Glu Asp Phe Ala Val Tyr Tyr Cys His Gln Tyr Asn Asn Trp Pro Leu
                85                  90                  95
Thr Phe Gly Gly Gly Thr Lys Val Glu Ile Lys Arg
            100                 105
```

<210> SEQ ID NO 214
<211> LENGTH: 339
<212> TYPE: DNA
<213> ORGANISM: Homo sapiens

<400> SEQUENCE: 214

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaaccccg   300
tggacgttcg gccaagggac caaggtggaa atcaaacga                          339
```

<210> SEQ ID NO 215
<211> LENGTH: 113
<212> TYPE: PRT
<213> ORGANISM: Homo sapiens

<400> SEQUENCE: 215

```
Asp Ile Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
            20                  25                  30
```

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Trp Thr Phe Gly Gln Gly Thr Lys Val Glu Ile Lys
             100                 105                 110

Arg

<210> SEQ ID NO 216
<211> LENGTH: 372
<212> TYPE: DNA
<213> ORGANISM: Homo sapiens

<400> SEQUENCE: 216
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccagacaagg ggctggagtg ggtggcagtt atatggtatg atggaagtta taaatactat     180
gcagactccg tgaagggccg attcaccatc tccagagaca attccaagaa cacgctgtat     240
ctgcaaatga acagcctgag agccgaggac acggctgtgt attactgtgc gagaggaggc     300
cctctgtata gcaactcctt ttactacttt gactactggg gccagggaac cctggtcacc     360
gtctcctcag ct                                                        372

<210> SEQ ID NO 217
<211> LENGTH: 124
<212> TYPE: PRT
<213> ORGANISM: Homo sapiens

<400> SEQUENCE: 217

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Asp Lys Gly Leu Glu Trp Val
             35                  40                  45

Ala Val Ile Trp Tyr Asp Gly Ser Tyr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Pro Leu Tyr Ser Asn Ser Phe Tyr Tyr Phe Asp Tyr
             100                 105                 110

Trp Gly Gln Gly Thr Leu Val Thr Val Ser Ser Ala
             115                 120

<210> SEQ ID NO 218
<211> LENGTH: 324
<212> TYPE: DNA
<213> ORGANISM: Homo sapiens

<400> SEQUENCE: 218

```
gacatccaga tgacccagtc tccatcctcc ctgtctgcat ctgtaggaga cagagtcacc    60
atcacttgcc aggcgagtca ggacattaga aactatttaa attggtatca gcagaaacca   120
gggaaagccc ctaagctcct gatctacgat gcatccaatt tggaaacagg ggtcccgtca   180
aggttcagtg gaagtggatc tgggacagat tttactttca ccatcagcag cctgcagcct   240
gaagatattg caacatatta ctgtcaacag tatgataatc tcccgatcac cttcggccaa   300
ggggcacgac tggagattaa acga                                          324
```

```
<210> SEQ ID NO 219
<211> LENGTH: 108
<212> TYPE: PRT
<213> ORGANISM: Homo sapiens

<400> SEQUENCE: 219
```

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile
                85                  90                  95

Thr Phe Gly Gln Gly Ala Arg Leu Glu Ile Lys Arg
            100                 105

```
<210> SEQ ID NO 220
<211> LENGTH: 354
<212> TYPE: DNA
<213> ORGANISM: Homo sapiens

<400> SEQUENCE: 220
```

```
caggtgcagc tggtggagtc tgggggaggc gtggtccagc ctgggaggtc cctgagactc    60
ccctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagataag   300
gccttggctt ttgatatctg ggccaaggg acaatggtca ccgtctcttc agct          354
```

```
<210> SEQ ID NO 221
<211> LENGTH: 118
<212> TYPE: PRT
<213> ORGANISM: Homo sapiens

<400> SEQUENCE: 221
```

Gln Val Gln Leu Val Glu Ser Gly Gly Gly Val Val Gln Pro Gly Arg
1               5                   10                  15

Ser Leu Arg Leu Pro Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Lys Ala Leu Ala Phe Asp Ile Trp Gly Gln Gly Thr Met
            100                 105                 110

Val Thr Val Ser Ser Ala
            115

<210> SEQ ID NO 222
<211> LENGTH: 324
<212> TYPE: DNA
<213> ORGANISM: Homo sapiens

<400> SEQUENCE: 222
gacatccaga tgacccagtc tccatcctcc ctgtctgcat ctgtaggaga cagagtcacc    60
atcacttgcc gggcaagtca gagcattagc aactatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta tccccattca ctttcggccct   300 gggaccaaag tggatatcaa acga                                          324

<210> SEQ ID NO 223
<211> LENGTH: 108
<212> TYPE: PRT
<213> ORGANISM: Homo sapiens

<400> SEQUENCE: 223

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ile Pro Phe
                 85                  90                  95

Thr Phe Gly Pro Gly Thr Lys Val Asp Ile Lys Arg
            100                 105

<210> SEQ ID NO 224
<211> LENGTH: 377
<212> TYPE: DNA
<213> ORGANISM: Homo sapiens

<400> SEQUENCE: 224
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaggtaa taaatactat   180
acagactccg tgaagggccg attcaccatc tccagagaca attccaagaa cacgctgtat   240
```

```
ctgcaaatga acagcctgag agccgaggac acggctgtgt attactgtgc gagagatgag    300
gatatagtgg ctacgattaa ctactactac ggtatggacg tctggggcca agggaccacg    360
gtcaccgtct cctcagc                                                    377
```

<210> SEQ ID NO 225
<211> LENGTH: 126
<212> TYPE: PRT
<213> ORGANISM: Homo sapiens

<400> SEQUENCE: 225

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Gly Asn Lys Tyr Tyr Thr Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Glu Asp Ile Val Ala Thr Ile Asn Tyr Tyr Gly Met
            100                 105                 110

Asp Val Trp Gly Gln Gly Thr Thr Val Thr Val Ser Ser Ala
            115                 120                 125
```

<210> SEQ ID NO 226
<211> LENGTH: 324
<212> TYPE: DNA
<213> ORGANISM: Homo sapiens

<400> SEQUENCE: 226

```
gacatccaga tgacccagtc tccatcctcc ctgtctgcat ctgtaggaga cagagtcacc    60
atcacttgcc gggcaagtca gagcattagc aactatttaa attggtatca gcagaaacca    120
gggaaagccc ctaagctcct gatctatgct gcatccagtt tgcaaagtgg ggtcccatca    180
aggttcagtg gcagtggatc tgggacagat tcactctca  ccatcagcag tctgcaacct    240
gaagattttg caacttacta ctgtcaacag agttacagta tcccattcac tttcggccct    300
gggaccaaag tggatatcaa acga                                           324
```

<210> SEQ ID NO 227
<211> LENGTH: 108
<212> TYPE: PRT
<213> ORGANISM: Homo sapiens

<400> SEQUENCE: 227

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Ile Pro Phe
                    85                  90                  95
Thr Phe Gly Pro Gly Thr Lys Val Asp Ile Lys Arg
                100                 105

<210> SEQ ID NO 228
<211> LENGTH: 366
<212> TYPE: DNA
<213> ORGANISM: Homo sapiens

<400> SEQUENCE: 228
gaggtgcagc tggtggagtc tgggggaggc ttggtccagc ctggggggtc cctgagactc     60
tcctgtgcag cctctggatt cacctttagt agctattgga tgagctgggt ccgccaggct    120
ccagggaagg ggctggagtg ggtggccaac ataaagcaag atggaagtga aaaatactat    180
gtggactctg tgaagggccg attcaccatc tccagagaca acgccaagaa ctcactgtat    240
ctgcaaatga acagcctgag agccgaggac acggctgtgt attactgtgc gagagatccg    300
ggtatagcag tggctggccc ctttgactac tggggccagg aaccctggt caccgtctcc    360 tcagct                                                                366

<210> SEQ ID NO 229
<211> LENGTH: 122
<212> TYPE: PRT
<213> ORGANISM: Homo sapiens

<400> SEQUENCE: 229

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
                20                  25                  30
Trp Met Ser Trp Val Arg Gln Ala Pro Gly Lys Gly Leu Glu Trp Val
            35                  40                  45
Ala Asn Ile Lys Gln Asp Gly Ser Glu Lys Tyr Tyr Val Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Pro Gly Ile Ala Val Ala Gly Pro Phe Asp Tyr Trp Gly
                100                 105                 110
Gln Gly Thr Leu Val Thr Val Ser Ser Ala
            115                 120

<210> SEQ ID NO 230
<211> LENGTH: 321
<212> TYPE: DNA
<213> ORGANISM: Homo sapiens

<400> SEQUENCE: 230
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataatcact ggtggacgtt cggccaaggg   300
```
accaaggtgg aaatcaaacg a                                                  321

<210> SEQ ID NO 231
<211> LENGTH: 107
<212> TYPE: PRT
<213> ORGANISM: Homo sapiens

<400> SEQUENCE: 231

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn His Trp Trp Thr
                85                  90                  95

Phe Gly Gln Gly Thr Lys Val Glu Ile Lys Arg
            100                 105

<210> SEQ ID NO 232
<211> LENGTH: 365
<212> TYPE: DNA
<213> ORGANISM: Homo sapiens

<400> SEQUENCE: 232
caggtgcagc tggtgcagtc tggggctgag gtgaagaagc ctggggcctc agtgaaggtc    60
tcctgcaagg cttctggata caccttcacc ggctattata tgtactgggt gcgacaggcc   120
cctggacaag gcttgagtg gatgggatgg atcaaccctaacagtggtgg cacaaactat   180 gcacagaagt tcagggcag ggtcaccatg accagggaca cgtccatcag cacagcctac   240
atggagctga gcaggctgag atctgacgac acggccgtgt attactgtgc gagagatcag   300
ggtataacag tggctggccc ctttgactac tggggccagg gaagcctggt caccgtctcc   360
tcagc                                                              365

<210> SEQ ID NO 233
<211> LENGTH: 122
<212> TYPE: PRT
<213> ORGANISM: Homo sapiens

<400> SEQUENCE: 233

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gln Gly Ile Thr Val Ala Gly Pro Phe Asp Tyr Trp Gly
            100                 105                 110

Gln Gly Ser Leu Val Thr Val Ser Ser Ala
        115                 120

<210> SEQ ID NO 234
<211> LENGTH: 348
<212> TYPE: DNA
<213> ORGANISM: Homo sapiens

<400> SEQUENCE: 234
caggtgcagc tgcaggagtc gggcccagga ctggtgaagc cttcggagac cctgtccctc      60
acctgcactg tctctggtgg ctccatcagt ggttactact ggagctggat ccggcagccc     120
ccagggaagg gactggagtg gattgggtat atctattaca gtgggagcac caactacaac     180
ccctccctca gagtcgagt caccatatca gtagacacgt ccaagaacca gttctccctg      240
aagctgagct ctgtgaccgc tgcggacacg gccgtgtatt actgtgcgag agatcggcag     300
tggcttgact actggggcca gggaaccctg gtcaccgtct cctcagct                  348

<210> SEQ ID NO 235
<211> LENGTH: 116
<212> TYPE: PRT
<213> ORGANISM: Homo sapiens

<400> SEQUENCE: 235

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Gly Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Arg Gln Trp Leu Asp Tyr Trp Gly Gln Gly Thr Leu Val Thr
            100                 105                 110

Val Ser Ser Ala
        115

<210> SEQ ID NO 236
<211> LENGTH: 322
<212> TYPE: DNA
<213> ORGANISM: Homo sapiens

<400> SEQUENCE: 236
gaaatagtga tgacgcagtc tccagccacc ctgtctgtgt ctccagggga aagagccacc      60
ctctcctgca gggccagtca gactgttatc agcaacttag cctggtacca gcagaaacct     120
ggccaggctc ccaggctcct catctatggt gcatccacca gggccactgg tatcccagcc     180
aggttcagtg gcagtgggtc tgggacagaa ttcactctca ccatcagcag cctgcagtct     240
gaagattttg cactttatta ctgtcagcag tataataact ggtggacgtt cggccaaggg     300
accaaggtgg aaatcaaacg aa                                               322

<210> SEQ ID NO 237
<211> LENGTH: 107
<212> TYPE: PRT
<213> ORGANISM: Homo sapiens

<400> SEQUENCE: 237

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Thr Val Ile Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Leu Tyr Tyr Cys Gln Gln Tyr Asn Asn Trp Trp Thr
                 85                  90                  95

Phe Gly Gln Gly Thr Lys Val Glu Ile Lys Arg
            100                 105
```

<210> SEQ ID NO 238
<211> LENGTH: 365
<212> TYPE: DNA
<213> ORGANISM: Homo sapiens

<400> SEQUENCE: 238

```
caggtacagc tggtgcagtc tggggctgag gtgaagaagc ctggggcctc agtgaaggtc      60
tcctgcaagg cttctggata caccttcacc ggcttctata tgtactgggt gcgacaggcc    120
cctggacaag gcttgagtg gatgggatgg atcaaccta acagtagtgg cacaaaccat      180
gcacagaagt tcagggcag ggtcaccatg accaggaca cgtccatcag cacagcctac      240
atggagctga gcaggctgag atctgacgac acggccgtgt attactgtgc gagagatcag    300
gatatagcaa cagctggtcc ctttgactac tggggccagg gaaccctggt caccgtctcc    360
tcagc                                                                365
```

<210> SEQ ID NO 239
<211> LENGTH: 122
<212> TYPE: PRT
<213> ORGANISM: Homo sapiens

<400> SEQUENCE: 239

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Phe
             20                  25                  30

Tyr Met Tyr Trp Val Arg Gln Ala Pro Gly Gln Gly Leu Glu Trp Met
         35                  40                  45

Gly Trp Ile Asn Pro Asn Ser Ser Gly Thr Asn His Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Gln Asp Ile Ala Thr Ala Gly Pro Phe Asp Tyr Trp Gly
            100                 105                 110
```

```
Gln Gly Thr Leu Val Thr Val Ser Ser Ala
        115                 120
```

<210> SEQ ID NO 240
<211> LENGTH: 322
<212> TYPE: DNA
<213> ORGANISM: Homo sapiens

<400> SEQUENCE: 240

```
gaaatagtga tgacgcagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catctttggt gcatccaccc gggccactgg tatcccagcc    180
aggttcagtg gcagtgggtc tgggacagag ttcactctca ccatcagcag cctgcagtct    240
gaagattttg cagtttatta ctgtcagcag tataataact ggtggacgtt cggccgaggg    300
accaaggtgg aaatcaaacg aa                                             322
```

<210> SEQ ID NO 241
<211> LENGTH: 107
<212> TYPE: PRT
<213> ORGANISM: Homo sapiens

<400> SEQUENCE: 241

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Arg Gly Thr Lys Val Glu Ile Lys Arg
            100                 105
```

<210> SEQ ID NO 242
<211> LENGTH: 370
<212> TYPE: DNA
<213> ORGANISM: Homo sapiens

<400> SEQUENCE: 242

```
caggtgcagc tggtggagtc tgggggaggc gtggtccagc ctgggaggtc cctgagactc      60
tcctgtgcag cgtctggatt caccttcagt agctatggca tgcactgggt ccgccaggct    120
ccaggcaagg gctggagtg gtgacagtt atatggtatg atggaagtaa taatactat        180
gcagactccg tgaagggccg attcaccatc tccagagaca gttccaagaa cacgctgtat    240
ctgcaaatga acagcctgag agccgaggac acggctgtgt attactgtgc gagaggaggc    300
cctctgtata gcaactcctt ttactacttt gactactggg gccagggaac cctggtcacc    360
gtctcctcag                                                           370
```

<210> SEQ ID NO 243
<211> LENGTH: 124
<212> TYPE: PRT

<213> ORGANISM: Homo sapiens

<400> SEQUENCE: 243

| | | | | | | | | | | | | | |
|---|---|---|---|---|---|---|---|---|---|---|---|---|---|
|Gln|Val|Gln|Leu|Val|Glu|Ser|Gly|Gly|Val|Val|Gln|Pro|Gly|Arg|
|1| | | |5| | | | |10| | | | |15|
|Ser|Leu|Arg|Leu|Ser|Cys|Ala|Ala|Ser|Gly|Phe|Thr|Phe|Ser|Ser|Tyr|
| | | |20| | | | |25| | | | |30| | |
|Gly|Met|His|Trp|Val|Arg|Gln|Ala|Pro|Gly|Lys|Gly|Leu|Glu|Trp|Val|
| | | |35| | | | |40| | | | |45| | |
|Thr|Val|Ile|Trp|Tyr|Asp|Gly|Ser|Asn|Lys|Tyr|Tyr|Ala|Asp|Ser|Val|
| |50| | | | |55| | | | |60| | | | |
|Lys|Gly|Arg|Phe|Thr|Ile|Ser|Arg|Asp|Ser|Ser|Lys|Asn|Thr|Leu|Tyr|
|65| | | | |70| | | | |75| | | | |80|
|Leu|Gln|Met|Asn|Ser|Leu|Arg|Ala|Glu|Asp|Thr|Ala|Val|Tyr|Tyr|Cys|
| | | | |85| | | | |90| | | | |95| |
|Ala|Arg|Gly|Gly|Pro|Leu|Tyr|Ser|Asn|Ser|Tyr|Tyr|Phe|Asp|Tyr|
| | | | |100| | | | |105| | | | |110| |
|Trp|Gly|Gln|Gly|Thr|Leu|Val|Thr|Val|Ser|Ser|Ala|
| | | | |115| | | | |120| | |

<210> SEQ ID NO 244
<211> LENGTH: 324
<212> TYPE: DNA
<213> ORGANISM: Homo sapiens

<400> SEQUENCE: 244

```
gacatccaga tgacccagtc tccatcctcc ctgtctacat ctgtaggaga cagagtcacc      60
atcacttgcc aggcgagtca ggacattaga aactatttaa attggtatca gcagaaacca    120
gggaaagccc ctaagctcct gatccacgat gcatccaatt tggaaacagg ggtcccatca    180
agattcagtg gaaatggatc tgggacagat tttactttca ccatcaccag cctgcagcct    240
gaagatattg caacctatta ctgtcaacag tatgctaatc tcccgatcac cttcggccaa    300
gggacacgac tggagattaa acga                                            324
```

<210> SEQ ID NO 245
<211> LENGTH: 108
<212> TYPE: PRT
<213> ORGANISM: Homo sapiens

<400> SEQUENCE: 245

| | | | | | | | | | | | | | | |
|---|---|---|---|---|---|---|---|---|---|---|---|---|---|---|
|Asp|Ile|Gln|Met|Thr|Gln|Ser|Pro|Ser|Ser|Leu|Ser|Thr|Ser|Val|Gly|
|1| | | |5| | | | |10| | | | |15| |
|Asp|Arg|Val|Thr|Ile|Thr|Cys|Gln|Ala|Ser|Gln|Asp|Ile|Arg|Asn|Tyr|
| | | |20| | | | |25| | | | |30| | | |
|Leu|Asn|Trp|Tyr|Gln|Gln|Lys|Pro|Gly|Lys|Ala|Pro|Lys|Leu|Leu|Ile|
| | | |35| | | | |40| | | | |45| | | |
|His|Asp|Ala|Ser|Asn|Leu|Glu|Thr|Gly|Val|Pro|Ser|Arg|Phe|Ser|Gly|
| |50| | | | |55| | | | |60| | | | |
|Asn|Gly|Ser|Gly|Thr|Asp|Phe|Ser|Phe|Thr|Ile|Thr|Ser|Leu|Gln|Pro|
|65| | | | |70| | | | |75| | | | |80|
|Glu|Asp|Ile|Ala|Thr|Tyr|Tyr|Cys|Gln|Gln|Tyr|Ala|Asn|Leu|Pro|Ile|
| | | | |85| | | | |90| | | | |95| |
|Thr|Phe|Gly|Gln|Gly|Thr|Arg|Leu|Glu|Ile|Lys|Arg|
| | | | |100| | | | |105| | |

<210> SEQ ID NO 246

<211> LENGTH: 357
<212> TYPE: DNA
<213> ORGANISM: Homo sapiens

<400> SEQUENCE: 246

```
caggtgcagc tgcaggagtc gggcccagga ctggtgaagc cttcggagac cctgtccctc    60
acctgcactg tctctggtgg ctccatcagt agttactact ggagctggat ccggcagccc   120
gccgggaagg gactggagtg gattgggcgt atctatacca gtgggttcac caactacaac   180
ccctccctca agagtcgagt caccatgtca gtagacacgt ccaagaacca gttctccctg   240
aagctgagct ctgtgaccgc cgcggacacg gccgtgtatt actgtgcgag gtataactgg   300
aactactggt acttcgatct ctggggccgt ggcatcctgg tcactgtctc ctcagct     357
```

<210> SEQ ID NO 247
<211> LENGTH: 119
<212> TYPE: PRT
<213> ORGANISM: Homo sapiens

<400> SEQUENCE: 247

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Ile Ser Ser Tyr
             20                  25                  30
Tyr Trp Ser Trp Ile Arg Gln Pro Ala Gly Lys Gly Leu Glu Trp Ile
         35                  40                  45
Gly Arg Ile Tyr Thr Ser Gly Phe Thr Asn Tyr Asn Pro Ser Leu Lys
     50                  55                  60
Ser Arg Val Thr Met Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Arg Tyr Asn Trp Asn Tyr Trp Tyr Phe Asp Leu Trp Gly Arg Gly Ile
            100                 105                 110
Leu Val Thr Val Ser Ser Ala
        115
```

<210> SEQ ID NO 248
<211> LENGTH: 324
<212> TYPE: DNA
<213> ORGANISM: Homo sapiens

<400> SEQUENCE: 248

```
gacatccaga tgacccagtc tccatcctcc ctgtctgcat ctgtaggaga cagagtcacc    60
atcacttgcc aggcgagtca ggacattacc aactatttaa attggtatca gaagaaacca   120
gggaaagccc ctaaggtcct gatctacgat gcatccaatt tggaaacagg ggtcccatca   180
aggttcagtg aagtggatc tgggacaggt tttactttca ccatcagcag cctgcagcct   240
gaagatattg caacatatta ctgtcaacag tatgatcata tcccgctcac tttcggcgga   300
gggaccaagg tggagatcaa acga                                          324
```

<210> SEQ ID NO 249
<211> LENGTH: 108
<212> TYPE: PRT
<213> ORGANISM: Homo sapiens

<400> SEQUENCE: 249

Asp Ile Gln Met Thr Gln Ser Pro Ser Ser Leu Ser Ala Ser Val Gly

```
                1               5                  10                  15
              Asp Arg Val Thr Ile Thr Cys Gln Ala Ser Gln Asp Ile Thr Asn Tyr
                              20                  25                  30

Leu Asn Trp Tyr Gln Lys Lys Pro Gly Lys Ala Pro Lys Val Leu Ile
                          35                  40                  45

Tyr Asp Ala Ser Asn Leu Glu Thr Gly Val Pro Ser Arg Phe Ser Gly
                      50                  55                  60

Ser Gly Ser Gly Thr Gly Phe Thr Phe Thr Ile Ser Ser Leu Gln Pro
              65                  70                  75                  80

Glu Asp Ile Ala Thr Tyr Tyr Cys Gln Gln Tyr Asp His Ile Pro Leu
                              85                  90                  95

Thr Phe Gly Gly Gly Thr Lys Val Glu Ile Lys Arg
                              100                 105
```

<210> SEQ ID NO 250
<211> LENGTH: 360
<212> TYPE: DNA
<213> ORGANISM: Homo sapiens

<400> SEQUENCE: 250

```
gaggtgcagc tggtggagtc tgggggaggt gtggtacggc ctgggggtc  cctgagactc        60
tcctgtgcag cctctggatt cagctttgat gattatggca tgagctgggt ccgccaagct       120
ccagggaagg gctggagtg  gtctctggt  attaattgga atggtggtag  acagtttat       180
gcagactctg tgaagggccg attcaccatc tccagagaca gcgccaagaa ctccctgtat       240
ctgcaaatga acagtctgag agccgaggac acggccttgt atcactgtgc gagaaataag      300
cagtggctct ggtacttcga tctctggggc cgtggcaccc tggtcactgt ctcctcagct      360
```

<210> SEQ ID NO 251
<211> LENGTH: 120
<212> TYPE: PRT
<213> ORGANISM: Homo sapiens

<400> SEQUENCE: 251

```
              Glu Val Gln Leu Val Glu Ser Gly Gly Gly Val Val Arg Pro Gly Gly
              1               5                  10                  15

Ser Leu Arg Leu Ser Cys Ala Ala Ser Gly Phe Ser Phe Asp Asp Tyr
                              20                  25                  30

Gly Met Ser Trp Val Arg Gln Ala Pro Gly Lys Gly Leu Glu Trp Val
                          35                  40                  45

Ser Gly Ile Asn Trp Asn Gly Gly Arg Thr Val Tyr Ala Asp Ser Val
                      50                  55                  60

Lys Gly Arg Phe Thr Ile Ser Arg Asp Ser Ala Lys Asn Ser Leu Tyr
              65                  70                  75                  80

Leu Gln Met Asn Ser Leu Arg Ala Glu Asp Thr Ala Leu Tyr His Cys
                              85                  90                  95

Ala Arg Asn Lys Gln Trp Leu Trp Tyr Phe Asp Leu Trp Gly Arg Gly
                              100                 105                 110

Thr Leu Val Thr Val Ser Ser Ala
                              115                 120
```

<210> SEQ ID NO 252
<211> LENGTH: 369
<212> TYPE: DNA
<213> ORGANISM: Homo sapiens

<400> SEQUENCE: 252

```
caggtgcagc tggtggagtc tgggggaggc gtggtccagc ctgggaggtc cctgagactc      60
tcctgtgcag cctctggatt caccttcagt acctatggca tgcactgggt ccgccaggct     120
ccaggcaagg ggctggagtg ggtggcagtt atatcatatg atggaagtaa aaaatactat     180
gcagactccg tgaagggccg attcaccatc tccagagaca attccaagaa cacgctgtat     240
ctgcaaatga acagcctgag agctgaggac acggctctgt attactgtgc gagaggaggg     300
tatagcactg gctggggccc cgactttgac tactggggcc agggaaccct ggtcaccgtc     360
tcctcagct                                                              369
```

<210> SEQ ID NO 253
<211> LENGTH: 123
<212> TYPE: PRT
<213> ORGANISM: Homo sapiens

<400> SEQUENCE: 253

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Gly Gly Tyr Ser Thr Gly Trp Gly Pro Asp Phe Asp Tyr Trp
            100                 105                 110

Gly Gln Gly Thr Leu Val Thr Val Ser Ser Ala
        115                 120
```

<210> SEQ ID NO 254
<211> LENGTH: 369
<212> TYPE: DNA
<213> ORGANISM: Homo sapiens

<400> SEQUENCE: 254

```
caggtgcagc tggtggagtc tgcgggaggc gtggtccagc ctgggaggtc cctgagactc      60
tcctgtgcag cctctggatt caccttcagt atctatggca tgcactgggt ccgccaggct     120
ccaggcaagg ggctggagtg ggtggcagtt atatcatatg atggaagtaa taaatactat     180
gcagactccg tgaagggccg attcaccatc tccagagacg attccaagaa cacgctgtat     240
ctgcaaatga acagcctgag agctgaggac acggctgtgt attactgtgc gagaaattac     300
tatggttcgg ggagtcccta cggtatggac gtctggggcc aagggaccac ggtcaccgtc     360
tcctcagct                                                              369
```

<210> SEQ ID NO 255
<211> LENGTH: 123
<212> TYPE: PRT
<213> ORGANISM: Homo sapiens

<400> SEQUENCE: 255

```
Gln Val Gln Leu Val Glu Ser Ala Gly Gly Val Val Gln Pro Gly Arg
 1               5                  10                  15
```

Ser Leu Arg Leu Ser Cys Ala Ala Ser Gly Phe Thr Phe Ser Ile Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Tyr Tyr Gly Ser Gly Ser Pro Tyr Gly Met Asp Val Trp
            100                 105                 110

Gly Gln Gly Thr Thr Val Thr Val Ser Ser Ala
            115                 120

<210> SEQ ID NO 256
<211> LENGTH: 324
<212> TYPE: DNA
<213> ORGANISM: Homo sapiens

<400> SEQUENCE: 256
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtagatc tgggacagat ttcactctca ccatcagcag tctgcaacct    240
gaagattttg caacttacta ctgtcaacag agttacagtg tccccctgcag ttttggccag    300 gggaccaagc tggagatcaa acga                                            324

<210> SEQ ID NO 257
<211> LENGTH: 108
<212> TYPE: PRT
<213> ORGANISM: Homo sapiens

<400> SEQUENCE: 257

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Val Pro Cys
                85                  90                  95

Ser Phe Gly Gln Gly Thr Lys Leu Glu Ile Lys Arg
            100                 105

<210> SEQ ID NO 258
<211> LENGTH: 372
<212> TYPE: DNA
<213> ORGANISM: Homo sapiens

<400> SEQUENCE: 258

```
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagaggaggc   300
cctctgtata gcaactcctt ttactacttt gactactggg gccagggaac cctggtcacc   360
gtctcctcag ct                                                       372
```

<210> SEQ ID NO 259
<211> LENGTH: 124
<212> TYPE: PRT
<213> ORGANISM: Homo sapiens

<400> SEQUENCE: 259

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Leu Tyr Ser Asn Ser Phe Tyr Tyr Phe Asp Tyr
            100                 105                 110

Trp Gly Gln Gly Thr Leu Val Thr Val Ser Ser Ala
        115                 120
```

<210> SEQ ID NO 260
<211> LENGTH: 324
<212> TYPE: DNA
<213> ORGANISM: Homo sapiens

<400> SEQUENCE: 260

```
gacatccgga tgacccagtc tccatcctcc ctgtctgcat ctgtaggaga cagcgtcacc    60
atcacttgcc aggcgagtca ggacattaga aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatattg caacatatta ctgtcaacag tatgataatc tcccgatcac cttcggccaa   300
gggacacgac tggagattaa acga                                          324
```

<210> SEQ ID NO 261
<211> LENGTH: 108
<212> TYPE: PRT
<213> ORGANISM: Homo sapiens

<400> SEQUENCE: 261

```
Asp Ile Arg Met Thr Gln Ser Pro Ser Ser Leu Ser Ala Ser Val Gly
 1               5                  10                  15

Asp Ser Val Thr Ile Thr Cys Gln Ala Ser Gln Asp Ile Arg Asn Tyr
            20                  25                  30
```

```
Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Ile
                 85                  90                  95

Thr Phe Gly Gln Gly Thr Arg Leu Glu Ile Lys Arg
             100                 105
```

<210> SEQ ID NO 262
<211> LENGTH: 357
<212> TYPE: DNA
<213> ORGANISM: Homo sapiens

<400> SEQUENCE: 262

```
caggtgcagc tgcaggagtc gggcccagga ctggtgaagc cttcggagac cctgtccctc      60
acctgcactg tctctggtga ctccatcaat agttactact ggagctggat ccggcagccc     120
gccgggaagg gactggagtg gattgggcgt atctatacca gtgggagcac caactacaac     180
ccctccctca agagtcgagt caccatgtca gtagacacgt ccaagaacca gttctccctg     240
aagctgagct ctgtgaccgc cgcggacacg gccgtgtatt actgtgcgag aggtataact     300
ggttacgggg ggttcgaccc ctggggccag ggaaccctgg tcaccgtctc ctcagct        357
```

<210> SEQ ID NO 263
<211> LENGTH: 119
<212> TYPE: PRT
<213> ORGANISM: Homo sapiens

<400> SEQUENCE: 263

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Asn Ser Tyr
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
     50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Ile Thr Gly Tyr Gly Gly Phe Asp Pro Trp Gly Gln Gly Thr
             100                 105                 110

Leu Val Thr Val Ser Ser Ala
         115
```

<210> SEQ ID NO 264
<211> LENGTH: 324
<212> TYPE: DNA
<213> ORGANISM: Homo sapiens

<400> SEQUENCE: 264

```
gacatccaga tgacccagtc tccatcctcc ctgtctgcat ctgtaggaga cagagtcacc      60
atcacttgcc aggcgagtca ggacattagc aactatttaa attggtatca gcagaaacca     120
```

```
gggaaagccc ctaacctcct gatctacgat gcatccaatt tggaaacagg ggtcccatca    180
aggttcagtg aagtggatc tgggacagat tttactttca ccatcagcag cctgcagcct    240
gaagatattg caacatatta ctgtcaacag tattataatc tcccgatcac cttcggccaa    300
gggacacgac tggagattaa acga                                          324
```

<210> SEQ ID NO 265
<211> LENGTH: 108
<212> TYPE: PRT
<213> ORGANISM: Homo sapiens

<400> SEQUENCE: 265

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Asn Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Tyr Asn Leu Pro Ile
                 85                  90                  95

Thr Phe Gly Gln Gly Thr Arg Leu Glu Ile Lys Arg
             100                 105
```

<210> SEQ ID NO 266
<211> LENGTH: 354
<212> TYPE: DNA
<213> ORGANISM: Homo sapiens

<400> SEQUENCE: 266

```
caggtgcgcc tggtggagtc tgggggaggc ctggtcaagc ctggagggtc cctgagactc    60
tcctgtgcag cctctggatt caccttcagt gactactaca tgagctggat ccgccaggct   120
ccagggaagg ggctggagtg ggcttcatac attagtagta gtggttatag catatactac   180
gcagactctg tgaagggccg attcaccatc tccagggaca cgccaagaa ctcactgtat    240 ctgcaaatga acagcctgag agccgaggac acggccgtgt attactgtgc gagagaaaga   300
ggggatgctt ttgatatctg gggccaaggg acaatggtca ccgtctcttc agct          354
```

<210> SEQ ID NO 267
<211> LENGTH: 118
<212> TYPE: PRT
<213> ORGANISM: Homo sapiens

<400> SEQUENCE: 267

```
Gln Val Arg Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Ala
         35                  40                  45

Ser Tyr Ile Ser Ser Ser Gly Tyr Ser Ile Tyr Tyr Ala Asp Ser Val
     50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                        85                  90                  95
Ala Arg Glu Arg Gly Asp Ala Phe Asp Ile Trp Gly Gln Gly Thr Met
                100                 105                 110
Val Thr Val Ser Ser Ala
            115

<210> SEQ ID NO 268
<211> LENGTH: 325
<212> TYPE: DNA
<213> ORGANISM: Homo sapiens

<400> SEQUENCE: 268
gaaacgacac tcacgcagtc tccagcattc atgtcagcga ctccaggaga caaagtcaac    60
atctcctgca aagccagcca agacattgat gatgatatga actggtacca acagaaacca   120
ggagaagttg ctatttttcat tattcaagaa gctactactc tcgttcctgg aatcccacct   180
cgattcagtg gcagcgggta tggaacagat tttacccctca caattaataa catagaatct   240
gaggatgctg catattactt ctgtctacaa catgataatt tccctctcac tttcggcgga   300
gggaccaagg tggagatcaa acgaa                                         325

<210> SEQ ID NO 269
<211> LENGTH: 108
<212> TYPE: PRT
<213> ORGANISM: Homo sapiens

<400> SEQUENCE: 269

Glu Thr Thr Leu Thr Gln Ser Pro Ala Phe Met Ser Ala Thr Pro Gly
 1               5                  10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Val Ala Ile Phe Ile Ile
            35                  40                  45

Gln Glu Ala Thr Thr Leu Val Pro Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gly Gly Thr Lys Val Glu Ile Lys Arg
                100                 105

<210> SEQ ID NO 270
<211> LENGTH: 324
<212> TYPE: DNA
<213> ORGANISM: Homo sapiens

<400> SEQUENCE: 270
gacatccgga tgacccagtc tccatcctcc ctgtctgcat ctgttggaga cagagtcacc    60
atcacttgcc gggcaagtca gcgcattagc agctatttaa attggtttca gcagaaacca   120
gggaaagccc ctaagttcct gatctatgct gcatctagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccccattca cttcggccct   300
gggaccaaag tggatatcaa acga                                          324
```

<210> SEQ ID NO 271
<211> LENGTH: 108
<212> TYPE: PRT
<213> ORGANISM: Homo sapiens

<400> SEQUENCE: 271

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Ser Tyr
            20                  25                  30

Leu Asn Trp Phe Gln Gln Lys Pro Gly Lys Ala Pro Lys Phe Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg
            100                 105

<210> SEQ ID NO 272
<211> LENGTH: 363
<212> TYPE: DNA
<213> ORGANISM: Homo sapiens

<400> SEQUENCE: 272
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atgaaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagatccc    300
tttgaaactg gaactacttt tgactactgg ggccagggaa ccctggtcac cgtctcctca    360
gct                                                                  363

<210> SEQ ID NO 273
<211> LENGTH: 121
<212> TYPE: PRT
<213> ORGANISM: Homo sapiens

<400> SEQUENCE: 273

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Phe Glu Thr Gly Thr Thr Phe Asp Tyr Trp Gly Gln 100                 105                 110
Gly Thr Leu Val Thr Val Ser Ser Ala
            115                 120

<210> SEQ ID NO 274
<211> LENGTH: 330
<212> TYPE: DNA
<213> ORGANISM: Homo sapiens

<400> SEQUENCE: 274
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaaaatcct gatctatgct gcatccagtt tgcaaagtgg ggtcccatca     180
aggttcagtg gcagtggatc tgggacagat ttcactctca ccatcagcag tctgcaacct     240
gaagattttg cgacttacta ctgtcaacag agttgcagta ccccteegga gtgcagtttt     300 ggccagggga ccaagctgga gatcaaacga                                      330

<210> SEQ ID NO 275
<211> LENGTH: 110
<212> TYPE: PRT
<213> ORGANISM: Homo sapiens

<400> SEQUENCE: 275

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Ile Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Cys Ser Thr Pro Pro
                85                  90                  95

Glu Cys Ser Phe Gly Gln Gly Thr Lys Leu Glu Ile Lys Arg
            100                 105                 110

<210> SEQ ID NO 276
<211> LENGTH: 369
<212> TYPE: DNA
<213> ORGANISM: Homo sapiens

<400> SEQUENCE: 276
gaagtgcagc tggtggagtc tgggggaatc gtggtacagc ctgggggtc cctgagactc       60 tcctgtgcag cctctggatt cacctttgat gattatacca tgcactgggt ccgtcaaact     120
ccggggaagg gtctggagtg gtctctcttt attagttggg atggtggtag cacatactat     180
gcagactctg tgaagggccg attcaccatc tccagagaca acagcaaaaa ctccctgtat     240
ctgcaaatga acagtctgag aactgaggac accgccttgt attactgtgc aaaagatata     300
gatatagcag tggctggtac aggatttgac cactgggggcc agggaaccct ggtcaccgtc     360
tcctcagct                                                             369

<210> SEQ ID NO 277
<211> LENGTH: 123

```
<212> TYPE: PRT
<213> ORGANISM: Homo sapiens

<400> SEQUENCE: 277

Glu Val Gln Leu Val Glu Ser Gly Gly Ile Val Val Gln Pro Gly Gly
 1               5                  10                  15

Ser Leu Arg Leu Ser Cys Ala Ala Ser Gly Phe Thr Phe Asp Asp Tyr
            20                  25                  30

Thr Met His Trp Val Arg Gln Thr Pro Gly Lys Gly Leu Glu Trp Val
        35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Ile Asp Ile Ala Val Ala Gly Thr Gly Phe Asp His Trp
            100                 105                 110

Gly Gln Gly Thr Leu Val Thr Val Ser Ser Ala
        115                 120

<210> SEQ ID NO 278
<211> LENGTH: 324
<212> TYPE: DNA
<213> ORGANISM: Homo sapiens

<400> SEQUENCE: 278
gaaatagtga tgacgcagtc tccagccacc ctgtctgtgt ctccagggga aagagccacc        60
ctctcctgca gggccagtca gagtgttacc agcaacctag cctggtacca gcagaaacct       120
ggccaggctc ccaggctcct catctatggt gcattaatta gggccactgg tatcccagcc       180
aggttcagtg gcagtgggtc tgggacagag ttcactctca ccatcagcag cctgcagtct       240
gaagattttg cagtttatta ctgtcagcaa tataataact ggccattcac tttcggccct       300
gggaccaaag tggatatcaa acga                                             324

<210> SEQ ID NO 279
<211> LENGTH: 108
<212> TYPE: PRT
<213> ORGANISM: Homo sapiens

<400> SEQUENCE: 279

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Thr Ser Asn
            20                  25                  30

Leu Ala Trp Tyr Gln Gln Lys Pro Gly Gln Ala Pro Arg Leu Leu Ile
        35                  40                  45

Tyr Gly Ala Leu Ile Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys Arg
            100                 105
```

<210> SEQ ID NO 280
<211> LENGTH: 369
<212> TYPE: DNA
<213> ORGANISM: Homo sapiens

<400> SEQUENCE: 280

| | | |
|---|---|---|
| gtcaggtgca gctggtggag tctgggggag gcgtggtcca gcctgggagg tccctgagac | 60 |
| tctcctgtgc agcgtctgga ttcaccttca gtagctatgg catgcactgg gtccgccagg | 120 |
| ctccaggcaa ggggctggaa tgggtggcag ttatatggta tgatggaagt aataaatact | 180 |
| atgcagactc cgtgaagggc cgattcacca tctccagaga caattccaag aacacgctgt | 240 |
| atctgcaaat gaacagcctg agagccgagg acacggctgt gtattactgt gcgagagctc | 300 |
| cgtatgactg gaactcatac tacggttttgg acgtctgggg ccaagggacc acggtcaccg | 360 |
| tctcctcag | 369 |

<210> SEQ ID NO 281
<211> LENGTH: 123
<212> TYPE: PRT
<213> ORGANISM: Homo sapiens

<400> SEQUENCE: 281

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Pro Tyr Asp Trp Asn Ser Tyr Tyr Gly Leu Asp Val Trp
            100                 105                 110

Gly Gln Gly Thr Thr Val Thr Val Ser Ser Ala
        115                 120

<210> SEQ ID NO 282
<211> LENGTH: 324
<212> TYPE: DNA
<213> ORGANISM: Homo sapiens

<400> SEQUENCE: 282

| | | |
|---|---|---|
| gacatccaga tgacccagtc tccatcctcc ctgtctgcat ctgtaggaga cagagtcacc | 60 |
| atcacttgcc aggcgagtca ggacattagg aactatttaa attggtatca gcagaaacca | 120 |
| gggaaagccc ctaagctcct gatctacgat gcatccaatt tggaaacagg ggtcccatca | 180 |
| aggttcagtg aagtggatc tgggacagat tttactttca ccatcagcag cctgcagcct | 240 |
| gaagatattg caacatatta ctgtcaacag tatgataatc tcccgatcac cttcggccaa | 300 |
| gggacacgac tggagattaa acga | 324 |

<210> SEQ ID NO 283
<211> LENGTH: 108
<212> TYPE: PRT
<213> ORGANISM: Homo sapiens

<400> SEQUENCE: 283

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile
                85                  90                  95

Thr Phe Gly Gln Gly Thr Arg Leu Glu Ile Lys Arg
            100                 105

<210> SEQ ID NO 284
<211> LENGTH: 351
<212> TYPE: DNA
<213> ORGANISM: Homo sapiens

<400> SEQUENCE: 284
caggttcagc tggtgcagtc tggagctgag gtgaagaagc ctggggcctc agtgaaggtc      60
tcctgcaagg cttctggtta caccttacc agctatggta tcagctgggt gcgacaggcc     120
cctggacaag gcttgagtg gatgggatgg atcagcgctc acaatggtaa cacaaactat     180
gcacagaagc tccagggcag agtcaccatg accacagaca catccacgag cacagcctac     240
atggagctga ggagcctgag atctgacgac acggccgtgt attattgtgc gagaggcgtg     300
ggatctaagg attactgggg ccagggaacc ctggtcaccg tctcctcagc t              351

<210> SEQ ID NO 285
<211> LENGTH: 117
<212> TYPE: PRT
<213> ORGANISM: Homo sapiens

<400> SEQUENCE: 285

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala His Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Val Gly Ser Lys Asp Tyr Trp Gly Gln Gly Thr Leu Val
            100                 105                 110

Thr Val Ser Ser Ala
            115

<210> SEQ ID NO 286
<211> LENGTH: 324
<212> TYPE: DNA

<213> ORGANISM: Homo sapiens

<400> SEQUENCE: 286

```
gacatccaga tgacccagtc tccatcctca ctgtctgcat ctgtaggaga cagagtcacc      60
atcacttgtc gggcgagtca ggacattagc aattatttag cctggtttca gcagaaacca     120
gggaaagccc ctaagtccct gatctatgct gcatccagtt tgcaaagtgg ggtcccatca     180
aagttcagcg gcagtggatc tgggaccgat tcactctcac ccatcagcag cctgcagcct     240
gaagattttg caacttatta ctgccaacag tataatagtt accctcggac gttcggccaa     300
gggaccaagg tggaaatcaa acga                                            324
```

<210> SEQ ID NO 287
<211> LENGTH: 108
<212> TYPE: PRT
<213> ORGANISM: Homo sapiens

<400> SEQUENCE: 287

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys Arg
            100                 105
```

<210> SEQ ID NO 288
<211> LENGTH: 372
<212> TYPE: DNA
<213> ORGANISM: Homo sapiens

<400> SEQUENCE: 288

```
caggtgcagc tggtggagtc tgggggaggc gtggtccagc ctgggaggtc cctgagactc      60
tcctgtgcag cgtctggatt caccttcagt agttatggca tgcactgggt ccgccaggct     120
ccaggcaagg ggctggagtg ggtggcaatt atttggtttg atggaagtaa tgaatactat     180
gcagactccg tgaagggccg attcaccatc tccagagaca attccaagaa cacgctgtat     240
ctgcaaatga acagcctgag agccgaggac acggctgtgt atttctgtgc gagaggaggc     300
cctctgtata gcaactcctt ttactacttt gactactggg gccagggaac cctggtcacc     360
gtctcctcag ct                                                         372
```

<210> SEQ ID NO 289
<211> LENGTH: 124
<212> TYPE: PRT
<213> ORGANISM: Homo sapiens

<400> SEQUENCE: 289

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
```

```
                    20                  25                  30
Gly Met His Trp Val Arg Gln Ala Pro Gly Lys Gly Leu Glu Trp Val
            35                  40                  45

Ala Ile Ile Trp Phe Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Gly Gly Pro Leu Tyr Ser Asn Ser Phe Tyr Tyr Phe Asp Tyr
            100                 105                 110

Trp Gly Gln Gly Thr Leu Val Thr Val Ser Ser Ala
            115                 120
```

<210> SEQ ID NO 290
<211> LENGTH: 324
<212> TYPE: DNA
<213> ORGANISM: Homo sapiens

<400> SEQUENCE: 290

```
gacatccaga tgacccagtc tccatcctcc ctgtctgcat ctgtaggaga cagagtcacc    60
atcacttgcc aggcgagtca ggacattaga aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatattg caacatatta ctgtcaacag tatgataatc tcccgatcac cttcggccaa   300
gggacacgac tggagattaa acga                                          324
```

<210> SEQ ID NO 291
<211> LENGTH: 108
<212> TYPE: PRT
<213> ORGANISM: Homo sapiens

<400> SEQUENCE: 291

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile
                85                  90                  95

Thr Phe Gly Gln Gly Thr Arg Leu Glu Ile Lys Arg
            100                 105
```

<210> SEQ ID NO 292
<211> LENGTH: 365
<212> TYPE: DNA
<213> ORGANISM: Homo sapiens

<400> SEQUENCE: 292

```
gaggtgcagc tggtggagtc tgggggaggc ttggtaaagc ctggggggtc ccttagactc    60
```

```
tcctgtgcag cctctggatt cactttcagt aacacctgga tgagctgggt ccgccaggct    120
ccagggaagg ggctggagtg ggttggccgt attaaaagca aaactgatgg tgggacaaca    180
gactacgctg cacccgtgaa ggcagattc accatctcaa gagatgattc aaaaaacacg    240
ctgtgtctgc aactgaacag cctgaaaacc gaggacacag ccgtgtatta ctgttccgca    300
ggctacggtg actaccccta ctttgacttc tggggccagg aaccctggt caccgtctcc    360 tcagc    365
```

<210> SEQ ID NO 293
<211> LENGTH: 122
<212> TYPE: PRT
<213> ORGANISM: Homo sapiens

<400> SEQUENCE: 293

```
Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Ser Asn Thr
            20                  25                  30
Trp Met Ser Trp Val Arg Gln Ala Pro Gly Lys Gly Leu Glu Trp Val
        35                  40                  45
Gly Arg Ile Lys Ser Lys Thr Asp Gly Gly Thr Thr Asp Tyr Ala Ala
    50                  55                  60
Pro Val Lys Gly Arg Phe Thr Ile Ser Arg Asp Asp Ser Lys Asn Thr
65                  70                  75                  80
Leu Cys Leu Gln Leu Asn Ser Leu Lys Thr Glu Asp Thr Ala Val Tyr
                85                  90                  95
Tyr Cys Ser Ala Gly Tyr Gly Asp Tyr Pro Tyr Phe Asp Phe Trp Gly
            100                 105                 110
Gln Gly Thr Leu Val Thr Val Ser Ser Ala
        115                 120
```

<210> SEQ ID NO 294
<211> LENGTH: 324
<212> TYPE: DNA
<213> ORGANISM: Homo sapiens

<400> SEQUENCE: 294

```
gacatccaga tgacccagtc tccatcttcc gtgtctgcat ctgtaggaga cagagtcacc    60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt tcccgtggac gttcggccaa    300
gggaccaagg tggaaatcaa acga    324
```

<210> SEQ ID NO 295
<211> LENGTH: 108
<212> TYPE: PRT
<213> ORGANISM: Homo sapiens

<400> SEQUENCE: 295

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
```

```
                35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Trp
                 85                  90                  95

Thr Phe Gly Gln Gly Thr Lys Val Glu Ile Lys Arg
            100                 105
```

<210> SEQ ID NO 296
<211> LENGTH: 360
<212> TYPE: DNA
<213> ORGANISM: Homo sapiens

<400> SEQUENCE: 296

```
gaggtgcagc tggtggagtc tgggggaggt gtggtacggc ctgggggggtc cctgagactc      60 tcctgtacaa cctctggatt caccttttgat gattatggca tgagctgggt ccgccaagct     120
ccagggaagg gctggagtg gtctctggt attaattgga atggtggtag cacagtttat        180
gcagactctg tgaagggccg attcaccatc tccagagaca cgccaagaa ctccctgtat       240 ctgcaaatga acagtctgag agccgaggac acggccttgt atcactgtgc gagaaataag     300
cagtggctct ggtacttcga tctctgggggc cgtggcaccc tggtcactgt ctcctcagct    360
```

<210> SEQ ID NO 297
<211> LENGTH: 120
<212> TYPE: PRT
<213> ORGANISM: Homo sapiens

<400> SEQUENCE: 297

```
Glu Val Gln Leu Val Glu Ser Gly Gly Gly Val Val Arg Pro Gly Gly
 1               5                  10                  15

Ser Leu Arg Leu Ser Cys Thr Thr Ser Gly Phe Thr Phe Asp Asp Tyr
            20                  25                  30

Gly Met Ser Trp Val Arg Gln Ala Pro Gly Lys Gly Leu Glu Trp Val
         35                  40                  45

Ser Gly Ile Asn Trp Asn Gly Gly Ser Thr Val Tyr Ala Asp Ser Val
     50                  55                  60

Lys Gly Arg Phe Thr Ile Ser Arg Asp Ser Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg Asn Lys Gln Trp Leu Trp Tyr Phe Asp Leu Trp Gly Arg Gly
            100                 105                 110

Thr Leu Val Thr Val Ser Ser Ala
        115                 120
```

<210> SEQ ID NO 298
<211> LENGTH: 324
<212> TYPE: DNA
<213> ORGANISM: Homo sapiens

<400> SEQUENCE: 298

```
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg gattccagcc     180
```

```
aggttcagtg gcagtgggtc tgggacagag ttcactctca ccatcagcag cctgcagtct    240
gaagattttg cagtttatta ctgtgagcag tataataact ggcctctcac tttcggcggt    300
gggaccaagg tggagatcaa acga                                           324
```

<210> SEQ ID NO 299
<211> LENGTH: 108
<212> TYPE: PRT
<213> ORGANISM: Homo sapiens

<400> SEQUENCE: 299

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg
            100                 105
```

<210> SEQ ID NO 300
<211> LENGTH: 372
<212> TYPE: DNA
<213> ORGANISM: Homo sapiens

<400> SEQUENCE: 300

```
caggtgcagc tgcaggagtc gggcccagga ctggtgaagc cttcggagac cctgtccctc     60
acctgcactg tctctggtgg ctccgtcagc agtggtggtt actactggag ctggatccgg    120
cagcccccag ggaagggact ggagtggatt ggatatatca attacagtcg agcaccaac    180 cacaacccct ccctcaagag tcgagtcacc atatcagtag acacgtccaa gaatcagttc    240
tccctgaagc tgagctctgt gaccgctgcg gacacggccg tgtattactg tgcgagagag    300
ggacgtggag acagctatgg ttactacttt gactattggg gccagggaac cctggtcacc    360
gtctcctcag ct                                                        372
```

<210> SEQ ID NO 301
<211> LENGTH: 124
<212> TYPE: PRT
<213> ORGANISM: Homo sapiens

<400> SEQUENCE: 301

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Asn Tyr Ser Arg Ser Thr Asn His Asn Pro Ser
    50                  55                  60

Leu Lys Ser Arg Val Thr Ile Ser Val Asp Thr Ser Lys Asn Gln Phe
```

```
                65                  70                  75                  80
Ser Leu Lys Leu Ser Ser Val Thr Ala Ala Asp Thr Ala Val Tyr Tyr
                        85                  90                  95

Cys Ala Arg Glu Gly Arg Gly Asp Ser Tyr Gly Tyr Tyr Phe Asp Tyr
            100                 105                 110

Trp Gly Gln Gly Thr Leu Val Thr Val Ser Ser Ala
            115                 120

<210> SEQ ID NO 302
<211> LENGTH: 324
<212> TYPE: DNA
<213> ORGANISM: Homo sapiens

<400> SEQUENCE: 302
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatggt gcatccagtt tgcaaagtgg ggtcccatca    180
aggttcagtg gcagtggatc tgggacagat ttcactctca ccatcagcag tctgcagcct    240
gaagattttg caacttacta ctgtcagcag agttacagta tccctcgcac gttcggccaa    300
gggaccaagg tggaaatcaa acga                                           324

<210> SEQ ID NO 303
<211> LENGTH: 108
<212> TYPE: PRT
<213> ORGANISM: Homo sapiens

<400> SEQUENCE: 303

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Gly Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ile Pro Arg
             85                  90                  95

Thr Phe Gly Gln Gly Thr Lys Val Glu Ile Lys Arg
            100                 105

<210> SEQ ID NO 304
<211> LENGTH: 371
<212> TYPE: DNA
<213> ORGANISM: Homo sapiens

<400> SEQUENCE: 304
caggtgcaac tggtggagtc tgggggaggc gtggtccagc ctgggaggtc cctgagactc      60
tcctgtgcag cgtctggatt caccttcagt aactatggca tgcactgggt ccgccaggct    120
ccaggcaagg ggctggagtg ggtggcagtt atctggtatg atggaagtca taatactat     180 gcagactccg tgaagggccg attcaccatc tccagagaca attccaagaa ctcgctgtat    240
ctgcaaatga acagcctgag agccgaggac acggctgtgt attactgtgc gagaggaggc    300
cctctgtata gcaactcctt ttactacttt gactactggg gccagggaac cctggtcacc    360
```
gtctcctcag c                                                          371

<210> SEQ ID NO 305
<211> LENGTH: 124
<212> TYPE: PRT
<213> ORGANISM: Homo sapiens

<400> SEQUENCE: 305

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Val Arg Gln Ala Pro Gly Lys Gly Leu Glu Trp Val
        35                  40                  45

Ala Val Ile Trp Tyr Asp Gly Ser His Lys Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Leu Tyr Ser Asn Ser Phe Tyr Tyr Phe Asp Tyr
            100                 105                 110

Trp Gly Gln Gly Thr Leu Val Thr Val Ser Ser Ala
        115                 120

<210> SEQ ID NO 306
<211> LENGTH: 324
<212> TYPE: DNA
<213> ORGANISM: Homo sapiens

<400> SEQUENCE: 306
gacatccaga tgacccagtc tccatcctcc ctgtctgcat ctgtaggaga cagagtcacc     60
atcacttgcc aggcgagtca ggacattaga aactatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaacag tatgataatc tcccgatcac cttcggccaa    300
gggacacgac tggagattaa acga                                           324

<210> SEQ ID NO 307
<211> LENGTH: 108
<212> TYPE: PRT
<213> ORGANISM: Homo sapiens

<400> SEQUENCE: 307

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile

```
              85                  90                  95
Thr Phe Gly Gln Gly Thr Arg Leu Glu Ile Lys Arg
            100                 105

<210> SEQ ID NO 308
<211> LENGTH: 360
<212> TYPE: DNA
<213> ORGANISM: Homo sapiens

<400> SEQUENCE: 308
gaggtgaagc tggtggagtc tgggggagga atggtccggc ctgggggtc cctgagactc      60 tcctgtgcag cctctggatt cacctttgat gattacggca tgagctgggt ccgccaagct    120
ccagggaagg gctggagtg gtctctggt attaattgga atggtggtgg cacagcttat     180
gcagactctg tgaagggccg attcaccatc tccagagaca cgccaagaa ctccctgtat     240 ctgcaattga acagtctgag agccgaggac acggccttgt atcactgtgc gagaaataag    300
cagtggctct ggtacttcga tctctggggc cgtggcaccc tggtcactgt ctcctcagct    360

<210> SEQ ID NO 309
<211> LENGTH: 120
<212> TYPE: PRT
<213> ORGANISM: Homo sapiens

<400> SEQUENCE: 309

Glu Val Lys Leu Val Glu Ser Gly Gly Gly Met Val Arg Pro Gly Gly
  1               5                  10                  15

Ser Leu Arg Leu Ser Cys Ala Ala Ser Gly Phe Thr Phe Asp Asp Tyr
             20                  25                  30

Gly Met Ser Trp Val Arg Gln Ala Pro Gly Lys Gly Leu Glu Trp Val
         35                  40                  45

Ser Gly Ile Asn Trp Asn Gly Gly Gly Thr Ala Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr His Cys
                 85                  90                  95

Ala Arg Asn Lys Gln Trp Leu Trp Tyr Phe Asp Leu Trp Gly Arg Gly
            100                 105                 110

Thr Leu Val Thr Val Ser Ser Ala
        115                 120

<210> SEQ ID NO 310
<211> LENGTH: 324
<212> TYPE: DNA
<213> ORGANISM: Homo sapiens

<400> SEQUENCE: 310
gaaatagtga tgacgcagtc tccagccacc ctgtctgtgt ctccagggga aagagtcacc      60
ctctcctgca gggccagtca gagtgttagc ggcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcac tataataact ggcctctcac tttcggcggt    300
gggaccaagg tggagatcaa acga                                            324

<210> SEQ ID NO 311
```

```
<211> LENGTH: 108
<212> TYPE: PRT
<213> ORGANISM: Homo sapiens

<400> SEQUENCE: 311

Glu Ile Val Met Thr Gln Ser Pro Ala Thr Leu Ser Val Ser Pro Gly
 1               5                  10                  15

Glu Arg Val Thr Leu Ser Cys Arg Ala Ser Gln Ser Val Ser Gly Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Tyr Asn Asn Trp Pro Leu
                85                  90                  95

Thr Phe Gly Gly Gly Thr Lys Val Glu Ile Lys Arg
            100                 105

<210> SEQ ID NO 312
<211> LENGTH: 366
<212> TYPE: DNA
<213> ORGANISM: Homo sapiens

<400> SEQUENCE: 312
caggtgcagc tggtgcagtc tggggctgag gtgacgaagc ctggggcctc agtgaaggtc     60
tcctgcaagg cttctggata caccttcacc gcctaccata tgtactgggt gcgacaggcc    120
cctggacaag gcttgagtg gatgggatgg atcaaccota acagtggtgg cacaaactat    180
gcacagaagt tcagggcag gtcaccatg accagggaca cgtccatcag cacagcctac    240
atggaactga gcaggctgag atctgacgac tcgcccgtgt attactgtgc gagagatcag    300
ggtatagcag cagctggtcc ctttgactac tggggccagg gaaccctggt caccgtctcc    360
tcagct                                                               366

<210> SEQ ID NO 313
<211> LENGTH: 122
<212> TYPE: PRT
<213> ORGANISM: Homo sapiens

<400> SEQUENCE: 313

Gln Val Gln Leu Val Gln Ser Gly Ala Glu Val Thr Lys Pro Gly Ala
 1               5                  10                  15

Ser Val Lys Val Ser Cys Lys Ala Ser Gly Tyr Thr Phe Thr Ala Tyr
            20                  25                  30

His Met Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Ser Pro Val Tyr Tyr Cys
                85                  90                  95

Ala Arg Asp Gln Gly Ile Ala Ala Gly Pro Phe Asp Tyr Trp Gly
            100                 105                 110

Gln Gly Thr Leu Val Thr Val Ser Ser Ala
```

<210> SEQ ID NO 314
<211> LENGTH: 321
<212> TYPE: DNA
<213> ORGANISM: Homo sapiens

<400> SEQUENCE: 314

```
gaaatagtga tgacgcagtc tccagccacc ctgtctgtgt ctccagggga tagagccacc    60
ctctcctgca gggccagtca gagtgttagc agcaactttg cctggtacca gcagaaacct   120
ggccaggctc ccaggctcct catctatggt tcatccacca gggccactgg tatcccagcc   180
aggttcagtg gcagtgggtc tgggacagag ttcactctca ccatcagcag cctgcagtct   240
gaagattttg cagtttatta ctgtcagcag tatcattact ggtggacgtt cggccaaggg   300
accaaggtgg aattcaaacg a                                             321
```

<210> SEQ ID NO 315
<211> LENGTH: 107
<212> TYPE: PRT
<213> ORGANISM: Homo sapiens

<400> SEQUENCE: 315

Glu Ile Val Met Thr Gln Ser Pro Ala Thr Leu Ser Val Ser Pro Gly
1               5                   10                  15

Asp Arg Ala Thr Leu Ser Cys Arg Ala Ser Gln Ser Val Ser Ser Asn
            20                  25                  30

Phe Ala Trp Tyr Gln Gln Lys Pro Gly Gln Ala Pro Arg Leu Leu Ile
        35                  40                  45

Tyr Gly Ser Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Tyr Trp Trp Thr
                85                  90                  95

Phe Gly Gln Gly Thr Lys Val Glu Phe Lys Arg
            100                 105

<210> SEQ ID NO 316
<211> LENGTH: 369
<212> TYPE: DNA
<213> ORGANISM: Homo sapiens

<400> SEQUENCE: 316

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggttatag cacatactac   180
gcagactccg tgaagggccg gttcaccatc tccagagaca attccaagaa cacgctgtat   240
ctgcaaatga acagcctgag agccgaggac acggccgtat attactgtgc gaaagatctg   300
cagcagtggc tggtaccgac cgtctttgac tactggggcc agggaaccct ggtcaccgtc   360
tcctcagct                                                          369
```

<210> SEQ ID NO 317
<211> LENGTH: 123
<212> TYPE: PRT
<213> ORGANISM: Homo sapiens

<400> SEQUENCE: 317

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Leu Gln Gln Trp Leu Val Pro Thr Val Phe Asp Tyr Trp
            100                 105                 110
Gly Gln Gly Thr Leu Val Thr Val Ser Ser Ala
            115                 120

<210> SEQ ID NO 318
<211> LENGTH: 322
<212> TYPE: DNA
<213> ORGANISM: Homo sapiens

<400> SEQUENCE: 318
gaaatagtga tgacgcagtc tccagccacc ctgtctgtgt ctccagggga aagagccacc      60
ctctcctgca gggccagtca gagtgttagc agcaacttag tctggtacca gcagaaacct     120
ggccaggctc ccaggctcct catctatgat tcatccacca gggccactgg tatcccagtc     180
aggttcagtg gcagtgggtc tgggacagag ttcactctca ccatcagcag cctgcagtct     240
gaagattttg cagtgtatta ctgtcagcag tataatcact ggtggacgtt cggccaaggg     300
accaaggtgg aaatcaaacg aa                                              322

<210> SEQ ID NO 319
<211> LENGTH: 107
<212> TYPE: PRT
<213> ORGANISM: Homo sapiens

<400> SEQUENCE: 319

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Val Trp Tyr Gln Gln Lys Pro Gly Gln Ala Pro Arg Leu Leu Ile
        35                  40                  45
Tyr Asp Ser Ser Thr Arg Ala Thr Gly Ile Pro Val Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn His Trp Trp Thr
                85                  90                  95
Phe Gly Gln Gly Thr Lys Val Glu Ile Lys Arg
            100                 105

<210> SEQ ID NO 320
<211> LENGTH: 357
<212> TYPE: DNA

<213> ORGANISM: Homo sapiens

<400> SEQUENCE: 320

```
gaggtgcagt tggtggagtc tgggggaggc ttggtccagc ctgggggtc cctgagactc    60
tcctgtgcag cctctggatt caccttagt agctattgga tgagctgggt ccgccaggct   120
ccagggaagg gctggagtg gtggccaac ataaaggaag atggaagtga aaatactat    180
gtggactctg tgaagggccg attcaccatc tccagagaca acgccaagaa ctcactgtat   240
ctgcaaatga acagcctgag agccgaggac acggctgtgt tttactgtgc gagagatcgg   300
agcagtggct tttttgacta ctggggccag ggaaccctgg tcaccgtctc ctcagct    357
```

<210> SEQ ID NO 321
<211> LENGTH: 119
<212> TYPE: PRT
<213> ORGANISM: Homo sapiens

<400> SEQUENCE: 321

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Lys Glu Asp Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Phe Tyr Cys
                 85                  90                  95

Ala Arg Asp Arg Ser Ser Gly Phe Phe Asp Tyr Trp Gly Gln Gly Thr
            100                 105                 110

Leu Val Thr Val Ser Ser Ala
        115
```

<210> SEQ ID NO 322
<211> LENGTH: 321
<212> TYPE: DNA
<213> ORGANISM: Homo sapiens

<400> SEQUENCE: 322

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggttcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataatcact ggtggacgtt cggccaaggg   300
accaaggtgg aaatcaaacg a                                              321
```

<210> SEQ ID NO 323
<211> LENGTH: 107
<212> TYPE: PRT
<213> ORGANISM: Homo sapiens

<400> SEQUENCE: 323

```
Glu Ile Val Met Thr Gln Ser Pro Ala Thr Leu Ser Val Ser Pro Gly
 1               5                  10                  15
```

```
Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Phe Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn His Trp Trp Thr
                85                  90                  95

Phe Gly Gln Gly Thr Lys Val Glu Ile Lys Arg
            100                 105
```

<210> SEQ ID NO 324
<211> LENGTH: 357
<212> TYPE: DNA
<213> ORGANISM: Homo sapiens

<400> SEQUENCE: 324

```
gtgaggtgca gctggtggag tctgggggag gcttggtaca gcctgggggg tccctgagac    60
tctcctgtgc agcctctgga ttcaccttca gtacctatag catgaactgg gtccgccagg   120
ctccagggaa ggggctggag tggatttcat acattagtcg tagtagtaga accataaacc   180
acgcagactc tgtgaagggc cgattcaccg tctccagaga caatgccaag aactcactgt   240
atctgcaaat gatcagcctg agagacgagg acacggctgt gtattactgt gcgagaaagg   300
cagcagctgg tccctttgac tactggggcc agggaaccct ggtcaccgtc gcctcag      357
```

<210> SEQ ID NO 325
<211> LENGTH: 119
<212> TYPE: PRT
<213> ORGANISM: Homo sapiens

<400> SEQUENCE: 325

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Ile
        35                  40                  45

Ser Tyr Ile Ser Arg Ser Ser Arg Thr Ile Asn His Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Ile Ser Leu Arg Asp Glu Asp Thr Ala Val Tyr Tyr Cys
                85                  90                  95

Ala Arg Lys Ala Ala Ala Gly Pro Phe Asp Tyr Trp Gly Gln Gly Thr
            100                 105                 110

Leu Val Thr Val Ala Ser Ala
            115
```

<210> SEQ ID NO 326
<211> LENGTH: 342
<212> TYPE: DNA
<213> ORGANISM: Homo sapiens

<400> SEQUENCE: 326

```
gacatcgtga tgacccagtc tccagactcc ctggctgtgt ctctgggcga gagggccacc    60
```

```
atcaactgca agtccagcca gagtgtttta tacagctcca acaataagaa ctacttagct    120
tggtaccagc agaaaccagg acagcctcct aagctgctca ttcactggtc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgctcactt tcggcggagg gaccaaggtg gagatcaaac ga                      342
```

<210> SEQ ID NO 327
<211> LENGTH: 114
<212> TYPE: PRT
<213> ORGANISM: Homo sapiens

<400> SEQUENCE: 327

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile His Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys Arg

<210> SEQ ID NO 328
<211> LENGTH: 360
<212> TYPE: DNA
<213> ORGANISM: Homo sapiens

<400> SEQUENCE: 328

```
gaggtgcagc tggtggagtc tgggggaggt gtggtacgga ctgggggtc cctgagactc      60 tcctgtgcag cctctggatt cagctttgat gattatggca tgagctgggt ccgccaagct    120
ccagggaagg ggctggagtg ggtctctggt attaattgga tggtggtag acagtttat      180 gcagactctg tgaagggccg attcaccatc tccagagaca cgccaagaa ctccctgtat     240 ctgcaaatga acagtctgag agccgaggac acggccttgt atcactgtgc gagaaataag    300
cagtggctct ggtacttcga tctctggggc cgtggcaccc tggtcactgt ctcctcagct    360
```

<210> SEQ ID NO 329
<211> LENGTH: 120
<212> TYPE: PRT
<213> ORGANISM: Homo sapiens

<400> SEQUENCE: 329

Glu Val Gln Leu Val Glu Ser Gly Gly Gly Val Val Arg Thr Gly Gly
1               5                   10                  15

Ser Leu Arg Leu Ser Cys Ala Ala Ser Gly Phe Ser Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Arg Thr Val Tyr Ala Asp Ser Val
         50                  55                  60

Lys Gly Arg Phe Thr Ile Ser Arg Asp Ser Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg Asn Lys Gln Trp Leu Trp Tyr Phe Asp Leu Trp Gly Arg Gly
            100                 105                 110

Thr Leu Val Thr Val Ser Ser Ala
        115                 120

<210> SEQ ID NO 330
<211> LENGTH: 324
<212> TYPE: DNA
<213> ORGANISM: Homo sapiens

<400> SEQUENCE: 330
gaaatagtga tgacgcagtc tccagccacc ctgtctgtgt ctccagggga aagagccacc      60
ctctcctgca gggccagtca gagtattagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagcct    240
gaagattttg cagtttatta ctgtcagcag tataataact ggcctctcac tttcggccgt    300
gggaccaagg tggagatcaa acga                                            324

<210> SEQ ID NO 331
<211> LENGTH: 108
<212> TYPE: PRT
<213> ORGANISM: Homo sapiens

<400> SEQUENCE: 331

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Ile Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Val Tyr Tyr Cys Gln Gln Tyr Asn Asn Trp Pro Leu
                 85                  90                  95

Thr Phe Gly Arg Gly Thr Lys Val Glu Ile Lys Arg
            100                 105

<210> SEQ ID NO 332
<211> LENGTH: 375
<212> TYPE: DNA
<213> ORGANISM: Homo sapiens

<400> SEQUENCE: 332
gaggtgcagc tggtggagtc tgggggaggc ttggtaaagc ctggggggtc ccttagactc      60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240

```
ctgtatctgc aaatgaacag cctgaaaacc gaggacacag ccgtgtatta ctgtaccaca      300
tcgtatagca gtggctggtt ctactggtac ttcgatatct ggggccgtgg cacccggtc       360 actgtctcct cagct                                                       375
```

<210> SEQ ID NO 333
<211> LENGTH: 125
<212> TYPE: PRT
<213> ORGANISM: Homo sapiens

<400> SEQUENCE: 333

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ser Tyr Ser Ser Gly Trp Phe Tyr Trp Tyr Phe Asp
            100                 105                 110

Ile Trp Gly Arg Gly Thr Pro Val Thr Val Ser Ser Ala
        115                 120                 125
```

<210> SEQ ID NO 334
<211> LENGTH: 324
<212> TYPE: DNA
<213> ORGANISM: Homo sapiens

<400> SEQUENCE: 334

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctgagctcct gatctatgct gcatccagtt tgcaaagtgg agtcccatca     180
aggttcagtg gcagtggatc tgggacagat ttcactctca ccatcagcag tctgcaacct     240
gaagattttg caacttacta ctgtcaacag agttacatta cccattcac tttcggccct      300 gggaccaaag tggatatcaa acga                                            324
```

<210> SEQ ID NO 335
<211> LENGTH: 108
<212> TYPE: PRT
<213> ORGANISM: Homo sapiens

<400> SEQUENCE: 335

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Glu Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ile Asn Pro Phe
                 85                  90                  95

Thr Phe Gly Pro Gly Thr Lys Val Asp Ile Lys Arg
            100                 105
```

```
<210> SEQ ID NO 336
<211> LENGTH: 366
<212> TYPE: DNA
<213> ORGANISM: Homo sapiens

<400> SEQUENCE: 336
gaggtgcagc tggtggagtc tgggggaggc ttggtaaagc ctgggggtc ccttagactc      60 tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatgtcaa gagatgattc aaaaaacacg    240
ctgtatctgc aaatgaacag cctgaaaacc gaggacacag ccgtgtatta ttgtaccatc    300
ctctacggtg acttctggta cttcgatctc tggggccgtg caccctggt cactgtctcc    360 tcagct                                                               366

<210> SEQ ID NO 337
<211> LENGTH: 122
<212> TYPE: PRT
<213> ORGANISM: Homo sapiens

<400> SEQUENCE: 337

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
     50                  55                  60

Pro Val Lys Gly Arg Phe Thr Met Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Ile Leu Tyr Gly Asp Phe Trp Tyr Phe Asp Leu Trp Gly
            100                 105                 110

Arg Gly Thr Leu Val Thr Val Ser Ser Ala
        115                 120

<210> SEQ ID NO 338
<211> LENGTH: 389
<212> TYPE: DNA
<213> ORGANISM: Homo sapiens

<400> SEQUENCE: 338
caggtgcagc tggtggagtc gggggaggc gtggtccagc ctggaggtc cctgagactc      60 tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
```

```
ctgcaaatga acagcctgag agccgaggac acggctgtgt attactgtgc gagagaaaat      300
tgtggtggtg actgctatca gctaaattac tactactact acggtatgga cgtctggggc      360
caagggacca cggtcaccgt ctcctcagc                                        389
```

```
<210> SEQ ID NO 339
<211> LENGTH: 130
<212> TYPE: PRT
<213> ORGANISM: Homo sapiens

<400> SEQUENCE: 339
```

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Cys Gly Gly Asp Cys Tyr Gln Leu Asn Tyr Tyr Tyr
            100                 105                 110

Tyr Tyr Gly Met Asp Val Trp Gly Gln Gly Thr Thr Val Thr Val Ser
        115                 120                 125

Ser Ala
    130

```
<210> SEQ ID NO 340
<211> LENGTH: 348
<212> TYPE: DNA
<213> ORGANISM: Homo sapiens

<400> SEQUENCE: 340
```

```
caggtgcagc tgcaggagtc ggccccagga ctggtgaagc cttcggagac cctgtccctc      60
acctgcactg tctctggtgg ctccatcagt agttactact ggagctggat ccggcagccc     120
ccagggaagg gactggagtg gattgggtat atctcttaca gtgggagcac caactacaac     180
ccctccctca agagtcgagt caccacatca gtagacacgt ccaagaacca gttctccctg     240
aagctgagct ctgtgaccgc cgcggacacg gccgtgtatt actgtacgag gggaactggg     300
gcctctgact actggggcca gggaaccctg gtcaccgtct cctcagct                  348
```

```
<210> SEQ ID NO 341
<211> LENGTH: 116
<212> TYPE: PRT
<213> ORGANISM: Homo sapiens

<400> SEQUENCE: 341
```

Gln Val Gln Leu Gln Glu Ser Ala Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Ser Tyr Ser Gly Ser Thr Asn Tyr Asn Pro Ser Leu Lys

```
                    50                  55                  60
Ser Arg Val Thr Thr Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Thr
                 85                  90                  95

Arg Gly Thr Gly Ala Ser Asp Tyr Trp Gly Gln Gly Thr Leu Val Thr
            100                 105                 110

Val Ser Ser Ala
        115

<210> SEQ ID NO 342
<211> LENGTH: 324
<212> TYPE: DNA
<213> ORGANISM: Homo sapiens

<400> SEQUENCE: 342
gacatccaga tgacccagtc tccatcctcc ctgtctgcat ctgtaggaga cagagtcacc      60
atcacttgcc aggcgagtca ggacattacc aactatttaa attggtatca gcagaaacca     120
gggaaagccc ctaagctcct gatctacgat gcatccaatt tggaaacagg gtcccatca     180 aggttcagtg aagtggatc tgggacagat tttactttca ccatcagcag cctgcagcct     240
gaagatattg caacatattt ctgtcaacag tatgataatc tcccgctcac tttcggcgga     300
gggaccaagg tggagatcaa acga                                            324

<210> SEQ ID NO 343
<211> LENGTH: 108
<212> TYPE: PRT
<213> ORGANISM: Homo sapiens

<400> SEQUENCE: 343

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Thr Asn Tyr
                 20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Tyr Asp Asn Leu Pro Leu
                 85                  90                  95

Thr Phe Gly Gly Gly Thr Lys Val Glu Ile Lys Arg
            100                 105

<210> SEQ ID NO 344
<211> LENGTH: 390
<212> TYPE: DNA
<213> ORGANISM: Homo sapiens

<400> SEQUENCE: 344
tcaggtgcag ctggtggagt cgggggggagg cgtggtccag cctggggaggt ccctgagact      60 ctcctgtgca gcgtctggat tcaccttcag tagctatggc atgcactggg tccgccaggc     120
tccaggcaag gggctggagt gggtggcagt tatatggtat gatggaagta ataaatacta     180
tgcagactcc gtgaagggcc gattcaccat ctccagagac aattccaaga acacgctgta     240
```

```
tctgcaaatg aacagcctga gagccgagga cacggctgtg tattactgtg cgagagaaaa    300
ttgtggtggt gactgctatc agctaaatta ctactactac tacggtatgg acgtctgggg    360
ccaagggacc acggtcaccg tctcctcagc                                     390
```

```
<210> SEQ ID NO 345
<211> LENGTH: 130
<212> TYPE: PRT
<213> ORGANISM: Homo sapiens

<400> SEQUENCE: 345
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Cys Gly Gly Asp Cys Tyr Gln Leu Asn Tyr Tyr Tyr
            100                 105                 110

Tyr Tyr Gly Met Asp Val Trp Gly Gln Gly Thr Thr Val Thr Val Ser
        115                 120                 125

Ser Ala
    130

```
<210> SEQ ID NO 346
<211> LENGTH: 362
<212> TYPE: DNA
<213> ORGANISM: Homo sapiens

<400> SEQUENCE: 346
```

```
caggtgcagc tggtggagtc tgggggaggc gtggtccagc ctggggaggtc cctgagactc    60 tcctgtgcag cgtctggatt caccttcagt agttatggca tgcactgggt ccgccaggct   120
ccaggcaagg gctggagtg gtggcagtt agatggtatg atgaaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagatccc   300
tttgaaactg gaactacttt tgactactgg ggccagggaa ccctggtcac cgtctcctca   360
gc                                                                   362
```

```
<210> SEQ ID NO 347
<211> LENGTH: 121
<212> TYPE: PRT
<213> ORGANISM: Homo sapiens

<400> SEQUENCE: 347
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Val Arg Trp Tyr Asp Glu Ser Asn Lys Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asp Pro Phe Glu Thr Gly Thr Thr Phe Asp Tyr Trp Gly Gln
            100                 105                 110

Gly Thr Leu Val Thr Val Ser Ser Ala
            115                 120

<210> SEQ ID NO 348
<211> LENGTH: 322
<212> TYPE: DNA
<213> ORGANISM: Homo sapiens

<400> SEQUENCE: 348
gaaatagtga tgacgcagtc tccagccacc ctggctgtgt ctccagggga aagagccacc      60
ctctcctgca gggccaggca gagtgttagc agcaacttag cctggtacca gcagaaacct     120
ggccaggctc ccaggctcct catctatggt gcatccacca tggccactgg tttcccagcc     180
aggttcagtg gcagagggtc tgggacagag ttcactctca ccatcagcag cctgcagtct     240
gaagattttg cagtttatta ctgtcaacag tataataact ggtggacgtt cggccaaggg     300
accaaggtgg aaatcaaacg aa                                              322

<210> SEQ ID NO 349
<211> LENGTH: 107
<212> TYPE: PRT
<213> ORGANISM: Homo sapiens

<400> SEQUENCE: 349

Glu Ile Val Met Thr Gln Ser Pro Ala Thr Leu Ala Val Ser Pro Gly
 1               5                  10                  15

Glu Arg Ala Thr Leu Ser Cys Arg Ala Arg Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Met Ala Thr Gly Phe Pro Ala Arg Phe Ser Gly
     50                  55                  60

Arg Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                 85                  90                  95

Phe Gly Gln Gly Thr Lys Val Glu Ile Lys Arg
            100                 105

<210> SEQ ID NO 350
<211> LENGTH: 362
<212> TYPE: DNA
<213> ORGANISM: Homo sapiens

<400> SEQUENCE: 350
caggtgcagc tggtggagtc tgggggaggc gtggtccagc ctggagggtc cctgagactc      60
tcctgtgcag cgtctggatt caccttcagt agtt atggca tgcactgggt ccgccaggct    120
ccaggcaagg ggctggagtg ggtggcagtt agatggtatg atgaaagtaa taatactat     180
```

```
gcagactccg tgaagggccg attcaccatc tccagagaca attccaagaa cacgctgtat    240
ctgcaaatga acagcctgag agccgaggac acggctgtgt attactgtgc gagagatccc    300
tttgaaactg aactactttt gactactgg ggccaggga cctggtcac cgtctcctca     360 gc                                                                  362
```

<210> SEQ ID NO 351
<211> LENGTH: 121
<212> TYPE: PRT
<213> ORGANISM: Homo sapiens

<400> SEQUENCE: 351

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Arg Trp Tyr Asp Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Phe Glu Thr Gly Thr Thr Phe Asp Tyr Trp Gly Gln
            100                 105                 110

Gly Thr Leu Val Thr Val Ser Ser Ala
        115                 120
```

<210> SEQ ID NO 352
<211> LENGTH: 313
<212> TYPE: DNA
<213> ORGANISM: Homo sapiens

<400> SEQUENCE: 352

```
gacatccaga tgacccagtc tccttcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gtatccagtt tggaaagtgg ggtcccatca    180
aggttcagcg gcagtggatc tgggacagat ttcactctca ccatcagcag cctgcagcct    240
gaagattttg caacttacta ttgtcaacag gctctcactt tcggcggagg gaccaaggtg    300
gagatcaaac gaa                                                      313
```

<210> SEQ ID NO 353
<211> LENGTH: 104
<212> TYPE: PRT
<213> ORGANISM: Homo sapiens

<400> SEQUENCE: 353

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Val Ser Ser Leu Glu Ser Gly Val Pro Ser Arg Phe Ser Gly
    50                  55                  60
```

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Leu Thr Phe Gly Gly
                 85                  90                  95

Gly Thr Lys Val Glu Ile Lys Arg
            100

<210> SEQ ID NO 354
<211> LENGTH: 363
<212> TYPE: DNA
<213> ORGANISM: Homo sapiens

<400> SEQUENCE: 354
caggtgcagc tggtggagtc tgggggaggc gtggtccagc ctggggaggtc cctgagactc      60 tcctgtgcag cgtctggatt caccttcagt gactatggca tgcactgggt ccgccaggct     120
ccaggcaagg ggctggagtg gatggcagtt ttatggtatg atgaaagtaa taaatactat     180
gcagactccg tgaagggccg attcaccatc tccagagaca gttccaagaa cacgctgtat     240
ctgcaaatga acagcctgag agccgaggac acggctgtgt attactgtgc gagagatccc     300
tttgaaactg aactactttt tgactactgg ggccagggaa ccctggtcac cgtctcctca     360
gct                                                                   363

<210> SEQ ID NO 355
<211> LENGTH: 121
<212> TYPE: PRT
<213> ORGANISM: Homo sapiens

<400> SEQUENCE: 355

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asp Tyr
                 20                  25                  30

Gly Met His Trp Val Arg Gln Ala Pro Gly Lys Gly Leu Glu Trp Met
             35                  40                  45

Ala Val Leu Trp Tyr Asp Glu Ser Asn Lys Tyr Tyr Ala Asp Ser Val
         50                  55                  60

Lys Gly Arg Phe Thr Ile Ser Arg Asp Ser Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Phe Glu Thr Gly Thr Thr Phe Asp Tyr Trp Gly Gln
            100                 105                 110

Gly Thr Leu Val Thr Val Ser Ser Ala
        115                 120

<210> SEQ ID NO 356
<211> LENGTH: 368
<212> TYPE: DNA
<213> ORGANISM: Homo sapiens

<400> SEQUENCE: 356
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaacccta acagtggtgg cacaaactat     180
gcacagaagt ttcagggcag ggtcaccatg accagggaca cgtccatcag cacagcctac     240

```
atggagctga gcaggctgag atctgacgac acggccgtgt attactgtgc gagagatggg      300
ggcagtatag cagtggctgg tcactttgag tactggggcc agggaaccct ggtcaccgtc      360
tcctcagc                                                                368
```

<210> SEQ ID NO 357
<211> LENGTH: 123
<212> TYPE: PRT
<213> ORGANISM: Homo sapiens

<400> SEQUENCE: 357

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Gly Ser Ile Ala Val Ala Gly His Phe Glu Tyr Trp
            100                 105                 110

Gly Gln Gly Thr Leu Val Thr Val Ser Ser Ala
        115                 120
```

<210> SEQ ID NO 358
<211> LENGTH: 322
<212> TYPE: DNA
<213> ORGANISM: Homo sapiens

<400> SEQUENCE: 358

```
gaaatagtga tgacgcagtc tccagccacc ctgtctgtgt ctccagggga aagagccacc       60
ctctcctgca gggccagtca gagtcttatc agcaacttag cctggtacca gcagaaacct      120
ggccaggctc ccaggctcct catctttggt gcatccacca gggccactgg tatcccagcc      180
aggttcagtg gcagtgggtc tgggacagag ttcactctca ccatcagcag cctgcagtct      240
gaagattttg caatttatta ctgtcatcag tataataact ggtggacgtt cggccaaggg      300
accaaggtgg aaatcaaacg aa                                                322
```

<210> SEQ ID NO 359
<211> LENGTH: 107
<212> TYPE: PRT
<213> ORGANISM: Homo sapiens

<400> SEQUENCE: 359

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Leu Ile Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60
```

Ser Gly Ser Gly Thr Glu Phe Thr Leu Thr Ile Ser Ser Leu Gln Ser
65                  70                  75                  80

Glu Asp Phe Ala Ile Tyr Tyr Cys His Gln Tyr Asn Asn Trp Trp Thr
                85                  90                  95

Phe Gly Gln Gly Thr Lys Val Glu Ile Lys Arg
            100                 105

<210> SEQ ID NO 360
<211> LENGTH: 383
<212> TYPE: DNA
<213> ORGANISM: Homo sapiens

<400> SEQUENCE: 360
gaggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccata    300
ggtagcagtg gctggtacga ggcctactat tactacggta tggacgtctg gggccaaggg    360
accacggtca ccgtctcctc agc                                            383

<210> SEQ ID NO 361
<211> LENGTH: 128
<212> TYPE: PRT
<213> ORGANISM: Homo sapiens

<400> SEQUENCE: 361

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ile Gly Ser Ser Gly Trp Tyr Glu Ala Tyr Tyr Tyr
            100                 105                 110

Gly Met Asp Val Trp Gly Gln Gly Thr Thr Val Thr Val Ser Ser Ala
            115                 120                 125

<210> SEQ ID NO 362
<211> LENGTH: 360
<212> TYPE: DNA
<213> ORGANISM: Homo sapiens

<400> SEQUENCE: 362
caggtgcagc tggtggagtc tgggggaggc gtggtccagc ctggggaggtc cctgagactc     60 tcctgtgcag cgtctggatt cacccttcagt agctatggca tgcactgggt ccgccaggct    120
ccaggcaagg ggctggagtg ggtggcagtt atatggtatg atggaagtaa taatactat    180 gcagactccg tgaagggccg attcaccatc tccagagaca attccaagaa cacgctgtat    240

```
ctgcaaatga acagcctgag agccgaggac acggctgtgt attactgtgc gagagaggat      300
aactggaact tctactttga ctactggggc cagggaaccc tggtcaccgt ctcctcagct      360
```

<210> SEQ ID NO 363
<211> LENGTH: 120
<212> TYPE: PRT
<213> ORGANISM: Homo sapiens

<400> SEQUENCE: 363

Gln Val Gln Leu Val Glu Ser Gly Gly Gly Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Asn Trp Asn Phe Tyr Phe Asp Tyr Trp Gly Gln Gly
            100                 105                 110

Thr Leu Val Thr Val Ser Ser Ala
        115                 120

<210> SEQ ID NO 364
<211> LENGTH: 324
<212> TYPE: DNA
<213> ORGANISM: Homo sapiens

<400> SEQUENCE: 364

```
gacatccaga tgacccagtc tccatcctcc ctgtctgcat ctgtaggaga cagagtcacc       60
atcacttgcc gggcgagtca gggcattagc tattatttag cctggtatca gcagaaacca      120
gggaaagttc ctaagctcct gatctatgct gcatccactt tgcaatcagg ggtcccatct      180
cggttcagtg aagtggatc tgggacagat ttcactctca ccatcagcag cctgcagcct      240
gaagatgttg caacttatta ctgtcaaaag tataacagtg ccccattcac tttcggccct      300
gggaccaaag tggatatcaa acga                                              324
```

<210> SEQ ID NO 365
<211> LENGTH: 108
<212> TYPE: PRT
<213> ORGANISM: Homo sapiens

<400> SEQUENCE: 365

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Tyr Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Phe
                85                  90                  95

Thr Phe Gly Pro Gly Thr Lys Val Asp Ile Lys Arg
            100                 105

<210> SEQ ID NO 366
<211> LENGTH: 372
<212> TYPE: DNA
<213> ORGANISM: Homo sapiens

<400> SEQUENCE: 366
gaggtgcagt tggtggagtc tgggggaggc ctggtcaagc ctgggggtc cctgagactc      60 tcctgtgcag cctctggatt caccttcagt agctatagca tgaactgggt ccgccaggct    120
ccagggaagg gctggagtg gtctcatcc attagtagta gtagtagtta tatatattac     180
gcagactcag tgaagggccg attcaccatc tccagagaca acgccaagaa ctccctgtat    240
ctgcaaatga acagcctgag agccgaggac acggctgtgt attactgtgc gagagatggg    300 gcgattttg gagtggttaa ctggtacttc gatctctggg gccgtggcac cctggtcact     360
gtctcctcag cc                                                        372

<210> SEQ ID NO 367
<211> LENGTH: 124
<212> TYPE: PRT
<213> ORGANISM: Homo sapiens

<400> SEQUENCE: 367

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ile Phe Gly Val Val Asn Trp Tyr Phe Asp Leu
            100                 105                 110

Trp Gly Arg Gly Thr Leu Val Thr Val Ser Ser Ala
        115                 120

<210> SEQ ID NO 368
<211> LENGTH: 328
<212> TYPE: DNA
<213> ORGANISM: Homo sapiens

<400> SEQUENCE: 368
gaaattgtgt tgacgcagtc tccaggcacc ctgtctttgt ctccagggga aagagccacc    60
ctctcctgta gggccagtca gagtgttagc agcagctact tagcctggta ccagcagaaa   120
gctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggtt ggtcatcgat cacccttcggc    300 caagggacac gactggagat caaacgaa                                        328

<210> SEQ ID NO 369
<211> LENGTH: 109
<212> TYPE: PRT
<213> ORGANISM: Homo sapiens

<400> SEQUENCE: 369

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Ala Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Trp Ser Ser
                85                  90                  95

Ile Thr Phe Gly Gln Gly Thr Arg Leu Glu Ile Lys Arg
            100                 105

<210> SEQ ID NO 370
<211> LENGTH: 374
<212> TYPE: DNA
<213> ORGANISM: Homo sapiens

<400> SEQUENCE: 370
caggtgcagc tggtggagtc tgggggaggc gtggtccagc ctgggaggtc cctgagactc      60
tcctgtgcag cgtctggatt caccttcagt agttatggca tgcactgggt ccgccaggct     120
ccaggcaagg ggctggagtg ggtggcaatt atatggtatg atggaagtaa taaatactat     180
gcagactccg tgaagggccg attcaccatt tccagagaca attccaagaa cacgctgcat     240
ctgcaaatga acagcctgag agccgaggac acggctgtgt attactgtgc gagaaaggga     300
tattgtagtg gtggtagctg tgtctacggt atggacgtct ggggccaagg gaccacggtc     360
accgtctcct cagc                                                       374

<210> SEQ ID NO 371
<211> LENGTH: 125
<212> TYPE: PRT
<213> ORGANISM: Homo sapiens

<400> SEQUENCE: 371

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Arg Lys Gly Tyr Cys Ser Gly Gly Ser Cys Val Tyr Gly Met Asp

```
                  100                 105                 110
Val Trp Gly Gln Gly Thr Thr Val Thr Val Ser Ser Ala
            115                 120                 125

<210> SEQ ID NO 372
<211> LENGTH: 357
<212> TYPE: DNA
<213> ORGANISM: Homo sapiens

<400> SEQUENCE: 372
caggtgcagc tggtggagtc tgggggaggc gtggtccagc ctggggaggtc cctgagactc      60 tcctgtgcag cctctggatt caccttcagt ggctatgaca tccactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gagagagaga     300
cagctatggt tgattgacta ctggggccag ggaaccctgg tcaccgtctc ctcagct       357

<210> SEQ ID NO 373
<211> LENGTH: 119
<212> TYPE: PRT
<213> ORGANISM: Homo sapiens

<400> SEQUENCE: 373

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Gly Tyr
            20                  25                  30

Asp Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gln Leu Trp Leu Ile Asp Tyr Trp Gly Gln Gly Thr
            100                 105                 110

Leu Val Thr Val Ser Ser Ala
        115

<210> SEQ ID NO 374
<211> LENGTH: 342
<212> TYPE: DNA
<213> ORGANISM: Homo sapiens

<400> SEQUENCE: 374
gacatcgtga tgacccagtc tccagactcc ctggctgtgt ctctgggcga gagggccacc      60
atcaactgca agtccagcca gagtgtttta tacagctcca acaataagaa ctacttagtt     120
tggtaccagc agaaaccagg gcagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttataatact     300
ccgtgcagtt ttggccaggg gaccaagctg gagatcaaac ga                       342

<210> SEQ ID NO 375
```

```
<211> LENGTH: 114
<212> TYPE: PRT
<213> ORGANISM: Homo sapiens

<400> SEQUENCE: 375

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Thr Pro Cys Ser Phe Gly Gln Gly Thr Lys Leu Glu Ile
            100                 105                 110

Lys Arg

<210> SEQ ID NO 376
<211> LENGTH: 369
<212> TYPE: DNA
<213> ORGANISM: Homo sapiens

<400> SEQUENCE: 376
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaatgacat actacaggtc caagtggtct     180
aatgattatg cagtatctct gaaaagtcga ataaccatca acccagacac atccaagaac     240
cagttctccc tgcagctgaa ctctgtgact cccgaggaca cggctgtgta ttactgtgca     300 agggggtaact ggttctactg gtacttcgat ctctggggcc gtggcaccct ggtcactgtc     360
tcctcagct                                                             369

<210> SEQ ID NO 377
<211> LENGTH: 123
<212> TYPE: PRT
<213> ORGANISM: Homo sapiens

<400> SEQUENCE: 377

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Met Thr Tyr Tyr Arg Ser Lys Trp Ser Asn Asp Tyr Ala
50                  55                  60

Val Ser Leu Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Asn Trp Phe Tyr Trp Tyr Phe Asp Leu Trp
            100                 105                 110
```

Gly Arg Gly Thr Leu Val Thr Val Ser Ser Ala
        115                 120

<210> SEQ ID NO 378
<211> LENGTH: 322
<212> TYPE: DNA
<213> ORGANISM: Homo sapiens

<400> SEQUENCE: 378
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag gctgcagcct   240
gaagatattg caacatatta ctgtcaacag tatgataatc tgtgcagttt tggccagggg   300
accaagttgg agatcaaacg aa                                            322

<210> SEQ ID NO 379
<211> LENGTH: 107
<212> TYPE: PRT
<213> ORGANISM: Homo sapiens

<400> SEQUENCE: 379

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Arg Leu Gln Pro
65                  70                  75                  80

Glu Asp Ile Ala Thr Tyr Tyr Cys Gln Gln Tyr Asp Asn Leu Cys Ser
                85                  90                  95

Phe Gly Gln Gly Thr Lys Leu Glu Ile Lys Arg
            100                 105

<210> SEQ ID NO 380
<211> LENGTH: 364
<212> TYPE: DNA
<213> ORGANISM: Homo sapiens

<400> SEQUENCE: 380
gaggtgcagc tggtggagtc tgggggaggc ttggtccagc ctgggggtc cctgagactc    60 tcctgtgcag cctctggatt cacctttagt agctattgga tgagctgggt ccgccaggct   120
ccagggaagg ggctggagtg ggtggccaac ataaagcaag atggaagtga aaatactat    180 gtggactctg tgaagggccg attcaccatc tccagagaca acgccaagaa ctcactgtat   240
ctgcaaatga acagcctgag agccgaggac acggctgtgt attactgtgc gagagatccg   300
ggtatagcag tggctggccc ctttgactac tggggccagg gaaccctggt caccgtctcc   360
tcag                                                               364

<210> SEQ ID NO 381
<211> LENGTH: 122
<212> TYPE: PRT

<213> ORGANISM: Homo sapiens

<400> SEQUENCE: 381

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ile Ala Val Ala Gly Pro Phe Asp Tyr Trp Gly
            100                 105                 110

Gln Gly Thr Leu Val Thr Val Ser Ser Ala
        115                 120

<210> SEQ ID NO 382
<211> LENGTH: 321
<212> TYPE: DNA
<213> ORGANISM: Homo sapiens

<400> SEQUENCE: 382
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcattcacca gggccactgg tatcccagcc     180
aggttcagtg gcagtgggtc tgggacagag ttcactctca ccatcagcag cctgcagtct     240
gaagattttg cggtttatta ctgtcagcag tataatcact ggtggacgtt cggccaaggg     300
accaaggtgg aatcaaacg a                                                321

<210> SEQ ID NO 383
<211> LENGTH: 107
<212> TYPE: PRT
<213> ORGANISM: Homo sapiens

<400> SEQUENCE: 383

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Phe Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn His Trp Trp Thr
                85                  90                  95

Phe Gly Gln Gly Thr Lys Val Gly Ile Lys Arg
            100                 105

<210> SEQ ID NO 384

<211> LENGTH: 360
<212> TYPE: DNA
<213> ORGANISM: Homo sapiens

<400> SEQUENCE: 384

| gaggtgcagc | tggtggagtc | tgggggaggc | ctggtcaagc | ctgggggtc | cctgagactc | 60 |
| tcctgtgcag | cctctggatt | caccttcaat | agctatagaa | tgaactgggt | ccgccaggct | 120 |
| ccagggaagg | gctggagtg | gtctcatcc | attactagta | gtagtcatta | catatactat | 180 |
| gcagactcag | tgaagggccg | attcaccatc | tccagagaca | acgccaagaa | ctcactgtat | 240 |
| ctgcaaatga | acagcctgag | agccgaggac | acggctgtgt | attactgtgc | gagagatcgc | 300 |
| ggtatagcag | ccccctttga | ctactggggc | cagggaaccc | tggtcaccgt | ctcctcagct | 360 |

<210> SEQ ID NO 385
<211> LENGTH: 120
<212> TYPE: PRT
<213> ORGANISM: Homo sapiens

<400> SEQUENCE: 385

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ser Tyr
            20                  25                  30

Arg Met Asn Trp Val Arg Gln Ala Pro Gly Lys Gly Leu Glu Trp Val
        35                  40                  45

Ser Ser Ile Thr Ser Ser Ser His Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Pro Phe Asp Tyr Trp Gly Gln Gly
            100                 105                 110

Thr Leu Val Thr Val Ser Ser Ala
        115                 120

<210> SEQ ID NO 386
<211> LENGTH: 321
<212> TYPE: DNA
<213> ORGANISM: Homo sapiens

<400> SEQUENCE: 386

| gaaatagtga | tgacgcagtc | tccagccacc | ctgtctgtgt | ctccagggga | aagagccacc | 60 |
| ctctcctgca | gggccagtca | gagtgttagc | agcaacttag | cctggtacca | gcagaaacct | 120 |
| ggccaggctc | ccaggctcct | catctatggt | gcatccacca | gggccactgg | tttcccagcc | 180 |
| aggttcagtg | gcagtgggtc | tgggacagag | ttcactctca | ccatcagcag | cctgcagtct | 240 |
| gaagattttg | cagtttatta | ctgtcagcag | tataataact | ggtggacgtt | cggccaaggg | 300 |
| accaaggtgg | aaatcaaacg | a | | | | 321 |

<210> SEQ ID NO 387
<211> LENGTH: 107
<212> TYPE: PRT
<213> ORGANISM: Homo sapiens

<400> SEQUENCE: 387

Glu Ile Val Met Thr Gln Ser Pro Ala Thr Leu Ser Val Ser Pro Gly

```
                1               5                   10                  15
            Glu Arg Ala Thr Leu Ser Cys Arg Ala Ser Gln Ser Val Ser Ser Asn
                            20                  25                  30
            Leu Ala Trp Tyr Gln Gln Lys Pro Gly Gln Ala Pro Arg Leu Leu Ile
                        35                  40                  45
            Tyr Gly Ala Ser Thr Arg Ala Thr Gly Phe Pro Ala Arg Phe Ser Gly
                    50                  55                  60
            Ser Gly Ser Gly Thr Glu Phe Thr Leu Thr Ile Ser Ser Leu Gln Ser
             65                 70                  75                  80
            Glu Asp Phe Ala Val Tyr Tyr Cys Gln Gln Tyr Asn Asn Trp Trp Thr
                            85                  90                  95
            Phe Gly Gln Gly Thr Lys Val Glu Ile Lys Arg
                        100                 105

<210> SEQ ID NO 388
<211> LENGTH: 337
<212> TYPE: DNA
<213> ORGANISM: Homo sapiens

<400> SEQUENCE: 388
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggttt atctattaca gtgggaccac caactacaac    180
ccctccctca gagtcgagt caccatatca gtagacacgt ccaagaacca gttctccctg    240
aagctgagtt ctgtgaccgc tgcggacacg gccgtgtatt actgtgcgag agcgtacgat    300
ccctggggcc aggaaccct ggtcaccgtc tcctcag                              337

<210> SEQ ID NO 389
<211> LENGTH: 113
<212> TYPE: PRT
<213> ORGANISM: Homo sapiens

<400> SEQUENCE: 389

Gln Val Gln Leu Gln Glu Ser Gly Pro Gly Leu Val Lys Pro Ser Glu
             1               5                   10                  15
            Thr Leu Ser Leu Thr Cys Thr Val Ser Gly Gly Ser Ile Ser Ser Tyr
                            20                  25                  30
            Tyr Trp Ser Trp Ile Arg Gln Pro Pro Gly Lys Gly Leu Glu Trp Ile
                        35                  40                  45
            Gly Phe Ile Tyr Tyr Ser Gly Thr Thr Asn Tyr Asn Pro Ser Leu Lys
                    50                  55                  60
            Ser Arg Val Thr Ile Ser Val Asp Thr Ser Lys Asn Gln Phe Ser Leu
             65                 70                  75                  80
            Lys Leu Ser Ser Val Thr Ala Ala Asp Thr Ala Val Tyr Tyr Cys Ala
                            85                  90                  95
            Arg Ala Tyr Asp Pro Trp Gly Gln Gly Thr Leu Val Thr Val Ser Ser
                        100                 105                 110
            Ala

<210> SEQ ID NO 390
<211> LENGTH: 324
<212> TYPE: DNA
<213> ORGANISM: Homo sapiens

<400> SEQUENCE: 390
```

```
gacatccaga tgacccagtc tccatcctcc ctgtctgcat ctgtaggaga cagagtcacc    60
atcacttgcc gggcaagtca gagtataagc agctatttta attggtatca gcagaaacca   120
gggaaagccc ctaaactcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac tttcggcgga   300
gggaccaagg tggagatcaa acga                                          324
```

<210> SEQ ID NO 391
<211> LENGTH: 108
<212> TYPE: PRT
<213> ORGANISM: Homo sapiens

<400> SEQUENCE: 391

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Phe Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105
```

<210> SEQ ID NO 392
<211> LENGTH: 342
<212> TYPE: DNA
<213> ORGANISM: Homo sapiens

<400> SEQUENCE: 392

```
caggtgcagc tggtggagtc tgggggaggc gtggtccagc ctggggaggtc cctgagactc    60 tcctgtgcag cgtctggatt caccttcagt agttatggca tgcactgggt ccgccaggct   120
ccaggcaagg ggctggagtg gtggcagtt atatggtatg atggaagtaa taatactat    180 gcagactccg tgaagggccg attcaccatc tccagagaca attccaagaa cacgctgtat   240
ctgcaaatga acagcctgag agccgaggac acggctgtgt attactgtgc gagagagctt   300
gcctactggg gccagggaac cctggtcacc gtctcctcag ct                      342
```

<210> SEQ ID NO 393
<211> LENGTH: 114
<212> TYPE: PRT
<213> ORGANISM: Homo sapiens

<400> SEQUENCE: 393

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Ala Tyr Trp Gly Gln Gly Thr Leu Val Thr Val Ser
            100                 105                 110

Ser Ala
```

<210> SEQ ID NO 394
<211> LENGTH: 324
<212> TYPE: DNA
<213> ORGANISM: Homo sapiens

<400> SEQUENCE: 394

```
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctgagtccct gatctatgct gcatccagtt tgcaaactgg ggtcccatca   180
aagttcagcg gcaatggatc tgggacagat ttcactctca ccatcagcag cctgcagcct   240
gaagattttg caacctatta ttgccaacag tataatagtt acccgctcac tttcggcgga   300
gggaccaagg tggagatcaa acga                                         324
```

<210> SEQ ID NO 395
<211> LENGTH: 108
<212> TYPE: PRT
<213> ORGANISM: Homo sapiens

<400> SEQUENCE: 395

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
             20                  25                  30

Leu Ala Trp Phe Gln Gln Lys Pro Gly Lys Ala Pro Glu Ser Leu Ile
         35                  40                  45

Tyr Ala Ala Ser Ser Leu Gln Thr Gly Val Pro Ser Lys Phe Ser Gly
 50                  55                  60

Asn Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys Arg
            100                 105
```

<210> SEQ ID NO 396
<211> LENGTH: 357
<212> TYPE: DNA
<213> ORGANISM: Homo sapiens

<400> SEQUENCE: 396

```
caggtgcagc tgcaggagtc gggcccagga ctggtgaagc cttcggagac cctgtccctc    60
acctgcactg tctctggtgg ctccatcagt agtcactact ggatctggat ccggcagccc   120
gccgggaagg gactggagtg gattggccgt atctatagca gtgggagtac caactacaac   180
ccctccctca gagtcgagt caccatgtca ggagacacgc caagaaccag gttctccctg   240
aagctgagct ctgtgaccgc cgcggacacg gccgtgtatt actgtgcgag agggaggtgg   300
```

```
ggatcctggt acttcgatct ctggggccgt ggcaccctgg tcactgtctc ctcagct        357
```

<210> SEQ ID NO 397
<211> LENGTH: 119
<212> TYPE: PRT
<213> ORGANISM: Homo sapiens

<400> SEQUENCE: 397

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser His
            20                  25                  30

Tyr Trp Ile Trp Ile Arg Gln Pro Ala Gly Lys Gly Leu Glu Trp Ile
        35                  40                  45

Gly Arg Ile Tyr Ser Ser Gly Ser Thr Asn Tyr Asn Pro Ser Leu Lys
    50                  55                  60

Ser Arg Val Thr Met Ser Gly Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Trp Gly Ser Trp Tyr Phe Asp Leu Trp Gly Arg Gly Thr
            100                 105                 110

Leu Val Thr Val Ser Ser Ala
        115

<210> SEQ ID NO 398
<211> LENGTH: 372
<212> TYPE: DNA
<213> ORGANISM: Homo sapiens

<400> SEQUENCE: 398

```
gaggtgcagt tggtggagtc tgggggaggc ctggtcaagc ctggggggtc cctgagactc        60
tcctgtgcag cctctggatt caccttcagt agctatagca tgaactgggt ccgccaggct       120
ccagggaagg ggctggagtg ggtctcatcc attagtagta gtagtagtta tatatattac       180
gcagactcag tgaagggccg attcaccatc tccagagaca acgccaagaa ctccctgtat       240
ctgcaaatga acagcctgag agccgaggac acggctgtgt attactgtgc gagagatggg       300
gcgattttg gagtggttaa ctggtacttc gatctctggg gccgtggcac cctggtcact       360
gtctcctcag cc                                                           372
```

<210> SEQ ID NO 399
<211> LENGTH: 124
<212> TYPE: PRT
<213> ORGANISM: Homo sapiens

<400> SEQUENCE: 399

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                 85                  90                  95

Ala Arg Asp Gly Ala Ile Phe Gly Val Val Asn Trp Tyr Phe Asp Leu
            100                 105                 110

Trp Gly Arg Gly Thr Leu Val Thr Val Ser Ser Ala
        115                 120
```

<210> SEQ ID NO 400
<211> LENGTH: 375
<212> TYPE: DNA
<213> ORGANISM: Homo sapiens

<400> SEQUENCE: 400

```
caggtgcagc tggtggagtc tgggggaggc gtggtccagc ctggaaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagagggc     300
ctggattttt ggagtgattt ttacaactgg ttcgacccct ggggccaggg aaccctggtc     360
accgtctcct cagct                                                     375
```

<210> SEQ ID NO 401
<211> LENGTH: 125
<212> TYPE: PRT
<213> ORGANISM: Homo sapiens

<400> SEQUENCE: 401

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Glu Gly Leu Asp Phe Trp Ser Asp Phe Tyr Asn Trp Phe Asp
            100                 105                 110

Pro Trp Gly Gln Gly Thr Leu Val Thr Val Ser Ser Ala
        115                 120                 125
```

<210> SEQ ID NO 402
<211> LENGTH: 324
<212> TYPE: DNA
<213> ORGANISM: Homo sapiens

<400> SEQUENCE: 402

```
gacatccaga tgacccagtc tccatcctcc ctgtctgcat ctgtaggaga cagagtcacc      60
atcacttgcc gggcaagtca gagcattagc aactatttaa attggtatca gcagaaacca     120
gggaaagccc ctaagctcct gatctttact gcatccagtt tacaaagtgg ggtcccatca     180
agattcagtg gcagtggatc tgggacagat ttcactctca ccatcagcag tctgcaacct     240
```

```
gaagattttg caacttactt ctgtcaacag agttacagta ccccattcac tttcggccct    300
gggaccaaag tgggtatcaa acga                                            324
```

<210> SEQ ID NO 403
<211> LENGTH: 108
<212> TYPE: PRT
<213> ORGANISM: Homo sapiens

<400> SEQUENCE: 403

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Phe Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Phe
                85                  90                  95

Thr Phe Gly Pro Gly Thr Lys Val Gly Ile Lys Arg
               100                 105
```

<210> SEQ ID NO 404
<211> LENGTH: 365
<212> TYPE: DNA
<213> ORGANISM: Homo sapiens

<400> SEQUENCE: 404

```
gaggtgcagc tggtggagtc tgggggaggc ttggtaaagc ctggggggtc ccttagactc    60
tcctgtgcag cctctggatt cactttcagt aacgcctgga tgagctgggt ccgccaggct   120
ccagggaagg ggctggagtg ggttggccgt attaaaagca aaactgatgg tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtaccaac   300
tactacggtg acttttatgc ttttgatatc tggggccaag ggacaatggt caccgtctct   360
tcagc                                                                365
```

<210> SEQ ID NO 405
<211> LENGTH: 122
<212> TYPE: PRT
<213> ORGANISM: Homo sapiens

<400> SEQUENCE: 405

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

Leu Tyr Leu Gln Met Asn Ser Leu Lys Thr Glu Asp Thr Ala Val Tyr
                85                  90                  95

Tyr Cys Thr Asn Tyr Tyr Gly Asp Phe Tyr Ala Phe Asp Ile Trp Gly
            100                 105                 110

Gln Gly Thr Met Val Thr Val Ser Ser Ala
        115                 120

<210> SEQ ID NO 406
<211> LENGTH: 324
<212> TYPE: DNA
<213> ORGANISM: Homo sapiens

<400> SEQUENCE: 406
gacatccaga tgacccagtc tccatcctcc ctgtctgcat ctgtaggaga cagagtcacc      60
atcacttgcc gggcaagtca gaccattagc agctatttaa attggtatca gcagaaacca     120
gggaaagccc ctaagctcct gatctatgct gcatccagtt tacaaagtgg ggtcccatca     180
aggttcagtg gcagtggatc tgggacagat ttcactctca ccatcagcag tctgcaacct     240
gaagattttg caacttacta ctgtcaacag acttacagta atcgctcac tttcggcgga      300 gggaccaagg tggagatcaa acga                                            324

<210> SEQ ID NO 407
<211> LENGTH: 108
<212> TYPE: PRT
<213> ORGANISM: Homo sapiens

<400> SEQUENCE: 407

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Lys Ser Leu
                85                  90                  95

Thr Phe Gly Gly Gly Thr Lys Val Glu Ile Lys Arg
            100                 105

<210> SEQ ID NO 408
<211> LENGTH: 368
<212> TYPE: DNA
<213> ORGANISM: Homo sapiens

<400> SEQUENCE: 408
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg gtggcagtt atatggtatg atggaagtaa taaatactat      180
gcagactccg tgaagggccg attcaccatc tccagagaca attccaagaa cacgctgtat     240
ctgcaaatga acagcctgag agccgaggac acggctgtgt attactgtgc gagaggggat     300
aactggaact acgaggggga cggtatggac gtctggggcc aagggaccac ggtcaccgtc     360
tcctcagc                                                              368

<210> SEQ ID NO 409
<211> LENGTH: 123
<212> TYPE: PRT
<213> ORGANISM: Homo sapiens

<400> SEQUENCE: 409

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Asn Trp Asn Tyr Glu Gly Asp Gly Met Asp Val Trp
            100                 105                 110

Gly Gln Gly Thr Thr Val Thr Val Ser Ser Ala
        115                 120

<210> SEQ ID NO 410
<211> LENGTH: 324
<212> TYPE: DNA
<213> ORGANISM: Homo sapiens

<400> SEQUENCE: 410
gacatccaga tgacccagtc tccatcttcc gtgtctgcat ctgtaggaga cagagtcacc      60
atcacttgtc gggcgagtca gggtattagc aggtggttag cctggtatca gcagaaacca    120
gggaaagccc ctaagctcct gatctatgtt gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt tccctcggac gttcggccaa    300
gggaccaagg tggaaatcaa acga                                            324

<210> SEQ ID NO 411
<211> LENGTH: 108
<212> TYPE: PRT
<213> ORGANISM: Homo sapiens

<400> SEQUENCE: 411

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg
                100                 105

<210> SEQ ID NO 412
<211> LENGTH: 362
<212> TYPE: DNA
<213> ORGANISM: Homo sapiens

<400> SEQUENCE: 412
caggttcagc tggtgcagtc tggagctgag gtgaagaagc ctggggcctc agtgaaggtc      60
tcctgcaagg cttctggtta cacctttacc agctattgta tcagctgggt gcgacaggcc     120
cctggacgag gcttgagtg gatgggttgg atctgctctt acaatggtaa cacaaactgt     180
gcacagaagc tccagggcag agtcaccatg accacagaca catccacgac tacagcctac    240
atggagctga ggggcctgag atctgacgac acggccgtgt attactgtgc gagagagtcc    300
ctttatagca gtggctggtt tgactactgg ggccagggaa ccctggtcac cgtctcctca    360
gc                                                                   362

<210> SEQ ID NO 413
<211> LENGTH: 121
<212> TYPE: PRT
<213> ORGANISM: Homo sapiens

<400> SEQUENCE: 413

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Cys Ile Ser Trp Val Arg Gln Ala Pro Gly Arg Gly Leu Glu Trp Met
        35                  40                  45

Gly Trp Ile Cys Ser Tyr Asn Gly Asn Thr Asn Cys Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Gly Leu Arg Ser Asp Asp Thr Ala Val Tyr Tyr Cys
                85                  90                  95

Ala Arg Glu Ser Leu Tyr Ser Ser Gly Trp Phe Asp Tyr Trp Gly Gln
            100                 105                 110

Gly Thr Leu Val Thr Val Ser Ser Ala
        115                 120

<210> SEQ ID NO 414
<211> LENGTH: 324
<212> TYPE: DNA
<213> ORGANISM: Homo sapiens

<400> SEQUENCE: 414
gacatccgga tgacccagtc tccatcctcc ctgtctgcat ctgttggaga cagagtcacc      60
atcacttgcc gggcaagtca gcgcattagc acctatttaa attggtatca gcagaaacca    120
gggaaagccc ctaagttcct gatctatgct gcatctagtt tgcaaagtgg ggtcccatca    180
aggttcagtg gcagtggatc tgggacagat ttcactctca ccatcagcag tctgcaacct    240
gaagattttg caacttacta ctgtcaacag agttacacta ccccattcac tttcggccct    300
gggaccaaag tggatatcaa acga                                           324

<210> SEQ ID NO 415

```
<211> LENGTH: 108
<212> TYPE: PRT
<213> ORGANISM: Homo sapiens

<400> SEQUENCE: 415

Asp Ile Arg Met Thr Gln Ser Pro Ser Ser Leu Ser Ala Ser Val Gly
  1               5                  10                  15

Asp Arg Val Thr Ile Thr Cys Arg Ala Ser Gln Arg Ile Ser Thr Tyr
             20                  25                  30

Leu Asn Trp Tyr Gln Gln Lys Pro Gly Lys Ala Pro Lys Phe Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Phe
                 85                  90                  95

Thr Phe Gly Pro Gly Thr Lys Val Asp Ile Lys Arg
            100                 105

<210> SEQ ID NO 416
<211> LENGTH: 372
<212> TYPE: DNA
<213> ORGANISM: Homo sapiens

<400> SEQUENCE: 416
caggtgcagc tggtggagtc tgggggaggc gtggtccagc ctgggaggtc cctgagactc     60
tcctgtgcag cctctggatt caccttcagt ggctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gagagatagg    300
ggtatagcag tggctgggta ttacggtatg gacgtctggg gccaagggaa cacggtcacc    360
gtctcctcag ct                                                       372

<210> SEQ ID NO 417
<211> LENGTH: 124
<212> TYPE: PRT
<213> ORGANISM: Homo sapiens

<400> SEQUENCE: 417

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Gly Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Ile Ala Val Ala Gly Tyr Tyr Gly Met Asp Val
            100                 105                 110

Trp Gly Gln Gly Asn Thr Val Thr Val Ser Ser Ala
```

<210> SEQ ID NO 418
<211> LENGTH: 372
<212> TYPE: DNA
<213> ORGANISM: Homo sapiens

<400> SEQUENCE: 418
caggtacaac tggtggagtc tgggggaggc gtggtccagc ctgggaggtc cctgagactc    60
tcctgtgtag cgtctggatt caccttcagt agctatggca tgcactgggt ccgccaggct   120
ccaggcaagg gctggagtg gtggcagtt atatggtatg atggaagtaa taaatactat    180
gcagactccg tgaagggccg attcaccatc tccagagaca attccaagaa cacgctgtat   240
ctgcaaatga acagcctgag agccgaggac acggctgtgt attactgtgc gagaggaggt   300
cctctgtata gcaactcctt ttactacttt gactactggg gccagggaac cctggtcacc   360
gtctcctcag ct                                                       372

<210> SEQ ID NO 419
<211> LENGTH: 124
<212> TYPE: PRT
<213> ORGANISM: Homo sapiens

<400> SEQUENCE: 419

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Leu Tyr Ser Asn Ser Phe Tyr Tyr Phe Asp Tyr
            100                 105                 110

Trp Gly Gln Gly Thr Leu Val Thr Val Ser Ser Ala
        115                 120

<210> SEQ ID NO 420
<211> LENGTH: 324
<212> TYPE: DNA
<213> ORGANISM: Homo sapiens

<400> SEQUENCE: 420
gacatccaga tgacccagtc tccatcctcc ctgtctgcat ctgtaggaga cagagtcacc    60
atcacttgcc aggcgagtca ggacattaga aactatttaa attggtatca gcagaaacca   120
gggacagccc ctaaactcct gatctacgat gcatccaatt ggaaacaggg gtcccatca   180 aggttcagtg aagtggatc tgggacagat tttactttca ccatcagcag cctgcagcct    240
gaagatattg caacatatta ctgtcaacag tatgataatc tcccgatcac cttcggccaa   300
gggacacgac tggagattaa acga                                          324

<210> SEQ ID NO 421
<211> LENGTH: 108

<210> TYPE: PRT
<213> ORGANISM: Homo sapiens

<400> SEQUENCE: 421

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Thr Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile
            85                  90                  95

Thr Phe Gly Gln Gly Thr Arg Leu Glu Ile Lys Arg
            100                 105

<210> SEQ ID NO 422
<211> LENGTH: 327
<212> TYPE: DNA
<213> ORGANISM: Homo sapiens

<400> SEQUENCE: 422
gaagttgtgt tgacgcagtc tccaggcacc ctgtctttgt ctccagggga tagagccacc      60
ctctcctgca gggccagtca gagtgttagc agcagctact tagcctggta caaccagaaa     120
cctggccagg ctcccaggct cctcatcttt ggtgcatcca gcagggccac tggcatccca     180
gacaggttca gtggcagtgg gtctgggaca gacttcactc tcaccatcag cagactggag     240
cctgaagatt ttgcagtgta ttactgtcta cagtatggta gctcaccgtg gacgttcggc     300
caagggacca aggtggaaat caaacga                                          327

<210> SEQ ID NO 423
<211> LENGTH: 109
<212> TYPE: PRT
<213> ORGANISM: Homo sapiens

<400> SEQUENCE: 423

Glu Val Val Leu Thr Gln Ser Pro Gly Thr Leu Ser Leu Ser Pro Gly
1               5                   10                  15

Asp Arg Ala Thr Leu Ser Cys Arg Ala Ser Gln Ser Val Ser Ser Ser
            20                  25                  30

Tyr Leu Ala Trp Tyr Asn Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Leu Gln Tyr Gly Ser Ser Pro
            85                  90                  95

Trp Thr Phe Gly Gln Gly Thr Lys Val Glu Ile Lys Arg
            100                 105

<210> SEQ ID NO 424
<211> LENGTH: 378
<212> TYPE: DNA

<213> ORGANISM: Homo sapiens

<400> SEQUENCE: 424

```
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccctaa acagtggtgg cacaaactat   180
gcacagaagt ttcagggcag ggtcaccatg accagggaca cgtccatcag cacagcctac   240
atggagctga gcaggctgag atctgacgac acggccgtgt attactgtgc gagagatagg   300
ggctggaact acgcagacta ctactactac ggtatggacg tctggggcca agggaccacg   360
gtcaccgtct cctcagct                                                 378
```

<210> SEQ ID NO 425
<211> LENGTH: 126
<212> TYPE: PRT
<213> ORGANISM: Homo sapiens

<400> SEQUENCE: 425

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Gly Trp Asn Tyr Ala Asp Tyr Tyr Tyr Gly Met
            100                 105                 110

Asp Val Trp Gly Gln Gly Thr Thr Val Thr Val Ser Ser Ala
        115                 120                 125

<210> SEQ ID NO 426
<211> LENGTH: 342
<212> TYPE: DNA
<213> ORGANISM: Homo sapiens

<400> SEQUENCE: 426

```
gacatcgtga tgacccagtc tccagactcc ctggctgtgt ctctgggcga gagggccacc    60
atcaactgca gtccagcca gagtgtttta tacagttcca acaatcagaa cttcttagct   120
tggtatcagc agaaaccagg acagcctcct aaactgctca tttactgggc atctacccgg   180
gaatccgggg tccctgaccg attcagtggc agcgggtctg ggacagattt cactctcacc   240
atcagcagcc tgcaggctga agatgtggca gtttattact gtcaccaata ttatagtact   300
ccgatcacct tcggccaagg gacacgactg gagattaaac ga                     342
```

<210> SEQ ID NO 427
<211> LENGTH: 114
<212> TYPE: PRT
<213> ORGANISM: Homo sapiens

<400> SEQUENCE: 427

Asp Ile Val Met Thr Gln Ser Pro Asp Ser Leu Ala Val Ser Leu Gly

```
            1               5                   10                  15
          Glu Arg Ala Thr Ile Asn Cys Lys Ser Ser Gln Ser Val Leu Tyr Ser
                          20                  25                  30

Ser Asn Asn Gln Asn Phe Leu Ala Trp Tyr Gln Gln Lys Pro Gly Gln
                          35                  40                  45

Pro Pro Lys Leu Leu Ile Tyr Trp Ala Ser Thr Arg Glu Ser Gly Val
                          50                  55                  60

Pro Asp Arg Phe Ser Gly Ser Gly Ser Gly Thr Asp Phe Thr Leu Thr
           65                  70                  75                  80

Ile Ser Ser Leu Gln Ala Glu Asp Val Ala Val Tyr Tyr Cys His Gln
                          85                  90                  95

Tyr Tyr Ser Thr Pro Ile Thr Phe Gly Gln Gly Thr Arg Leu Glu Ile
                          100                 105                 110

Lys Arg
```

<210> SEQ ID NO 428
<211> LENGTH: 378
<212> TYPE: DNA
<213> ORGANISM: Homo sapiens

<400> SEQUENCE: 428

```
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctaa cagtggtgg cacaaactat     180
gcacagaagt ttcagggcag ggtcaccatg accaggaca cgtccatcag cacagcctac     240
atggagctga gcaggctgag atctgacgac acggccgtgt attactgtgc gagagatagg     300
ggctggaact acgcagacta ctactactac ggtatggacg tctggggcca agggaccacg     360
gtcaccgtct cctcagct                                                   378
```

<210> SEQ ID NO 429
<211> LENGTH: 126
<212> TYPE: PRT
<213> ORGANISM: Homo sapiens

<400> SEQUENCE: 429

```
          Gln Val Gln Leu Val Gln Ser Gly Ala Glu Val Lys Lys Pro Gly Ala
           1               5                   10                  15

Ser Val Lys Val Ser Cys Lys Ala Ser Gly Tyr Thr Phe Thr Gly Tyr
                          20                  25                  30

Tyr Met His Trp Val Arg Gln Ala Pro Gly Gln Gly Leu Glu Trp Met
                          35                  40                  45

Gly Trp Ile Asn Pro Asn Ser Gly Gly Thr Asn Tyr Ala Gln Lys Phe
                          50                  55                  60

Gln Gly Arg Val Thr Met Thr Arg Asp Thr Ser Ile Ser Thr Ala Tyr
           65                  70                  75                  80

Met Glu Leu Ser Arg Leu Arg Ser Asp Asp Thr Ala Val Tyr Tyr Cys
                          85                  90                  95

Ala Arg Asp Arg Gly Trp Asn Tyr Ala Asp Tyr Tyr Tyr Gly Met
                          100                 105                 110

Asp Val Trp Gly Gln Gly Thr Thr Val Thr Val Ser Ser Ala
                          115                 120                 125
```

<210> SEQ ID NO 430
<211> LENGTH: 342

```
<212> TYPE: DNA
<213> ORGANISM: Homo sapiens

<400> SEQUENCE: 430
gacatcgtga tgacccagtc tccagactcc ctggctgtgt ctctgggcga gagggccacc      60
atcaactgca gtccagcca gagtgtttta tacagttcca acaatcagaa cttcttagct      120
tggtatcagc agaaaccagg acagcctcct aaactgctca tttactgggc atctacccgg     180
gaatccgggg tccctgaccg attcagtggc agcgggtctg ggacagattt cactctcacc     240
atcagcagcc tgcaggctga agatgtggca gtttattact gtcaccaata ttatagtact     300
ccgatcacct tcggccaagg gacacgactg gagattaaac ga                        342

<210> SEQ ID NO 431
<211> LENGTH: 114
<212> TYPE: PRT
<213> ORGANISM: Homo sapiens

<400> SEQUENCE: 431

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Gln Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Thr Pro Ile Thr Phe Gly Gln Gly Thr Arg Leu Glu Ile
            100                 105                 110

Lys Arg

<210> SEQ ID NO 432
<211> LENGTH: 357
<212> TYPE: DNA
<213> ORGANISM: Homo sapiens

<400> SEQUENCE: 432
caggtgcagc tgcaggagtc gggcccagga ctggtgaagc cttcggagac cctgtccctc      60
acctgcactg tctctggtgg ctccatcagt agttactact ggagctggat ccggcagccc     120
gccgggaagg gactggagtg gattgggcgt atctacacca gtgggagcac caactacaac     180
ccctccctca gagtcgagt caccatgtcc gtagacacgt ccaagaacca gttctccctg     240
aagctgagct ctgtgaccgc cgcggacacg gccgtgtatt actgtgcgag aggtataact     300
ggttacgggg ggttcgaccc ctggggccag ggaaccctgg tcaccgtctc ctcagct       357

<210> SEQ ID NO 433
<211> LENGTH: 119
<212> TYPE: PRT
<213> ORGANISM: Homo sapiens

<400> SEQUENCE: 433

Gln Val Gln Leu Gln Glu Ser Gly Pro Gly Leu Val Lys Pro Ser Glu
 1               5                  10                  15
```

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ile Thr Gly Tyr Gly Gly Phe Asp Pro Trp Gly Gln Gly Thr
            100                 105                 110

Leu Val Thr Val Ser Ser Ala
        115

<210> SEQ ID NO 434
<211> LENGTH: 360
<212> TYPE: DNA
<213> ORGANISM: Homo sapiens

<400> SEQUENCE: 434
gaggtgcagc tggtggagtc tgggggaggc ctggtcaagc ctggggggtc cctgagactc      60
tcctgtgcag cctctggatt caccttcagt agctatcgca tgaactgggt ccgccaggct     120
ccagggaagg gctggagtg gtctcatcc attagcagta gtggtagcta catatactac      180
gcagactcag tgaagggccg attcaccatc tccagagaca acgccaagaa ctcactgtat     240
ctgcaaatga acagcctgag agccgaggac acggctgttt attactttgc gagagatcgg     300
ggagtgggag ctgcctttga ctactgggggc cagggaaccc tggtcaccgt ctcctcagct    360

<210> SEQ ID NO 435
<211> LENGTH: 120
<212> TYPE: PRT
<213> ORGANISM: Homo sapiens

<400> SEQUENCE: 435

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Phe
                85                  90                  95

Ala Arg Asp Arg Gly Val Gly Ala Ala Phe Asp Tyr Trp Gly Gln Gly
            100                 105                 110

Thr Leu Val Thr Val Ser Ser Ala
        115                 120

<210> SEQ ID NO 436
<211> LENGTH: 324
<212> TYPE: DNA
<213> ORGANISM: Homo sapiens

<400> SEQUENCE: 436

```
gacatccaga tgacccagtc tccatcctca ctgtctgcat ctgtaggaga cagagtcacc      60
atcacttgtc gggcgagtca ggacattagc aattatttag cctggtttca gcagaaacca    120
gggaaagccc ctaagtccct gatctatgct gcatccagtt tgcaaagtgg ggtcccatca    180
aaattcagcg gcagtggatc tgggaccgat ttcactctca ccatcagcag cctgcagcct    240
gaagattttg caacttatta ctgccaacag tataatagtt accctcggac gttcggccaa    300
gggaccaagg tggaaatcaa acga                                           324
```

<210> SEQ ID NO 437
<211> LENGTH: 108
<212> TYPE: PRT
<213> ORGANISM: Homo sapiens

<400> SEQUENCE: 437

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Asn Tyr
            20                  25                  30
Leu Ala Trp Phe Gln Gln Lys Pro Gly Lys Ala Pro Lys Ser Leu Ile
        35                  40                  45
Tyr Ala Ala Ser Ser Leu Gln Ser Gly Val Pro Ser Lys Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Arg
                85                  90                  95
Thr Phe Gly Gln Gly Thr Lys Val Glu Ile Lys Arg
            100                 105

<210> SEQ ID NO 438
<211> LENGTH: 372
<212> TYPE: DNA
<213> ORGANISM: Homo sapiens

<400> SEQUENCE: 438

```
caggtgcagc tgcaggagtc gggcccagga ctggtgaagc cttcggagac cctgtccctc      60
acctgcactg tctctggtgg ctccatcagt agttactact ggagctggat ccggcagccc    120
gccgggaagg gactggagtg gattgggcgt atctatacca gtgggagcac caactacaac    180
ccctccctca gagtcgagt caccatgtca gtagacacgc ccaagaacca gttctccctg    240
aagctgagct ctgtgaccgc cgcggacacg gccgtgtatt actgtgcgag agatgactac    300
agtcactctt actactacta ctacggtatg gacgtctggg gccaagggac cacggtcacc    360
gtctcctcag ct                                                       372
```

<210> SEQ ID NO 439
<211> LENGTH: 124
<212> TYPE: PRT
<213> ORGANISM: Homo sapiens

<400> SEQUENCE: 439

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
 50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Asp Tyr Ser His Ser Tyr Tyr Tyr Tyr Gly Met Asp Val
                100                 105                 110

Trp Gly Gln Gly Thr Thr Val Thr Val Ser Ser Ala
            115                 120

<210> SEQ ID NO 440
<211> LENGTH: 324
<212> TYPE: DNA
<213> ORGANISM: Homo sapiens

<400> SEQUENCE: 440
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt ccctcggacg ttcggccaa    300 gggaccaagg tggaaatcaa acga                                           324

<210> SEQ ID NO 441
<211> LENGTH: 108
<212> TYPE: PRT
<213> ORGANISM: Homo sapiens

<400> SEQUENCE: 441

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Arg
                 85                  90                  95

Thr Phe Gly Gln Gly Thr Lys Val Glu Ile Lys Arg
            100                 105

<210> SEQ ID NO 442
<211> LENGTH: 375
<212> TYPE: DNA
<213> ORGANISM: Homo sapiens

<400> SEQUENCE: 442
caggtgcagc tggtggagtc tgggggaggc gtggtccagc ctgggaggtc cctgagactc     60
tcctgtgcag cgtctggatt caccttcagt agctatggca tgcactgggt ccgccaggct    120

```
ccaggcaagg ggctggagtg ggtggctatt atatggtttg atggaagtaa taaatactat    180
gcagactccg tgaagggccg attcaccatc tccagagaca attccaagaa cacgctgtat    240
ctgcaagtga acagcctgcg agccgaggac acggctgtgt attactgtgc gagaaaggga    300
tattgtagtg gtggtagatg tgtctacggt atggacgtct ggggccaagg gaccacggtc    360
accgtctcct cagct                                                     375
```

<210> SEQ ID NO 443
<211> LENGTH: 125
<212> TYPE: PRT
<213> ORGANISM: Homo sapiens

<400> SEQUENCE: 443

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Arg Lys Gly Tyr Cys Ser Gly Gly Arg Cys Val Tyr Gly Met Asp
            100                 105                 110

Val Trp Gly Gln Gly Thr Thr Val Thr Val Ser Ser Ala
        115                 120                 125

<210> SEQ ID NO 444
<211> LENGTH: 339
<212> TYPE: DNA
<213> ORGANISM: Homo sapiens

<400> SEQUENCE: 444

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacagatt cggtggcagt ggatcaggca cagattttac actgaaaatc   240
agcagagtgg aggctgagga tgttggggtt tattactgca tgcaagctct acaaactcct   300
atcaccttcg gccaagggac acgactggag attaaacga                           339
```

<210> SEQ ID NO 445
<211> LENGTH: 113
<212> TYPE: PRT
<213> ORGANISM: Homo sapiens

<400> SEQUENCE: 445

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

```
Pro Gln Leu Leu Ile Tyr Leu Gly Ser Asn Arg Ala Ser Gly Val Pro
     50                  55                  60

Asp Arg Phe Gly Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Ile Thr Phe Gly Gln Gly Thr Arg Leu Glu Ile Lys
            100                 105                 110

Arg

<210> SEQ ID NO 446
<211> LENGTH: 366
<212> TYPE: DNA
<213> ORGANISM: Homo sapiens

<400> SEQUENCE: 446
gaggtgcagc tggtggtgtc tgggggaggc ttggtccagc ctgggggtc cctgagactc      60 tcctgtgaag cctctggatt cacctttagt aactattgga tgacctgggt ccgccaggct   120
ccagggaagg ggctggagtg ggtggccaac ataaagcaag atggaagtga aaatactat    180 gtggactctg tgaagggccg attcaccatc tccagagaca cgccaagaa ctcactgtat    240 ctgcaaatga acagcctgag agccgaggac acggctgtgt attactgtgc gagagatgcc   300
ggtatggaag tggctggccc ttttgactac tggggccagg gaaccctggt caccgtctcc   360
tcagct                                                              366

<210> SEQ ID NO 447
<211> LENGTH: 122
<212> TYPE: PRT
<213> ORGANISM: Homo sapiens

<400> SEQUENCE: 447

Glu Val Gln Leu Val Val Ser Gly Gly Gly Leu Val Gln Pro Gly Gly
 1               5                  10                  15

Ser Leu Arg Leu Ser Cys Glu Ala Ser Gly Phe Thr Phe Ser Asn Tyr
             20                  25                  30

Trp Met Thr Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Asp Ala Gly Met Glu Val Ala Gly Pro Phe Asp Tyr Trp Gly
            100                 105                 110

Gln Gly Thr Leu Val Thr Val Ser Ser Ala
        115                 120

<210> SEQ ID NO 448
<211> LENGTH: 368
<212> TYPE: DNA
<213> ORGANISM: Homo sapiens

<400> SEQUENCE: 448
caggtgcagc tggtgcagtc tggggctgag gtgaagaagc ctggggcctc agtgaaggtc      60
tcctgcaagg cttctggata cacctttacc ggctactata tgcactgggt gcgacaggcc   120
```

```
cctggacaag ggcttgagtg gatgggatgg atcaaccta acagtggtgg cacaaactat    180
gcacagaagt tcagggcag ggtcaccatg accaggaca cgtccatcag cacagcctac    240
atggagctga gcaggctgag atctgacgac acggccgtgt attactgtgc gagagatggg    300
ggcagtatag cagtgctgg tcactttgac tactggggcc agggaaccct ggtcaccgtc    360
tcctcagc                                                             368
```

<210> SEQ ID NO 449
<211> LENGTH: 123
<212> TYPE: PRT
<213> ORGANISM: Homo sapiens

<400> SEQUENCE: 449

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Gly Gly Ser Ile Ala Val Ala Gly His Phe Asp Tyr Trp
            100                 105                 110

Gly Gln Gly Thr Leu Val Thr Val Ser Ser Ala
        115                 120
```

<210> SEQ ID NO 450
<211> LENGTH: 321
<212> TYPE: DNA
<213> ORGANISM: Homo sapiens

<400> SEQUENCE: 450

```
gaaatagtga tgacgcagtc tccagccacc ctgtctgtgt ctccagggga aagagccacc    60
ctctcctgca gggccagtca gagtcttatc agcaacttag cctggtacca gcagaaacct   120
ggccaggctc ccaggctcct catctttggt gcatccacca gggccactgg tatcccagcc   180
aggttcagtg gcagtgggtc tgggacagag ttcactctca ccatcagcag cctgcagtct   240
gaagattttg cagtttatta ctgtcatcag tataataact ggtggacgtt cggccaaggg   300
accaaggtgg aaatcaaacg a                                             321
```

<210> SEQ ID NO 451
<211> LENGTH: 107
<212> TYPE: PRT
<213> ORGANISM: Homo sapiens

<400> SEQUENCE: 451

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Leu Ile Ser Asn
             20                  25                  30

Leu Ala Trp Tyr Gln Gln Lys Pro Gly Gln Ala Pro Arg Leu Leu Ile
         35                  40                  45
```

```
Phe Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys His Gln Tyr Asn Asn Trp Trp Thr
                85                  90                  95
Phe Gly Gln Gly Thr Lys Val Glu Ile Lys Arg
            100                 105
```

<210> SEQ ID NO 452
<211> LENGTH: 366
<212> TYPE: DNA
<213> ORGANISM: Homo sapiens

<400> SEQUENCE: 452

```
caggtgcagc tggtgcagtc cggggctgag gtgaagaagc ctggggcctc agtgaaggtc      60
tcctgcaagg cttctggata caccttcacc ggctaccata tgtactgggt gcgacaggcc     120
cctggacaag gcttgagtg gctgggatgg atcaacccta cagtggtgg cacaaactat       180
gcacagaagt tccagggcag ggtcaccatg accagggaca cgtccatcag cacagcctac     240
atggagctga gcaggctgag atctgacgac acggccgtgt attactgtgt gagagatcag     300
ggtatagcag cagctggtcc ctttgactac tggtgccagg gaaccctggt caccgtctcc     360
tcagct                                                                366
```

<210> SEQ ID NO 453
<211> LENGTH: 122
<212> TYPE: PRT
<213> ORGANISM: Homo sapiens

<400> SEQUENCE: 453

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
                20                  25                  30
His Met Tyr Trp Val Arg Gln Ala Pro Gly Gln Gly Leu Glu Trp Leu
            35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Val Arg Asp Gln Gly Ile Ala Ala Ala Gly Pro Phe Asp Tyr Trp Cys
            100                 105                 110
Gln Gly Thr Leu Val Thr Val Ser Ser Ala
        115                 120
```

<210> SEQ ID NO 454
<211> LENGTH: 324
<212> TYPE: DNA
<213> ORGANISM: Homo sapiens

<400> SEQUENCE: 454

```
gacatccgga tgacccagtc tccatcctcc ctgtctgcat ctgttggaga cagagtcacc      60
atcacttgcc gggcaagtca gcgcattagc acctatttaa attggtatca gcagaaacca    120
```

```
gggaaagccc ctaagttcct gatctatgct gcatctagtt tgcaaagtgg ggtcccatca      180
aggttcagtg gcagtggatc tgggacagat ttcactctca ccatcagcag tctgcaacct      240
gaagattttg caacttacta ctgtcaacag agttacacta ccccattcac tttcggccct      300
gggaccaaag tggatatcaa acga                                             324
```

```
<210>   SEQ ID NO 455
<211>   LENGTH: 108
<212>   TYPE: PRT
<213>   ORGANISM: Homo sapiens

<400>   SEQUENCE: 455
```

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Thr Tyr
            20                  25                  30

Leu Asn Trp Tyr Gln Gln Lys Pro Gly Lys Ala Pro Lys Phe Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Phe
                85                  90                  95

Thr Phe Gly Pro Gly Thr Lys Val Asp Ile Lys Arg
            100                 105

```
<210>   SEQ ID NO 456
<211>   LENGTH: 352
<212>   TYPE: DNA
<213>   ORGANISM: Homo sapiens

<400>   SEQUENCE: 456 caggtgcagc tggtggagtc tgggggaggc gtggtccagc ctggggaggtc cctgagactc       60 tcctgtgcag cgtctggatt caccttcagt agctatggca tgcactgggt ccgccaggct      120
ccaggcaagg ggctggagtg gtggcagtt atatggtatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc cggggggagct      300 acggccatgg acgtctgcgg ccaagggagc acgggcaccg tctcctcagc ct              352
```

```
<210>   SEQ ID NO 457
<211>   LENGTH: 117
<212>   TYPE: PRT
<213>   ORGANISM: Homo sapiens

<400>   SEQUENCE: 457
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95
Ala Gly Gly Ala Thr Ala Met Asp Val Cys Gly Gln Gly Ser Thr Gly
            100                 105                 110
Thr Val Ser Ser Ala
        115

<210> SEQ ID NO 458
<211> LENGTH: 324
<212> TYPE: DNA
<213> ORGANISM: Homo sapiens

<400> SEQUENCE: 458
gacatccgga tgacccagtc tccatcctcc ctgtctgcat ctgtaggaga cagagtcacc    60
atcacttgcc gggcaagtca gggcattaga acctatttaa actggtatca gcagaaacca   120
gggaaagccc ctaagctcct gatctatgct gcatctagtt tgcaaagtgg ggtcccatca   180
aggttcagcg gcagtggatc tgggacagat ttcactctca ccatcagcag tctgcagcct   240
gaagattttg caacttacta ctgtcaacag aattacacta ccccattcac tttcggccct   300
gggaccaaag tggatatcaa acga                                          324

<210> SEQ ID NO 459
<211> LENGTH: 108
<212> TYPE: PRT
<213> ORGANISM: Homo sapiens

<400> SEQUENCE: 459

Asp Ile Arg Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Thr Thr Pro Phe
                85                  90                  95

Thr Phe Gly Pro Gly Thr Lys Val Asp Ile Lys Arg
            100                 105

<210> SEQ ID NO 460
<211> LENGTH: 363
<212> TYPE: DNA
<213> ORGANISM: Homo sapiens

<400> SEQUENCE: 460
gaggtgcaga tggtggagtc tgggggaggc ttggtccagc cggggggggtc cctgagactc    60 tcctgtgcag cctctggatt caccttaaga agctactgga tgagctgggt ccgccaggct   120
ccagggaagg ggctggagtg ggtggccaac ataaaggaag acggaagtga aaataccat    180 gtggactctg tgaagggccg attcaccatc tccagagaca acgccgagaa ctcactgttt   240
ctgcaaatga gcagcctgcg agccgaggac acggctgtgt attactgtgc gagagatatg   300
gaagcatcag ctggcctctt tgactactgg ggccagggaa ccctggtcac cgtctcctca   360
```

```
gct                                                               363
```

<210> SEQ ID NO 461
<211> LENGTH: 121
<212> TYPE: PRT
<213> ORGANISM: Homo sapiens

<400> SEQUENCE: 461

| Glu | Val | Gln | Met | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Leu | Arg | Ser | Tyr |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Asn | Ile | Lys | Glu | Asp | Gly | Ser | Glu | Lys | Tyr | His | Val | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ala | Glu | Asn | Ser | Leu | Phe |
|---|---|---|---|---|---|---|---|---|---|---|---|---|---|---|---|
| 65 | | | | | 70 | | | | | 75 | | | | | 80 |

| Leu | Gln | Met | Ser | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Met | Glu | Ala | Ser | Ala | Gly | Leu | Phe | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser | Ala |
|---|---|---|---|---|---|---|---|---|
| | | | 115 | | | | | 120 |

<210> SEQ ID NO 462
<211> LENGTH: 321
<212> TYPE: DNA
<213> ORGANISM: Homo sapiens

<400> SEQUENCE: 462

```
gaaatagtga tgacgcagtc cccagccacc ctgtctgtgt ctccagggga aagagccatc    60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataattact ggtggacgtt cggccaaggg   300
accaaggtgg aaatcaaacg a                                             321
```

<210> SEQ ID NO 463
<211> LENGTH: 107
<212> TYPE: PRT
<213> ORGANISM: Homo sapiens

<400> SEQUENCE: 463

| Glu | Ile | Val | Met | Thr | Gln | Ser | Pro | Ala | Thr | Leu | Ser | Val | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Ile | Leu | Ser | Cys | Arg | Ala | Ser | Gln | Ser | Ile | Ser | Ser | Asn |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Gln | Ala | Pro | Arg | Leu | Leu | Ile |
|---|---|---|---|---|---|---|---|---|---|---|---|---|---|---|---|
| | | 35 | | | | | 40 | | | | | 45 | | | |

| Tyr | Gly | Ala | Ser | Thr | Arg | Ala | Thr | Gly | Ile | Pro | Ala | Arg | Phe | Ser | Gly |
|---|---|---|---|---|---|---|---|---|---|---|---|---|---|---|---|
| 50 | | | | | 55 | | | | | 60 | | | | | |

| Ser | Gly | Ser | Gly | Thr | Glu | Phe | Thr | Leu | Thr | Ile | Ser | Ser | Leu | Gln | Ser |
|---|---|---|---|---|---|---|---|---|---|---|---|---|---|---|---|
| 65 | | | | | 70 | | | | | 75 | | | | | 80 |

| Glu | Asp | Phe | Ala | Val | Tyr | Tyr | Cys | Gln | Gln | Tyr | Asn | Tyr | Trp | Trp | Thr |
|---|---|---|---|---|---|---|---|---|---|---|---|---|---|---|---|
| | | | | 85 | | | | | 90 | | | | | 95 | |

Phe Gly Gln Gly Thr Lys Val Glu Ile Lys Arg
            100                 105

<210> SEQ ID NO 464
<211> LENGTH: 363
<212> TYPE: DNA
<213> ORGANISM: Homo sapiens

<400> SEQUENCE: 464
gaggtgcaga tggtggagtc tgggggaggc ttggtccagc cggggggggtc cctgagactc      60 tcctgtgcag cctctggatt caccttaaga agctactgga tgagctgggt ccgccaggct     120
ccagggaagg ggctggagtg ggtggccaac ataaaggaag acggaagtga aaataccat      180 gtggactctg tgaagggccg attcaccatc tccagagaca acgccgagaa ctcactgttt     240
ctgcaaatga gcagcctgcg agccgaggac acggctgtgt attactgtgc gagagatatg     300
gaagcatcag ctggcctctt tgactactgg ggccaggaaa ccctggtcac cgtctcctca     360
gct                                                                    363

<210> SEQ ID NO 465
<211> LENGTH: 121
<212> TYPE: PRT
<213> ORGANISM: Homo sapiens

<400> SEQUENCE: 465

Glu Val Gln Met Val Glu Ser Gly Gly Gly Leu Val Gln Pro Gly Gly
 1               5                  10                  15

Ser Leu Arg Leu Ser Cys Ala Ala Ser Gly Phe Thr Leu Arg Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr His Val Asp Ser Val
    50                  55                  60

Lys Gly Arg Phe Thr Ile Ser Arg Asp Asn Ala Glu Asn Ser Leu Phe
65                  70                  75                  80

Leu Gln Met Ser Ser Leu Arg Ala Glu Asp Thr Ala Val Tyr Tyr Cys
                85                  90                  95

Ala Arg Asp Met Glu Ala Ser Ala Gly Leu Phe Asp Tyr Trp Gly Gln
            100                 105                 110

Gly Thr Leu Val Thr Val Ser Ser Ala
            115                 120

<210> SEQ ID NO 466
<211> LENGTH: 321
<212> TYPE: DNA
<213> ORGANISM: Homo sapiens

<400> SEQUENCE: 466
gaaatagtga tgacgcagtc cccagccacc ctgtctgtgt ctccagggga aagagccatc      60
ctctcctgca gggccagtca gagtattagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataattact ggtggacgtt cggccaaggg    300
accaaggtgg aaatcaaacg a                                                321

<210> SEQ ID NO 467
<211> LENGTH: 107
<212> TYPE: PRT
<213> ORGANISM: Homo sapiens

<400> SEQUENCE: 467

```
Glu Ile Val Met Thr Gln Ser Pro Ala Thr Leu Ser Val Ser Pro Gly
 1               5                  10                  15

Glu Arg Ala Ile Leu Ser Cys Arg Ala Ser Gln Ser Ile Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Tyr Trp Trp Thr
                 85                  90                  95

Phe Gly Gln Gly Thr Lys Val Glu Ile Lys Arg
            100                 105
```

<210> SEQ ID NO 468
<211> LENGTH: 363
<212> TYPE: DNA
<213> ORGANISM: Homo sapiens

<400> SEQUENCE: 468

```
gaggtgcaga tggtggagtc tgggggaggc ttggtccagc cggggggggtc cctgagactc      60 tcctgtgcag cctctggatt caccttaaga agctactgga tgagctgggt ccgccaggct     120
ccagggaagg ggctggagtg ggtggccaac ataaaggaag acggaagtga aaataccat      180 gtggactctg tgaagggccg attcaccatc tccagagaca acgccgagaa ctcactgttt     240
ctgcaaatga gcagcctgcg agccgaggac acggctgtgt attactgtgc gagagatatg     300
gaagcatcag ctggcctctt tgactactgg ggccagggaa ccctggtcac cgtctcctca     360
gct                                                                    363
```

<210> SEQ ID NO 469
<211> LENGTH: 121
<212> TYPE: PRT
<213> ORGANISM: Homo sapiens

<400> SEQUENCE: 469

```
Glu Val Gln Met Val Glu Ser Gly Gly Gly Leu Val Gln Pro Gly Gly
 1               5                  10                  15

Ser Leu Arg Leu Ser Cys Ala Ala Ser Gly Phe Thr Leu Arg Ser Tyr
             20                  25                  30

Trp Met Ser Trp Val Arg Gln Ala Pro Gly Lys Gly Leu Glu Trp Val
         35                  40                  45

Ala Asn Ile Lys Glu Asp Gly Ser Glu Lys Tyr His Val Asp Ser Val
     50                  55                  60

Lys Gly Arg Phe Thr Ile Ser Arg Asp Asn Ala Glu Asn Ser Leu Phe
 65                  70                  75                  80

Leu Gln Met Ser Ser Leu Arg Ala Glu Asp Thr Ala Val Tyr Tyr Cys
                 85                  90                  95

Ala Arg Asp Met Glu Ala Ser Ala Gly Leu Phe Asp Tyr Trp Gly Gln
            100                 105                 110
```

```
<210> SEQ ID NO 470
<211> LENGTH: 321
<212> TYPE: DNA
<213> ORGANISM: Homo sapiens

<400> SEQUENCE: 470
gaaatagtga tgacgcagtc cccagccacc ctgtctgtgt ctccagggga aagagccatc    60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataattact ggtggacgtt cggccaaggg   300
accaaggtgg aaatcaaacg a                                              321

<210> SEQ ID NO 471
<211> LENGTH: 107
<212> TYPE: PRT
<213> ORGANISM: Homo sapiens

<400> SEQUENCE: 471

Glu Ile Val Met Thr Gln Ser Pro Ala Thr Leu Ser Val Ser Pro Gly
 1               5                  10                  15

Glu Arg Ala Ile Leu Ser Cys Arg Ala Ser Gln Ser Ile Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Tyr Trp Trp Thr
                 85                  90                  95

Phe Gly Gln Gly Thr Lys Val Glu Ile Lys Arg
            100                 105

<210> SEQ ID NO 472
<211> LENGTH: 363
<212> TYPE: DNA
<213> ORGANISM: Homo sapiens

<400> SEQUENCE: 472
caggtgcagc tggtggagtc tgggggaggc gtggtccagc ctgggaggtc cctgagactc    60
tcctgtgcag cgtctggatt caccttcagg agctatggca tgcactgggt ccgccaggct   120
ccaggcaagg ggctggagtg ggtggcagtt atatggtatg atggaagtta taaaaactat   180
ggagactccg tgaagggccg attcaccatc tccagagaca attccaagaa cacgctgtat   240
ctgcaaatga acagcctgag agccgaggac acggctgtgt attactgtgc gagggactac   300
agtaactacg aggagtactt tgactactgg ggccagggaa ccctggtcac cgtctcctca   360
gct                                                                  363

<210> SEQ ID NO 473
<211> LENGTH: 121
<212> TYPE: PRT
<213> ORGANISM: Homo sapiens
```

Gly Thr Leu Val Thr Val Ser Ser Ala
        115                 120

<400> SEQUENCE: 473

```
Gln Val Gln Leu Val Glu Ser Gly Gly Val Val Gln Pro Gly Arg
1               5                   10                  15
Ser Leu Arg Leu Ser Cys Ala Ala Ser Gly Phe Thr Phe Arg Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Tyr Lys Asn Tyr Gly Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Tyr Ser Asn Tyr Glu Glu Tyr Phe Asp Tyr Trp Gly Gln
            100                 105                 110
Gly Thr Leu Val Thr Val Ser Ser Ala
        115                 120
```

<210> SEQ ID NO 474
<211> LENGTH: 354
<212> TYPE: DNA
<213> ORGANISM: Homo sapiens

<400> SEQUENCE: 474

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagttc aaaaactac      180
gcagactctg tgaagggccg aatcaccatc tccagggaca acgccaagaa ctcactgtat     240
ctgcaaatga acagcctgag agccgaggac acggccgtgt attactgtgc gagagagagg     300
ggggatgctt ttgatatctg gggccaaggg acaatggtca ccgtctcttc agct           354
```

<210> SEQ ID NO 475
<211> LENGTH: 118
<212> TYPE: PRT
<213> ORGANISM: Homo sapiens

<400> SEQUENCE: 475

```
Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Tyr Met Ser Trp Ile Arg Gln Ala Pro Gly Lys Gly Leu Glu Trp Val
        35                  40                  45
Ser Tyr Ile Ser Ser Ser Gly Ser Ser Lys Asn Tyr Ala Asp Ser Val
    50                  55                  60
Lys Gly Arg Ile Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Arg Gly Asp Ala Phe Asp Ile Trp Gly Gln Gly Thr Met
            100                 105                 110
Val Thr Val Ser Ser Ala
        115
```

<210> SEQ ID NO 476
<211> LENGTH: 342
<212> TYPE: DNA
<213> ORGANISM: Homo sapiens

<400> SEQUENCE: 476

```
gacatcgtga tgacccagtc tccagactcc ctggctgtgt ctctgggcga aaggccacc      60
atcaactgca gtccagcca gagtgttata tacagttcca acaatcagaa cttcttagct     120
tggtatcagc ataaaccagg acagcctcct aaactgctca tttactgggc atctacccgg   180
gaatccgggg tccctgaccg attcagtgac agcgggtctg ggacagattt cactctcacc   240
atcagcagcc tgcaggctga agatgtggca gtttattact gtcaccaata ttatagtact   300
ccgatcacct tcggccaagg gacacgactg gagattaaac ga                       342
```

<210> SEQ ID NO 477
<211> LENGTH: 114
<212> TYPE: PRT
<213> ORGANISM: Homo sapiens

<400> SEQUENCE: 477

Asp Ile Val Met Thr Gln Ser Pro Asp Ser Leu Ala Val Ser Leu Gly
1               5                   10                  15

Glu Lys Ala Thr Ile Asn Cys Lys Ser Ser Gln Ser Val Ile Tyr Ser
            20                  25                  30

Ser Asn Asn Gln Asn Phe Leu Ala Trp Tyr Gln His Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Asp Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Thr Pro Ile Thr Phe Gly Gln Gly Thr Arg Leu Glu Ile
            100                 105                 110

Lys Arg

<210> SEQ ID NO 478
<211> LENGTH: 354
<212> TYPE: DNA
<213> ORGANISM: Homo sapiens

<400> SEQUENCE: 478

```
gaggtgcagc tggtggagtc tgggggaggc ttggtccagc ctggggggtc cctgagactc      60
tcctgtgcag cctctggatt cacctttagt agctattgga tgagctgggt ccgccaggct    120
ccagggaagg ggctggagtg ggtggccaac ataaagcaag atggaagtga aaatactat     180
gtggactctg tgaagggccg attcaccatc tccagagaca acgccaagaa ctcactgtat   240
ctgcaaatga acagcctgag agccgaggac acggctgtat attactgtgc gagagatagc   300
tggtggtact cgatctctg gggccgtggc accctggtca ctgtctcctc agct           354
```

<210> SEQ ID NO 479
<211> LENGTH: 118
<212> TYPE: PRT
<213> ORGANISM: Homo sapiens

<400> SEQUENCE: 479

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Ser Trp Trp Tyr Phe Asp Leu Trp Gly Arg Gly Thr Leu
            100                 105                 110

Val Thr Val Ser Ser Ala
            115
```

<210> SEQ ID NO 480
<211> LENGTH: 375
<212> TYPE: DNA
<213> ORGANISM: Homo sapiens

<400> SEQUENCE: 480

```
caggtgcagc tggtggagtc tgggggaggc gtggtccagc ctggggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taatactat   180
gcagactccg tgaagggccg attcaccatc tccagagaca attccaagaa cacgctgtat   240
ctgcaaatga acagcctgag agccgaggac acggctgtgt attactgtgc gagaaaggga   300
tattgtagtg gtggtaggtg tgtctacggt atggacgtct ggggccaagg gaccacggtc   360
accgtctcct cagct                                                     375
```

<210> SEQ ID NO 481
<211> LENGTH: 125
<212> TYPE: PRT
<213> ORGANISM: Homo sapiens

<400> SEQUENCE: 481

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Lys Gly Tyr Cys Ser Gly Arg Cys Val Tyr Gly Met Asp
            100                 105                 110

Val Trp Gly Gln Gly Thr Thr Val Thr Val Ser Ser Ala
            115                 120                 125
```

-continued

<210> SEQ ID NO 482
<211> LENGTH: 339
<212> TYPE: DNA
<213> ORGANISM: Homo sapiens

<400> SEQUENCE: 482

```
gatattgtga tgactcagtc tccactctcc ctgcccgtca cccctggaga gccggcctcc      60
atctcctgca ggtctagtca gagcctcctg tatagtaatg gatacaacta tttggattgg     120
tacctgcaga agccagggca gtctccacag gtcctgatct atttgggttc taatcgggcc     180
tccggggtcc ctgacaggtt cagtggcagt ggatcaggca cagatttac actgaaaatc      240 agcagagtgg aggctgagga tgttggggtt tattactgca tgcaagctct acaaactcct     300
atcaccttcg gccaagggac acgactggag attaaacga                            339
```

<210> SEQ ID NO 483
<211> LENGTH: 113
<212> TYPE: PRT
<213> ORGANISM: Homo sapiens

<400> SEQUENCE: 483

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

Arg

<210> SEQ ID NO 484
<211> LENGTH: 324
<212> TYPE: DNA
<213> ORGANISM: Homo sapiens

<400> SEQUENCE: 484

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaaggtcct gatctatggt gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctgtgca gttttggccag    300 gggaccaagc tggagatcaa acga                                            324
```

<210> SEQ ID NO 485
<211> LENGTH: 108
<212> TYPE: PRT
<213> ORGANISM: Homo sapiens

<400> SEQUENCE: 485

Asp Ile Gln Met Thr Gln Ser Pro Ser Ser Leu Ser Ala Ser Val Gly

```
               1               5                  10                 15
Asp Arg Val Thr Ile Thr Cys Arg Ala Ser Gln Ser Ile Ser Ser Tyr
                    20                 25                 30

Leu Asn Trp Tyr Gln Gln Lys Pro Gly Lys Ala Pro Lys Val Leu Ile
            35                 40                 45

Tyr Gly Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ser Tyr Ser Thr Leu Cys
                    85                 90                 95

Ser Phe Gly Gln Gly Thr Lys Leu Glu Ile Lys Arg
                    100                105
```

```
<210> SEQ ID NO 486
<211> LENGTH: 372
<212> TYPE: DNA
<213> ORGANISM: Homo sapiens

<400> SEQUENCE: 486
gaggtgcagt tggtggagtc tgggggaggc ctgttcaagc ctggggggtc cctgagactc      60
tcctgtgcag cctctggatt caccttcagt agctatagca tgaactgggt ccgccaggct     120
ccagggaagg ggctggagtg ggtctcatcc attagtagta gtagtagtta tatatattac     180
gcagactcag tgaagggccg attcaccatc tccagagaca acgccaagaa ctccctgtat     240
ctgcaaatga acagcctgag agccgaggac acggctgtgt attactgtgc gagagatggg     300 gcgattttg gagtggttaa ctggtacttc gatctctggg gccgtggcac cctggtcact     360
gtctcctcag cc                                                         372
```

```
<210> SEQ ID NO 487
<211> LENGTH: 124
<212> TYPE: PRT
<213> ORGANISM: Homo sapiens

<400> SEQUENCE: 487

Glu Val Gln Leu Val Glu Ser Gly Gly Gly Leu Phe Lys Pro Gly Gly
1               5                  10                 15

Ser Leu Arg Leu Ser Cys Ala Ala Ser Gly Phe Thr Phe Ser Ser Tyr
            20                 25                 30

Ser Met Asn Trp Val Arg Gln Ala Pro Gly Lys Gly Leu Glu Trp Val
        35                 40                 45

Ser Ser Ile Ser Ser Ser Ser Tyr Ile Tyr Tyr Ala Asp Ser Val
    50                 55                 60

Lys Gly Arg Phe Thr Ile Ser Arg Asp Asn Ala Lys Asn Ser Leu Tyr
65                 70                 75                 80

Leu Gln Met Asn Ser Leu Arg Ala Glu Asp Thr Ala Val Tyr Tyr Cys
                    85                 90                 95

Ala Arg Asp Gly Ala Ile Phe Gly Val Val Asn Trp Tyr Phe Asp Leu
                    100                105                110

Trp Gly Arg Gly Thr Leu Val Thr Val Ser Ser Ala
            115                120
```

```
<210> SEQ ID NO 488
<211> LENGTH: 324
<212> TYPE: DNA
<213> ORGANISM: Homo sapiens
```

<400> SEQUENCE: 488

| | | | |
|---|---|---|---|
| gacatccaga tgacccagtc tccatcttcc gtgtctgcat ctgtaggaga cagagtcacc | 60 |
| atcacttgtc gggcgagtca gggtattagc agctggttag cctggtatca gcagaaacca | 120 |
| gggaaagccc ctaagctcct gatctttgct gcatccagtt tgcaaagtgg ggtcccatcc | 180 |
| aggttcagcg gcagtggatc tgggacagat tcactctcac catcagcag cctgcagcct | 240 |
| gaagattttg caacttacta ttgtcaacag gctaacagtt tccctctcac tttcggcgga | 300 |
| gggaccaagg tggagatcaa acga | 324 |

<210> SEQ ID NO 489
<211> LENGTH: 108
<212> TYPE: PRT
<213> ORGANISM: Homo sapiens

<400> SEQUENCE: 489

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 490
<211> LENGTH: 366
<212> TYPE: DNA
<213> ORGANISM: Homo sapiens

<400> SEQUENCE: 490

| | | | |
|---|---|---|---|
| gaggtgcagc tgttggagtc tgggggaggc ttggtacagc ctgggggtc cctgagactc | 60 |
| tcctgtgctg cctctggatt caccttcagc agctatgcca tgagctgggt ccgccaggct | 120 |
| ccagggaagg ggctggagtg ggtctcaggt attagtggta gtggtggtaa cacataccac | 180 |
| gcagactccg tgaagggccg gttcaccatc tccagagaca attccaagaa cacgctgtat | 240 |
| ctgcaaatga acagcctgag agccgaggac acggccgtat attactgtgc gaaagatgaa | 300 |
| gactacggtg gctactccga ctttgactac tggggccagg gaaccctggt caccgtctcc | 360 |
| tcagct | 366 |

<210> SEQ ID NO 491
<211> LENGTH: 122
<212> TYPE: PRT
<213> ORGANISM: Homo sapiens

<400> SEQUENCE: 491

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
        35                  40                  45

Ser Gly Ile Ser Gly Ser Gly Gly Asn Thr Tyr His Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Glu Asp Tyr Gly Gly Tyr Ser Asp Phe Asp Tyr Trp Gly
            100                 105                 110

Gln Gly Thr Leu Val Thr Val Ser Ser Ala
        115                 120

<210> SEQ ID NO 492
<211> LENGTH: 327
<212> TYPE: DNA
<213> ORGANISM: Homo sapiens

<400> SEQUENCE: 492
gacatccaga tgacccagtc tccatcctcc ctgtctgcat ctgtaggaac cagagtcacc     60
atcacttgcc gggcaagtca gagcattcgc agctatttaa attggtatca gcagaaacca    120
gggaaagccc ctaagctcct gatctatgct gcatccagtt tacaaagagg ggtcccatca    180
aggttcagtg gcagtggatc tgggacagat ttcactctca ccatcagcag tctgcaagct    240
gaagattttg caacttacta ctgtcaacag agttacacta ccccccctgtg cagttttggc    300 caggggacca ggctggagat caaacga                                        327

<210> SEQ ID NO 493
<211> LENGTH: 109
<212> TYPE: PRT
<213> ORGANISM: Homo sapiens

<400> SEQUENCE: 493

Asp Ile Gln Met Thr Gln Ser Pro Ser Ser Leu Ser Ala Ser Val Gly
 1               5                  10                  15

Thr Arg Val Thr Ile Thr Cys Arg Ala Ser Gln Ser Ile Arg Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Arg Gly Val Pro Ser Arg Phe Ser Gly
     50                  55                  60

Ser Gly Ser Gly Thr Asp Phe Thr Leu Thr Ile Ser Ser Leu Gln Ala
 65                  70                  75                  80

Glu Asp Phe Ala Thr Tyr Tyr Cys Gln Gln Ser Tyr Thr Thr Pro Leu
                 85                  90                  95

Cys Ser Phe Gly Gln Gly Thr Arg Leu Glu Ile Lys Arg
            100                 105

<210> SEQ ID NO 494
<211> LENGTH: 324
<212> TYPE: DNA
<213> ORGANISM: Homo sapiens

<400> SEQUENCE: 494
gacatccaga tgacccagtc tccatcctca ctgtctgcat ctgtaggaga cagagtcacc     60
atcacttgtc gggcgagtca ggacattagc aattatttag cctggtttca gcagaaacca    120
```
gggaaagccc ctaagtccct gatctatgct gcatccagtt tgcaaagtgg ggtcccatca   180
cagttcagcg gcagtggctc tgggacagat ttcactctca ccatcagcag cctgcagcct   240
gaagattttg caacttatta ctgccaacaa tataataatt acccattcac tttcggccct   300
gggaccaaag tggatgtcaa acga   324

<210> SEQ ID NO 495
<211> LENGTH: 108
<212> TYPE: PRT
<213> ORGANISM: Homo sapiens

<400> SEQUENCE: 495

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Gln Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Pro Gly Thr Lys Val Asp Val Lys Arg
            100                 105

<210> SEQ ID NO 496
<211> LENGTH: 369
<212> TYPE: DNA
<213> ORGANISM: Homo sapiens

<400> SEQUENCE: 496
caggtgcagc tggtgcagtc tggggctgag gtgaagaagc ctggggcctc agtgaaggtc   60
tcctgcaagg cttctggata caccttcacc ggctactata tgcactgggt gccacaggcc   120
cctggacaag gcttgagtg atgggatgg atcaaccta acagtggtgg cacaaactat   180
gcacagaagt tcagggcag ggtcaccatg accagggaca cgtccatcag cacagcttac   240
atggagctga ggaggctgag atctgacgac acggccgtgt attactgtgc gagagatggg   300
ggtagtatac cagtgtctgg tcactttgac tactgggggc agggaaccct ggtcaccgtc   360
tcctcagct   369

<210> SEQ ID NO 497
<211> LENGTH: 123
<212> TYPE: PRT
<213> ORGANISM: Homo sapiens

<400> SEQUENCE: 497

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Pro Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Arg Asp Gly Gly Ser Ile Pro Val Ser Gly His Phe Asp Tyr Trp
            100                 105                 110

Gly Gln Gly Thr Leu Val Thr Val Ser Ser Ala
        115                 120

<210> SEQ ID NO 498
<211> LENGTH: 321
<212> TYPE: DNA
<213> ORGANISM: Homo sapiens

<400> SEQUENCE: 498
gaaatagtga tgacgcagtc tccagccacc ctgtctgtgt ctccagggga aagagccacc      60
ctctcctgca gggccagtca gagtcttatc agcaacttag cctggtacca gcagaaacct     120
ggccaggctc ccaggctcct catctttggt gcatccacca gggccactgg tatcccagcc     180
aggttcagtg gcagtgggtc tgggacagag ttcactctca ccatcagcag cctgcagtct     240
gaagattttg cagtttatta ctgtcatcag tataataact ggtggacgtt cggccaaggg     300
accaaggtgg aaatcaaacg a                                              321

<210> SEQ ID NO 499
<211> LENGTH: 107
<212> TYPE: PRT
<213> ORGANISM: Homo sapiens

<400> SEQUENCE: 499

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ile Ser Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Asn Asn Trp Trp Thr
                85                  90                  95

Phe Gly Gln Gly Thr Lys Val Glu Ile Lys Arg
            100                 105

<210> SEQ ID NO 500
<211> LENGTH: 354
<212> TYPE: DNA
<213> ORGANISM: Homo sapiens

<400> SEQUENCE: 500
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagggaca cgccaagaa ctcactgtat      240 ctgcaaatga atagcctgag agccgaggac acggccgtgt attactgtgc gagagaaaga     300

```
ggggatgctt tgatatctg gggccaaggg acaatggtca ccgtctcttc agct        354
```

<210> SEQ ID NO 501
<211> LENGTH: 118
<212> TYPE: PRT
<213> ORGANISM: Homo sapiens

<400> SEQUENCE: 501

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Asp Ala Phe Asp Ile Trp Gly Gln Gly Thr Met
            100                 105                 110

Val Thr Val Ser Ser Ala
        115

<210> SEQ ID NO 502
<211> LENGTH: 366
<212> TYPE: DNA
<213> ORGANISM: Homo sapiens

<400> SEQUENCE: 502

```
caggtgcagc tggtgcagtc tggggctgag gtgaaaaagc ctggggcctc agtcaaggtc     60
tcctgcaagg cttctggata caccttcacc ggctactatt tgtactgggt gccacaggcc    120
cctggacaag gcttgagtg gatgggatgg atcagcccta acagtggtgg cacaaactat     180
gcacagaagt tcagggcag ggtcaccatg accaggaca cgtccatcag cacagcctac      240
atggagctga gcaggctgag atctgacgac acggccgtgt attactgtgc gagagatcag    300
gtcatagcag tagctggtcc ctttgactac tgggcccaag gaaccctggt caccgtctcc    360
tcagct                                                              366
```

<210> SEQ ID NO 503
<211> LENGTH: 122
<212> TYPE: PRT
<213> ORGANISM: Homo sapiens

<400> SEQUENCE: 503

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu Tyr Trp Val Pro Gln Ala Pro Gly Gln Gly Leu Glu Trp Met
        35                  40                  45

Gly Trp Ile Ser Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

```
Met Glu Leu Ser Arg Leu Arg Ser Asp Asp Thr Ala Val Tyr Tyr Cys
                85                  90                  95

Ala Arg Asp Gln Val Ile Ala Val Ala Gly Pro Phe Asp Tyr Trp Ala
            100                 105                 110

Gln Gly Thr Leu Val Thr Val Ser Ser Ala
        115                 120
```

<210> SEQ ID NO 504
<211> LENGTH: 321
<212> TYPE: DNA
<213> ORGANISM: Homo sapiens

<400> SEQUENCE: 504

```
gaaacagtga tgacgcagtc tccagccacc ctgtctgtgt ctccagggga aagagtcacc    60
ctctcctgca gggccagtca gagtgttatc agcagcttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataatt ggtggacgtt cggccaaggg   300
accaaggtgg aaatcaaacg a                                             321
```

<210> SEQ ID NO 505
<211> LENGTH: 107
<212> TYPE: PRT
<213> ORGANISM: Homo sapiens

<400> SEQUENCE: 505

```
Glu Thr Val Met Thr Gln Ser Pro Ala Thr Leu Ser Val Ser Pro Gly
 1               5                  10                  15

Glu Arg Val Thr Leu Ser Cys Arg Ala Ser Gln Ser Val Ile Ser Ser
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys Arg
            100                 105
```

<210> SEQ ID NO 506
<211> LENGTH: 369
<212> TYPE: DNA
<213> ORGANISM: Homo sapiens

<400> SEQUENCE: 506

```
caggtgcagc tggtggagtc tgggggaggc gtggtccagc ctggggaggtc cctgagactc    60
tcctgtgcag cgtctggatt caccttcagt agctatggca tgcactgggt ccgccaggct   120
ccaggcaagg ggctggaatg ggtggcagtt atatggtatg atggaagtaa taatactat    180
gcagactccg tgaaggaccg attcaccatc tccagagaca attccaagaa cacgctgtat   240
ctgcaaatga acagcctgag agccgaggac acggctgtgt attactgtgc gagagctccg   300
tatgactgga actcatacta cggtttggac gtctggggcc aagggaccac ggtcaccgtc   360
```

```
tcctcagct                                                                369
```

<210> SEQ ID NO 507
<211> LENGTH: 123
<212> TYPE: PRT
<213> ORGANISM: Homo sapiens

<400> SEQUENCE: 507

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Pro Tyr Asp Trp Asn Ser Tyr Tyr Gly Leu Asp Val Trp
            100                 105                 110

Gly Gln Gly Thr Thr Val Thr Val Ser Ser Ala
        115                 120

<210> SEQ ID NO 508
<211> LENGTH: 348
<212> TYPE: DNA
<213> ORGANISM: Homo sapiens

<400> SEQUENCE: 508

```
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caacttcaac     180
ccctccctca agagtcgagt caccacatca gtagacacgt ccaagaacca gttctccctg     240
aacctgaggt ctgtgaccgc tgcggacacg gccgtgtatt actgtgcgag gggaactggg     300
gcctctgact actggggcca gggaaccctg gtcaccgtct cctcagct                  348
```

<210> SEQ ID NO 509
<211> LENGTH: 116
<212> TYPE: PRT
<213> ORGANISM: Homo sapiens

<400> SEQUENCE: 509

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Phe Asn Pro Ser Leu Lys
    50                  55                  60

Ser Arg Val Thr Thr Ser Val Asp Thr Ser Lys Asn Gln Phe Ser Leu
65                  70                  75                  80

Asn Leu Arg Ser Val Thr Ala Ala Asp Thr Ala Val Tyr Tyr Cys Ala
                85                  90                  95

```
Arg Gly Thr Gly Ala Ser Asp Tyr Trp Gly Gln Gly Thr Leu Val Thr
            100                 105                 110
Val Ser Ser Ala
        115
```

<210> SEQ ID NO 510
<211> LENGTH: 371
<212> TYPE: DNA
<213> ORGANISM: Homo sapiens

<400> SEQUENCE: 510

```
caggtgcagc tgcaggagtc gggcccagga ctggtgaagc cttcggagac cctgtccctc      60
acctgcactg tctctggtgg ctccgtcagc agtggtggtt actactggag ctggatccgg     120
cagcccccag ggaagggact ggagtggatt ggatatatct attacagtcg gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcgagagag     300
ggacgtggaa acagttatgg ttactacttt gactactggg gccagggaac cctggtcacc     360
gtctcctcag c                                                          371
```

<210> SEQ ID NO 511
<211> LENGTH: 124
<212> TYPE: PRT
<213> ORGANISM: Homo sapiens

<400> SEQUENCE: 511

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Val Ser Ser Gly
             20                  25                  30
Gly Tyr Tyr Trp Ser Trp Ile Arg Gln Pro Pro Gly Lys Gly Leu Glu
         35                  40                  45
Trp Ile Gly Tyr Ile Tyr Tyr Ser Arg Ser Thr Asn Tyr Asn Pro Ser
     50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg Glu Gly Arg Gly Asn Ser Tyr Gly Tyr Tyr Phe Asp Tyr
            100                 105                 110
Trp Gly Gln Gly Thr Leu Val Thr Val Ser Ser Ala
        115                 120
```

<210> SEQ ID NO 512
<211> LENGTH: 342
<212> TYPE: DNA
<213> ORGANISM: Homo sapiens

<400> SEQUENCE: 512

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa caaatactat     180
gcagactccg tgaagggccg attcaccatc tccagagaca attccaagaa cacgctatat     240
ctgcaaatga acagcctgag agccgaggac acagctatgt attactgtgc gagagaactg     300
```

```
gcactgtggg gccagggaac cctggtcacc gtctcctcag ct                        342
```

<210> SEQ ID NO 513
<211> LENGTH: 114
<212> TYPE: PRT
<213> ORGANISM: Homo sapiens

<400> SEQUENCE: 513

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Glu Leu Ala Leu Trp Gly Gln Gly Thr Leu Val Thr Val Ser
            100                 105                 110

Ser Ala
```

<210> SEQ ID NO 514
<211> LENGTH: 321
<212> TYPE: DNA
<213> ORGANISM: Homo sapiens

<400> SEQUENCE: 514

```
gaaatagtga tgacgcagtc tccagccacc ctgtctgtgt ctccagggga aagagccacc     60
ctctcctgca gggccagtca gagtgttagc agctacttag cctggtacca gcagaaacct    120
ggccaggctc ccaggctcct catttatggt gcattcacca gggccactgg aattccagcc    180
aggttcagag gcagtgggtc tgggccagaa ttcacgctca ccatcagcag cctgcagtct    240
gaagattttg cagtttatta ctgtcagcag tatagtcact ggtggacgtt cggccaaggg    300
accaaggtgg aaatcaaacg a                                              321
```

<210> SEQ ID NO 515
<211> LENGTH: 107
<212> TYPE: PRT
<213> ORGANISM: Homo sapiens

<400> SEQUENCE: 515

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Phe Thr Arg Ala Thr Gly Ile Pro Ala Arg Phe Arg Gly
    50                  55                  60

Ser Gly Ser Gly Pro Glu Phe Thr Leu Thr Ile Ser Ser Leu Gln Ser
65                  70                  75                  80

Glu Asp Phe Ala Val Tyr Tyr Cys Gln Gln Tyr Ser His Trp Trp Thr
                85                  90                  95
```

```
Phe Gly Gln Gly Thr Lys Val Glu Ile Lys Arg
            100                 105
```

<210> SEQ ID NO 516
<211> LENGTH: 366
<212> TYPE: DNA
<213> ORGANISM: Homo sapiens

<400> SEQUENCE: 516

```
gaggtgcagc tggtggagtc tgggggaggc ttggtccagc ctggggggtc cctgagactc      60
tcctgtgcag cctctggatt cacctttagt agttattgga tgagctgggt ccgccaggct     120
ccagggaagg ggctggagtg ggtggccaac ataaagcaag atggaagtga gcaatactct     180
gtggactctg tgaagggccg attcaccatc tccagagaca acgccaagaa ctcactgtat     240
ctgcaaatga acaccctgag agccgaggac acggctgtgt attactgtgt gagagatccg     300
ggtatagaag tggctggccc ctttgactac tggggccagg aaccctggt caccgtctcc      360 tcagct                                                                366
```

<210> SEQ ID NO 517
<211> LENGTH: 122
<212> TYPE: PRT
<213> ORGANISM: Homo sapiens

<400> SEQUENCE: 517

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Gln Tyr Ser Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Glu Asp Thr Ala Val Tyr Tyr Cys
                85                  90                  95

Val Arg Asp Pro Gly Ile Glu Val Ala Gly Pro Phe Asp Tyr Trp Gly
            100                 105                 110

Gln Gly Thr Leu Val Thr Val Ser Ser Ala
        115                 120
```

<210> SEQ ID NO 518
<211> LENGTH: 321
<212> TYPE: DNA
<213> ORGANISM: Homo sapiens

<400> SEQUENCE: 518

```
gaaatagtga tgacgcagtc tccagccacc ctgtctgtgt ctccagggga aagagccacc      60
ctctcctgca gggccagtca gagtgttagc agctacttag cctggtacca gcagaaacct     120
ggccaggctc ccaggctcct catttatggt gcattcacca gggccactgg aattccagcc     180
aggttcagag gcagtgggtc tgggccagaa ttcacgctca ccatcagcag cctgcagtct     240
gaagattttg cagtttatta ctgtcagcag tatagtcact ggtggacgtt cggccaaggg     300
accaaggtgg aaatcaaacg a                                               321
```

<210> SEQ ID NO 519

```
<211> LENGTH: 107
<212> TYPE: PRT
<213> ORGANISM: Homo sapiens

<400> SEQUENCE: 519

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Phe Thr Arg Ala Thr Gly Ile Pro Ala Arg Phe Arg Gly
50                  55                  60

Ser Gly Ser Gly Pro Glu Phe Thr Leu Thr Ile Ser Ser Leu Gln Ser
65                  70                  75                  80

Glu Asp Phe Ala Val Tyr Tyr Cys Gln Gln Tyr Ser His Trp Trp Thr
                85                  90                  95

Phe Gly Gln Gly Thr Lys Val Glu Ile Lys Arg
            100                 105

<210> SEQ ID NO 520
<211> LENGTH: 378
<212> TYPE: DNA
<213> ORGANISM: Homo sapiens

<400> SEQUENCE: 520
caggtgcagc tggtggagtc tgggggagac gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatgc acagcctgag agctgaggac acggctgtgt attactgtgc gagagacggg     300
gggtggctac gattggacta ctactactac ggtatggacg tctggggcca ggggaccacg     360
gtcaccgtct cctcagct                                                   378

<210> SEQ ID NO 521
<211> LENGTH: 126
<212> TYPE: PRT
<213> ORGANISM: Homo sapiens

<400> SEQUENCE: 521

Gln Val Gln Leu Val Glu Ser Gly Gly Asp Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Arg Asp Gly Gly Trp Leu Arg Leu Asp Tyr Tyr Tyr Tyr Gly Met
            100                 105                 110

Asp Val Trp Gly Gln Gly Thr Thr Val Thr Val Ser Ser Ala
```

<210> SEQ ID NO 522
<211> LENGTH: 324
<212> TYPE: DNA
<213> ORGANISM: Homo sapiens

<400> SEQUENCE: 522

```
gacatccaga tgacccagtc tccatcctcc ctgtctgcat ctgtaggaga cagagtcacc    60
ttcacttgcc gggcaagtca gagcattatc acctttttaa attggtttca gcataaacca   120
gggaaagccc ctaagctcct gttctatggt gcatccagtt tggagagtgg ggtcccatca   180
aggttcagtg gcagtggatc tgggacaaat ttcactctca ccatcagcag tctgcaacct   240
gaagattttg caacttacta ctgtcaacag agttacagtg acccattcac tttcggccct   300
gggaccaaag tggatatcaa acga                                          324
```

<210> SEQ ID NO 523
<211> LENGTH: 108
<212> TYPE: PRT
<213> ORGANISM: Homo sapiens

<400> SEQUENCE: 523

Asp Ile Gln Met Thr Gln Ser Pro Ser Ser Leu Ser Ala Ser Val Gly
1               5                   10                  15

Asp Arg Val Thr Phe Thr Cys Arg Ala Ser Gln Ser Ile Ile Thr Phe
            20                  25                  30

Leu Asn Trp Phe Gln His Lys Pro Gly Lys Ala Pro Lys Leu Leu Phe
        35                  40                  45

Tyr Gly Ala Ser Ser Leu Glu Ser Gly Val Pro Ser Arg Phe Ser Gly
    50                  55                  60

Ser Gly Ser Gly Thr Asn Phe Thr Leu Thr Ile Ser Ser Leu Gln Pro
65                  70                  75                  80

Glu Asp Phe Ala Thr Tyr Tyr Cys Gln Gln Ser Tyr Ser Asp Pro Phe
                85                  90                  95

Thr Phe Gly Pro Gly Thr Lys Val Asp Ile Lys Arg
            100                 105

<210> SEQ ID NO 524
<211> LENGTH: 372
<212> TYPE: DNA
<213> ORGANISM: Homo sapiens

<400> SEQUENCE: 524

```
caggtgcagc tggtggagtc tgggggaggc gtggtccagc ctggaggtc cctgagactc     60
tcctgtgcag cgtctggatt caccttcagt agctatggca tgcactgggt ccgccaggct   120
ccaggcaagg gctggagtg gtggcaatt ctatggtatg atggaagtaa taaatactat     180
gcagactccg tgaagggccg attcaccatc tccagagaca attccaagaa cacgctgtat   240
ctgcaaatga acagcctgag agccgaggac acggctgtgt attactgtgc gagaggaggc   300
cctctgtata ccaactcctt ttactacttt gactactggg gccagggaac cctggtcacc   360
gtctcctcag ct                                                       372
```

<210> SEQ ID NO 525
<211> LENGTH: 124
<212> TYPE: PRT
<213> ORGANISM: Homo sapiens

<400> SEQUENCE: 525

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Leu Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Leu Tyr Thr Asn Ser Phe Tyr Tyr Phe Asp Tyr
            100                 105                 110

Trp Gly Gln Gly Thr Leu Val Thr Val Ser Ser Ala
        115                 120

<210> SEQ ID NO 526
<211> LENGTH: 324
<212> TYPE: DNA
<213> ORGANISM: Homo sapiens

<400> SEQUENCE: 526
gacatcgaga tgacccagtc tccatcctcc ctgtctgcat ctgtaggaga cagagtcacc      60
atcacttgcc gggcaagtca gaacattagc agctatttaa attggtatca gcagaagcca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagtt ccccgctcac tttcggcgga     300
gggaccaagg tggagatcaa acga                                            324

<210> SEQ ID NO 527
<211> LENGTH: 108
<212> TYPE: PRT
<213> ORGANISM: Homo sapiens

<400> SEQUENCE: 527

Asp Ile Glu Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gly Gly Thr Lys Val Glu Ile Lys Arg
            100                 105

<210> SEQ ID NO 528
<211> LENGTH: 365
<212> TYPE: DNA

<213> ORGANISM: Homo sapiens

<400> SEQUENCE: 528

```
cagatcacct tgaaggagtc tggtcctacg ctggtgaaac ccacacagac cctcacgctg    60
acctgtaccc tctctgggtt ctcactcagt attagtggag tgggtgtggg ctggatccgt   120
cagcccccag gaaaggccct ggagtggctt gcattcattt attggaatga tgataagcgc   180
tacagcccat ctctgaagag caggctcacc atcaccaagg acacctccaa aaaccaggtg   240
gtccttacaa tgaccaacat ggaccctgtg acacagcca catattactg cacacaga     300
ccggatagca gcagctggga ctttgactac tggggccagg gaaccctggt caccgtctcc   360
tcagc                                                              365
```

<210> SEQ ID NO 529
<211> LENGTH: 122
<212> TYPE: PRT
<213> ORGANISM: Homo sapiens

<400> SEQUENCE: 529

```
Gln Ile Thr Leu Lys Glu Ser Gly Pro Thr Leu Val Lys Pro Thr Gln
  1               5                  10                  15

Thr Leu Thr Leu Thr Cys Thr Leu Ser Gly Phe Ser Leu Ser Ile Ser
             20                  25                  30

Gly Val Gly Val Gly Trp Ile Arg Gln Pro Pro Gly Lys Ala Leu Glu
         35                  40                  45

Trp Leu Ala Phe Ile Tyr Trp Asn Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg Pro Asp Ser Ser Ser Trp Asp Phe Asp Tyr Trp Gly
            100                 105                 110

Gln Gly Thr Leu Val Thr Val Ser Ser Ala
        115                 120
```

<210> SEQ ID NO 530
<211> LENGTH: 324
<212> TYPE: DNA
<213> ORGANISM: Homo sapiens

<400> SEQUENCE: 530

```
gacatcgaga tgacccagtc tccatcctcc ctgtctgcat ctgtaggaga cagagtcacc    60
atcacttgcc gggcaagtca gaacattagc agctatttaa attggtatca gcagaagcca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagtt ccccgctcac tttcggcgga   300
gggaccaagg tggagatcaa acga                                         324
```

<210> SEQ ID NO 531
<211> LENGTH: 108
<212> TYPE: PRT
<213> ORGANISM: Homo sapiens

<400> SEQUENCE: 531

```
Asp Ile Glu Met Thr Gln Ser Pro Ser Ser Leu Ser Ala Ser Val Gly
```

```
                1               5                  10                 15
            Asp Arg Val Thr Ile Thr Cys Arg Ala Ser Gln Asn Ile Ser Ser Tyr
                            20                  25                  30

Leu Asn Trp Tyr Gln Gln Lys Pro Gly Lys Ala Pro Lys Leu Leu Ile
                            35                  40                  45

Tyr Ala Ala Ser Ser Leu Gln Ser Gly Val Pro Ser Arg Phe Ser Gly
                            50                  55                  60

Ser Gly Ser Gly Thr Asp Phe Thr Leu Thr Ile Ser Ser Leu Gln Pro
             65                 70                  75                  80

Glu Asp Phe Ala Thr Tyr Tyr Cys Gln Gln Ser Tyr Ser Ser Pro Leu
                            85                  90                  95

Thr Phe Gly Gly Gly Thr Lys Val Glu Ile Lys Arg
                            100                 105
```

<210> SEQ ID NO 532
<211> LENGTH: 343
<212> TYPE: DNA
<213> ORGANISM: Homo sapiens

<400> SEQUENCE: 532

```
caggtgctac tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtttg atggaagtaa aaaatactat     180
gcagactccg tgaagggccg attcaccatc tccagagaca attccaagaa ctcgctgtat     240
ctgcaaatga acagcctgag agccgaggac acggctgtat attactgtgc gagagaactg     300
gaactgtggg gcctgggaac cctggtcacc gtctcctcag ctt                       343
```

<210> SEQ ID NO 533
<211> LENGTH: 114
<212> TYPE: PRT
<213> ORGANISM: Homo sapiens

<400> SEQUENCE: 533

```
            Gln Val Leu Leu Val Glu Ser Gly Gly Val Val Gln Pro Gly Arg
             1               5                  10                  15

Ser Leu Arg Leu Ser Cys Ala Ala Ser Gly Phe Thr Phe Ser Ser Tyr
                            20                  25                  30

Gly Met His Trp Val Arg Gln Ala Pro Gly Lys Gly Leu Glu Trp Val
                            35                  40                  45

Ala Val Ile Trp Phe Asp Gly Ser Lys Lys Tyr Tyr Ala Asp Ser Val
                            50                  55                  60

Lys Gly Arg Phe Thr Ile Ser Arg Asp Asn Ser Lys Asn Ser Leu Tyr
             65                 70                  75                  80

Leu Gln Met Asn Ser Leu Arg Ala Glu Asp Thr Ala Val Tyr Tyr Cys
                            85                  90                  95

Ala Arg Glu Leu Glu Leu Trp Gly Leu Gly Thr Leu Val Thr Val Ser
                            100                 105                 110

Ser Ala
```

<210> SEQ ID NO 534
<211> LENGTH: 366
<212> TYPE: DNA
<213> ORGANISM: Homo sapiens

<400> SEQUENCE: 534

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtgtcactt atatggtatg ctggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagaggacct     300
ctacgatatt ttgactggcc cagtgactac tggggccagg gaaccctggt caccgtctcc     360
tcagct                                                                366
```

<210> SEQ ID NO 535
<211> LENGTH: 122
<212> TYPE: PRT
<213> ORGANISM: Homo sapiens

<400> SEQUENCE: 535

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Leu Ile Trp Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Leu Arg Tyr Phe Asp Trp Pro Ser Asp Tyr Trp Gly
            100                 105                 110

Gln Gly Thr Leu Val Thr Val Ser Ser Ala
        115                 120
```

<210> SEQ ID NO 536
<211> LENGTH: 327
<212> TYPE: DNA
<213> ORGANISM: Homo sapiens

<400> SEQUENCE: 536

```
gaaattgtgt tgacgcagtc tccaggcacc ctgtctttgt ctccagggga aagagccacc      60
ctctcctgca gggccagtca gagttttagc agcagctact tagcctggtt ccagcagaaa     120
cctggccagg ctcccaggct cctcatctat ggtgcatcca cagggccac tggcatccca      180 gacaggttca gtggcagtgg gtctgggaca gacttcactc tcaccatcag cagactggag     240
cctgaagatt ttgcagtgta ttactgtcat cattttggta cctcaccgct cactttcggc     300
ggagggacca aggtggagat caaacga                                         327
```

<210> SEQ ID NO 537
<211> LENGTH: 109
<212> TYPE: PRT
<213> ORGANISM: Homo sapiens

<400> SEQUENCE: 537

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30
```

```
    Tyr Leu Ala Trp Phe Gln Gln Lys Pro Gly Gln Ala Pro Arg Leu Leu
                 35                  40                  45

Ile Tyr Gly Ala Ser Asn Arg Ala Thr Gly Ile Pro Asp Arg Phe Ser
     50                  55                  60

Gly Ser Gly Ser Gly Thr Asp Phe Thr Leu Thr Ile Ser Arg Leu Glu
     65                  70                  75                  80

Pro Glu Asp Phe Ala Val Tyr Tyr Cys His His Phe Gly Thr Ser Pro
                     85                  90                  95

Leu Thr Phe Gly Gly Gly Thr Lys Val Glu Ile Lys Arg
                    100                 105

<210> SEQ ID NO 538
<211> LENGTH: 366
<212> TYPE: DNA
<213> ORGANISM: Homo sapiens

<400> SEQUENCE: 538
caggtgcagc tggtgcagtc tggggctgag gtgaagaagc ctggggcctc agtgaaggtc      60
tcctgcaagg cttctggata caccttcacc ggctacttta tgcactgggt gccacaggcc    120
cctggacaag gcttgagtg gatgggatgg atcaaccctaa acagtggtgg cacaaactat    180
gcacagaatt ttcagggcag ggtcaccatg accagggaca cgtccatcag cacagcctac    240
atggagctga gcaggctgag atctgacgac acgcccgtgt attactgtgc gagagatccc    300
tggcaaaact ggaactctta ctttgactac tggggccagg gaaccctggt caccgtctcc    360
tcagct                                                                366

<210> SEQ ID NO 539
<211> LENGTH: 122
<212> TYPE: PRT
<213> ORGANISM: Homo sapiens

<400> SEQUENCE: 539

Gln Val Gln Leu Val Gln Ser Gly Ala Glu Val Lys Lys Pro Gly Ala
     1               5                  10                  15

Ser Val Lys Val Ser Cys Lys Ala Ser Gly Tyr Thr Phe Thr Gly Tyr
                     20                  25                  30

Phe Met His Trp Val Pro Gln Ala Pro Gly Gln Gly Leu Glu Trp Met
                 35                  40                  45

Gly Trp Ile Asn Pro Asn Ser Gly Gly Thr Asn Tyr Ala Gln Asn Phe
     50                  55                  60

Gln Gly Arg Val Thr Met Thr Arg Asp Thr Ser Ile Ser Thr Ala Tyr
     65                  70                  75                  80

Met Glu Leu Ser Arg Leu Arg Ser Asp Asp Thr Pro Val Tyr Tyr Cys
                     85                  90                  95

Ala Arg Asp Pro Trp Gln Asn Trp Asn Ser Tyr Phe Asp Tyr Trp Gly
                    100                 105                 110

Gln Gly Thr Leu Val Thr Val Ser Ser Ala
                    115                 120

<210> SEQ ID NO 540
<211> LENGTH: 324
<212> TYPE: DNA
<213> ORGANISM: Homo sapiens

<400> SEQUENCE: 540
gacatccaga tgacccagtc tccatcctcc ctgtctgcat ctgtaggaga cagagtcacc      60
```

```
atcacttgcc gggcaagtca gagcattaga agctatttaa attggtatca gcagaaacca    120
gggaaagccc ctaaggtcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccctgtgcag ttttggccag    300
gggaccaagc tggagatcaa acga                                           324
```

<210> SEQ ID NO 541
<211> LENGTH: 108
<212> TYPE: PRT
<213> ORGANISM: Homo sapiens

<400> SEQUENCE: 541

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Arg Ser Tyr
             20                  25                  30

Leu Asn Trp Tyr Gln Gln Lys Pro Gly Lys Ala Pro Lys Val Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Leu Cys
                 85                  90                  95

Ser Phe Gly Gln Gly Thr Lys Leu Glu Ile Lys Arg
            100                 105
```

<210> SEQ ID NO 542
<211> LENGTH: 321
<212> TYPE: DNA
<213> ORGANISM: Homo sapiens

<400> SEQUENCE: 542

```
gaaatagtga tgacgcagtc tccagccacc ctgtctgtgt ctccagggga aagagccacc     60
ctctcctgca gggccagtca gagtcttatc agcaacttag cctggtacca gcagaaacct    120
ggccaggctc ccaggctcct catctttggt gcatccacca gggccactgg tatcccagcc    180
aggttcagtg gcagtgggtc tgggacagag ttcactctca ccatcagcag cctgcagtct    240
gaagattttg cagtttatta ctgtcatcag tataataact ggtggacgtt cggccaaggg    300
accaaggtgg aaatcaaacg a                                              321
```

<210> SEQ ID NO 543
<211> LENGTH: 107
<212> TYPE: PRT
<213> ORGANISM: Homo sapiens

<400> SEQUENCE: 543

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Leu Ile Ser Asn
             20                  25                  30

Leu Ala Trp Tyr Gln Gln Lys Pro Gly Gln Ala Pro Arg Leu Leu Ile
         35                  40                  45

Phe Gly Ala Ser Thr Arg Ala Thr Gly Ile Pro Ala Arg Phe Ser Gly
     50                  55                  60
```

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Asn Asn Trp Trp Thr
                85                  90                  95

Phe Gly Gln Gly Thr Lys Val Glu Ile Lys Arg
            100                 105

<210> SEQ ID NO 544
<211> LENGTH: 366
<212> TYPE: DNA
<213> ORGANISM: Homo sapiens

<400> SEQUENCE: 544
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagaggacct     300
ctacgatatt ttgactggcc cagtgactac tggggccagg gaaccctggt caccgtctcc     360
tcagct                                                                366

<210> SEQ ID NO 545
<211> LENGTH: 122
<212> TYPE: PRT
<213> ORGANISM: Homo sapiens

<400> SEQUENCE: 545

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Leu Arg Tyr Phe Asp Trp Pro Ser Asp Tyr Trp Gly
            100                 105                 110

Gln Gly Thr Leu Val Thr Val Ser Ser Ala
        115                 120

<210> SEQ ID NO 546
<211> LENGTH: 343
<212> TYPE: DNA
<213> ORGANISM: Homo sapiens

<400> SEQUENCE: 546
ctggtgcagt ctggagctga ggtgaagaag cctggggcct cagtgaaggt ctcctgcaag      60
gcttctggtt acacctttac cagctatggt atcagctggg tgcgacaggc ccctggacaa     120
gggcttgagt ggatgggatg gatcagcgct tacaatggta acacaaacta tgcacagaag     180
ctccaggaca gagtcaccat gaccacagac acatccacga gcacagccta catggagctg     240

```
aggagcctga gatctgacga cacggccgtg tattactgtg cgagaggcgt gggagctaag    300
gactactggg gccagggaac cctggtcacc gtctcctcag ctt                      343
```

<210> SEQ ID NO 547
<211> LENGTH: 114
<212> TYPE: PRT
<213> ORGANISM: Homo sapiens

<400> SEQUENCE: 547

Leu Val Gln Ser Gly Ala Glu Val Lys Lys Pro Gly Ala Ser Val Lys
1               5                   10                  15

Val Ser Cys Lys Ala Ser Gly Tyr Thr Phe Thr Ser Tyr Gly Ile Ser
            20                  25                  30

Trp Val Arg Gln Ala Pro Gly Gln Gly Leu Glu Trp Met Gly Trp Ile
        35                  40                  45

Ser Ala Tyr Asn Gly Asn Thr Asn Tyr Ala Gln Lys Leu Gln Asp Arg
    50                  55                  60

Val Thr Met Thr Thr Asp Thr Ser Thr Ser Thr Ala Tyr Met Glu Leu
65                  70                  75                  80

Arg Ser Leu Arg Ser Asp Asp Thr Ala Val Tyr Tyr Cys Ala Arg Gly
                85                  90                  95

Val Gly Ala Lys Asp Tyr Trp Gly Gln Gly Thr Leu Val Thr Val Ser
            100                 105                 110

Ser Ala

<210> SEQ ID NO 548
<211> LENGTH: 324
<212> TYPE: DNA
<213> ORGANISM: Homo sapiens

<400> SEQUENCE: 548

```
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tggaaagtgg agtcccatca   180
aagttcagcg gcagtggatc tgggacagat ttcaatctca ccatcagcag cctgcagcct   240
gaagattttg caacttatta ctgccaacag tataatagtt atcctcggac gttcggccaa   300
gggaccaagg tggaaagcaa acga                                          324
```

<210> SEQ ID NO 549
<211> LENGTH: 108
<212> TYPE: PRT
<213> ORGANISM: Homo sapiens

<400> SEQUENCE: 549

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Glu Ser Gly Val Pro Ser Lys Phe Ser Gly
    50                  55                  60

Ser Gly Ser Gly Thr Asp Phe Asn Leu Thr Ile Ser Ser Leu Gln Pro
65                  70                  75                  80

Glu Asp Phe Ala Thr Tyr Tyr Cys Gln Gln Tyr Asn Ser Tyr Pro Arg
            85                  90                  95

Thr Phe Gly Gln Gly Thr Lys Val Glu Ser Lys Arg
        100                 105

<210> SEQ ID NO 550
<211> LENGTH: 372
<212> TYPE: DNA
<213> ORGANISM: Homo sapiens

<400> SEQUENCE: 550
caggtgcagc tgcaggagtc gggcccagga ctggtgaagc cttcggagac cctgtccctc        60
acctgcactg tctctggtgg ctccgtcagc agtggtggtt actactggag ctggatccgg       120
cagcccccag ggaagggact ggagtggatt ggatatatct attacagtcg gagcaccaac       180
tacaacccct ccctcaagag tcgagtcacc atatcagtag acacgtccaa gaaccagttc       240
tccctgaaac tgagctctgt gaccgctgcg gacacggccg tgtattactg tgcgagagag       300
ggacgtggat acagctatgg ttactacttt gactactggg gccagggaac cctggtcacc       360
gtctcctcag ct                                                            372

<210> SEQ ID NO 551
<211> LENGTH: 124
<212> TYPE: PRT
<213> ORGANISM: Homo sapiens

<400> SEQUENCE: 551

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Arg Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Arg Gly Tyr Ser Tyr Gly Tyr Tyr Phe Asp Tyr
            100                 105                 110

Trp Gly Gln Gly Thr Leu Val Thr Val Ser Ser Ala
        115                 120

<210> SEQ ID NO 552
<211> LENGTH: 366
<212> TYPE: DNA
<213> ORGANISM: Homo sapiens

<400> SEQUENCE: 552
gaggtgcagc tgttggagtc tgggggaggc ttggtacagc ctgggggtc cctgagactc         60 tcctgtgcag cctctggatt cacctttagc agctatgcca tgagctgggt ccgccaggct       120
ccagggaagg ggctggagtg ggtctcagct attagtggta gtggtggtag tacatactac       180
gcagactccg taaagggccg gttcaccatc tccagagaca attccaagaa cacgctgtat       240
ctgcaaatga acagcctgag agccgaggac acggccgtat attactgtgc gaaagatgaa       300
gactacggtg gtaactccga ctttgactac tggggccagg gaaccctggt caccgtctcc       360
tcagct    366

<210> SEQ ID NO 553
<211> LENGTH: 122
<212> TYPE: PRT
<213> ORGANISM: Homo sapiens

<400> SEQUENCE: 553

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Glu Asp Tyr Gly Gly Asn Ser Asp Phe Asp Tyr Trp Gly
            100                 105                 110

Gln Gly Thr Leu Val Thr Val Ser Ser Ala
            115                 120

<210> SEQ ID NO 554
<211> LENGTH: 363
<212> TYPE: DNA
<213> ORGANISM: Homo sapiens

<400> SEQUENCE: 554
gaggtgcagc tggtggaatc tggaggaggc ttgatccagt ctggggggtc cctgagactc    60
tcctgtgcag cctctgggtt caccgtcagt agcaaataca tgagctgggt ccgccaggct    120
ccagggaagg ggctggagtg ggtctcagtt atttatagcg gaggtttcac atactacgca    180
gactccgtga agggccgatt caccgtctcc agagacaatt ccaagaacac gctgtatctt    240
caaatgaaca gcctgggagc cgaggacacg gccgtgtatt actgtgcgac ctatagcagt    300
ggctggcact actacggtat ggacgtctgg ggccaaggga ccacggtcac cgtctcctca    360
gct    363

<210> SEQ ID NO 555
<211> LENGTH: 121
<212> TYPE: PRT
<213> ORGANISM: Homo sapiens

<400> SEQUENCE: 555

Glu Val Gln Leu Val Glu Ser Gly Gly Gly Leu Ile Gln Ser Gly Gly
1               5                   10                  15

Ser Leu Arg Leu Ser Cys Ala Ala Ser Gly Phe Thr Val Ser Ser Lys
            20                  25                  30

Tyr Met Ser Trp Val Arg Gln Ala Pro Gly Lys Gly Leu Glu Trp Val
        35                  40                  45

Ser Val Ile Tyr Ser Gly Gly Phe Thr Tyr Tyr Ala Asp Ser Val Lys
    50                  55                  60

Gly Arg Phe Thr Val Ser Arg Asp Asn Ser Lys Asn Thr Leu Tyr Leu
65                  70                  75                  80

```
Gln Met Asn Ser Leu Gly Ala Glu Asp Thr Ala Val Tyr Tyr Cys Ala
                85                  90                  95

Thr Tyr Ser Ser Gly Trp His Tyr Tyr Gly Met Asp Val Trp Gly Gln
            100                 105                 110

Gly Thr Thr Val Thr Val Ser Ser Ala
        115                 120

<210> SEQ ID NO 556
<211> LENGTH: 324
<212> TYPE: DNA
<213> ORGANISM: Homo sapiens

<400> SEQUENCE: 556
gacatccaga tgacccagtc tccatcctca ctgtctgcat ctgtaggaga cagagtcacc    60
atcacttgtc gggcgagtca ggacattagc aattatttag cctggtttca gcagaaacca   120
gggaaagccc ctaagtccct gatctatgct gtatccagtt tgcaaagtgg ggtcccatca   180
aagttcagcg gcagtggatc tgggaccgat ttcactctca ccatcagcag cctgcagcct   240
gaagattttg caacttatta ctgccaacag tataatagtt accctcggac gttcggccaa   300
gggaccaagg tggaaatcaa acga                                          324

<210> SEQ ID NO 557
<211> LENGTH: 108
<212> TYPE: PRT
<213> ORGANISM: Homo sapiens

<400> SEQUENCE: 557

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
             20                  25                  30

Leu Ala Trp Phe Gln Gln Lys Pro Gly Lys Ala Pro Lys Ser Leu Ile
         35                  40                  45

Tyr Ala Val Ser Ser Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys Arg
            100                 105

<210> SEQ ID NO 558
<211> LENGTH: 121
<212> TYPE: PRT
<213> ORGANISM: Homo sapiens

<400> SEQUENCE: 558

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
     50                  55                  60
```

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Tyr Gly Asp Tyr Gly Met Asp Val Trp Gly Gln
            100                 105                 110

Gly Thr Thr Val Thr Val Ser Ser Ala
        115                 120

<210> SEQ ID NO 559
<211> LENGTH: 118
<212> TYPE: PRT
<213> ORGANISM: Homo sapiens

<400> SEQUENCE: 559

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ile Ala Val Ala Gly Phe Asp Tyr Trp Gly Gln Gly Thr Leu
            100                 105                 110

Val Thr Val Ser Ser Ala
        115

<210> SEQ ID NO 560
<211> LENGTH: 118
<212> TYPE: PRT
<213> ORGANISM: Homo sapiens

<400> SEQUENCE: 560

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Gly Asn Phe Asp Tyr Trp Gly Gln Gly Thr Leu
            100                 105                 110

Val Thr Val Ser Ser Ala
        115

<210> SEQ ID NO 561
<211> LENGTH: 114

<212> TYPE: PRT
<213> ORGANISM: Homo sapiens

<400> SEQUENCE: 561

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Phe Asp Ile Trp Gly Gln Gly Thr Met Val Thr Val Ser
            100                 105                 110

Ser Ala

<210> SEQ ID NO 562
<211> LENGTH: 112
<212> TYPE: PRT
<213> ORGANISM: Homo sapiens

<400> SEQUENCE: 562

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Trp Gly Gln Gly Thr Leu Val Thr Val Ser Ser Ala
            100                 105                 110

<210> SEQ ID NO 563
<211> LENGTH: 118
<212> TYPE: PRT
<213> ORGANISM: Homo sapiens

<400> SEQUENCE: 563

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Leu Tyr His Cys
                85                  90                  95

Ala Arg Gln Trp Leu Trp Tyr Phe Asp Leu Trp Gly Arg Gly Thr Leu
            100                 105                 110

Val Thr Val Ser Ser Ala
        115
```

<210> SEQ ID NO 564
<211> LENGTH: 123
<212> TYPE: PRT
<213> ORGANISM: Homo sapiens

<400> SEQUENCE: 564

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Gly Gly Asn Ser Tyr Tyr Tyr Tyr Gly Met Asp Val Trp
            100                 105                 110

Gly Gln Gly Thr Thr Val Thr Val Ser Ser Ala
        115                 120
```

<210> SEQ ID NO 565
<211> LENGTH: 119
<212> TYPE: PRT
<213> ORGANISM: Homo sapiens

<400> SEQUENCE: 565

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Ile Ala Val Ala Gly Phe Asp Tyr Trp Gly Gln Gly Thr
            100                 105                 110

Leu Val Thr Val Ser Ser Ala
        115
```

<210> SEQ ID NO 566
<211> LENGTH: 117
<212> TYPE: PRT
<213> ORGANISM: Homo sapiens

<400> SEQUENCE: 566

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Asn Tyr Phe Asp Tyr Trp Gly Gln Gly Thr Leu Val
            100                 105                 110

Thr Val Ser Ser Ala
        115
```

<210> SEQ ID NO 567
<211> LENGTH: 116
<212> TYPE: PRT
<213> ORGANISM: Homo sapiens

<400> SEQUENCE: 567

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Asp Phe Asp Tyr Trp Gly Gln Gly Thr Leu Val Thr
            100                 105                 110

Val Ser Ser Ala
        115
```

<210> SEQ ID NO 568
<211> LENGTH: 121
<212> TYPE: PRT
<213> ORGANISM: Homo sapiens

<400> SEQUENCE: 568

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60
```

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Tyr Ser Tyr Gly Tyr Tyr Phe Asp Tyr Trp Gly Gln
            100                 105                 110

Gly Thr Leu Val Thr Val Ser Ser Ala
            115                 120

<210> SEQ ID NO 569
<211> LENGTH: 121
<212> TYPE: PRT
<213> ORGANISM: Homo sapiens

<400> SEQUENCE: 569

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Leu Arg Tyr Tyr Tyr Gly Met Asp Val Trp Gly Gln
            100                 105                 110

Gly Thr Thr Val Thr Val Ser Ser Ala
            115                 120

<210> SEQ ID NO 570
<211> LENGTH: 123
<212> TYPE: PRT
<213> ORGANISM: Homo sapiens

<400> SEQUENCE: 570

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
                 20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Thr Asp Tyr Ala Ala
         50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Tyr Ser Ser Gly Trp Tyr Trp Tyr Phe Asp Leu Trp
            100                 105                 110

Gly Arg Gly Thr Leu Val Thr Val Ser Ser Ala
            115                 120

<210> SEQ ID NO 571
<211> LENGTH: 117
```

```
<212> TYPE: PRT
<213> ORGANISM: Homo sapiens

<400> SEQUENCE: 571

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Ala Ala Ala Gly Phe Asp Tyr Trp Gly Gln Gly Thr Leu Val
            100                 105                 110

Thr Val Ser Ser Ala
        115

<210> SEQ ID NO 572
<211> LENGTH: 118
<212> TYPE: PRT
<213> ORGANISM: Homo sapiens

<400> SEQUENCE: 572

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Gly Gly Asn Phe Asp Tyr Trp Gly Gln Gly Thr Leu
            100                 105                 110

Val Thr Val Ser Ser Ala
        115

<210> SEQ ID NO 573
<211> LENGTH: 120
<212> TYPE: PRT
<213> ORGANISM: Homo sapiens

<400> SEQUENCE: 573

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
```

```
                50              55              60
Val Ser Val Lys Ser Arg Ile Thr Ile Asn Pro Asp Thr Ser Lys Asn
 65              70              75              80

Gln Phe Ser Leu Gln Leu Asn Ser Val Thr Pro Glu Asp Thr Ala Val
                 85              90              95

Tyr Tyr Cys Ala Trp Phe Tyr Trp Tyr Phe Asp Leu Trp Gly Arg Gly
                100             105             110

Thr Leu Val Thr Val Ser Ser Ala
            115             120

<210> SEQ ID NO 574
<211> LENGTH: 114
<212> TYPE: PRT
<213> ORGANISM: Homo sapiens

<400> SEQUENCE: 574

Gln Val Gln Leu Val Glu Ser Gly Gly Gly Val Val Gln Pro Gly Arg
 1               5              10              15

Ser Leu Arg Leu Ser Cys Ala Ala Ser Gly Phe Thr Phe Ser Ser Tyr
                20              25              30

Gly Met His Trp Val Arg Gln Ala Pro Gly Lys Gly Leu Glu Trp Val
             35              40              45

Ala Val Ile Trp Tyr Asp Gly Ser Asn Lys Tyr Tyr Ala Asp Ser Val
 50              55              60

Lys Gly Arg Phe Thr Ile Ser Arg Asp Asn Ser Lys Asn Thr Leu Tyr
 65              70              75              80

Leu Gln Met Asn Ser Leu Arg Ala Glu Asp Thr Ala Val Tyr Tyr Cys
                 85              90              95

Ala Arg Thr Gly Asp Tyr Trp Gly Gln Gly Thr Leu Val Thr Val Ser
                100             105             110

Ser Ala

<210> SEQ ID NO 575
<211> LENGTH: 119
<212> TYPE: PRT
<213> ORGANISM: Homo sapiens

<400> SEQUENCE: 575

Gln Val Gln Leu Val Glu Ser Gly Gly Gly Val Val Gln Pro Gly Arg
 1               5              10              15

Ser Leu Arg Leu Ser Cys Ala Ala Ser Gly Phe Thr Phe Ser Ser Tyr
                20              25              30

Gly Met His Trp Val Arg Gln Ala Pro Gly Lys Gly Leu Glu Trp Val
             35              40              45

Ala Val Ile Ser Tyr Asp Gly Ser Asn Lys Tyr Tyr Ala Asp Ser Val
 50              55              60

Lys Gly Arg Phe Thr Ile Ser Arg Asp Asn Ser Lys Asn Thr Leu Tyr
 65              70              75              80

Leu Gln Met Asn Ser Leu Arg Ala Glu Asp Thr Ala Val Tyr Tyr Cys
                 85              90              95

Ala Arg Gly Tyr Ser Ser Gly Trp Phe Asp Tyr Trp Gly Gln Gly Thr
                100             105             110

Leu Val Thr Val Ser Ser Ala
        115

<210> SEQ ID NO 576
```

```
<211> LENGTH: 125
<212> TYPE: PRT
<213> ORGANISM: Homo sapiens

<400> SEQUENCE: 576

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Cys Gly Gly Asp Cys Tyr Tyr Tyr Tyr Tyr Gly Met Asp
            100                 105                 110

Val Trp Gly Gln Gly Thr Thr Val Thr Val Ser Ser Ala
        115                 120                 125

<210> SEQ ID NO 577
<211> LENGTH: 116
<212> TYPE: PRT
<213> ORGANISM: Homo sapiens

<400> SEQUENCE: 577

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Trp Asp Phe Asp Tyr Trp Gly Gln Gly Thr Leu Val Thr
            100                 105                 110

Val Ser Ser Ala
        115

<210> SEQ ID NO 578
<211> LENGTH: 110
<212> TYPE: PRT
<213> ORGANISM: Homo sapiens

<400> SEQUENCE: 578

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45
```

```
Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Pro Trp Gly Gln Gly Thr Leu Val Thr Val Ser Ser Ala
                100                 105                 110

<210> SEQ ID NO 579
<211> LENGTH: 121
<212> TYPE: PRT
<213> ORGANISM: Homo sapiens

<400> SEQUENCE: 579

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Trp Asn Tyr Tyr Tyr Gly Met Asp Val Trp Gly Gln
                100                 105                 110

Gly Thr Thr Val Thr Val Ser Ser Ala
            115                 120

<210> SEQ ID NO 580
<211> LENGTH: 121
<212> TYPE: PRT
<213> ORGANISM: Homo sapiens

<400> SEQUENCE: 580

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Gly Ser Gly Ser Tyr Gly Met Asp Val Trp Gly Gln
                100                 105                 110

Gly Thr Thr Val Thr Val Ser Ser Ala
            115                 120

<210> SEQ ID NO 581
<211> LENGTH: 124
```

<212> TYPE: PRT
<213> ORGANISM: Homo sapiens

<400> SEQUENCE: 581

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Tyr Gly Ser Gly Tyr Tyr Tyr Gly Met Asp Val
            100                 105                 110

Trp Gly Gln Gly Thr Thr Val Thr Val Ser Ser Ala
        115                 120

<210> SEQ ID NO 582
<211> LENGTH: 117
<212> TYPE: PRT
<213> ORGANISM: Homo sapiens

<400> SEQUENCE: 582

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Trp Asn Tyr Phe Asp Tyr Trp Gly Gln Gly Thr Leu Val
            100                 105                 110

Thr Val Ser Ser Ala
        115

<210> SEQ ID NO 583
<211> LENGTH: 118
<212> TYPE: PRT
<213> ORGANISM: Homo sapiens

<400> SEQUENCE: 583

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala

```
            50                  55                  60
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Tyr Gly Trp Tyr Phe Asp Leu Trp Gly Arg Gly Thr Leu
            100                 105                 110

Val Thr Val Ser Ser Ala
        115

<210> SEQ ID NO 584
<211> LENGTH: 115
<212> TYPE: PRT
<213> ORGANISM: Homo sapiens

<400> SEQUENCE: 584

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Ala Gly Lys Gly Leu Glu Trp Ile
             35                  40                  45

Gly Arg Ile Tyr Thr Ser Gly Ser Thr Asn Tyr Asn Pro Ser Leu Lys
         50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Trp Trp Tyr Phe Asp Leu Trp Gly Arg Gly Thr Leu Val Thr Val
            100                 105                 110

Ser Ser Ala
        115

<210> SEQ ID NO 585
<211> LENGTH: 111
<212> TYPE: PRT
<213> ORGANISM: Homo sapiens

<400> SEQUENCE: 585

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Gly Gln Gly Thr Leu Val Thr Val Ser Ser Ala
            100                 105                 110

<210> SEQ ID NO 586
<211> LENGTH: 121
<212> TYPE: PRT
```

<213> ORGANISM: Homo sapiens

<400> SEQUENCE: 586

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Tyr Tyr Tyr Tyr Tyr Gly Met Asp Val Trp Gly Gln
            100                 105                 110

Gly Thr Thr Val Thr Val Ser Ser Ala
            115                 120

<210> SEQ ID NO 587
<211> LENGTH: 116
<212> TYPE: PRT
<213> ORGANISM: Homo sapiens

<400> SEQUENCE: 587

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ala Phe Asp Tyr Trp Gly Gln Gly Thr Leu Val Thr
            100                 105                 110

Val Ser Ser Ala
        115

<210> SEQ ID NO 588
<211> LENGTH: 116
<212> TYPE: PRT
<213> ORGANISM: Homo sapiens

<400> SEQUENCE: 588

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ser Tyr Phe Asp Tyr Trp Gly Gln Gly Thr Leu Val Thr
            100                 105                 110

Val Ser Ser Ala
        115

<210> SEQ ID NO 589
<211> LENGTH: 122
<212> TYPE: PRT
<213> ORGANISM: Homo sapiens

<400> SEQUENCE: 589

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
 50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Asp Tyr Ser Tyr Tyr Tyr Tyr Gly Met Asp Val Trp Gly
            100                 105                 110

Gln Gly Thr Thr Val Thr Val Ser Ser Ala
        115                 120

<210> SEQ ID NO 590
<211> LENGTH: 122
<212> TYPE: PRT
<213> ORGANISM: Homo sapiens

<400> SEQUENCE: 590

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Tyr Gly Gly Asn Ser Tyr Gly Met Asp Val Trp Gly
            100                 105                 110

Gln Gly Thr Thr Val Thr Val Ser Ser Ala
        115                 120

<210> SEQ ID NO 591
```

```
<211> LENGTH: 118
<212> TYPE: PRT
<213> ORGANISM: Homo sapiens

<400> SEQUENCE: 591
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Asn | Ile | Lys | Gln | Asp | Gly | Ser | Glu | Lys | Tyr | Tyr | Val | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ala | Lys | Asn | Ser | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Ile | Ala | Val | Ala | Phe | Asp | Tyr | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser | Ala |
|---|---|---|---|---|---|
| | | | 115 | | |

```
<210> SEQ ID NO 592
<211> LENGTH: 117
<212> TYPE: PRT
<213> ORGANISM: Homo sapiens

<400> SEQUENCE: 592
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Gly | Ser | Gly | Gly | Ser | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Gln | Trp | Leu | Val | Phe | Asp | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser | Ala |
|---|---|---|---|---|
| | | | 115 | |

```
<210> SEQ ID NO 593
<211> LENGTH: 114
<212> TYPE: PRT
<213> ORGANISM: Homo sapiens

<400> SEQUENCE: 593
```

| Gln | Val | Gln | Leu | Gln | Glu | Ser | Gly | Pro | Gly | Leu | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Ile | Ser | Ser | Tyr |
|---|---|---|---|---|---|---|---|---|---|---|---|---|---|---|---|
| | | | 20 | | | | | 25 | | | | | 30 | | |

| Tyr | Trp | Ser | Trp | Ile | Arg | Gln | Pro | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

-continued

```
Gly Tyr Ile Tyr Tyr Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gln Trp Leu Asp Tyr Trp Gly Gln Gly Thr Leu Val Thr Val Ser
            100                 105                 110

Ser Ala
```

<210> SEQ ID NO 594
<211> LENGTH: 113
<212> TYPE: PRT
<213> ORGANISM: Homo sapiens

<400> SEQUENCE: 594

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Phe Asp Ile Trp Gly Gln Gly Thr Met Val Thr Val Ser Ser
            100                 105                 110

Ala
```

<210> SEQ ID NO 595
<211> LENGTH: 115
<212> TYPE: PRT
<213> ORGANISM: Homo sapiens

<400> SEQUENCE: 595

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Phe Asp Ile Trp Gly Gln Gly Thr Met Val Thr Val
            100                 105                 110

Ser Ser Ala
        115
```

<210> SEQ ID NO 596

```
<211> LENGTH: 119
<212> TYPE: PRT
<213> ORGANISM: Homo sapiens

<400> SEQUENCE: 596

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Asn Trp Asn Tyr Trp Tyr Phe Asp Leu Trp Gly Arg Gly Thr
            100                 105                 110

Leu Val Thr Val Ser Ser Ala
        115

<210> SEQ ID NO 597
<211> LENGTH: 118
<212> TYPE: PRT
<213> ORGANISM: Homo sapiens

<400> SEQUENCE: 597

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ile Ala Val Ala Gly Phe Asp Tyr Trp Gly Gln Gly Thr Leu
            100                 105                 110

Val Thr Val Ser Ser Ala
        115

<210> SEQ ID NO 598
<211> LENGTH: 119
<212> TYPE: PRT
<213> ORGANISM: Homo sapiens

<400> SEQUENCE: 598

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45
```

```
Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Tyr Ser Ser Gly Trp Tyr Tyr Gly Met Asp Val Trp Gly Gln Gly Thr
                100                 105                 110

Thr Val Thr Val Ser Ser Ala
            115
```

<210> SEQ ID NO 599
<211> LENGTH: 119
<212> TYPE: PRT
<213> ORGANISM: Homo sapiens

<400> SEQUENCE: 599

```
Gln Val Gln Leu Val Glu Ser Gly Gly Val Val Gln Pro Gly Arg
 1               5                   10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Leu Leu Leu Arg Tyr Gly Arg Leu Pro Arg Asp
                100                 105                 110

His Gly His Arg Leu Leu Ser
            115
```

<210> SEQ ID NO 600
<211> LENGTH: 124
<212> TYPE: PRT
<213> ORGANISM: Homo sapiens

<400> SEQUENCE: 600

```
Gln Val Gln Leu Val Glu Ser Gly Gly Val Val Gln Pro Gly Arg
 1               5                   10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ile Val Ala Thr Ile Asn Tyr Tyr Gly Met Asp Val
                100                 105                 110

Trp Gly Gln Gly Thr Thr Val Thr Val Ser Ser Ala
            115                 120
```

<210> SEQ ID NO 601
<211> LENGTH: 117
<212> TYPE: PRT
<213> ORGANISM: Homo sapiens

<400> SEQUENCE: 601

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Trp Tyr Phe Asp Leu Trp Gly Arg Gly Thr Leu Val
            100                 105                 110

Thr Val Ser Ser Ala
        115

<210> SEQ ID NO 602
<211> LENGTH: 115
<212> TYPE: PRT
<213> ORGANISM: Homo sapiens

<400> SEQUENCE: 602

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Phe Asp Leu Trp Gly Arg Gly Thr Leu Val Thr Val
            100                 105                 110

Ser Ser Ala
        115

<210> SEQ ID NO 603
<211> LENGTH: 116
<212> TYPE: PRT
<213> ORGANISM: Homo sapiens

<400> SEQUENCE: 603

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val

```
                35                  40                  45

Ala Asn Ile Lys Gln Asp Gly Ser Glu Lys Tyr Tyr Val Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ala Ala Phe Asp Tyr Trp Gly Gln Gly Thr Leu Val Thr
                100                 105                 110

Val Ser Ser Ala
        115

<210> SEQ ID NO 604
<211> LENGTH: 117
<212> TYPE: PRT
<213> ORGANISM: Homo sapiens

<400> SEQUENCE: 604

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
                 35                  40                  45

Ala Val Ile Trp Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Tyr Ser Asn Tyr Tyr Phe Asp Tyr Trp Gly Gln Gly Thr Leu Val
                100                 105                 110

Thr Val Ser Ser Ala
        115

<210> SEQ ID NO 605
<211> LENGTH: 119
<212> TYPE: PRT
<213> ORGANISM: Homo sapiens

<400> SEQUENCE: 605

Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Val Gly Val Gly Trp Ile Arg Gln Pro Pro Gly Lys Ala Leu Glu
                 35                  40                  45

Trp Leu Ala Leu Ile Tyr Trp Asn Asp Asp Lys Arg Tyr Ser Pro Ser
 50                      55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg Ser Ser Trp Phe Asp Tyr Trp Gly Gln Gly Thr
                100                 105                 110

Leu Val Thr Val Ser Ser Ala
```

-continued

115

<210> SEQ ID NO 606
<211> LENGTH: 116
<212> TYPE: PRT
<213> ORGANISM: Homo sapiens

<400> SEQUENCE: 606

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Ala Phe Asp Tyr Trp Gly Gln Gly Thr Leu Val Thr
            100                 105                 110

Val Ser Ser Ala
        115

<210> SEQ ID NO 607
<211> LENGTH: 119
<212> TYPE: PRT
<213> ORGANISM: Homo sapiens

<400> SEQUENCE: 607

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ile Ala Ala Ala Gly Phe Asp Tyr Trp Gly Gln Gly Thr
            100                 105                 110

Leu Val Thr Val Ser Ser Ala
        115

<210> SEQ ID NO 608
<211> LENGTH: 115
<212> TYPE: PRT
<213> ORGANISM: Homo sapiens

<400> SEQUENCE: 608

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

```
Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ile Thr Phe Asp Pro Trp Gly Gln Gly Thr Leu Val Thr Val
            100                 105                 110

Ser Ser Ala
        115

<210> SEQ ID NO 609
<211> LENGTH: 113
<212> TYPE: PRT
<213> ORGANISM: Homo sapiens

<400> SEQUENCE: 609

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Met Asp Val Trp Gly Gln Gly Thr Thr Val Thr Val Ser Ser
            100                 105                 110

Ala

<210> SEQ ID NO 610
<211> LENGTH: 116
<212> TYPE: PRT
<213> ORGANISM: Homo sapiens

<400> SEQUENCE: 610

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Trp Asn Phe Asp Ile Trp Gly Gln Gly Thr Met Val Thr
            100                 105                 110
```

Val Ser Ser Ala
        115

<210> SEQ ID NO 611
<211> LENGTH: 121
<212> TYPE: PRT
<213> ORGANISM: Homo sapiens

<400> SEQUENCE: 611

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ile Phe Gly Val Val Asn Trp Tyr Phe Asp Leu Trp Gly Arg
            100                 105                 110

Gly Thr Leu Val Thr Val Ser Ser Ala
            115                 120

<210> SEQ ID NO 612
<211> LENGTH: 123
<212> TYPE: PRT
<213> ORGANISM: Homo sapiens

<400> SEQUENCE: 612

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Asn Tyr Asp Phe Trp Ser Gly Tyr Gly Met Asp Val Trp
            100                 105                 110

Gly Gln Gly Thr Thr Val Thr Val Ser Ser Ala
            115                 120

<210> SEQ ID NO 613
<211> LENGTH: 115
<212> TYPE: PRT
<213> ORGANISM: Homo sapiens

<400> SEQUENCE: 613

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                    20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Gly Ala Asp Tyr Trp Gly Gln Gly Thr Leu Val Thr Val
            100                 105                 110

Ser Ser Ala
        115

<210> SEQ ID NO 614
<211> LENGTH: 124
<212> TYPE: PRT
<213> ORGANISM: Homo sapiens

<400> SEQUENCE: 614

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ser Ser Gly Trp Tyr Tyr Tyr Tyr Gly Met Asp Val
            100                 105                 110

Trp Gly Gln Gly Thr Thr Val Thr Val Ser Ser Ala
        115                 120

<210> SEQ ID NO 615
<211> LENGTH: 119
<212> TYPE: PRT
<213> ORGANISM: Homo sapiens

<400> SEQUENCE: 615

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Trp Ser Asn Trp Phe Asp Pro Trp Gly Gln Gly Thr
```

Leu Val Thr Val Ser Ser Ala
        115

<210> SEQ ID NO 616
<211> LENGTH: 118
<212> TYPE: PRT
<213> ORGANISM: Homo sapiens

<400> SEQUENCE: 616

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Tyr Gly Asp Ala Phe Asp Ile Trp Gly Gln Gly Thr Met
            100                 105                 110

Val Thr Val Ser Ser Ala
        115

<210> SEQ ID NO 617
<211> LENGTH: 121
<212> TYPE: PRT
<213> ORGANISM: Homo sapiens

<400> SEQUENCE: 617

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Cys Ser Gly Tyr Gly Met Asp Val Trp Gly Gln
            100                 105                 110

Gly Thr Thr Val Thr Val Ser Ser Ala
        115                 120

<210> SEQ ID NO 618
<211> LENGTH: 117
<212> TYPE: PRT
<213> ORGANISM: Homo sapiens

<400> SEQUENCE: 618

Gln Val Gln Leu Val Glu Ser Gly Gly Gly Val Val Gln Pro Gly Arg
 1               5                  10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Tyr Phe Asp Trp Asp Tyr Trp Gly Gln Gly Thr Leu Val
            100                 105                 110

Thr Val Ser Ser Ala
            115

<210> SEQ ID NO 619
<211> LENGTH: 116
<212> TYPE: PRT
<213> ORGANISM: Homo sapiens

<400> SEQUENCE: 619

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Ser Ser Phe Asp Tyr Trp Gly Gln Gly Thr Leu Val Thr
            100                 105                 110

Val Ser Ser Ala
        115

<210> SEQ ID NO 620
<211> LENGTH: 119
<212> TYPE: PRT
<213> ORGANISM: Homo sapiens

<400> SEQUENCE: 620

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Phe Trp Ser Asn Trp Phe Asp Pro Trp Gly Gln Gly Thr
            100                 105                 110

Leu Val Thr Val Ser Ser Ala
            115

<210> SEQ ID NO 621
<211> LENGTH: 110
<212> TYPE: PRT
<213> ORGANISM: Homo sapiens

<400> SEQUENCE: 621

Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser Ala
            100                 105                 110

<210> SEQ ID NO 622
<211> LENGTH: 112
<212> TYPE: PRT
<213> ORGANISM: Homo sapiens

<400> SEQUENCE: 622

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Gly Asp Tyr Trp Gly Gln Gly Thr Leu Val Thr Val Ser Ser Ala
            100                 105                 110

<210> SEQ ID NO 623
<211> LENGTH: 114
<212> TYPE: PRT
<213> ORGANISM: Homo sapiens

<400> SEQUENCE: 623

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
            20                  25                  30
```

```
Tyr Met Ser Trp Ile Arg Gln Ala Pro Gly Lys Gly Leu Glu Trp Val
         35                  40                  45

Ser Tyr Ile Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ala Phe Asp Ile Trp Gly Gln Gly Thr Met Val Thr Val Ser
                100                 105                 110

Ser Ala

<210> SEQ ID NO 624
<211> LENGTH: 119
<212> TYPE: PRT
<213> ORGANISM: Homo sapiens

<400> SEQUENCE: 624

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Tyr Gly Asp Tyr Tyr Phe Asp Tyr Trp Gly Gln Gly Thr
                100                 105                 110

Leu Val Thr Val Ser Ser Ala
        115

<210> SEQ ID NO 625
<211> LENGTH: 112
<212> TYPE: PRT
<213> ORGANISM: Homo sapiens

<400> SEQUENCE: 625

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Phe Asp Tyr Trp Gly Gln Gly Thr Leu Val Thr Val Ser Ser Ala
                100                 105                 110
```

```
<210> SEQ ID NO 626
<211> LENGTH: 115
<212> TYPE: PRT
<213> ORGANISM: Homo sapiens

<400> SEQUENCE: 626

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Gln Leu Trp Asp Tyr Trp Gly Gln Gly Thr Leu Val Thr Val
                100                 105                 110

Ser Ser Ala
        115

<210> SEQ ID NO 627
<211> LENGTH: 120
<212> TYPE: PRT
<213> ORGANISM: Homo sapiens

<400> SEQUENCE: 627

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Gly Ile Ala Val Ala Tyr Gly Met Asp Val Trp Gly Gln Gly
                100                 105                 110

Thr Thr Val Thr Val Ser Ser Ala
        115                 120

<210> SEQ ID NO 628
<211> LENGTH: 109
<212> TYPE: PRT
<213> ORGANISM: Homo sapiens

<400> SEQUENCE: 628

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45
```

```
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys Arg
            100                 105

<210> SEQ ID NO 629
<211> LENGTH: 104
<212> TYPE: PRT
<213> ORGANISM: Homo sapiens

<400> SEQUENCE: 629

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Phe Gly Gln
                 85                  90                  95

Gly Thr Lys Leu Glu Ile Lys Arg
            100

<210> SEQ ID NO 630
<211> LENGTH: 108
<212> TYPE: PRT
<213> ORGANISM: Homo sapiens

<400> SEQUENCE: 630

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Trp
                 85                  90                  95

Thr Phe Gly Gln Gly Thr Lys Val Glu Ile Lys Arg
            100                 105

<210> SEQ ID NO 631
<211> LENGTH: 108
<212> TYPE: PRT
<213> ORGANISM: Homo sapiens

<400> SEQUENCE: 631
```

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gly Gly Thr Lys Val Glu Ile Lys Arg
            100                 105

<210> SEQ ID NO 632
<211> LENGTH: 108
<212> TYPE: PRT
<213> ORGANISM: Homo sapiens

<400> SEQUENCE: 632

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Phe
                85                  90                  95

Thr Phe Gly Pro Gly Thr Lys Val Asp Ile Lys Arg
            100                 105

<210> SEQ ID NO 633
<211> LENGTH: 108
<212> TYPE: PRT
<213> ORGANISM: Homo sapiens

<400> SEQUENCE: 633

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg
            100                 105

<210> SEQ ID NO 634
<211> LENGTH: 108
<212> TYPE: PRT
<213> ORGANISM: Homo sapiens

<400> SEQUENCE: 634

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys Arg
            100                 105

<210> SEQ ID NO 635
<211> LENGTH: 108
<212> TYPE: PRT
<213> ORGANISM: Homo sapiens

<400> SEQUENCE: 635

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys Arg
            100                 105

<210> SEQ ID NO 636
<211> LENGTH: 106
<212> TYPE: PRT
<213> ORGANISM: Homo sapiens

<400> SEQUENCE: 636

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro

```
65                  70                  75                  80

Glu Asp Phe Ala Thr Tyr Tyr Cys Leu Gln His Asn Ser Tyr Pro Phe
                85                  90                  95

Gly Gln Gly Thr Lys Leu Glu Ile Lys Arg
            100                 105

<210> SEQ ID NO 637
<211> LENGTH: 108
<212> TYPE: PRT
<213> ORGANISM: Homo sapiens

<400> SEQUENCE: 637

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys Arg
            100                 105

<210> SEQ ID NO 638
<211> LENGTH: 108
<212> TYPE: PRT
<213> ORGANISM: Homo sapiens

<400> SEQUENCE: 638

Glu Ile Val Met Thr Gln Ser Pro Ala Thr Leu Ser Val Ser Pro Gly
1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys Arg
            100                 105

<210> SEQ ID NO 639
<211> LENGTH: 113
<212> TYPE: PRT
<213> ORGANISM: Homo sapiens

<400> SEQUENCE: 639

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
                20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
                100                 105                 110

Arg

<210> SEQ ID NO 640
<211> LENGTH: 114
<212> TYPE: PRT
<213> ORGANISM: Homo sapiens

<400> SEQUENCE: 640

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Arg Pro Gly Gln Ser
            35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
                100                 105                 110

Lys Arg

<210> SEQ ID NO 641
<211> LENGTH: 113
<212> TYPE: PRT
<213> ORGANISM: Homo sapiens

<400> SEQUENCE: 641

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
                100                 105                 110

Arg
```

-continued

```
<210> SEQ ID NO 642
<211> LENGTH: 114
<212> TYPE: PRT
<213> ORGANISM: Homo sapiens

<400> SEQUENCE: 642

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gln Gly Thr Arg Leu Glu Ile
            100                 105                 110

Lys Arg

<210> SEQ ID NO 643
<211> LENGTH: 110
<212> TYPE: PRT
<213> ORGANISM: Homo sapiens

<400> SEQUENCE: 643

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Phe Gly Gln Gly Thr Lys Leu Glu Ile Lys Arg
            100                 105                 110

<210> SEQ ID NO 644
<211> LENGTH: 112
<212> TYPE: PRT
<213> ORGANISM: Homo sapiens

<400> SEQUENCE: 644

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
```

```
                 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                     85                  90                  95

Tyr Tyr Ser Thr Thr Phe Gly Gly Gly Thr Lys Val Glu Ile Lys Arg
                100                 105                 110
```

<210> SEQ ID NO 645
<211> LENGTH: 113
<212> TYPE: PRT
<213> ORGANISM: Homo sapiens

<400> SEQUENCE: 645

```
Asp Val Val Met Thr Gln Ser Pro Leu Ser Leu Pro Val Thr Leu Gly
 1                   5                  10                  15

Gln Pro Ala Ser Ile Ser Cys Arg Ser Ser Gln Ser Leu Val Tyr Ser
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                     85                  90                  95

Thr His Trp Pro Pro Thr Phe Gly Gln Gly Thr Lys Val Glu Ile Lys
                100                 105                 110

Arg
```

<210> SEQ ID NO 646
<211> LENGTH: 111
<212> TYPE: PRT
<213> ORGANISM: Homo sapiens

<400> SEQUENCE: 646

```
Asp Ile Val Met Thr Gln Ser Pro Leu Ser Leu Pro Val Thr Pro Gly
 1                   5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Trp Thr Phe Gly Gln Gly Thr Lys Val Glu Ile Lys Arg
                100                 105                 110
```

<210> SEQ ID NO 647
<211> LENGTH: 113
<212> TYPE: PRT
<213> ORGANISM: Homo sapiens

<400> SEQUENCE: 647

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Trp Thr Phe Gly Gln Gly Thr Lys Val Glu Ile Lys
            100                 105                 110

Arg
```

<210> SEQ ID NO 648
<211> LENGTH: 106
<212> TYPE: PRT
<213> ORGANISM: Homo sapiens

<400> SEQUENCE: 648

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Thr Phe
            85                  90                  95

Gly Gly Gly Thr Lys Val Glu Ile Lys Arg
            100                 105
```

<210> SEQ ID NO 649
<211> LENGTH: 111
<212> TYPE: PRT
<213> ORGANISM: Homo sapiens

<400> SEQUENCE: 649

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Thr Phe Gly Gln Gly Thr Lys Leu Glu Ile Lys Arg
            100                 105
```

<210> SEQ ID NO 650
<211> LENGTH: 106
<212> TYPE: PRT
<213> ORGANISM: Homo sapiens

<400> SEQUENCE: 650

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ile Thr Phe
                85                  90                  95

Gly Gln Gly Thr Arg Leu Glu Ile Lys Arg
            100                 105

<210> SEQ ID NO 651
<211> LENGTH: 108
<212> TYPE: PRT
<213> ORGANISM: Homo sapiens

<400> SEQUENCE: 651

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 652
<211> LENGTH: 108
<212> TYPE: PRT
<213> ORGANISM: Homo sapiens

<400> SEQUENCE: 652

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Phe
                 85                  90                  95

Thr Phe Gly Pro Gly Thr Lys Val Asp Ile Lys Arg
            100                 105

<210> SEQ ID NO 653
<211> LENGTH: 107
<212> TYPE: PRT
<213> ORGANISM: Homo sapiens

<400> SEQUENCE: 653

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Thr
                 85                  90                  95

Phe Gly Gly Gly Thr Lys Val Glu Ile Lys Arg
            100                 105

<210> SEQ ID NO 654
<211> LENGTH: 108
<212> TYPE: PRT
<213> ORGANISM: Homo sapiens

<400> SEQUENCE: 654

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Ile
                 85                  90                  95

Thr Phe Gly Gln Gly Thr Arg Leu Glu Ile Lys Arg
            100                 105

<210> SEQ ID NO 655
<211> LENGTH: 106
<212> TYPE: PRT
<213> ORGANISM: Homo sapiens

<400> SEQUENCE: 655

Asp Ile Gln Met Thr Gln Ser Pro Ser Ser Leu Ser Ala Ser Val Gly
 1               5                  10                  15
```

Asp Arg Val Thr Ile Thr Cys Arg Ala Ser Gln Gly Ile Ser Asn Tyr
              20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Thr Phe
                 85                  90                  95

Gly Pro Gly Thr Lys Val Asp Ile Lys Arg
            100                 105

<210> SEQ ID NO 656
<211> LENGTH: 106
<212> TYPE: PRT
<213> ORGANISM: Homo sapiens

<400> SEQUENCE: 656

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
              20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                 85                  90                  95

Gly Gln Gly Thr Lys Leu Glu Ile Lys Arg
            100                 105

<210> SEQ ID NO 657
<211> LENGTH: 108
<212> TYPE: PRT
<213> ORGANISM: Homo sapiens

<400> SEQUENCE: 657

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Ser Tyr
              20                  25                  30

Leu Asn Trp Tyr Gln Gln Lys Pro Gly Lys Ala Pro Lys Val Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Cys
                 85                  90                  95

Ser Phe Gly Gln Gly Thr Lys Leu Glu Ile Lys Arg
            100                 105

<210> SEQ ID NO 658
<211> LENGTH: 108

```
<212> TYPE: PRT
<213> ORGANISM: Homo sapiens

<400> SEQUENCE: 658

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
             85                  90                  95

Thr Phe Gly Gly Gly Thr Lys Val Glu Ile Lys Arg
            100                 105

<210> SEQ ID NO 659
<211> LENGTH: 109
<212> TYPE: PRT
<213> ORGANISM: Homo sapiens

<400> SEQUENCE: 659

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
             85                  90                  95

Phe Thr Phe Gly Pro Gly Thr Lys Val Asp Ile Lys Arg
            100                 105

<210> SEQ ID NO 660
<211> LENGTH: 106
<212> TYPE: PRT
<213> ORGANISM: Homo sapiens

<400> SEQUENCE: 660

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Gln Tyr Asp Asn Leu Thr Phe
                85                  90                  95
Gly Gly Gly Thr Lys Val Glu Ile Lys Arg
            100                 105

<210> SEQ ID NO 661
<211> LENGTH: 107
<212> TYPE: PRT
<213> ORGANISM: Homo sapiens

<400> SEQUENCE: 661

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Thr
                85                  90                  95
Phe Gly Gln Gly Thr Lys Val Glu Ile Lys Arg
            100                 105

<210> SEQ ID NO 662
<211> LENGTH: 108
<212> TYPE: PRT
<213> ORGANISM: Homo sapiens

<400> SEQUENCE: 662

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Tyr
            20                  25                  30
Leu Ala Trp Phe Gln Gln Lys Pro Gly Lys Ala Pro Lys Ser Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Arg
                85                  90                  95
Thr Phe Gly Gln Gly Thr Lys Val Glu Ile Lys Arg
            100                 105
```